(12) United States Patent
Zhu et al.

(10) Patent No.: US 7,598,242 B2
(45) Date of Patent: Oct. 6, 2009

(54) COMPOUNDS FOR THE TREATMENT OF INFLAMMATORY DISORDERS

(75) Inventors: Zhaoning Zhu, Plainsboro, NJ (US); Robert Mazzola, Clinton, NJ (US); Zhuyan Guo, Scotch Plains, NJ (US); Brian J. Lavey, Chatham, NJ (US); Lisa Sinning, New Providence, NJ (US); Joseph Kozlowski, Princeton, NJ (US); Brian McKittrick, New Vernon, NJ (US); Neng-Yang Shih, North Caldwell, NJ (US)

(73) Assignee: Schering Corporation, Kenilworth, NJ (US)

( * ) Notice: Subject to any disclaimer, the term of this patent is extended or adjusted under 35 U.S.C. 154(b) by 707 days.

(21) Appl. No.: 11/255,130

(22) Filed: Oct. 20, 2005

(65) Prior Publication Data

US 2006/0063843 A1 Mar. 23, 2006

Related U.S. Application Data

(62) Division of application No. 10/716,890, filed on Nov. 19, 2003, now Pat. No. 7,034,057, which is a division of application No. 10/323,511, filed on Dec. 19, 2002, now Pat. No. 6,838,466.

(60) Provisional application No. 60/342,332, filed on Dec. 20, 2001.

(51) Int. Cl.
*A61K 31/535* (2006.01)
*A61K 31/497* (2006.01)
*C07D 401/12* (2006.01)
*C07D 413/04* (2006.01)
*C07D 295/02* (2006.01)
*C07D 217/06* (2006.01)
*C07C 255/03* (2006.01)
*C07C 69/76* (2006.01)

(52) U.S. Cl. ............... 514/231.5; 514/252.12; 514/252.13; 514/521; 514/402; 514/406; 514/572; 514/307; 514/311; 544/114; 544/363; 544/386; 546/146; 546/265; 548/255; 548/300.1; 560/52; 560/53; 558/414

(58) Field of Classification Search ............ 546/138, 546/146, 265; 514/231.5, 252.12, 402, 406; 544/114, 386; 548/255, 406; 560/52, 53
See application file for complete search history.

(56) References Cited

U.S. PATENT DOCUMENTS

| | | | |
|---|---|---|---|
| 3,740,412 A | 6/1973 | Ullman et al. | |
| 3,997,223 A | 12/1976 | Feldman et al. | |
| 4,166,452 A | 9/1979 | Generales, Jr. | |
| 4,256,108 A | 3/1981 | Theeuwes | |
| 4,265,874 A | 5/1981 | Bonsen et al. | |
| 4,267,333 A | 5/1981 | Tsao | |
| 4,431,661 A | 2/1984 | McKenzie et al. | |
| 4,435,419 A | 3/1984 | Epstein et al. | |
| 4,544,665 A | 10/1985 | Epstein et al. | |
| 5,037,853 A | 8/1991 | Brooks et al. | |
| 5,089,633 A | 2/1992 | Powers et al. | |
| 5,114,953 A | 5/1992 | Galardy et al. | |
| 5,120,752 A | 6/1992 | Brooks et al. | |
| 5,256,657 A | 10/1993 | Singh et al. | |
| 5,455,258 A | 10/1995 | MacPherson et al. | |
| 5,506,242 A | 4/1996 | MacPherson et al. | |
| 5,514,716 A | 5/1996 | Gowravaram et al. | |
| 5,552,419 A | 9/1996 | MacPherson et al. | |
| 5,594,106 A | 1/1997 | Black et al. | |
| 5,618,844 A | 4/1997 | Gowravaram et al. | |
| 5,646,167 A | 7/1997 | MacPherson et al. | |
| 5,665,777 A | 9/1997 | Fesik et al. | |
| 5,674,901 A | 10/1997 | Cook et al. | |
| 5,703,092 A | 12/1997 | Xue et al. | |
| 5,712,300 A | 1/1998 | Jacobsen | |
| 5,753,653 A | 5/1998 | Bender et al. | |
| 5,770,624 A | 6/1998 | Parker et al. | |
| 5,804,581 A | 9/1998 | Wolanin et al. | |
| 5,817,822 A | 10/1998 | Nantermet et al. | |
| 5,830,915 A | 11/1998 | Pikul et al. | |
| 5,837,696 A | 11/1998 | Golub et al. | |
| 5,853,977 A | 12/1998 | Dalie et al. | |
| 5,856,337 A | 1/1999 | Okazoe et al. | |
| 5,962,481 A | 10/1999 | Levin et al. | |
| 5,977,408 A | 11/1999 | Levin et al. | |

(Continued)

FOREIGN PATENT DOCUMENTS

AU 534404 B 1/1984

(Continued)

OTHER PUBLICATIONS

Anderson et al., The Practice of Medicinal Chemistry (1996) Academic Press, N.Y.

(Continued)

*Primary Examiner*—James O Wilson
*Assistant Examiner*—Ebenezer Sackey
(74) *Attorney, Agent, or Firm*—Palaiyur S. Kalyanaraman

(57) ABSTRACT

This invention relates to compounds of the Formula (I):

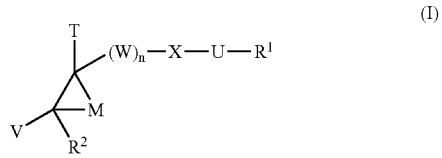

or a pharmaceutically acceptable salt, solvate or isomer thereof, which can be useful for the treatment of diseases or conditions mediated by MMPs, TNF-α or combinations thereof.

3 Claims, No Drawings

U.S. PATENT DOCUMENTS

| | | | |
|---|---|---|---|
| 5,985,900 | A | 11/1999 | Bender et al. |
| 6,034,096 | A | 3/2000 | Bertolini et al. |
| 6,057,336 | A | 5/2000 | Duane et al. |
| 6,066,633 | A | 5/2000 | De Nanteuil et al. |
| 6,071,903 | A | 6/2000 | Albright et al. |
| 6,103,739 | A | 8/2000 | Floyd et al. |
| 6,114,361 | A | 9/2000 | Robinson et al. |
| 6,153,757 | A | 11/2000 | Zook et al. |
| 6,172,057 | B1 | 1/2001 | Venkatesan et al. |
| 6,177,077 | B1 | 1/2001 | Tobinick et al. |
| 6,197,791 | B1 | 3/2001 | Venkatesan et al. |
| 6,200,996 | B1 | 3/2001 | Levin et al. |
| 6,225,311 | B1 | 5/2001 | Levin et al. |
| 6,277,885 | B1 | 8/2001 | Levin et al. |
| 6,294,539 | B1 | 9/2001 | Lou et al. |
| 6,313,123 | B1 | 11/2001 | Levin et al. |
| 6,326,516 | B1 | 12/2001 | Levin et al. |
| 6,372,747 | B1 | 4/2002 | Taveras et al. |
| 6,376,665 | B1 * | 4/2002 | Duan et al. .................. 544/60 |
| 2001/0046989 | A1 | 11/2001 | Levin et al. |

FOREIGN PATENT DOCUMENTS

| | | |
|---|---|---|
| CA | 2166168 A1 | 6/1996 |
| CA | 2281570 A1 | 9/1998 |
| CA | 2260337 A1 | 7/1999 |
| DE | 19831980 A1 | 1/2000 |
| EP | 818442 A2 | 1/1988 |
| EP | 0097816 B1 | 5/1988 |
| EP | 818442 A3 | 12/1988 |
| EP | 0887077 A1 | 12/1988 |
| EP | 641323 A1 | 9/1994 |
| EP | 498665 B1 | 4/1996 |
| EP | 757037 A2 | 2/1997 |
| EP | 667770 B1 | 3/1997 |
| EP | 863885 A2 | 5/1997 |
| EP | 871439 A1 | 7/1997 |
| EP | 574758 B1 | 9/1998 |
| EP | 922702 A1 | 6/1999 |
| EP | 00952148 A1 | 10/1999 |
| EP | 1004578 A2 | 5/2000 |
| EP | 684240 B1 | 8/2000 |
| EP | 1029851 A1 | 8/2000 |
| EP | 1041072 A1 | 10/2000 |
| EP | 1081137 A1 | 3/2001 |
| EP | 769947 B1 | 5/2001 |
| EP | 877019 B1 | 12/2001 |
| EP | 895988 B1 | 5/2002 |
| EP | 780386 B1 | 10/2002 |
| EP | 877018 B1 | 5/2003 |
| FR | 2780402 A1 | 12/1999 |
| FR | 2788525 A1 | 7/2000 |
| GB | 2200628 A | 8/1988 |
| GB | 2268934 A | 1/1994 |
| GB | 2333524 A | 7/1999 |
| JP | 95002797 | 1/1995 |
| JP | 98130217 | 5/1998 |
| JP | 98204054 | 8/1998 |
| JP | 98204059 | 8/1998 |
| WO | WO90/05719 A1 | 5/1990 |
| WO | WO93/07111 A1 | 4/1993 |
| WO | WO93/20047 A1 | 10/1993 |
| WO | WO94/00555 A2 | 1/1994 |
| WO | WO94/21612 A1 | 9/1994 |
| WO | WO94/24140 A1 | 10/1994 |
| WO | WO94/27947 A1 | 12/1994 |
| WO | WO95/06031 A1 | 3/1995 |
| WO | WO95/09841 A1 | 4/1995 |
| WO | WO95/19956 A1 | 7/1995 |
| WO | WO95/19957 A1 | 7/1995 |
| WO | WO95/19961 A1 | 7/1995 |
| WO | WO95/24501 A1 | 9/1995 |
| WO | WO95/29892 A1 | 11/1995 |
| WO | WO96/33166 A1 | 10/1996 |
| WO | WO96/33176 A1 | 10/1996 |
| WO | WO96/40204 A1 | 12/1996 |
| WO | WO97/03105 A1 | 1/1997 |
| WO | WO97/09066 A1 | 3/1997 |
| WO | WO97/12902 A1 | 4/1997 |
| WO | WO97/18188 A1 | 5/1997 |
| WO | WO97/18207 A2 | 5/1997 |
| WO | WO97/19053 A1 | 5/1997 |
| WO | WO97/20824 A1 | 6/1997 |
| WO | WO97/22587 A1 | 6/1997 |
| WO | WO97/24117 A1 | 7/1997 |
| WO | WO97/32846 A1 | 9/1997 |
| WO | WO97/40031 A1 | 10/1997 |
| WO | WO97/42168 A1 | 11/1997 |
| WO | WO98/02557 A2 | 1/1998 |
| WO | WO98/03164 A1 | 1/1998 |
| WO | WO98/03516 A1 | 1/1998 |
| WO | WO98/07697 A1 | 2/1998 |
| WO | WO98/08822 A1 | 3/1998 |
| WO | WO98/08823 A1 | 3/1998 |
| WO | WO98/08825 A1 | 3/1998 |
| WO | WO98/08827 A1 | 3/1998 |
| WO | WO98/09957 A1 | 3/1998 |
| WO | WO98/09961 A1 | 3/1998 |
| WO | WO98/12211 A1 | 3/1998 |
| WO | WO98/13340 A1 | 4/1998 |
| WO | WO98/15525 A1 | 4/1998 |
| WO | WO98/16503 A2 | 4/1998 |
| WO | WO98/16506 A1 | 4/1998 |
| WO | WO98/16514 A1 | 4/1998 |
| WO | WO98/16520 A1 | 4/1998 |
| WO | WO98/17643 A1 | 4/1998 |
| WO | WO98/17655 A1 | 4/1998 |
| WO | WO98/22436 A1 | 5/1998 |
| WO | 098/23588 A1 | 6/1998 |
| WO | WO98/24759 A1 | 6/1998 |
| WO | WO98/27069 A1 | 6/1998 |
| WO | WO98/30541 A1 | 7/1998 |
| WO | WO98/30551 A1 | 7/1998 |
| WO | WO98/30566 A1 | 7/1998 |
| WO | WO98/32748 A1 | 7/1998 |
| WO | WO98/33788 A1 | 8/1998 |
| WO | WO98/37877 A1 | 9/1998 |
| WO | WO98/38163 A1 | 9/1998 |
| WO | WO98/38167 A1 | 9/1998 |
| WO | WO98/38179 A1 | 9/1998 |
| WO | WO98/42662 A1 | 10/1998 |
| WO | WO98/43959 A1 | 10/1998 |
| WO | WO98/43963 A1 | 10/1998 |
| WO | WO98/45699 A1 | 10/1998 |
| WO | WO98/46563 A1 | 10/1998 |
| WO | WO98/50348 A1 | 11/1998 |
| WO | WO98/52910 A1 | 11/1998 |
| WO | WO99/02510 A1 | 1/1999 |
| WO | WO99/06410 A1 | 2/1999 |
| WO | WO99/18074 A1 | 4/1999 |
| WO | WO99/18076 A1 | 4/1999 |
| WO | WO99/18079 A1 | 4/1999 |
| WO | WO99/19296 A1 | 4/1999 |
| WO | WO99/24399 A1 | 5/1999 |
| WO | WO99/24408 A1 | 5/1999 |
| WO | WO99/24419 A1 | 5/1999 |
| WO | WO99/31052 A1 | 6/1999 |
| WO | WO99/37635 A2 | 6/1999 |
| WO | WO99/32413 A1 | 7/1999 |
| WO | WO99/32451 A1 | 7/1999 |
| WO | WO99/32452 A1 | 7/1999 |
| WO | WO99/32463 A1 | 7/1999 |
| WO | WO99/37625 A1 | 7/1999 |
| WO | WO99/38843 A1 | 8/1999 |

| | | | |
|---|---|---|---|
| WO | WO99/40080 A1 | 8/1999 |
| WO | WO99/42436 A1 | 8/1999 |
| WO | WO99/42443 A1 | 8/1999 |
| WO | WO99/52910 A1 | 10/1999 |
| WO | WO99/58528 A1 | 11/1999 |
| WO | WO99/58531 A1 | 11/1999 |
| WO | WO99/61413 A1 | 12/1999 |
| WO | WO99/65867 A1 | 12/1999 |
| WO | WO00/06560 A1 | 2/2000 |
| WO | WO00/06561 A1 | 2/2000 |
| WO | WO00/09485 A1 | 2/2000 |
| WO | WO00/12082 A1 | 3/2000 |
| WO | WO00/12083 A1 | 3/2000 |
| WO | WO00/12466 A1 | 3/2000 |
| WO | WO00/12477 A1 | 3/2000 |
| WO | WO00/12478 A1 | 3/2000 |
| WO | WO00/15603 A1 | 3/2000 |
| WO | WO00/16766 A1 | 3/2000 |
| WO | WO00/24720 A1 | 5/2000 |
| WO | WO00/32570 A1 | 6/2000 |
| WO | WO00/35885 A1 | 6/2000 |
| WO | WO00/37433 A1 | 6/2000 |
| WO | WO00/40564 A1 | 7/2000 |
| WO | WO00/40576 A2 | 7/2000 |
| WO | WO00/40578 A1 | 7/2000 |
| WO | WO00/42436 A1 | 7/2000 |
| WO | WO00/44709 A2 | 8/2000 |
| WO | WO00/44711 A1 | 8/2000 |
| WO | WO00/44713 A1 | 8/2000 |
| WO | WO00/44716 A1 | 8/2000 |
| WO | WO00/44723 A1 | 8/2000 |
| WO | WO00/44730 A1 | 8/2000 |
| WO | WO00/44740 A2 | 8/2000 |
| WO | WO00/44749 A1 | 8/2000 |
| WO | WO00/46189 A1 | 8/2000 |
| WO | WO00/46221 A1 | 8/2000 |
| WO | WO00/50391 A1 | 8/2000 |
| WO | WO00/58278 A1 | 10/2000 |
| WO | WO00/58280 A1 | 10/2000 |
| WO | WO00/58304 A1 | 10/2000 |
| WO | WO00/59874 A1 | 10/2000 |
| WO | WO00/63165 A1 | 10/2000 |
| WO | WO00/63194 A1 | 10/2000 |
| WO | WO00/63197 A1 | 10/2000 |
| WO | WO00/69812 A1 | 11/2000 |
| WO | WO00/69827 A1 | 11/2000 |
| WO | WO01/22952 A2 | 4/2001 |
| WO | WO01/30360 A1 | 5/2001 |
| WO | WO01/62704 A1 | 8/2001 |
| WO | WO01/67103 A1 | 9/2001 |
| WO | WO01/70673 A2 | 9/2001 |
| WO | WO01/70734 A2 | 9/2001 |
| WO | WO01/87870 A1 | 11/2001 |
| WO | WO02/04416 A2 | 1/2002 |
| WO | WO02/18326 A1 | 3/2002 |
| WO | WO02/096246 A1 | 12/2002 |
| WO | WO03/016248 A2 | 2/2003 |
| WO | WO03/024899 A2 | 3/2003 |

OTHER PUBLICATIONS

Mankin et al., Arthritis Rheum. 21 (1978) 761-66.
M. H. Rabinowitz et al., "Design of Selective and Soluble Inhibitors of Tumor Necrosis Factor-α Converting Enzyme (TACE)", J Med Chem, 44:4252-67 (2001).
J. W. Skiles et al., "The Design, Structure, and Therapeutic Application of Matrix Metalloproteinase Inhibitors" Current Medicinal Chem. 8:425-474 (2001).
R. Newton et al., "Biology of TACE Inhibition" Ann RheumDis 60iii 25-iii32 Dis(2001).
Delos Santos et al., "The Syntheses of 2,3,4,5-Tetrahydro-1H-[1, 4] Benzodiazepine-3-Hydroxamic Acids as Matrix Metalloproteinase and TACE Inhibitors", Wyeth-Ayerst Research-.
A. K. Ghose et al., "Determination of Pharmacophoric Geometry for Collagenase Inhibitors Using a Novel Computational Method and Its Verification Using Molecular Dynamics, NMR, and X-ray Crystallography".J. Am. Chem. Soc'y 117, 4671-4682 (1995).
S. F. Martin et al., "Cyclopropanes as Conformationally Restricted Peptide Isosteres. Design and Synthesis of Novel Collagenase Inhibitors"Tetrahedron 49:(17) 3521-32 (1993).
R. A. Black., "Tumor Necrosis Factor-α Converting Enzyme", The International J. Biocem. Cell Biology. (2002) 34(1): 1-5.
M. Moss et al., "TACE and other ADAM Proteases as Targets for Drug Discovery", Drug Discovery Today 6(8):417-26 (2001).
Feldman et al, Lancet (1994) 344,1105.
L. S. Lohmander et al., "The Structure of Aggrecan Fragments in Human Synovial Fluid", Arthritis Rheum. 36:(9) 1214-22 (1993).
T. T. Macdonald et al., "Tumor Necrosis Factor-alpha and Interferon-gamma Production measured at the single cell level in normal and inflamed human intestine", Clin. Exp. Immunol. 81:301-305 (1990).
H. Mankin et al., "Biochemical and Metabolic Abnormalities in Articular Cartilage from Osteo-Arthritic Human Hips", J. Bone Joint Surg. 52A (1970) 424-34.
J. F. Woessner et al., "Collagenase and Collagenolytic Activity in Human Osteoarthritic Cartilage", Arthritis and Rheum. 26(1), 63-68 (1983).
J. F. Woessner et al., "Neutral Proteases Capable of Proteoglycan Digesting Activity in Osteoarthritic and Normal Human Articular Cartilage", Arthritis Rheum 27:3, 305-312 (1984).
R. C. Wahl et al., "Chapter 19. Biochemistry and Inhibition of Collagenase and Stromelysin", Ann. Rep. Med. Chem. 25:177-184.
Gearing et al., Nature (1994) 370, 555.
J. Higuchi et al., Pro-Drugs as Novel Delivery Systems (1987) vol. 14 of the A.C.S. Symposium Series.
E. Roche (Ed.), Bioreversible Carriers in Drug Design (1987) Amer. Pharma. Assoc. and Pergannon Press.
S.M. Berge et al., "Pharmaceutical Salts", Journal of Pharm. Sciences 66(1) 1-19 (1977).
P. L. Gould, "Salt Selection for Basic Drugs", International J. of Pharmaceutics 33:201-217 (1986).
G. Kokotos and C. Noula, "Selective One-Pot Conversion of Carboxylic Acids into Alcohols", J. Org. Chem. 61:6994-6996 (1996).
F. J. Lotspeich, "The Reaction of Potassium Cyanide with p-Phenylsufonylbenzyl Bromide", J. Chem. Soc., J. Org. Chem. 32:12-74-1277 (1967).
G. Kottirsch et al., "β-Aryl—Succinic Acid Hydroxamates as Dual Inhibitors of Matrix Metalloproteinses and Tumor Necrosis Factor Alpha Converting Enzyme", J. Med. Chem. 45:2289-2293 (2002).
F. Nelson et al., "The Therapeutic Potential of Small Molecule TACE Inhibitors", Exp. Opin. Invest. Drugs, 9(4):393-92. (1999).
J. Duan et al., "Discovery of γ-Lactam Hydroxamic Acids as Selective Inhibitors of Tumor Necrosis Factor α Converting Enzyme: Design, Synthesis, and Structure-Activity Relationships", J. Med. Chem., 45:4954-4957 (2002).
D. Chantry, "Tumor Necrosis Factor Antagonists", Emerging Drugs, Annual Exec. Briefing 4: 5-13. (1999).
G. Van Assche et al., "Anti-TNF Agents in Crohn's Disease" 9(1) Exp. Opin. Invest. Drugs 9(1):103-111 (2000).
A. Dove, "MMP Inhibitors: Glimners of Hope Amidst Clinical Failures", Nature Medicine 8(2) (Feb. 2002) 95.
C. Brou et al., "A Novel Proteolytic Cleavage Involved in Notch Signaling: The role of the Disintegrin—Metalloprotease TACE", Molecular Cell 5:207-216 (2000).
C. Xue et al., "Design, Synthesis, and Structure-Activity Relationships of Macrocyclic Hydrosanic Acids that Inhibit Tumor Necrosis Factor & Release Invitro and InVivo", J. Med. Chem. 44:2636-2660 (2001).
D. M. Skovronsky et al., "Neuronal Localization of the TNF α Converting Enzyme (TACE) in Brain Tissue and Its Correlation to Amyloid Plaques", J. Neurobiol 49:40-46 (2001).
E. Kleinman et al., "Striking Effect of Hydroxamic Acid Substitution on the Phosphodiesterase Type 4 (PDE4) and TNFα Inhibitory Activity of Two Series of Rolipram Analogues: Implications for a New Active Site Model of PDE4", 41 J. Med. Chem. (Aug. 2, 2001) 2549-2502.

S. Pikul, "Potent and Selective Carboxylic Acid-Based Inhibitors of Matrix Metalloproteinases", J. Med. Chem. 44(16) 2549-2502 (Aug. 2, 2001).

T. Hirata et al., "Discovery of Potent, Highly Selective, and Orally Active Propenohydroxamate TNF-α Converting Enzyme (TACE) Inhibitors" Abstract # MEDI 262, 222$^{nd}$ National Meeting (ACS) Chicago.

Y. Tamura et al., "Highly Selective and Orally Active Inhibitors of Type IV Collagenase (MMP-9 and MMP-2): N-Sulfonylamino Acid Derivatives", J. Med. Chem. 41:640-49 (1998).

J. S. Tullis et al., "The Development of New Carboxylic Acid-Based MMP Inhibitors Derived from a Cycloexylglycine Scaffold", Bio. Org. Med. Chem. Letters. 11:1975-79 (2001).

R. Kiyama, "Homology Modeling of Gelatinase Catalytic Domains and Docking Simulations of Novel Sulfonamide Inhibitors", J. Med. Chem. 42:1723-38 (1999).

M. Whittaker et al., "Design and Therapeutic Application of Matrix Metalloproteinase Inhibitors", Chem. Rev. 99:2735-76 (1999).

J. El Yazal et al., "Ab Initio Calculations of Proton Dissociation Energies of Zinc Ligands: Hypothesis of Imidazolate as Zinc Ligand in Proteins", J. Phys. Chem. B. 103: 8773-79 (1999).

B. Barlaam et al., "New α-Substituted Succinate-Based Hdroxamic Acids as TNFα Convertase Inhibitors", J. Med. Chem. 42:4890-4908 (1999).

J. R. Doedens et al., "Stimulation-induced Down Regulation of Tumor Necrosis Factor-α Converting Enzyme", J. Biol. Chem. 275(19) 14598-14607 (May 12, 2000).

P. Reddy et al., "Functional Analysis of the Domain Structure of Tumor Necrosis Factor-α Converting Enzyme", J. Biol. Chem. 275(19) 14608-14614 (May 12, 2000).

N. Hooper et al., "Membrane Protein Secretases", BioChem. J., 321:265-79 (1977).

J. El Yazal, "Proton Dissociation Energies of Zinc-Coordinated Hydroxamic Acids and Their Relative Affinities for Zinc: Insight into Design of Inhibitors of Zinc-Containing Proteinases" J. Phys. Chem. B. 104:6499-6504 (2000).

T. Burton, "Research & Development: Abbott's Arthritis Drug Shows Promise, WSJ Says", Morning Highlight for Jun. 13, 2001, Wall Street Journal.

A. Reichelt et al., "Design, Synthesis, and Evaluation of Matrix Metalloprotease Inhibitors Bearing Cyclopropane-Derived Peptidomimetics as P1' and P2' Replacements", J. Org. Chem. 67:4062-75 (2002).

Patent Abastracts of Japan No. 018, No. 032 (C-1154), (Jan. 18, 1994) & JP 05 262698 A (Dainippon Ink & Chem Inc; Others: 01), (Oct. 12, 1993).

Database Crossfire Beilstein 'Online! Beilstein Institut zur Forderung der Chemischen Wissenschaften, Frankfurt am Main, DE; Database accession No. 3152815 XP002244521.

* cited by examiner

COMPOUNDS FOR THE TREATMENT OF INFLAMMATORY DISORDERS

CROSS-REFERENCE TO RELATED APPLICATIONS

The present application is a divisional of application U.S. Ser. No. 10/716,890, filed Nov. 19, 2003, now U.S. Pat. No. 7,034,057 now allowed, which itself was a divisional of application U.S. Ser. No. 10/323,511, filed Dec. 19, 2002, now U.S. Pat. No. 6,838,466, which claims the benefit of U.S. Provisional Application No. 60/342,332, filed Dec. 20, 2001, all incorporated herein by reference.

BACKGROUND OF THE INVENTION

1. Field of the Invention

This invention relates to hydroxamic or carboxylic acid functional compounds that can inhibit the production of tumor necrosis factor alpha (TNF-α), pharmaceutical compositions comprising such compounds, and methods of treatment using such compounds.

2. Description

Tumor necrosis factor alpha (TNF-α) has been shown to play a pivotal role in immune and inflammatory responses. Inappropriate or over-expression of TNF-α is a hallmark of a number of diseases, including rheumatoid arthritis (RA), Crohn's disease and sepsis. Inhibition of TNF-α production has been shown to be beneficial in many preclinical models of inflammatory disease, making inhibition of TNF-α production or signaling an appealing target for the development of novel anti-inflammatory drugs.

Tumor necrosis factor alpha is a cell-associated cytokine that is processed from a 26 kd precursor form to a 17 kd active form. See Black R. A. "Tumor necrosis factor-alpha converting enzyme" Int J Biochem Cell Biol. 2002 January; 34(1): 1-5 and Moss M L, White J M, Lambert M H, Andrews R C. "TACE and other ADAM proteases as targets for drug discovery" Drug Discov Today. 2001 Apr. 1; 6(8):417-426, each of which is incorporated by reference herein.

TNF-α has been shown to be a primary mediator in humans and animals of inflammation, fever and acute phase responses, similar to those observed during acute infection and shock. Excess TNF-α has been shown to be lethal. Blocking the effects of TNF-α with specific antibodies can be beneficial in a variety of conditions, including autoimmune diseases such as rheumatoid arthritis (Feldman et al, Lancet, (1994) 344, 1105), non-insulin dependent diabetes mellitus (Lohmander L. S. et al., Arthritis Rheum. 36 (1993) 1214-22) and Crohn's disease (Macdonald T. et al., Clin. Exp. Immunol. 81 (1990) 301).

Metalloproteinases (MP) are important in the uncontrolled breakdown of connective tissue, including proteoglycan and, collagen, leading to resorption of the extracellular matrix. This is a feature of many pathological conditions, such as rheumatoid and osteo-arthritis, corneal, epidermal or gastric ulceration; tumor metastasis or invasion; periodontal disease and bone disease. Normally these catabolic enzymes are tightly regulated at the level of their synthesis as well as at their level of extracellular activity through the action of specific inhibitors, such as alpha-2-macroglobulins and TIMP (tissue inhibitor of metalloproteinaase), which form inactive complexes with the MP's.

Osteo- and rheumatoid arthritis (OA and RA, respectively) are destructive diseases of articular cartilage characterized by localized erosion of the cartilage surface. Findings have shown that articular cartilage from the femoral heads of patients with OA, for example, had a reduced incorporation of radiolabeled sulfate over controls, suggesting that there must be an enhanced rate of cartilage degradation in OA (Mankin et al. J. Bone Joint Surg. 52A (1970) 424-434). There are four classes of protein degradative enzymes in mammalian cells: serine, cysteine, aspartic and metalloproteinases. The available evidence supports that it is the metalloproteinases that are responsible for the degradation of the extracellular matrix of articullar cartilage in OA and RA. Increased activities of collagenases and stromelysin have been found in OA cartilage and the activity correlates with severity of the lesion (Mankin et al. Arthritis Rheum. 21, 1978, 761-766, Woessner et al. Arthritis Rheum. 26, 1983, 63-68 and Ibid. 27, 1984, 305-312). In addition, aggrecanase (a newly identified metalloproteinase enzymatic activity) has been identified that provides the specific cleavage product of proteoglycan, found in RA and OA patients (Lohmander L. S. et al. Arthritis Rheum. 36, 1993, 1214-22).

Therefore, metalloproteinases (MP) have been implicated as the key enzymes in the destruction of mammalian cartilage and bone. It can be expected that the pathogenesis of such diseases can be modified in a beneficial manner by the administration of MP inhibitors, and many compounds have been suggested for this purpose (see Wahl et al. Ann. Rep. Med. Chem. 25, 175-184, AP, San Diego, 1990).

Compounds that inhibit the production of TNF-α are therefore of therapeutic importance for the treatment of inflammatory disorders. Recently it has been shown that a matrix metalloproteinase (MMP) or family of metalloproteinases, hereafter known as TNF-α convertases (TACE), as well as other MP's are capable of converting TNF-α from its inactive to active form (Gearing et al Nature, 1994, 370, 555). Since excessive TNF-α production has been noted in several disease conditions also characterized by MMP-mediated tissue degradation compounds which inhibit both MMPs and TNF-α production may also have a particular advantage in diseases where both mechanisms are involved.

There are several patents which disclose hydroxamate and carboxylate based MMP inhibitors.

WO95/09841 describes compounds that are hydroxamic acid derivatives and are inhibitors of cytokine production.

European Patent Application Publication No. 574,758 A1, discloses hydroxamic acid derivatives as collagenase inhibitors. GB 2 268 934 A and WO 94/24140 claim hydroxamate inhibitors of MMPs as inhibitors of TNF-α production.

There is a need in the art for inhibitors of MMPs, in particular TNF-α convertase, which can be useful as anti-inflammatory compounds and cartilage protecting therapeutics. The inhibition of TNF-α convertase and other metalloproteinases can prevent the degradation of cartilage by these enzymes, thereby alleviating the pathological conditions of osteo- and rheumatoid arthritis.

SUMMARY OF THE INVENTION

In one embodiment, the present invention provides a compound represented by Formula (I):

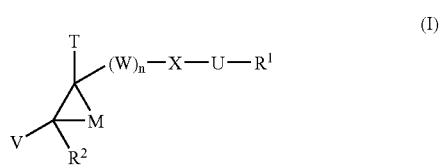

or a pharmaceutically acceptable salt, solvate or isomer thereof, wherein:

M is $-(C(R^{30})(R^{40}))_m-$, wherein m is 1 to 6;

T is selected from the group consisting of $R^{21}$-substituted alkyl, cycloalkyl, heterocycloalkyl, cycloalkenyl, heterocycloalkenyl, aryl, heteroaryl, $-OR^3$, $-C(O)R^4$, $-C(O)OR^3$, $-C(O)NR^{24}R^{25}$, $-C(O)NR^{24}OR^3$, $-C(O)SR^3$, $-NR^{24}R^{25}$, $-NR^{25}C(O)R^4$, $-NR^{25}C(O)OR^3$, $-NR^{25}C(O)NR^{24}R^{25}$, $-NR^{25}C(O)NR^{24}OR^3$, $-SR^3$, $-S(O)_x NR^{24}R^{25}$, $-S(O)_x NR^{25}OR^3$, $-CN$, $-P(O)(R^{24})(OR^{24})$, $-P(O)(OR^{24})(OR^{24})$ $-C(R^4)(=N(OR^3))$, $-C(O)\text{-AA-}NR^{24}R^{25}$ and $-C(O)\text{-AA-}NR^{25}OR^3$, wherein each of the cycloalkyl, heterocycloalkyl, cycoalkenyl, heterocycloalkenyl, aryl and heteroaryl groups of T is independently unsubstituted or substituted with one to five independently selected $R^{20}$ moieties which can be the same or different; each $R^{20}$ moiety being independently selected from the group of $R^{20}$ moieties below;

V is selected from the group consisting of alkyl, $R^{21}$-substituted alkyl, cycloalkyl, heterocycloalkyl, cycloalkenyl, heterocycloalkenyl, aryl, heteroaryl, $-OR^3$, $-C(O)R^4$, $-(CR^{23}R^{24})_{n1}C(O)OR^3$, $-C(O)NR^{24}R^{25}$, $-(CR^{23}R^{24})_{n1}C(O)NR^{25}OR^3$, $-C(O)SR^3$, $-NR^{24}R^{25}$, $-NR^{25}C(O)R^4$, $-NR^{25}C(O)OR^3$, $-NR^{25}C(O)NR^{24}R^{25}$, $-NR^{25}C(O)NR^{24}OR^3$, $-SR^3$, $-S(O)_x NR^{24}R^{25}$, $-S(O)_x NR^{25}OR^3$, $-CN$, $-P(O)(R^{24})(OR^{24})$, $-P(O)(OR^{24})(OR^{24})$, $-C(R^4)(=N(OR^3))$, $-C(O)\text{-AA-}NR^{24}R^{25}$ and $-C(O)\text{-AA-}NR^{25}OR^3$, wherein each of the cycloalkyl, heterocycloalkyl, cycloalkenyl, heterocycloalkenyl, aryl and heteroaryl groups of V is independently unsubstituted or substituted with one to three independently selected $R^{20}$ moieties which can be the same or different, each $R^{20}$ moiety being independently selected from the group of $R^{20}$ moieties below;

W is selected from the group consisting of

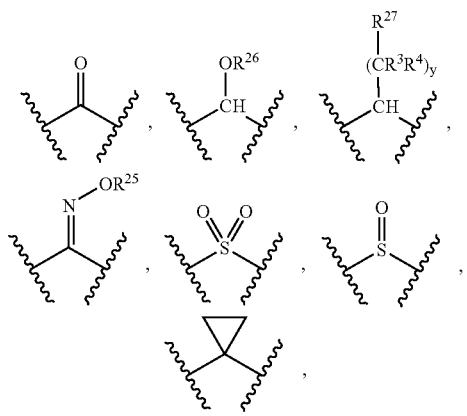

a covalent bond, $-(C(R^3)(R^4))_{n2}-$, $-O-$, $-S-$, and $-N(Z)-$;

X is selected from the group consisting of alkylene, cycloalkylene, heterocycloalkylene, arylene, heteroarylene and $-C\equiv C-$, wherein each of the alkylene, cycloalkylene, heterocycloalkylene, arylene or heteroarylene groups of X is independently unsubstituted or substituted with one to four independently selected $R^{20}$ moieties which can be the same or different, each $R^{20}$ moiety being independently selected from the group of $R^{20}$ moieties below;

U is selected from the group consisting of a covalent bond, $-(C(R^3)(R^4))_p-$, $-Y-(C(R^3)(R^4))_q-$; $-(C(R^3)(R^4))_t-Y-$, and $-Y-$;

Y is selected from the group consisting of $-O-$, $-S(O)_x-$, $-N(Z)-$, $-C(O)-$, $-OC(O)-$, $-C(O)N(R^{24})-$, $-N(R^{24})C(O)N(R^{25})-$, $-N(R^{24})S(O)-$, $-N(R^{14})S(O)_2-$, $-S(O)N(R^{24})-$, and $-S(O)_2N(R^{24})-$;

Z is selected from the group consisting of $-R^3$, $-C(O)R^3$, $-S(O)_x R^3$ and $-C(O)NR^3R^4$;

n is 0 to 2;

n1 is 0 to 2;

n2 is 1 to 2;

p is 1 to 4;

q is 1 to 4;

t is 1 to 4;

v is 1 to 3;

x is 0 to 2;

y is 0 to 3;

AA is

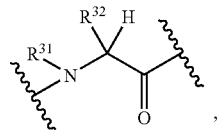

wherein $R^{31}$ and $R^{32}$ are the same or different and are each independently selected from the group consisting of H, alkyl, cycloalkyl, aryl, heteroaryl, $-NR^{24}R^{25}$, $-(CH_2)_3NH(C=NH)NH_2$, $-CH_2C(O)NH_2$, $-CH_2C(O)OH$, $-CH_2SH$, $-CH_2S-SCH_2CH(NH_2)C(O)OH$, $-CH_2CH_2C(O)OH$, $-CH_2CH_2C(O)NH_2$, $-(CH_2)_4NH_2$, $-CH_2CH_2CH(OH)CH_2NH_2$, $-CH_2CH(CH_3)_2$, $-CH(CH_3)CH_2(CH_3)$, $-CH_2CH_2SCH_3$, $-CH_2OH$, $-CH(OH)(CH_3)$,

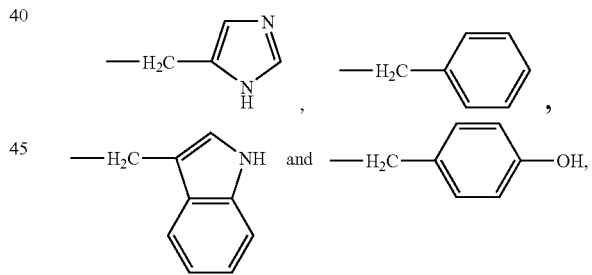

or $R^{31}$ and $R^{32}$, together with the N to which $R^{31}$ is attached and the C to which $R^{31}$ is attached, form a 5-membered ring which is unsubstituted or independently substituted with a hydroxyl group;

$R^1$ is selected from the group consisting of alkyl, $R^{21}$-substituted alkyl, cycloalkyl, heterocycloalkyl, cycloalkenyl, heterocycloalkenyl, aryl, heteroaryl, $-C\equiv CR^3$ and $-CR^3=CR^4R^5$, wherein each of the alkyl, cycloalkyl, heterocycloalkyl, cycloalkenyl, heterocycloalkenyl, aryl and heteroaryl groups of $R^1$ is independently unsubstituted or substituted with one to five independently selected $R^{20}$ moieties which can be the same or different, each $R^{20}$ moiety being independently selected from the group of $R^{20}$ moieties below, each $R^2$, $R^4$ and $R^5$ is the same or different and each is independently selected from the group consisting of H, halo, alkyl, $R^{22}$-substituted alkyl, cycloalkyl, heterocycloalkyl, cycloalkenyl, heterocycloalkenyl, aryl, heteroaryl, —$OR^6$, —$C(O)R^7$, —$C(O)OR^6$, —$NR^{24}R^{25}$, —$NR^{24}C(O)R^{25}$, —$N(=C-O-N^{24}R^{25})$, —$NR^{24}S(O)_2R^{25}$, wherein each of the cycloalkyl, heterocycloalkyl, cycloalkenyl, heterocycloalkenyl, aryl and heteroaryl groups of $R^2$, $R^4$ and $R^5$ is independently unsubstituted or substituted with one to four independently selected alkyl, $R^{22}$-substituted alkyl or $R^{22}$ moieties which can be the same or different, each $R^{22}$ moiety being independently selected from the group of $R^{22}$ moieties below;

each $R^3$ is the same or different and is independently selected from the group consisting of H, alkyl, $R^{22}$-substituted alkyl, cycloalkyl, heterocycloalkyl, cycloalkenyl, heterocycloalkenyl, aryl, heteroaryl, —$OR^6$, —$C(O)R^7$, —$C(O)OR^6$, —$NR^{24}R^{25}$, —$NR^{24}C(O)R^{25}$, —$N(=C-O-NR^{24}R^{25})$ and —$NR^{24}S(O)_2R^{25}$, each of the cycloalkyl, heterocycloalkyl, cycloalkenyl, heterocycloalkenyl, aryl and heteroaryl groups of $R^3$ is independently unsubstituted or substituted with one to four independently selected alkyl, $R^{22}$-substituted alkyl or $R^{22}$ moieties which can be the same or different, each $R^{22}$ moiety being independently selected from the group of $R^{22}$ moieties below;

each $R^6$ is independently selected from the group consisting of H, alkyl and —$OCF_3$;

each $R^7$ is independently selected from the group consisting of H, alkyl, heteroaryl and —$CF_3$;

each $R^{20}$ is independently selected from the group consisting of: alkyl, $R^{21}$-substituted alkyl, —$OR^3$, halo, —CN, —$NO_2$, —$NR^{24}R^{25}$, —$C(O)R^3$, —$C(O)OR^3$, —$C(O)NR^{24}R^{25}$, —$S(O)_xNR^{24}R^{25}$, —$S(O)_xR^5$, —$CF_3$, —$OCF_3$, —$CF_2CF_3$, —$C(=NOH)R^3$, aryl, halo-substituted aryl, heteroaryl, cycloalkyl, heterocycloalkyl, —$N(R^{25})S(O)_xR^5$, —$N(R^{25})C(O)R^5$, and —$N(R^{25})C(O)NR^{24}R^{25}$, wherein each of the aryl, halo-substituted aryl, heteroaryl, cycloalkyl and heterocycloalkyl groups of $R^{20}$ is independently unsubstituted or substituted with one to four independently selected $R^{22}$ moieties which can be the same or different, each $R^{22}$ moiety being independently selected from the group of $R^{23}$ moieties below, or two $R^{20}$ groups taken together with the carbon to which both $R^{20}$ groups are attached is

$R^{21}$ is one to three substituents independently selected from the group consisting of: —$OR^3$, halo, —CN, —$NO_2$, —$NR^{24}R^{25}$, —$C(O)R^3$, —$C(O)OR^3$, —$C(O)NR^{24}R^{25}$, —$S(O)_xNR^{24}R^{25}$, —$SO_xR^5$, —$CF_3$, —$OCF_3$, —$CF_2CF_3$, —$C(=NOH)R^3$, $R^{23}$-substituted alkyl, aryl, heteroaryl, cycloalkyl, heterocycloalkyl, —$N(R^{25})S(O)_xR^5$, —$N(R^{25})C(O)R^5$, and —$N(R^{25})C(O)NR^{24}R^{25}$;

wherein each of the aryl, halo-substituted aryl, heteroaryl, cycloalkyl, and heterocycloalkyl groups of $R^{21}$ is independently unsubstituted or substituted with one to four independently selected $R^{23}$ moieties which can be different, each $R^{23}$ moiety being independently selected from the group of $R^{23}$ moieties below, or two $R^{21}$ groups taken together with the carbon to which both $R^{21}$ groups are attached is

each $R^{22}$ is independently selected from the group consisting of, halo, alkynyl, aryl, heteroaryl, —$OR^{24}$, —$(C_1-C_6$ alkyl)-$OR^{24}$, —CN, —$NO_2$, —$NR^{24}R^{25}$, —$C(O)R^{23}$, —$C(O)OR^{23}$, —$C(O)NR^{24}R^{25}$, —$S(O)_xNR^{24}R^{25}$, —$S(O)_xR^{23}$, —$CF_3$, —$OCF_3$, —$CF_2CF_3$, —$C(=NOH)R^{23}$, —$N(R^{24})S(O)_xR^{25}$, —$N(R^{24})C(O)R^{25}$, and —$N(R^{24})C(O)NR^{24}R^{25}$, or two $R^{22}$ groups taken together with the carbon to which both $R^{22}$ groups are attached is

each $R^{23}$ is independently selected from the group consisting of H, hydroxyl, halo and alkyl;

each $R^{24}$ is independently selected from the group consisting of H and alkyl;

each $R^{25}$ is independently selected from the group consisting of H, hydroxyl, alkyl, hydroxyalkyl, aryl, cycloalkyl, heteroaryl, —$NR^{24}R^{24}$, —$(C_1$ to $C_6$ alkyl)$NR^{24}N^{24}$, —$CF_3$ and —$S(O)_xR^{23}$;

each $R^{26}$ is independently selected from the group consisting of H, hydroxyl, alkyl, hydroxyalkyl, aryl, cycloalkyl, heteroaryl and —$NR^3R^4$;

$R^{27}$ is independently selected from the group consisting of heteroaryl, heterocycloalkyl and —$NR^{24}R^{25}$;

$R^{30}$ is independently selected from the group consisting of H and $R^{20}$ substituent groups above;

$R^{40}$ is independently selected from the group consisting of H and $R^{20}$ substituent groups above, or $R^{30}$ and $R^{40}$, taken together with the carbon to which $R^{30}$ and $R^{40}$ are attached, is

with the proviso that at least one of V or T is selected from the group consisting of —$C(O)N(R^3)(OR^4)$, —$C(O)OR^3$ and —$C(O)NR^{24}R^{25}$, and when —$(W)_n$—X—U— is alkylene, $R^1$ is not alkyl.

In another embodiment, a compound of Formula I is provided with the provisos that at least one of V or T is selected from the group consisting of —$C(O)N(R^3)(OR^4)$, —$C(O)OR^3$ and —$C(O)NR^{24}R^{25}$, and when —$(W)_n$—X—U— is alkylene, $R^1$ is not alkyl, and when —$(W)_n$—X— is alkylene, —Y— is not —$N(R^{24})C(O)$—, and when one of T or V is —$NR^{25}S(O)_xR^3$, the other of T or V is not —$C(O)NR^{25}OR^3$.

Another aspect of the present invention is a composition comprising at least one of the above compounds. Methods of using the compounds for the treatment of MMP and TNF-α mediated diseases and conditions also are provided. The compounds of the invention may be used alone or in combination with other appropriate therapeutic agents.

DETAILED DESCRIPTION OF THE INVENTION

In its several embodiments, the present invention provides a novel class of inhibitors of MMP and TNF-α convertase, pharmaceutical compositions containing one or more of the compounds, methods of preparing pharmaceutical formulations comprising one or more such compounds, and methods of treatment, prevention or amelioration of one or more of the symptoms of inflammation.

In one embodiment, the present invention provides compounds which are represented by structural Formula (I) above or a pharmaceutically acceptable salt, solvate or isomer thereof, wherein the various moieties are as described above.

In one embodiment, m is 4. In another embodiment, m is 3. In another embodiment, m is 2. In another embodiment, m is 1.

In another embodiment, $R^{30}$ is H or —($C_1$-$C_6$)alkyl. In another embodiment, $R^{30}$ is H.

In another embodiment, $R^{40}$ is H or —($C_1$-$C_6$)alkyl. In another embodiment, $R^{40}$ is H.

In another embodiment, T is selected from the group consisting of —C(O)$R^4$, —C(O)O$R^3$, —C(O)N$R^{23}R^{25}$, and —C(O)N$R^{23}$O$R^3$.

In one embodiment, T is —C(O)$R^4$ in which $R^4$ is a pyrrolidinyl ring that is unsubstituted or substituted with one to three $R^{22}$ moieties which are each independently selected from the group consisting of —O$R^{24}$, —($C_1$-$C_6$ alkyl)-O$R^{24}$ and —N$R^{23}R^{24}$. Preferred $R^{22}$ moieties are hydroxyl, hydroxyalkyl and alkylamino and amino.

In another embodiment, T is —C(O)O$R^3$ in which $R^3$ is alkyl.

In another embodiment, T is —C(O)N$R^{23}R^{25}$ in which $R^{23}$ is H or alkyl and $R^{25}$ is H, alkyl or —($C_1$ to $C_6$ alkyl)N$R^{23}N^{24}$.

In another embodiment, T is —C(O)N$R^{23}$O$R^3$ in which $R^{23}$ is H or alkyl and $R^3$ is H or alkyl.

In another embodiment, V is —C(O)N$R^{23}$O$R^3$ in which $R^{23}$ is H or alkyl and $R^3$ is H or alkyl. In another embodiment, V is —C(O)O$R^3$ in which $R^3$ is H or alkyl, such as methyl.

In another embodiment, W is —C($R^3$)($R^4$)— in which $R^3$ is H and $R^4$ is H or W is a covalent bond.

In another embodiment, n is 1.

In another embodiment, X is arylene which is unsubstituted or substituted with one to two independently selected $R^{20}$ moieties which can be the same or different.

In another embodiment, X is phenylene which is unsubstituted or substituted with one or two halo substituents which can be the same or different.

In another embodiment, X is a heteroarylene which is unsubstituted or substituted with one to two independently selected $R^{20}$ moieties which can be the same or different.

In another embodiment, X is a heteroarylene selected from the group consisting of which is unsubstituted or substituted with one or two halo substituents, such as Cl, F or I, which can be the same or different.

In another embodiment, U is —Y—(C($R^3$)($R^4$))$_q$—. In another embodiment, Y is —O—. In another embodiment, q is 1, $R^3$ is H or alkyl and $R^4$ is H or alkyl.

In another embodiment, $R^1$ is selected from the group consisting of cycloalkyl, aryl and heteroaryl, wherein each of the cycloalkyl, aryl and heteroaryl groups of $R^1$ is independently unsubstituted or substituted with one to five independently selected $R^{20}$ moieties which can be the same or different, each $R^{20}$ moiety being independently selected from the group of $R^{20}$ moieties above.

In another embodiment, $R^1$ is a cycloalkyl group selected from the group consisting of cyclopropyl, cyclobutyl and cyclohexyl, wherein each of the cycloalkyl groups is independently unsubstituted or substituted with one to five independently selected $R^{20}$ moieties which can be the same or different, each $R^{20}$ moiety being independently selected from the group of $R^{20}$ moieties above, such as alkyl.

In another embodiment, $R^1$ is an aryl group selected from the group consisting of phenyl, naphthyl, indanyl and tetrahydronaphthalenyl, wherein each of the aryl groups is independently unsubstituted or substituted with one to five independently selected $R^{20}$ moieties which can be the same or different, each $R^{20}$ moiety being independently selected from the group of $R^{20}$ moieties above, such as alkyl.

In another embodiment, $R^1$ is a heteroaryl group selected from the group consisting of chromanyl, quinolyl, isoquinolyl, triazolyl, pyridyl, imidazolyl, thiazolyl, benzodioxolyl and wherein each of the heteroaryl groups is independently unsubstituted or substituted with one to five independently selected $R^{20}$ moieties which can be the same or different, each $R^{20}$ moiety being independently selected from the group of $R^{20}$ moieties, such as alkyl, $R^{21}$-substituted alkyl, halo, amino, carboxamide, aryl, heteroaryl, heterocycloalkyl and —O$R^3$.

In another embodiment, $R^1$ is a fused bicyclic aryl group which is unsubstituted or substituted with one to three independently selected $R^{20}$ moieties which can be the same or different.

In another embodiment, $R^1$ is a fused bicyclic heteroaryl group which is unsubstituted or substituted with one to three independently selected $R^{20}$ moieties which can be the same or different.

In another embodiment, $R^2$ is H.

In another embodiment, each $R^3$ is independently H, alkyl or aryl.

In another embodiment, each $R^4$ is independently H, alkyl or aryl.

In another embodiment, each $R^5$ is independently H, alkyl or aryl.

In another embodiment, each $R^{20}$ is independently selected from the group consisting of alkyl, $R^{21}$-substituted alkyl, $-OR^3$, halo, $-CN$, $-NO_2$, $-NR^3R^4$, $-C(O)OR^3$, $-S(O)_xR^5$, $-CF_3$, $-OCF_3$, aryl, heteroaryl, cycloalkyl, wherein each of the aryl, heteroaryl and cycloalkyl groups of $R^{20}$ is independently unsubstituted or substituted with one to four independently selected $R^{22}$ moieties which can be the same or different, each $R^{22}$ moiety being independently selected from the group of $R^{23}$ moieties.

In another embodiment, $R^{20}$ is a heteroaryl group selected from the group consisting of pyrazinyl, pyrrolyl, pyridyl and morpholinyl.

In another embodiment, $R^{20}$ is a cycloalkyl selected from the group consisting of cyclopropyl, cyclobutyl and cyclohexyl.

In another embodiment, $R^{20}$ is a heterocycloalkyl selected from the group consisting of piperazinyl and pyrrolidinyl.

In another embodiment, each $R^{20}$ moiety is selected from the group consisting of $-(C_1-C_6)$alkyl and aryl.

In another embodiment, M is $-(C(R^{30})(R^{40}))_m-$, wherein m is 1 to 4; V is $-C(O)OR^3$ or $-C(O)NR^{25}OR^3$; T is $R^{21}$-substituted alkyl, $-CN$, $-C(O)OR^3$, $-C(O)NR^{25}OR^3$, $-C(O)NR^{24}R^{25}$, $-C(O)R^4$ or $-C(R^4)(=N(OR^3))$; W is a covalent bond or $-(C(R^3)(R^4))_{n2}$; X is arylene or heteroarylene, each of which can be independently unsubstituted or substituted with one to four independently selected $R^{20}$ moieties; $R^1$ is cycloalkyl, aryl, heteroaryl, each of which can be independently unsubstituted or substituted with one to four independently selected $R^{20}$ moieties; $R^2$ is H; and each of the other variables are as above in the Summary of the Invention.

A preferred group of compounds are shown in Table 1 below.

Except where stated otherwise, the following definitions apply throughout the present specification and claims. Additionally, all technical and scientific terms used herein have the same meaning as is commonly understood by one skilled in the art to which this invention belongs. These definitions apply regardless of whether a term is used by itself or in combination with other terms. Hence the definition of "alkyl" applies to "alkyl" as well as to the "alkyl" portions of "alkoxy", etc.

"Patient" or "subject" includes both humans and animals.

"Mammal" includes humans and other mammalian animals.

"Alkyl" means an aliphatic hydrocarbon group that may be straight or branched and comprising 1 to about 20 carbon atoms in the chain. Preferred alkyl groups contain 1 to about 12 carbon atoms in the chain. More preferred alkyl groups contain 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. The alkyl may be substituted.

The phrase "$R^{21}$-substituted alkyl" means that the alkyl group can be substituted by one or more $R^{21}$ substituents that may be the same or different, each substituent being independently selected from the group consisting of $R^{21}$ substituents listed above. Each of the aryl, halo-substituted aryl, heteroaryl, cycloalkyl and heterocycloalkyl groups of $R^{21}$ can be unsubstituted or independently substituted with one to four independently selected $R^{23}$ moieties which can be the same or different, each $R^{23}$ moiety being independently selected from the group of $R^{23}$ moieties above.

The phrase "$R^{22}$-substituted alkyl" means that the alkyl group can be substituted bygone or more $R^{22}$ substituents that may be the same or different, each substituent being independently selected from the group consisting of $R^{22}$ substituents listed above.

The phrase "$R^{52}$-substituted alkyl" means that the alkyl group can be substituted by one or more $R^{52}$ substituents which may be the same or different, each substituent being independently selected from the group consisting of $R^{21}$ substituents listed above.

"Alkenyl" means an aliphatic hydrocarbon group comprising at least one carbon-carbon double bond and which may be straight or branched and comprising 2 to about 15 carbon atoms in the chain. Preferred alkenyl groups have 2 to about 12 carbon atoms in the chain; and more preferably 2 to about 6 carbon atoms in the chain. Branched means that one or more lower alkyl groups such as methyl, ethyl or propyl, are attached to a linear alkenyl chain. "Lower alkenyl" means 2 to about 6 carbon atoms in the chain which may be straight or branched. The alkenyl may be substituted and the term "$R^{35}$-substituted alkenyl" means that the alkenyl group may be substituted by one or more substituents which can be the same or different, each substituent being independently selected from the group consisting of $R^{35}$ substituents listed above.

"Aryl" means an aromatic monocyclic or multicyclic (for example, bicyclic) ring system comprising about 5 to about 14 carbon atoms, preferably about 6 to about 10 carbon atoms. The aryl groups of T, V, X (arylene) and $R^1$ can be unsubstituted or independently substituted with one to five independently selected $R^{20}$ moieties which can be the same or different, and are as defined herein. The aryl groups of $R^2$, $R^3$, $R^4$, $R^5$ and $R^{20}$ can be unsubstituted or independently substituted with one to four independently selected $R^{22}$ moieties which can be the same or different, and are as defined herein. The aryl groups of $R^{21}$ can be unsubstituted or independently substituted with one to four independently selected $R^{23}$ moieties which can be the same or different, and are as defined herein. Non-limiting examples of suitable aryl groups include phenyl, naphthyl, indenyl, tetrahydronaphthyl and indanyl.

"Alkylene" refers to an alkanediyl group commonly having free valencies on two carbon atoms. Non-limiting examples include methylene, propylene and the like.

"Arylene" is a bivalent group derived from an aromatic hydrocarbon by removal of a hydrogen atom from two ring carbon atoms. Non-limiting examples include phenylene and the like.

"Heteroarylene" is a bivalent group derived from a heterocyclic aromatic compound by removal of a hydrogen atom from two ring atoms such as, for example, the bivalent group derived from pyridine, pyrrole and the like. The bonds to the parent moiety can be through different carbon ring atoms, different hetero ring atoms or through a carbon ring atom and a hetero ring atom.

"Heteroaryl" represents cyclic aromatic groups of 5 or 6 atoms or bicyclic groups of 8 to 12 atoms having 1, 2 or 3 heteroatoms independently selected from O, S or N, said heteroatom (s) interrupting a carbocyclic ring structure and having a sufficient number of delocalized pi electrons to provide aromatic character, provided that the rings do not contain adjacent oxygen and/or sulfur atoms. Preferred monocyclic heteroaryls contain about 5 to about 6 ring atoms. Preferred bicyclic heteroaryls contain about 10 ring atoms. The heteroaryl groups of T, V, X (heteroarylene) and $R^1$ can be unsubstituted or independently substituted with one to five independently selected $R^{20}$ moieties which can be the same or different, and are as defined herein. The heteroaryl groups of $R^2$, $R^3$, $R^4$, $R^5$ and $R^{20}$ can be unsubstituted or independently substituted with one to four independently selected $R^{22}$ moieties which can be the same or different, and are as defined herein. The heteroaryl groups of $R^{21}$ can be unsubstituted or independently substituted with one to four independently selected $R^{23}$ moieties which can be the same or different, and are as defined herein. The prefix aza, oxa or thia before the heteroaryl root name means that at least a nitrogen, oxygen or sulfur atom respectively, is present as a ring atom. Nitrogen atoms can form an N-oxide. All regioisomers are contemplated, e.g., 2-pyridyl, 3-pyridyl and 4-pyridyl. Useful 6-membered heteroaryl groups include pyridyl, pyrimidinyl, pyrazinyl, pyridazinyl, morpholinyl and the like and the N-oxides thereof. Useful 5-membered heteroaryl rings include furyl, triazolyl, thienyl, pyrrolyl, thiazolyl, isothiazolyl, imidazolyl, pyrazolyl, isoxazolyl and the like. Typical bicyclic groups are benzo-fused ring systems derived from the heteroaryl groups named above, e.g. quinolyl, isoquinolyl, phthalazinyl, quinazolinyl, benzofuranyl, benzothienyl, benzodioxolyl, indolyl and the like.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl groups of T, V, X (cycloalkylene) and $R^1$ can be unsubstituted or independently substituted with one to five independently selected $R^{20}$ moieties which can be the same or different, and are as defined herein. The cycloalkyl groups of $R^2$, $R^3$, $R^4$, $R^5$ and $R^{20}$ can be unsubstituted or independently substituted with one to four independently selected $R^{22}$ moieties which can be the same or different, and are as defined herein. The cycloalkyl groups of $R^{21}$ can be unsubstituted or independently substituted with one to four independently selected $R^{23}$ moieties which can be the same or different, and are as defined herein. Non-limiting examples of suitable monocyclic cycloalkyls include cyclopropyl, cyclobutyl, cyclopentyl, cyclohexyl and the like. Non-limiting examples of suitable multicyclic cycloalkyls include 1-decalinyl, norbornyl, adamantyl and the like.

"Halo" means fluoro, chloro, bromo, or iodo groups. Preferred are fluoro, chloro or bromo, and more preferred are fluoro and chloro.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl groups of T, V and $R^1$ can be unsubstituted or independently substituted with one to five independently selected $R^{20}$ moieties which can be the same or different, and are as defined herein. The cycloalkenyl groups of $R^2$, $R^3$, $R^4$, $R^5$ and $R^{20}$ can be unsubstituted or independently substituted with one to four independently selected $R^{22}$ moieties which can be the same or different, and are as defined herein. The cycloalkenyl groups of $R^{21}$ can be unsubstituted or independently substituted with one to four independently selected $R^{23}$ moieties which can be the same or different, and are as defined herein. Non-limiting examples of suitable monocyclic cycloalkenyls include cyclopentenyl, cyclohexenyl, cycloheptenyl, and the like. Non-limiting example of a suitable multicyclic cycloalkenyl is norbornyl.

"Heterocycloalkenyl" means a non-aromatic monocyclic or multicyclic ring system comprising about 3 to about 10 ring-atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocycloalkenyl rings contain about 5 to about 6 ring atoms. The prefix aza, oxa or thia before the heterocyclenyl root name means that at least a nitrogen, oxygen or sulfur atom respectively is present as a ring atom. The heterocycloalkenyl groups of T, V and $R^1$ can be unsubstituted or independently substituted with one to five independently selected $R^{20}$ moieties which can be the same or different, and are as defined herein. The heterocycloalkenyl groups of $R^2$, $R^3$, $R^4$, $R^5$ and $R^{20}$ can be unsubstituted or independently substituted with one to four independently selected $R^{22}$ moieties which can be the same or different, and are as defined herein. The heterocycloalkenyl groups of $R^{21}$ can be unsubstituted or independently substituted with one to four independently selected $R^{23}$ moieties which can be the same or different, and are as defined herein. The nitrogen or sulfur atom of the heterocycloalkenyl can be optionally oxidized to the corresponding N-oxide, S-oxide or S,S-dioxide. Non-limiting examples of suitable monocyclic aza heterocycloalkenyl groups include 1,2,3,4-tetrahydropyridyl, 1,2-dihydropyridyl, 1,4,5,6-tetrahydropyrimidinyl, 2-pyrrolinyl, 2-imidazolinyl, 2-pyrazolinyl, and the like. Non-limiting examples of suitable oxa heterocycloalkenyl groups include 3,4-dihydro-2H-pyranyl, dihydrofuranyl, and the like. Non-limiting example of a suitable multicyclic oxa heterocycloalkenyl group is 7-oxabicyclo[2.2.1]heptenyl. Non-limiting examples of suitable monocyclic thia heterocycloalkenyl rings include dihydrothiophenyl, dihydrothiopyranyl, and the like.

"Heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms; present in the ring system. Preferred heterocycloalkyls contain about 5 to about 6 ring atoms. The prefix aza, oxa or thia before the heterocyclyl root name means that at least a nitrogen, oxygen or sulfur atom respectively is present as a ring atom. The heterocycloalkyl groups of T, V, X (cycloalkylene) and $R^1$ can be unsubstituted or independently substituted with one to five independently selected $R^{20}$ moieties which can be the same or different, and are as defined herein. The heterocycloalkyl groups of $R^2$, $R^3$, $R^4$, $R^5$ and $R^{20}$ can be unsubstituted or independently substituted with one to four independently selected $R^{22}$ moieties which can be the same or different, and are as defined herein. The heterocycloalkyl groups of $R^{21}$ can be unsubstituted or independently substituted with one to four independently selected $R^{23}$ moieties which can be the same or different, and are as defined herein. The nitrogen or sulfur atom of the heterocycloalkyl can be optionally oxidized to the corresponding N-oxide, S-oxide or S,S-dioxide. Non-limiting examples of suitable monocyclic heterocycloalkyl rings include piperidyl, pyrrolidinyl, piperazinyl, morpholinyl, 1,3-dioxolanyl, tetrahydrofuranyl, tetrahydrothiophenyl and the like.

"Heterocycloalkylene" is a bivalent group derived from a heterocyclic cycloalkyl compound by removal of a hydrogen atom from two ring atoms such as, for example, the bivalent group derived from piperazine and the like. The bonds to the parent moiety can be through different carbon ring atoms, different hetero ring atoms or through a carbon ring atom and a hetero ring atom.

"Hydroxyalkyl" means a HO-alkyl- group in which alkyl group is as previously defined. Preferred hydroxyalkyls contain lower alkyl. Non-limiting examples of suitable hydroxyalkyl groups include hydroxymethyl and 2-hydroxyethyl.

The term "optionally substituted" means optional substitution with the specified groups, radicals or moieties.

As a general note, any open-ended nitrogen atom with unfulfilled valence in the chemical structures in this application refers to NH, or in the case of a terminal nitrogen, —$NH_2$. Similarly, any open-ended oxygen atom with unfulfilled valence in the chemical structures in this application refers to —OH and any open-ended carbon atom with unfilled valence is appropriately filled with —H.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in Bioreversible Carriers in Drug Design, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound of the present invention effective in inhibiting TNF-α or MMP and thus producing the desired therapeutic, ameliorative, inhibitory or preventative effect.

The compounds of formula I can form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulforiates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates,) undecanoates, and the like. Additionally, acids which are generally considered suitable for the formation of pharmaceutically useful salts from basic pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; and Anderson et al, *The Practice of Medicinal Chemistry* (1996), Academic Press, N.Y.). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

When a variable appears more than once in the structural formula, for example $R^3$ or $R^5$, the identity of each variable appearing more than once may be independently selected from the definition for that variable.

The compounds of the present invention can have pharmacological properties, for example the compounds of Formula I can be inhibitors of TACE (TNF-α) and/or MMP activity. The compounds of Formula I can have anti-inflammatory activity and/or immunomodulatory activity and can be useful in the treatment of diseases including but not limited to septic shock, haemodynamic shock, sepsis syndrome, post ischaemic reperfusion injury, malaria, mycobacterial infection, meningitis, psoriasis, congestive heart failure, fibrotic diseases, cachexia, graft rejection, cancers such as cutaneous T-cell lymphoma, diseases involving angiogenesis, autoimmune diseases, skin inflammatory diseases, inflammatory bowel diseases such as Crohn's disease and colitis, osteo and rheumatoid arthritis, ankylosing spondylitis, psoriatic arthritis, adult Still's disease, ureitis, Wegener's granulomatosis, Behcehe disease, Sjogren's syndrome, sarcoidosis, polymyositis, dermatomyositis, multiple sclerosis, radiation damage, hyperoxic alveolar injury, periodontal disease, HIV, non-insulin dependent diabetes mellitus, systemic lupus erythematosus, glaucoma, sarcoidosis, idiopathic pulmonary fibrosis, bronchopulmonary dysplasia, retinal disease, scleroderma, osteoporosis, renal ischemia, myocardial infarction, cerebral stroke, cerebral ischemia, nephritis, hepatitis, glomerulonephritis, cryptogenic fibrosing aveolitis, psoriasis, transplant rejection, atopic dermatitis, vasculitis, allergy, seasonal allergic rhinitis, reversible airway obstruction, adult respiratory distress syndrome, asthma, chronic obstructive pulmonary disease (COPD) and/or bronchitis. It is contemplated that a compound of this invention may be useful in treating one or more of the diseases listed.

Additionally, a compound of the present invention may be co-administered or used in combination with disease-modifying antirheumatic drugs (DMARDS) such as methotrexate, azathioprine, leflunomide, pencillinamine, gold salts, mycophenolate mofetil, cyclophosphamide and other similar drugs. They may also be co-administered with or used in combination with NSAIDS such as piroxicam, naproxen, indomethacin, ibuprofen and the like; COX-2 selective inhibitors such as Vioxx® and Celebrex®; immunosuppressives such as steroids, cyclosporin, Tacrolimus, rapamycin and the like; biological response modifiers (BRMs) such as Enbrel®, Remicade®, IL-1 antagonists, anti-CD40, anti-CD28, IL-10, anti-adhesion molecules and the like; and other anti-inflammatory agents such as p38 kinase inhibitors, PDE4 inhibitors, other chemically different TACE inhibitors; chemokine receptor antagonists, Thalidomide and other small molecule inhibitors of pro-inflammatory cytokine production.

Also, a compound of the present invention may be co-administered or used in combination with an H1 antagonist for the treatment of seasonal allergic rhinitis and/or asthma. Suitable H1 antagonists may be, for example, Claritin®, Clarinex®, Allegra®, or Zyrtec®.

In another aspect, the invention provides a method for treating rheumatoid arthritis comprising administering a compound of the formula I in combination with compound selected from the class consisting of a COX-2 inhibitor e.g. Celebrex® or Vioxx®; a COX-1 inhibitor e.g. Feldene®; an immunosuppressive e.g. methotrexate or cyclosporin; a steroid e.g. β-methasone; and anti-TNF-α compound, e.g. Enbrel® or Remicade®; a PDE IV inhibitor, or other classes of compounds indicated for the treatment of rheumatoid arthritis.

In another aspect, the invention provides a method for treating multiple sclerosis comprising administering a compound of the formula I in combination with a compound selected from the group consisting of Avonex®, Betaseron, Copaxone or other compounds indicated for the treatment of multiple sclerosis.

TACE activity is determined by a kinetic assay measuring the rate of increase in fluorescent intensity generated by TACE catalyzed cleavage of an internally quenched peptide substrate (SPDL-3). The purified catalytic domain of recombinant human TACE (rhTACEc, Residue 215 to 477 with two mutation (S266A and N452Q) and a 6×His tail) is used in the assay. It is purified from the baculovirus/Hi5 cells expression system using affinity chromatography. The substrate SPDL-3 is an internally quenched peptide (MCA-Pro-Leu-Ala-Gln-Ala-Val-Arg-Ser-Ser-Ser-Dpa-Arg-NH2), with its sequence derived from the pro-TNFα cleavage site. MCA is (7-Methoxycoumarin-4-yl)acetyl. Dpa is N-3-(2,4-Dinitrophenyl)-L-2,3-diaminopropionyl.

A 50 µl assay mixture contains 20 mM HEPES, pH 7.3, 5 mM $CaCl_2$, 100 µM $ZnCl_2$, 2% DMSO, 0.04% Methylcellulose, 30 µM SPDL-3, 70 µM rhTACEc and a test compound. RhTACEc is pre-incubated with the testing compound for 90 min. at 25° C. Reaction is started by addition of the substrate. The fluorescent intensity (excitation at 320 nm, emission at 405 nm) was measured every 45 seconds for 30 min. using a fluorospectrometer (GEMINI XS, Molecular Devices). Rate of enzymatic reaction is shown as Units per second. Effect of a test compound is shown as % of TACE activity in the absence of the compound.

Useful compounds for TACE inhibitory activity can exhibit $K_i$ values of less than about 1000 nm, preferably about 0.01 nm to about 1000 nm, more preferably about 0.1 nm to about 100 nm, more preferably about 0.1 to about 15 nm, and most preferably less that about 15 nm. Representative compounds of the invention which exhibit excellent TACE inhibitory activity ($K_i$ values of less than about 20 nanomolar, m) are as follows: Compounds BX, JH, BD, BW, KM, BL, O, P, JY, JX, CV, CA, JG, BV, CC, JO, CP, JN, CT, FQ, DE, FN, KX, LB, IZ, GV, JB, JA, LA, KY, BY, JD, BO, BP, DA, FG, CU, CW, LC, JF, DB, CS, JC, JE, KZ, CO, JT, JU, JS, JR, FY, CR, GA, GB, CY, JV, BR, CZ, FZ, BQ, CQ, FX, FU, FW, JW, FV, CN, CA, JP, BS, LM, LI and LH. The Compound letter designations refer to the letter designations for the various structures in Table 1 in the EXAMPLES section found below.

The pharmaceutical compositions containing the active ingredient may be in a form suitable for oral use, for example, as tablets, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for controlled release.

Formulations for oral use may also be presented as hard gelatin capsules wherein the active ingredients is mixed with an inert solid diluent, for example, calcium carbonate, calcium phosphate or kaolin, or a soft gelatin capsules where in the active ingredient is mixed with water or an oil medium, for example peanut oil, liquid paraffin or olive oil.

Aqueous suspensions contain the active material in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example, heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example, ethyl or n-propyl, p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example, arachis oil, olive oil, sesame oil or coconut oil, or in mineral oil such as liquid paraffin. The oily suspensions may contain a thickening agent, for example, beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, e.g., sweetening, flavoring and coloring agents, may also be present.

The pharmaceutical compositions of the invention may also be in the form of an oil-in-water emulsions. The oily phase may be a vegetable oil, e.g., olive oil or arachis oil, or a mineral oil, e.g., liquid paraffin or mixtures of these. Suitable emulsifying agents may be naturally-occurring phosphatides, e.g., soy beans, lecithin, and esters or partial esters derived from fatty acids and hexitol anhydrides, for example, sorbitan monooleate, and condensation products of the said partial esters with ethylene oxide, e.g., polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, e.g., as a solution in 1,3-butane diol. Among the acceptable vehicles and solvents that may be employed are water, Ringer's solution and isotonic sodium chloride; solution. In addition, sterile fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of suppositories for rectal administration of the drug. The compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compound of The invention are employed. (For purposes of this application, topical application shall include mouthwashes and gargles.)

The compounds for the present invention can be administered in the intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The dosage regimen utilizing the compounds of the present invention is selected in accordance with a variety of factors including type, species, weight, sex and medical condition of the patient; the severity of the condition to be treated; the route of administration; the renal and hepatic function of the patient; and the particular compound thereof employed. A physician or veterinarian of ordinary skill can readily determine and prescribe the effective amount of the drug required to prevent, counter, arrest or reverse the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. Preferably, doses of the compound of Formula I useful in the method of the present invention: range from 0.01 to 1000 mg per day. Most preferably, dosages range from 0.1 to 500 mg/day. For oral administration, the compositions are preferably provided in the form of tablets containing 0.01 to 1000 milligrams of the active ingredient, particularly 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. An effective amount of the drug is ordinarily supplied at a dosage level of from about 0.0002 mg/kg to about 50 mg/kg of body weight per day. The range is more particularly from about 0.001 mg/kg to 1 mg/kg of body weight per day.

Advantageously, the active agent of the present invention may be administered in a single daily dose, or the total daily dosage may be administered in dividend doses of two, three or four time daily.

The amount of active ingredient that may be combined with the carrier materials to produce single dosage form will vary depending upon the host treated and the particular mode of administration.

It will be understood, however, that the specific dose level for any particular patient will depend upon a variety of factors including the age, body weight, general health, sex, diet, time of administration, route or administration, rate of excretion, drug combination and the severity of the particular disease undergoing therapy.

The compounds of the invention may be produced by processes known to those skilled in the art and as shown in the following reaction schemes and in the preparations and examples described below.

EXAMPLES

The following abbreviations are used in the procedures and schemes: dichloromethane (DCM); tetrabutylammonium bromide (TBAB); Benzyl (Bn); acetonitrile (MeCN); ethyl acetate (EtOAc); Tetrahydrofuran (THF); Trifluoroacetic acid (TFA); 1-hydroxy-7-aza-benzotriazole (HOAt); 1-hydroxylbenzotriazole (HOAt); N-methylmorpholine (NMM); 1-(3-dimethylaminopropyl)-3-ethylcarbodiimide hydrochloride (EDCl); diisopropylethyl amine (DIEA); 1-hydroxybenzotriazole (HOBt); Dimethoxyethane (DME). [1-(chloromethyl)-4-fluoro-1,4-diazoniabicyclo[2.2.2] octane bis(tetrafluoroborate)] (Selectfluor); 4-N,N-dimethylaminopyridine (DMAP); 1,8-diazabicyclo[5,4,0]undec-7-ene (DBU); Saturated (sat.); anhydrous (anhyd); room temperature (rt); hour (h); Minutes (Min), Retention Time ($R_t$); molecular weight (MW); milliliter (mL); gram (g). milligram (mg); equivalent (eq).

All NMR data were collected on 400 MHz NMR spectrometers unless otherwise indicated. LC-Electrospray-Mass spectroscopy with a C-18 column and 5% to 95% MeCN in water as the mobile phase was used to determine the molecular mass and retention time.

The compounds in the invention may be produced by processes known to those skilled in the art and as shown in the following reaction schemes and in the preparations and examples described below. Table 1 contains the compounds with retention time/observed MW and/or NMR data. The compounds of Table 1 can be obtained using synthetic methods similar to those below as listed in the last column of Table 1 using appropriate reagents known to those skilled in the art.

Method 1

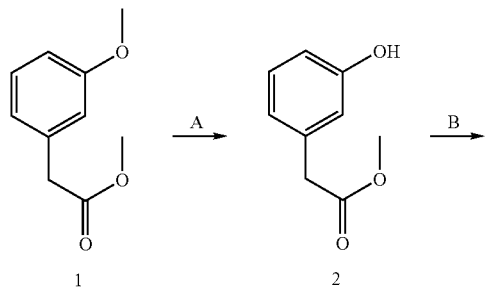

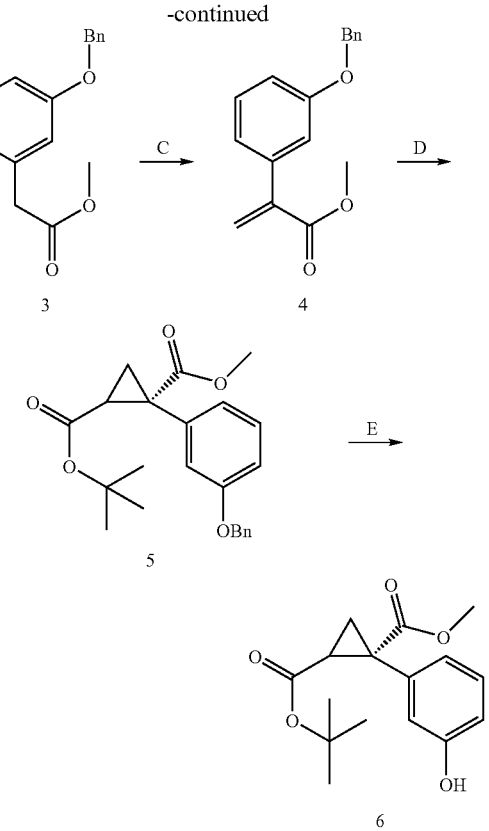

Synthesis of Compound 2

To a solution of 50 g (0.28 mol) of compound 1 in 500 mL of anhyd. DCM in an ice bath was added 560 mL 1N $BBr_3$ in DCM. The final solution was stirred for 30 min before it was quenched with 200 mL MeOH. After the solvent was evaporated, the residue was dissolved in 500 mL of DCM, washed with water, sat. $NaHCO_3$, and brine. The organic phase was dried over anhyd. sodium sulfate. The solvent was evaporated to give 41.5 g of desired compound 2 (90%) which was used in the next step without purification.

Synthesis of Compound 3

To a mixture of 41.5 g of Compound 2 in 500 mL DCM was added 10 eq. anhyd. $K_2CO_3$, 0.05 eq of tetrabutylammonium bromide (TBAB), and 1 eq. of benzylbromide. The mixture was stirred overnight, and the solid was filtered and washed with DCM. The combined organic solution was washed with water, saturated aqueous $Na_2CO_3$, brine, and dried over anhyd. sodium sulfate. The solvent was evaporated to give 57.6 g of compound 3 (90%), which was used in the next steps without purification.

Synthesis of Compound 4

To a solution of 57.6 g of Compound 3 in 500 mL of hexane was added $K_2CO_3$ (10 eq), TBAB (0.05 eq) and paraformaldehyde (20 eq), and the final mixture was refluxed overnight under effective stirring. The reaction mixture was partitioned between water and DCM, and the aqueous layer was extracted with DCM. The combined organic solution was washed with water, sat. $Na_2CO_3$, brine, and dried over anhyd. $Na_2SO_4$. The solvent was removed and the residue chromatographed with 1-10% ethylacetate in hexane to give 31 g of compound 4 (51%).

Synthesis of Compound 5

To a solution of 31 g of Compound 4 in 500 mL of MeCN was added S-carbo-tert-butoxymethyl-tetrahydrothiophene bromide (1.1 eq) and DBU (1.5 eq). The solution was stirred overnight and the solvent was evaporated. The residue dissolved in 500 mL DCM. The organic solution was washed with H₂O, 0.1 N HCl, water, brine, and dried over anhyd. Na₂SO₄. After removal of the solvent, the residue was chromatographed with 1-20% EtOAc/Hexane to give 32 g of compound 5 (73%).

Synthesis of 6

A mixture of 100 mL methanol solution of 2.0 g of Compound 5 with 200 mg of 10% Pd/C was stirred under H₂ until the starting material disappeared. The solution was filtered and the solvent evaporated to give compound 6 in quantitative yield.

Chiral Resolution of Compound 6

Compound 6 (1.0 g) was resolved with an OD chiral column eluted with 5% IPA/Hexane (120 mL/min). The first peak at 19.9 min was collected as enantiomer 6a and the second peak at 28.17 min was collected as enantiomer 6b.

Method 2

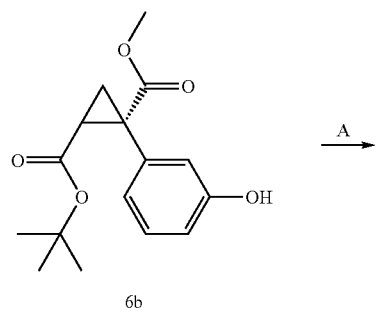

6b

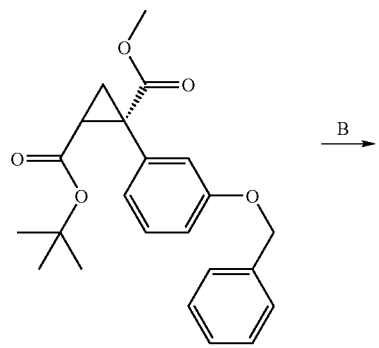

7

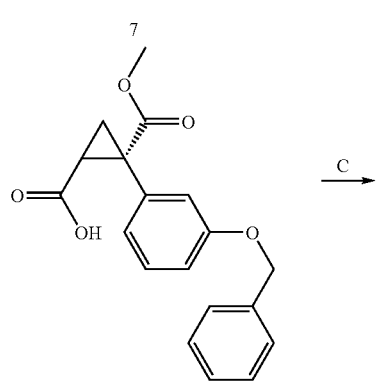

8

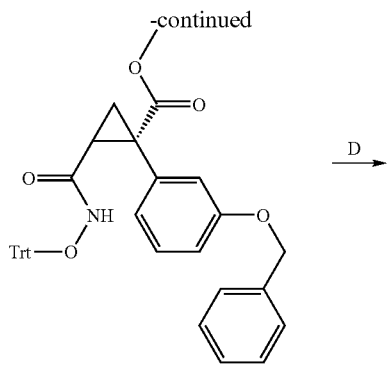

9

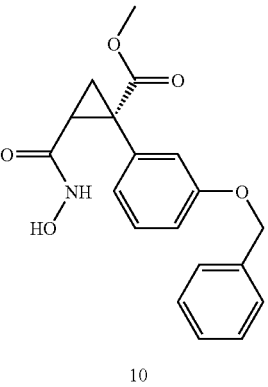

10

Synthesis of Compound 7

To a mixture of compound 6 (99 mg, 0.34 mmol), 31 mg of TBAB, 154 mg of anhyd K₂CO₃ in 2 mL of anhyd DCM was added 0.06 mL of benzyl bromide. The final solution was heated to 40° C. for 3 h. The mixture was diluted with 50 mL DCM and washed with water before the organic layer was dried over anhyd Na₂SO₄. The solvent was evaporated to give compound 7, which was used in the next step without purification.

Synthesis of Compound 8

A solution of Compound 7 (100 mg) in 30% TFA in DCM was kept for 4 h before the solvent was evaporated. The residue was adjusted to pH~9.5 with a 1:1 ratio of sat. NaHCO₃/Na₂CO₃ and the aqueous solution washed with ether. After acidification to pH~2, the aq layer was extracted with EtOAc. The combined organic layers were dried and solvent removed to give compound 8, which was used without purification for next step.

Synthesis of Compound 9

To a DCM solution of compound 8 at 0° C. were added HOAt (47 mg), O-tritylhydroxylamine (284 mg) and NMM 0.23 mL followed by 105 mg EDCl. The final solution was stirred overnight and the reaction mixture was diluted with 50 mL DCM and washed with NaHCO₃ and water. The organic layer was dried over anhyd Na₂SO₄. After removal of solvent the residue was chromatographed on a silica gel column eluting with 10-40% EtOAc in hexane to give 132 mg of Compound 9.

Synthesis of Compound 10

To a 2 mL solution of 60 mg of Compound 9 was added 55 mg of triethylsilane followed by 230 mg of TFA. The solution was evaporated and the residue was purified through a C-18 reverse phase HPLC column eluting with 5-95% of acetonitrile in water to give 32 mg of Compound 20 as a white solid.

$^1$H NMR (CD$_3$CN) of 10: δ 7.6-7.4 (m, 5H); 7.3 (m, 1H); 6.95 (m, 3H); 5.2 (m, 2H); 3.7 (s, 3H); 2.6 (m, 1H); 2.05 (m, 1H); 1.85 (m, 1H).

Method 3

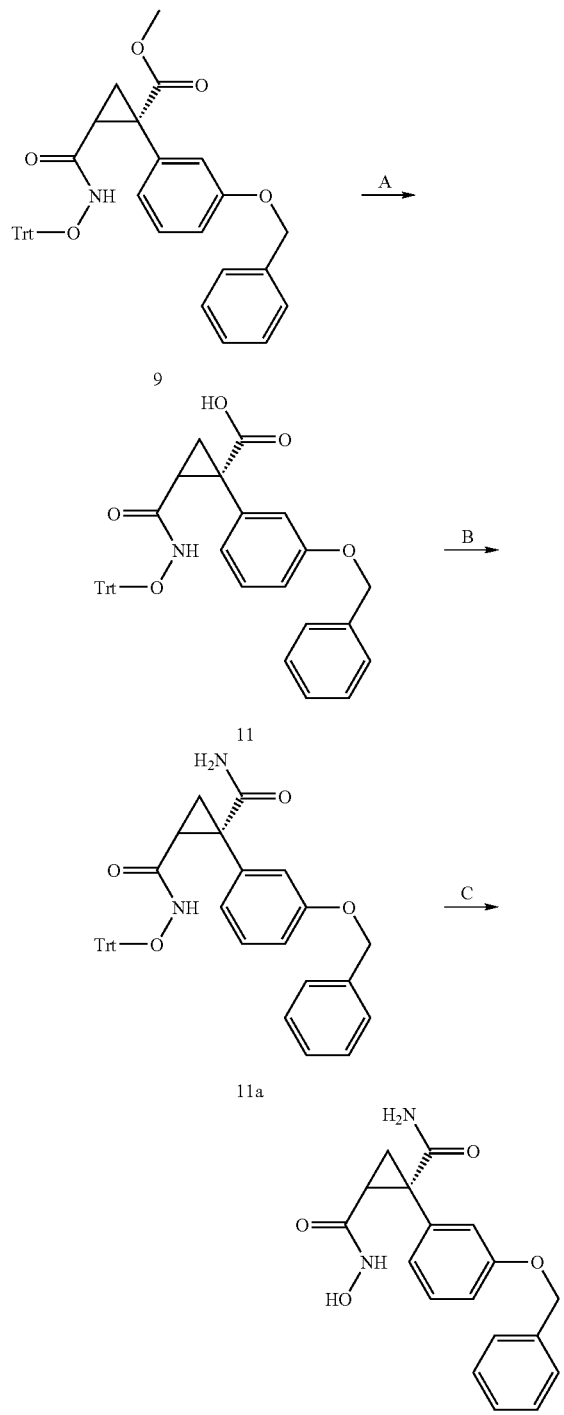

Synthesis of Compound 11

A solution 150 mg of Compound 9 and 1 g of LiOH.H$_2$O in a mixture of 20 mL MeOH, 10 mL THF and 10 mL H$_2$O was refluxed for 30 min. The solvent was evaporated and the residue was dissolved in a mixture of 100 mL DCM/100 mL of sat. aq ammonium chloride. The organic layer was separated, dried over anhyd sodium sulfate; and the solvent evaporated to give 150 mg of 11.

Synthesis of compound 11a

Compound 11 was dissolved in 2 ml of DMF followed by addition of 6 eq. of ammonium chloride, 2.5 eq. of HOBt, 25 eq of DIEA and 2.5 eq of EDCl. The mixture was stirred overnight followed by dilution with DCM and washed with water. The organic layer was dried over anhyd. sodium sulfate and the solvent was evaporated. The residue was chromatographed with a silica gel column to give 106 mg of Compound 11a.

Synthesis of Compound 12

Compound 12 was synthesized from 11a following a procedure similar to the transformation from 9 to 10 (Method 2).

$^1$H NMR(CDCl$_3$) of 12: δ 7.4-7.6 (m, 5H); 7.29 (m, 1H); 7.05 (m, 3H); 6.4 (br. s, 1H); 5.85 (br. s, 1H); 5.2 (m, 2H); 2.59 (m, 1H); 1.9 (m, 1H); 1.75 (m, 1H).

Method 4

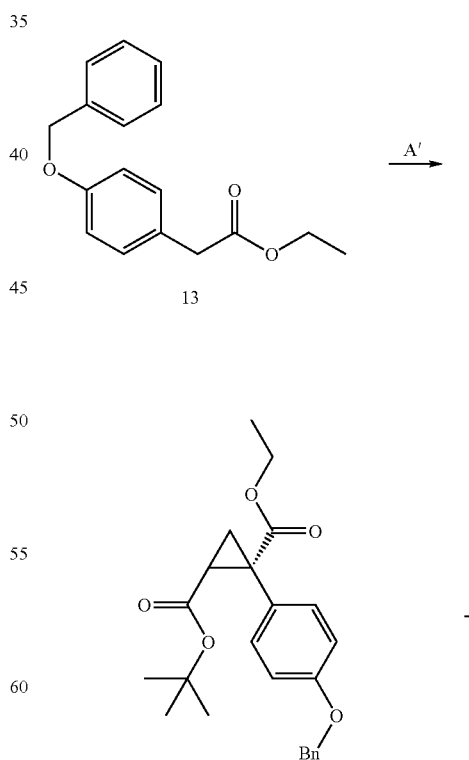

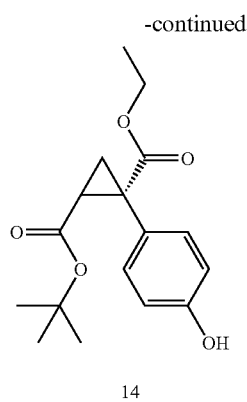

14

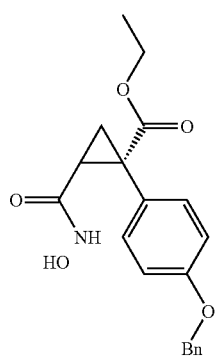

15

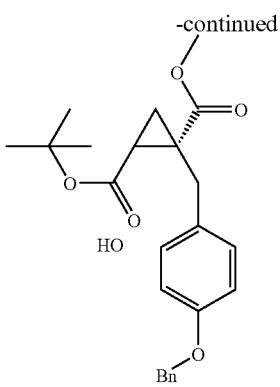

18

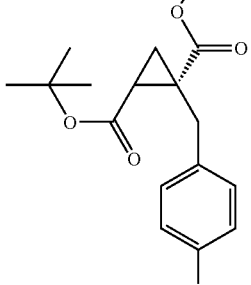

19

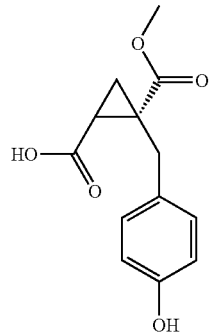

19c

Synthesis of Compound 14

Compound 14 was synthesized from 13 following procedures similar to the transformation from 3 to 6 (Method 1).

Synthesis of Compound 15

Compound 15 was synthesized from 14 following procedures similar to the transformation from 6 to 10 (Method 2).

$^1$H NMR(CD$_3$CN) of 15: δ 7.45-7.62 (m, 5H); 7.3 (m, 2H); 7.01 (m, 2H); 5.2 (s, 2H); 4.18 (m, 2H); 2.6 (m, 1H); 2.02 (m, 1H); 1.85 (m, 1H); 1.23 (m, 3H).

Method 5

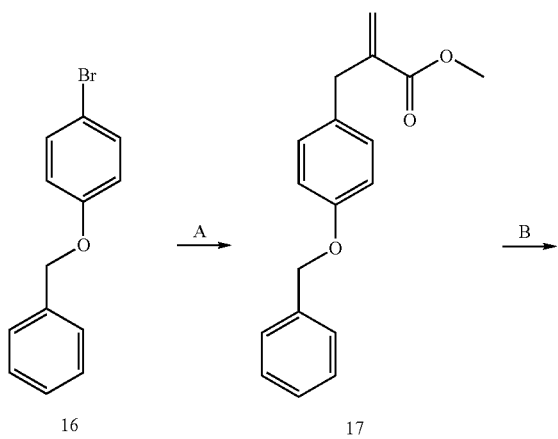

Synthesis of Compound 17

To a solution of 10.5 g of Compound 16 (40 mmol) in 100 mL of anhyd THF at −78° C. was added 53 mL of 1.5 M tert-Butyllithium in hexane over 5 min. After the solution was stirred at −78° C. for 1 h, it was added into a mixture of CuCN (40 mmol) in 20 mL of THF at 0° C. The solution was stirred for 30 min before it was cooled to −78. C and added to a solution of methyl 2-(bromomethyl)acrylate (29 mmol) in 20 mL of THF at −78° C. The reaction was stirred for 30 min at −78° C. followed by warming to −10° C. for 10 min before it was poured into a mixture of saturated NH$_4$Cl in ice. The mixture was extracted with DCM and the residue chromatographed with 10% EtOAc/Hexane to give 6.0 g of the desired product 17.

$^1$H NMR (CDCl$_3$) of 17: δ 7.5-7.3 (m, 5H); 7.13 (d, 2H); 6.94 (d, 2H); 6.22 (br s, 1H); 5.47 (br s, 1H); 5.05 (s, 2H); 3.75 (s, 3H); 3.59 (s, 2H).

Synthesis of Compound 18

Compound 18 was synthesized from 17 following a procedure similar to the transformation from 4 to 5 (Method 1).

Synthesis of Compound 19

Compound 19 was synthesized from 18 following a procedure similar to the transformation from 5 to 6 (Method 1).

Chiral Resolution of 19

Methods similar to the resolution of Compound 6 were used for the resolution of Compound 19. The first enantiomer was collected as 19a and the second enantiomer collected as 19b.

Synthesis of Compound 19c

Compound 19c was synthesized from 19a following a procedure similar to the transformation from 7 to 8 (Method 2).

Method 6

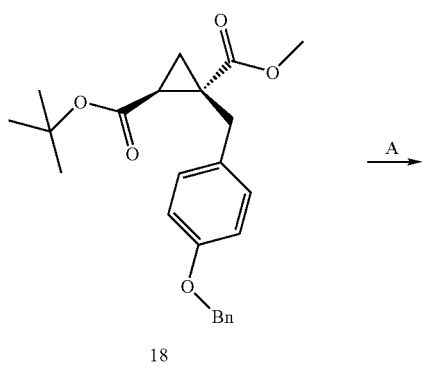

18

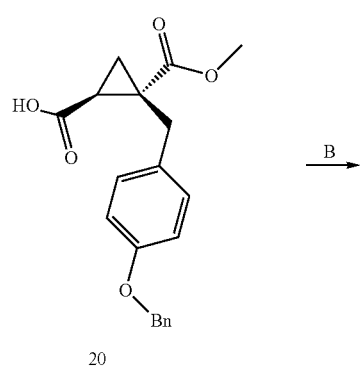

20

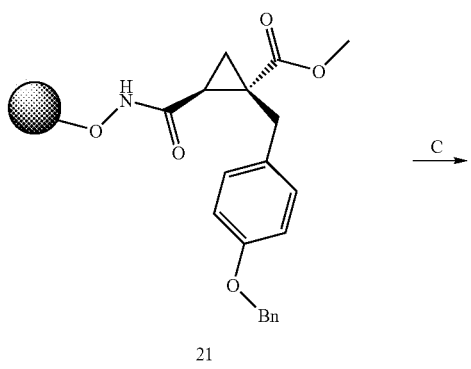

21

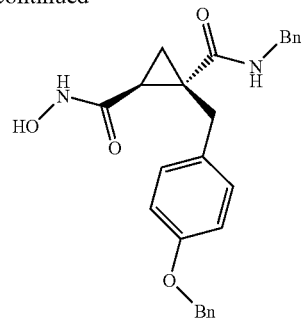

22

Synthesis of Compound 20

Compound 20 was synthesized from 18 following a procedure similar to the transformation of 7 to 8 (Method 2).

Synthesis of Compound 21

A solution of acid 20 (0.190 Mg, 0.56 mmol), Wang hydroxylamine resin (0.500 g, 1 mmol/g), EDCl (0.172 g, 0.90 mmol), NMM (0.400 mL, 3.64 mmol), and HOAt (0.075 g, 0.55 mmol) in DCM (7 mL), was agitated for 14 hours at room temperature. The liquid was drained, and the resin was washed with $CH_2Cl_2$ (3×), THF (3×), and MeOH (3×) in an alternating sequence. The resin was dried under high vacuum to yield resin 21 (0.630 g, 0.79 mmol/g).

Synthesis of Compound 22

A mixture of resin 21 (0.067 g, 0.79 mmol/g) and 1M $Bu_4NOH$ in THF (2 mL) was agitated at 60° C. for 4 h. The liquid was drained and the resin was washed with 1% AcOH in DMF (2×30 min.) followed by an alternating cycle of washes with MeOH (3×), THF (3×) and $CH_2Cl_2$ (3×). The resulting resin was dried under high vacuum for 4 hours.

A mixture of the carboxylic acid resin prepared above (0.067 g, 0.79 mmol/g), EDCl (0.045 g, 0.23 mmol), HOBt (0.030 g, 0.20 mmol) and NMM (0.026 mL, 0.24 mmol) in NMP (2 mL) was agitated for 20 minutes before the addition of benzyl amine (0.026 mL, 0.24 mmol). This mixture was agitated for 18 hours at rt. The liquid was drained, and the resin was washed with an alternating cycle of $CH_2Cl_2$ (3×), THF (3×), and MeOH (3×). The remaining resin was treated with 50% $TFA/CH_2Cl_2$ (2 mL) and agitated for 1 hour. The liquid was drained, and the remaining resin was washed with $CH_2Cl_2$ (2×). Concentration of the liquid afforded Compound 22 (10 mg, 0.023 mmol).

$^1$H NMR ($CD_3CN/D_2O$, 2:1) of 22: δ 7.29-7.44 (m, 6H), 7.14-7.07 (m, 4H), 6.84-6.81 (m, 4H), 5.03 (s, 2H), 4.22-4.13 (m, 2H), 3.12-2.93 (m, 2H), 2.07-2.03 (m, 1H), 1.49-1.46 (m, 1H), 1.40-1.38 (m, 1H).

Method 7

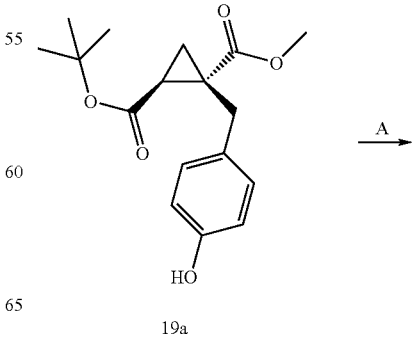

19a

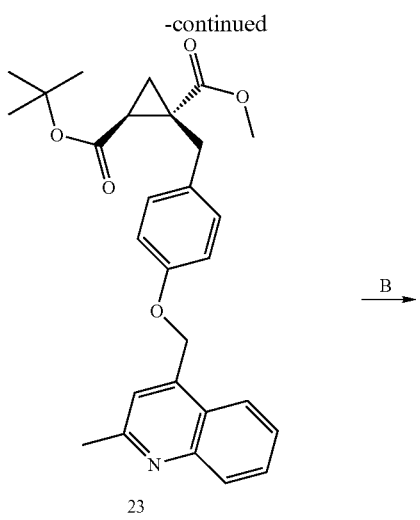

23

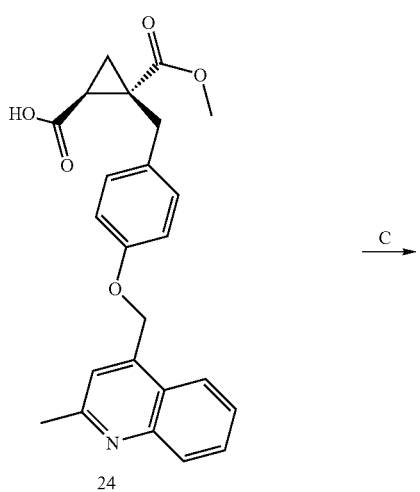

24

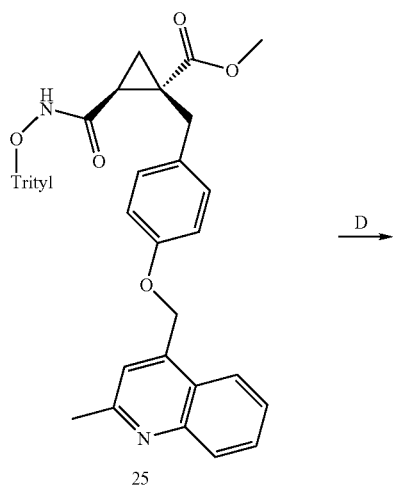

25

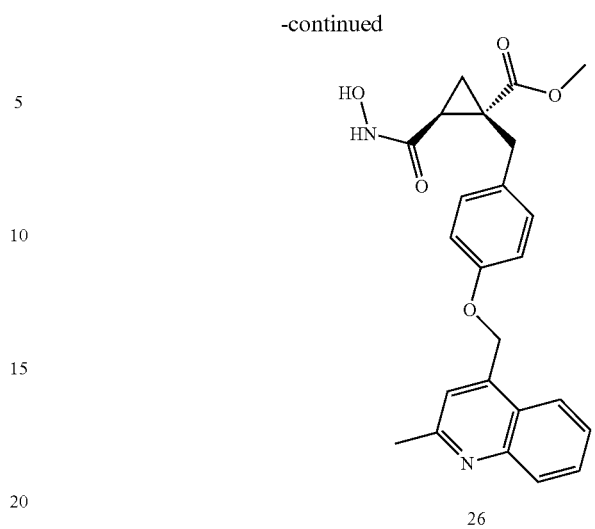

26

Synthesis of Compound 23

To a solution of compound 19a (0.04 g) and 4-chloromethyl-2-methylquinoline (1.5 eq) in 1 mL of DMF was added 0.25 g of potassium carbonate and 20 mg of tetrabutylammonium iodide. The mixture was stirred overnight before it was partitioned in a mixture of DCM/water. The aqueous layer was extracted twice with DCM and the combined organic layer was dried and solvent removed. The residue was chromatographed to give compound 23 (0.08 g).

Synthesis of Compound 24

Compound 24 was synthesized from 23 following a procedure similar to the transformation of 7 to 8 (Method 2).

Synthesis of Compound 25

Compound 25 was synthesized from 24 following a procedure similar to the transformation of 8 to 9 (Method 2).

Synthesis of Compound 26

Compound 26 was synthesized from 25 following a procedure similar to the transformation of 9 to 10 (Method 2).

$^1$H NMR (CD$_3$CN/D$_2$O, 2:1) of 26: δ 8.38 (m, 1H), 8.28 (m, 1H), 8.05 (m, 1H), 8.01 (s, 1H); 7.88 (m, 1H); 7.20 (m, 2H); 7.04 (m, 2H); 5.71 (s, 2H), 3.57 (s, 3H), 2.96-3.4 (m, 2H), 2.95 (s, 3H); 2.23 (m, 1H), 1.49-1.46 (m, 2H).

Method 8

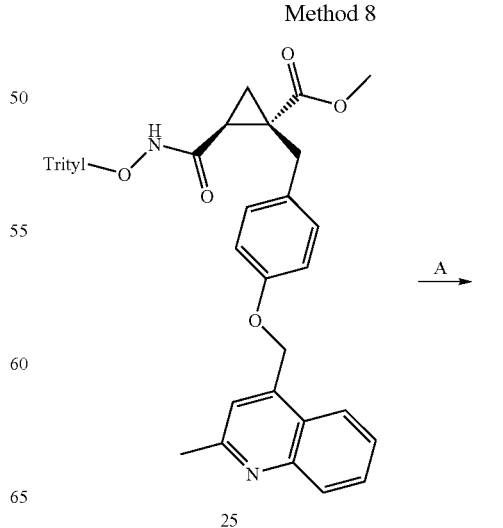

25

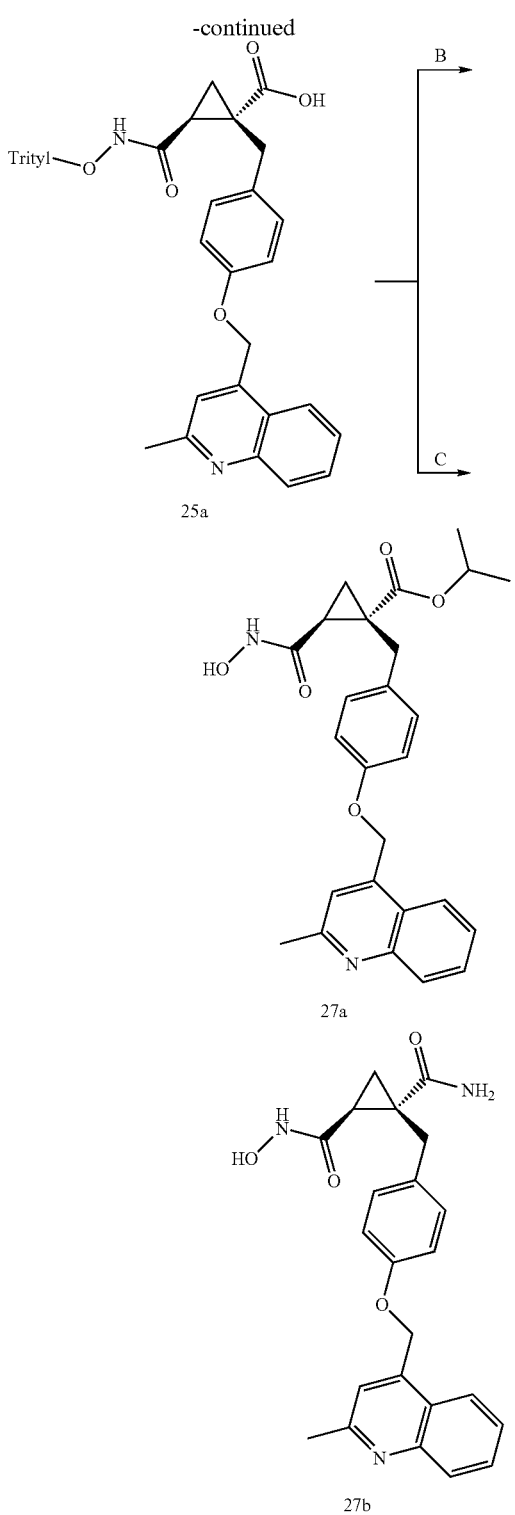

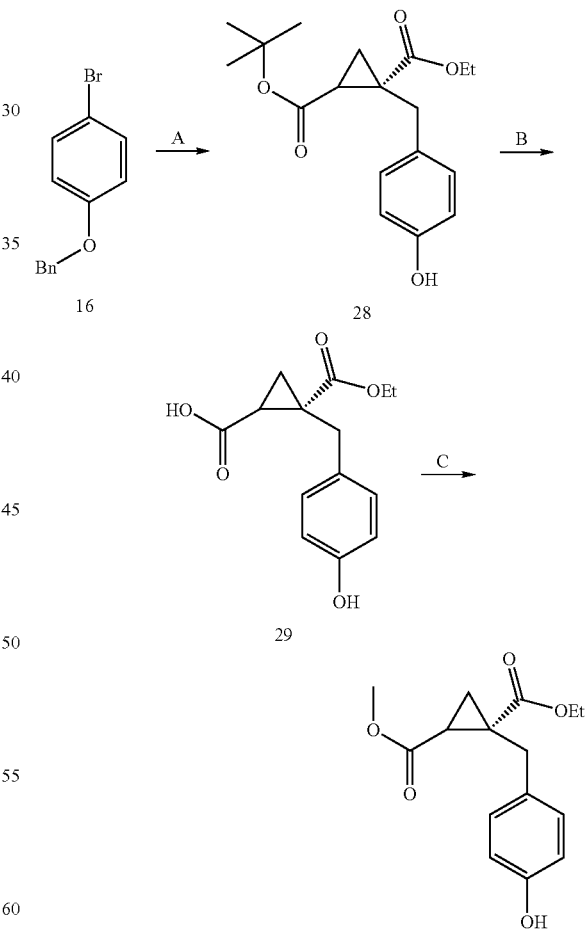

was stirred for 25 minutes and 2-propanol (0.20 mL, 2.6 mmol) was then added. The resulting mixture was stirred for 16 hours. The reaction was quenched with $H_2O$ and diluted with ethyl acetate. The organic phase was removed, and the aqueous layer was extracted with ethyl acetate (3×). The combined organic layers were washed with $H_2O$ (2×), brine (1×), dried ($Na_2SO_4$), filtered, and concentrated. The residue was purified by flash chromatography to afford compound 27a.

$^1$H NMR (CD$_3$OD): δ 8.4 (m, 1H), 8.05-8.02 (m, 3H), 7.93 (m, 1H), 7.25 (m, 2H); 7.05 (m, 2H); 5.8 (s, 2H), 4.88 (m, 1H); 3.0-3.24 (m, 2H), 2.96 (s, 3H); 2.24 (m, 1H); 1.5 (m, 2H); 1.1 (m, 6H).

Synthesis of Compound 27b

Compound 27b was synthesized from 25a following procedures similar to the transformation of 11 to 12 (Method 3).

$^1$H NMR (CD$_3$OD) of 27b: δ 8.12 (m, 1H), 8.01 (m, 1H), 7.80 (m, 1H), 7.62 (m, 2H); 7.23 (m, 2H); 7.01 (m, 2H); 5.57 (s, 2H), 3.1-3.3 (m, 2H); 2.74 (s, 3H); 2.14 (m, 1H), 1.54 (m, 1H); 1.46 (m, 1H).

Method 9

Synthesis of Compound 25a

Compound 25a was synthesized from 25 using a procedure similar to the transformation of 9 to 11 (Method 3).

Synthesis of Compound 27a

To a solution of acid 25a (0.043 g, 0.067 mmol) in CH$_2$Cl$_2$ (1 mL) at room temperature was added DMAP (6.025 mg, 0.20 mmol) and EDCl (0.033 g, 0.17 mmol). This mixture Synthesis of 28

Compound 28 was synthesized from 16 following procedures similar to the transformation of 16 to 19 (Method 5).

Synthesis of 29

Compound 28 was synthesized following a procedure similar to the transformation of 7 to 8 (Method 2).

Chiral Resolution of 29

Compound 29 was resolved with a Chiralpak AS column eluting with 40% iPrOH/hexanes (0.1% AcOH) at 70 mL/min. The first peak at was collected as enantiomer 29a and the second peak was collected as enantiomer 29b.

Synthesis of Compound 30

To a methanolic solution of 29a (0.5 g) was added 6 drops of sulfuric acid and the solution was refluxed for 1 h. After removal of methanol, the residue was partitioned in a mixture of DCM/water. The water layer was extracted with DCM (3×) and the combined organic layer was dried and solvent evaporated to give 0.51 g of product 30.

Method 10

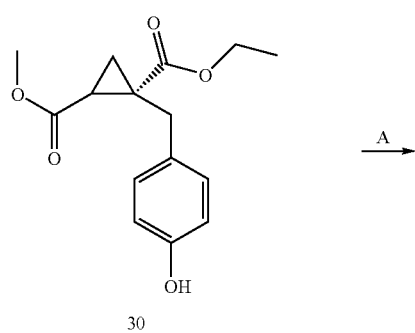

30

A →

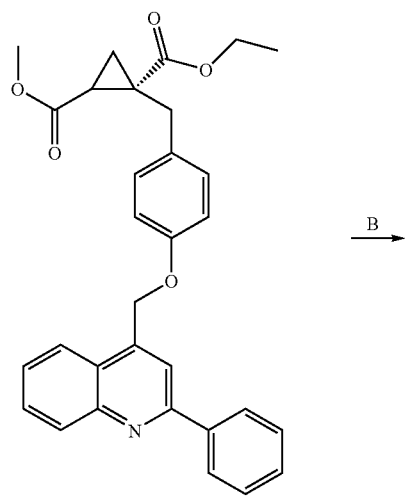

31

B →

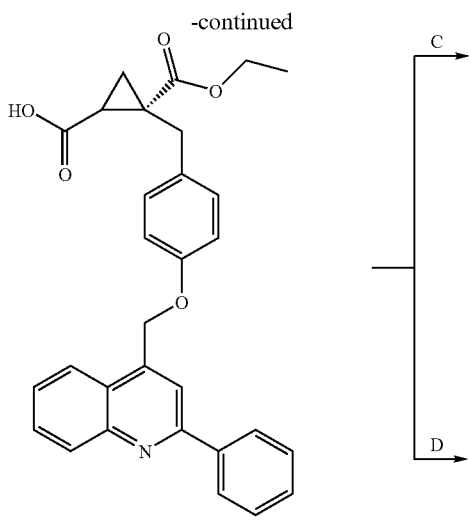

32

C →
D →

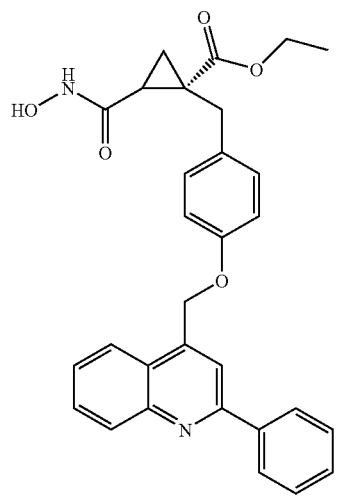

33

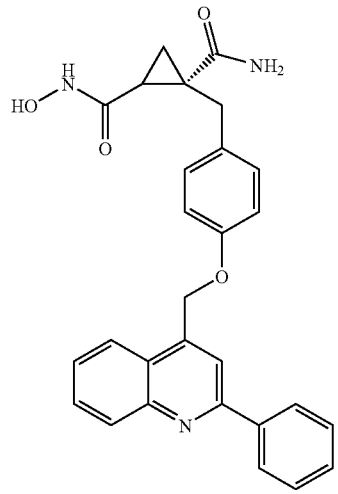

34

Synthesis of Compound 31

Compound 31 was synthesized from 30 following a procedure similar to the transformation of 6 to 7 (Method 2) or 19a to 23 (Method 7).

Synthesis of Compound 32

To a solution of Compound 31 (0.08 g) in 4 mL of methanol was added 100 mg LiOH in 1 mL of water. The suspension was stirred for 2 h at rt and the solution was partitioned in a mixture of DCM/saturated ammonium chloride. The aqueous layer was extracted with DCM and the combined organic layer was dried and solvent removed to give 75 mg of crude 32 which was used for next step without purification.

Synthesis of Compound 33

Compound 33 was synthesized from 32 following procedures similar to the transformation from 8 to 10 (Method 2).

$^1$H NMR (CD$_3$CN/D$_2$O, 2:1): δ 8.07-8.18 (m, 5H), 7.8 (m, 1H), 7.60 (m, 1H), 7.5 (m, 3H); 7.23 (m, 2H); 7.01 (m, 2H); 5.57 (m, 2H), 3.97 (m, 2H); 2.9-3.2 (m, 2H); 2.2 (m, 1H); 1.5 (m, 2H); 1.1 (m, 3H).

Synthesis of Compound 34

Compound 34 was synthesized from 32 following a procedure similar to the transformation from 8 to 9 (Method 2) and then 9 to 12 (Method 3).

$^1$H NMR (CD$_3$OD) of 34: δ 8.3-8.5 (m, 3H), 8.05-8.15 (m, 3H), 7.85-7.97 (m, 1H), 7.62-7.76 (m, 3H); 7.26 (m, 2H); 7.10 (m, 2H); 5.8 (s, 2H), 3.1-3.3 (m, 2H); 2.14 (m, 1H), 1.54 (m, 1H); 1.46 (m, 1H).

Method 11

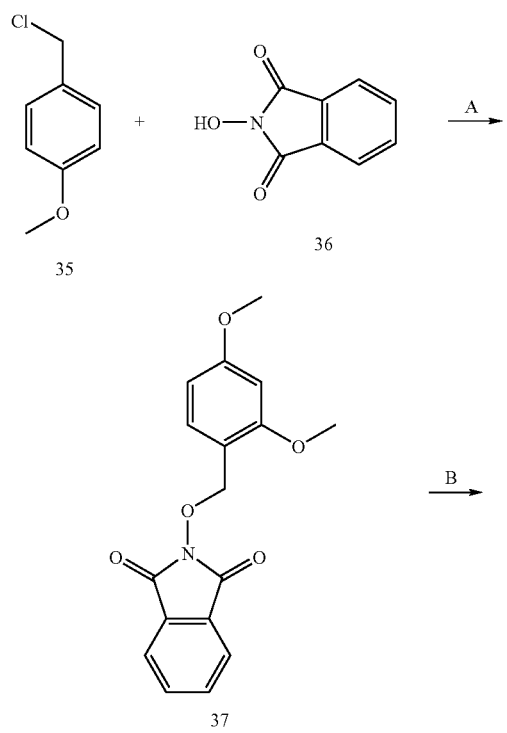

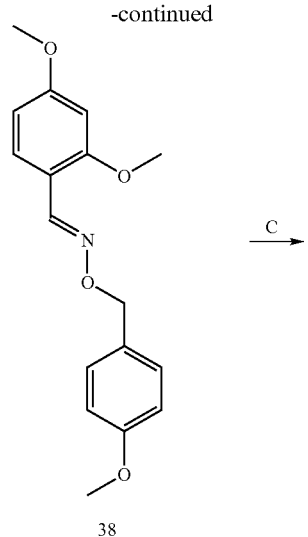

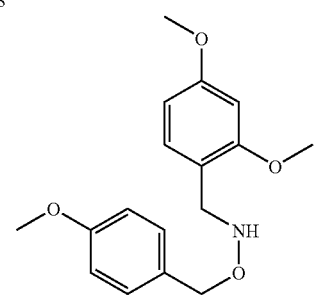

Synthesis of Compound 37

A solution of 11.5 g of 35 (7.4 mmol), 36 (1 eq) and Diisopropylethylamine (1.5 eq) in 200 mL Acetonitrile was refluxed for 3 h. After removing all the solvent, the solid (37, 22 g) was used for next step without purification.

Synthesis of Compound 38

A solution of compound 37 (22 g) and 300 mL of 20% hydrazine monohydrate in methanol was refluxed for 20 minutes. After removal of the solvents, the solid was partitioned between 1N NaOH and DCM. The aq layer was extracted with DCM (×3) before the combined organic layers were dried and evaporated to give 9.5 g crude product. The hydroxylamine was mixed with 9.0 g of 2,4-dimethoxybenzaldehyde, 10 g of sodium acetate in 200 mL of acetic acid. After the mixture was refluxed for 2 h, white precipitates formed upon cooling of the reaction. After removal of the solvent, the content was dissolved into DCM and the organic phase was washed with water. After removal of solvent, the solid was recrystalized from MeOH to give 11 g of 38 as a white solid.

Synthesis of Compound 39

To a solution of compound 38 (11 g, 36 mmol) in 200 mL acetic acid was added sodium cyanoborohydride (4 eq). The reaction was stirred for 30 min, and after removal of solvents, the solid was partitioned between saturated sodium carbonate/DCM and the aqueous layer was extracted with DCM (3×). The combined organic layers was dried and evaporated.

The residue was chromatographed with a silica gel column using ethyl acetate in hexane as elutant to give 9.5 gram crude product 39.

Method 12

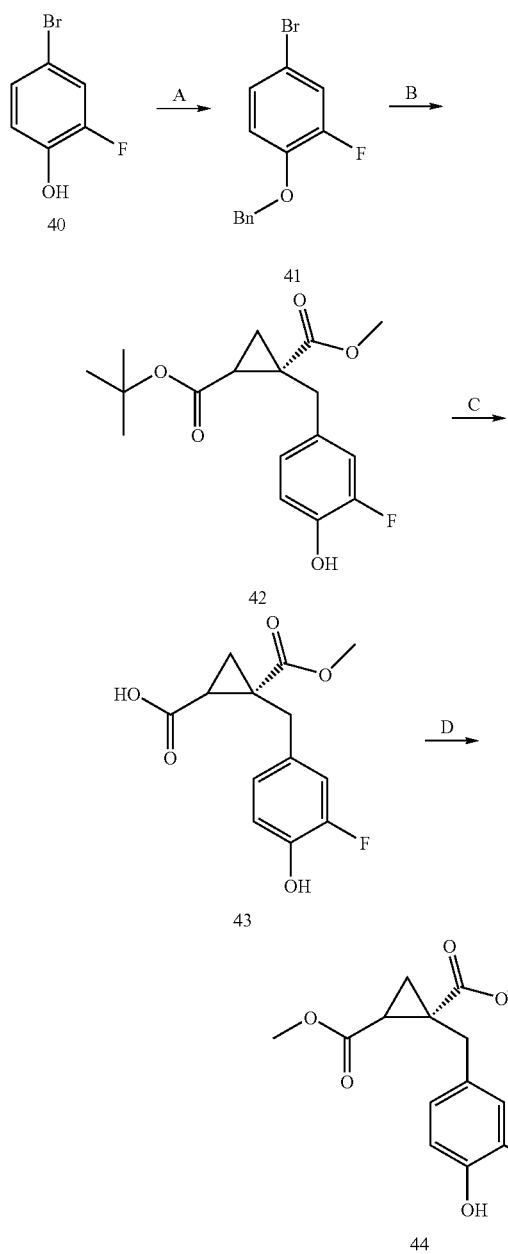

Chiral Resolution of 43

Compound 43 was resolved with a procedure similar to the resolution of compound 29. The first peak at was collected as enantiomer 43a and the second peak was collected as enantiomer 43b.

Synthesis of Compound 44

Compound 44 was synthesized from 43a following a procedure similar to the transformation from 29 to 30 (Method 9).

Method 13

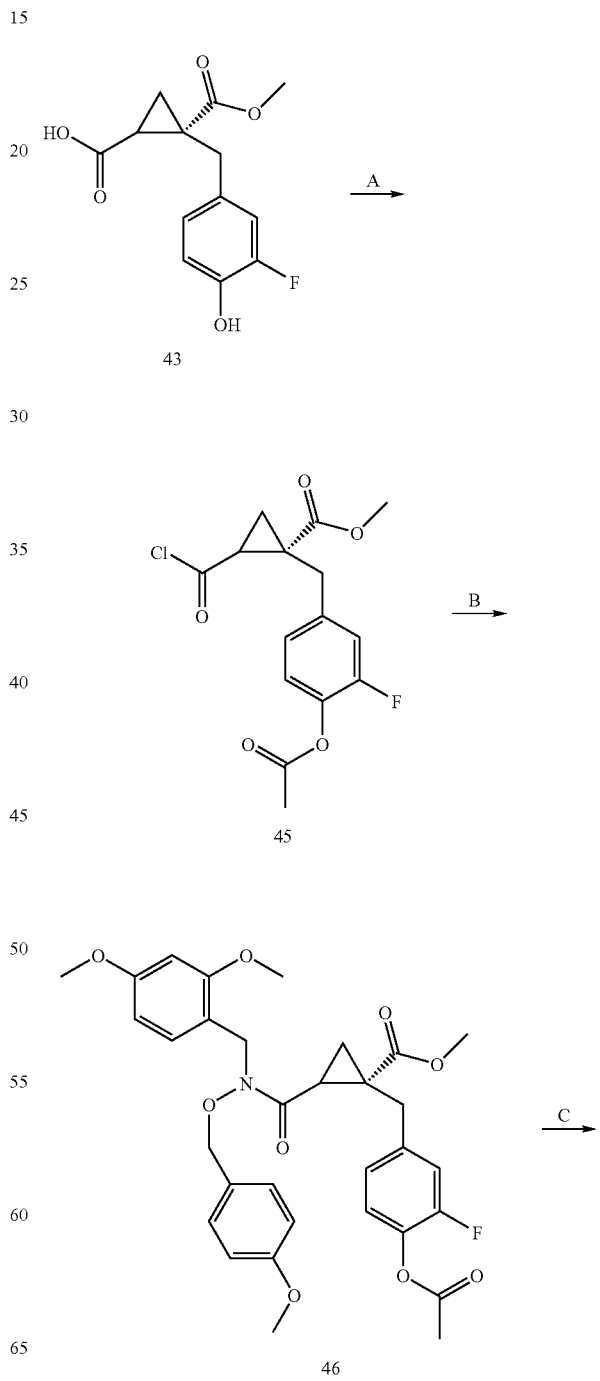

Synthesis of Compound 41

Compound 41 was synthesized from 40 following a procedure similar to the transformation from 2 to 3 (Method 1).

Synthesis of Compound 42

Compound 42 was synthesized from 41 following procedures similar to the transformation from 16 to 19 (Method 5);

Synthesis of Compound 43

Compound 43 was synthesized from 42 following a procedure similar to the transformation from 7 to 8 (Method 2).

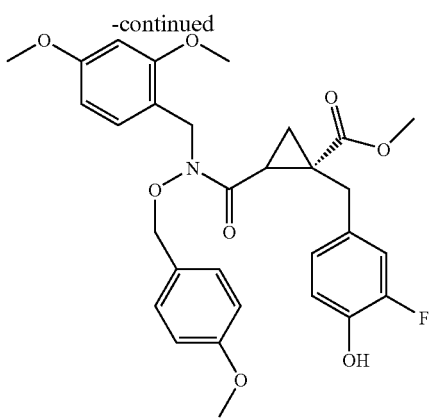

47

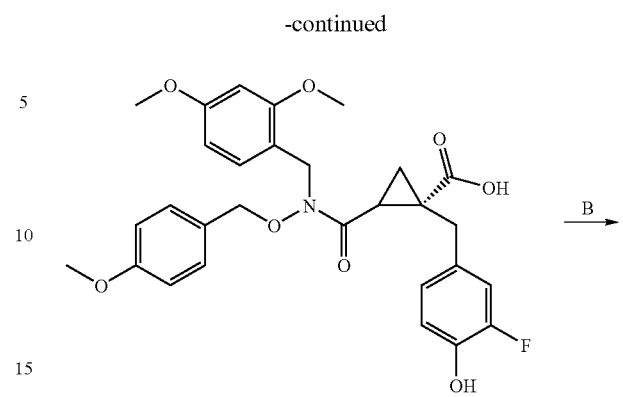

48

Synthesis of Compound 45

To a cooled solution of compound 43 (5.5 g, 20.5 mmol), DMAP (1 mmol), diisopropylethylamine (2.0 eq) in 40 mL anhyd. DCM at 0° C. was added acetyl chloride. The starting material disappeared in 30 min and the reaction mixture was washed with 0.5 N HCl. After removal of solvent, the residue was dissolved in 30 mL of anhyd. DCM followed by addition of oxalyl chloride (3 eq) and 2 drops of DMF. The reaction was kept overnight under rt and solvent evaporated to give a crude product 45 as an oil, which was used for next step without further purification.

Synthesis of Compound 47

After evaporating solvent from the DCM solution of 45 three times, the crude acid chloride was dissolved in 20 mL of DCM followed by addition of a 5 mL DCM solution of compound 39 with 2 eq of diisopropylethylamine. After the solution was stirred overnight at rt, the solvent was evaporated to give the crude product 46. After the crude product was treated with 7N ammonia in methanol for 30 min, the solvent was removed and the residue chromatographed on a silica gel column eluted with ethyl acetate and hexane to give 5.1 g of product 47.

Method 14

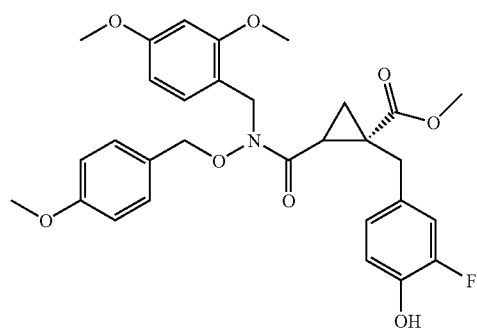

47

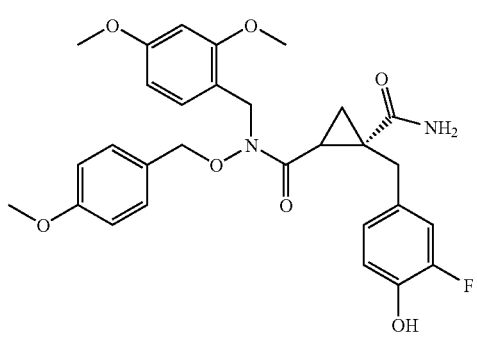

49

Synthesis of Compound 48

Compound 48 was synthesized from compound 47 following a procedure similar to the transformation from 9 to 11 (Method 3).

Synthesis of Compound 49

Compound 49 was synthesized from compound 48 following procedures similar to the transformation from 11 to 11a (Method 3).

Method 15

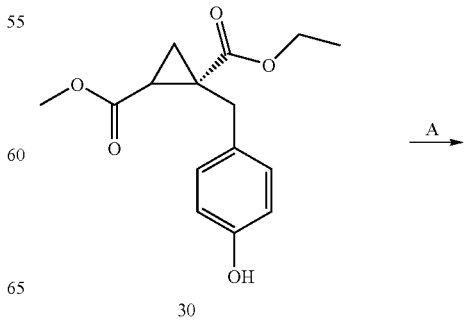

30

-continued

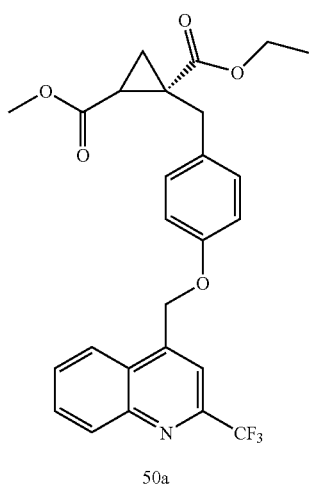

50a

Method 16

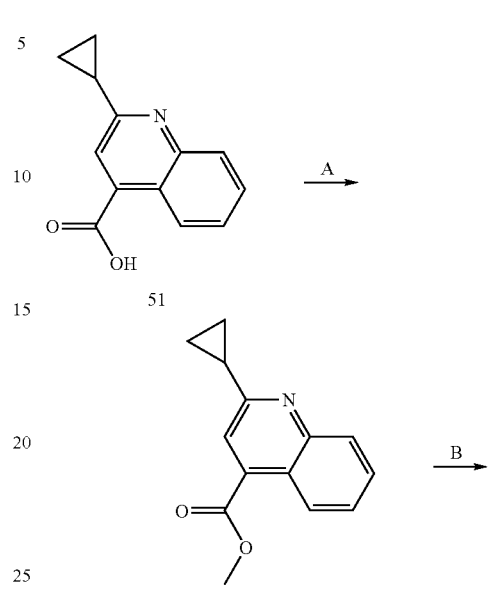

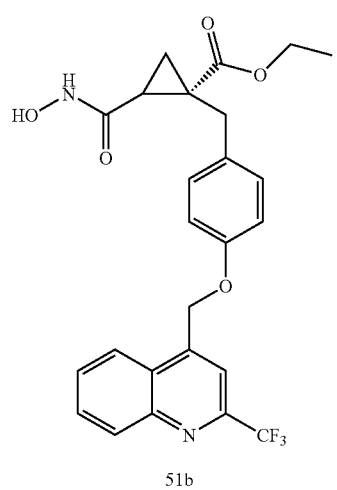

51b

Synthesis of Compound 50a

Compound 50a was synthesized following a procedure similar to the transformation from 30 to 31 (Method 10).

Synthesis of Compound 51b

Compound 50a (98 mg, 2 mmol) was dissolved in MeOH and hydroxylamine hydrochloride (440 mg, 6.3 mmol) and DBU (1.76 mL, 11.8 mmol) were added. The reaction mixture was stirred at rt for 2 h. AcOH (680 µL, 11.8 mmol) was added and the reaction mixture was concentrated to dryness. The crude product was purified via silica gel chromatography using 95:5 CH$_2$Cl$_2$:MeOH as the mobile phase to give 12 mg of 51 b.

$^1$H NMR (300 MHz, CDCl$_3$): δ 7.90 (m, 1H), 7.80 (m, 1H), 7.63 (s, 1H), 7.58-7.50 (m, 1H), 7.46-7.43 (m, 1H), 6.89 (m, 2H), 6.64 (m, 2H), 5.28 (s, 2H), 3.73-3.70 (m, 2H), 2.98 (s, 2H), 1.92 (m, 1H), 1.25-1.21 (m, 2H), 0.81 (m, 3H).

Synthesis of Compound 52

To a mixture of compound 51 (0.5 gram) in 30 mL of methanol was added sulfuric acid (1.5 eq) and the mixture was refluxed for 6 h. After removal of the solvent, the residue was dissolved in DCM and the solution was washed with sat sodium bicarbonate. The organic layer was dried and solvent evaporated to give 0.5 g of product 52, which was used without purification for next step.

Synthesis of Compound 53

To a solution of compound 52 (0.5 gram) in 20 mL of methanol was added sodium borohydride (2 eq), and the mixture was stirred overnight. After the removal of solvent, the residue was partitioned in DCM and water. The aqueous layer was extracted (3×) and the combined organic layer was dried, solvent evaporated to give compound 53 (0.45 g) which was used for next step without purification.

$^1$H NMR (CDCl$_3$) δ 7.96 (d, 1H); 7.81 (d, 1H); 7.61 (m, 1H); 7.41 (m, 1H); 7.21 (s, 1H); 5.13 (s, 2H); 2.20 (m, 1H); 1.06 (m, 4H).

Synthesis of Compound 54

To a solution of compound 53 (0.5 gram) in 20 mL of anhyd. DCM was added thionyl chloride (2 eq), and the mixture was stirred for 30 min. After removal of solvent, the residue was partitioned in DCM and water. The aqueous layer was extracted (3×) and the combined organic layer was dried, solvent evaporated to give compound 54 (0.55 g) which was used for next step without purification.

Method 17

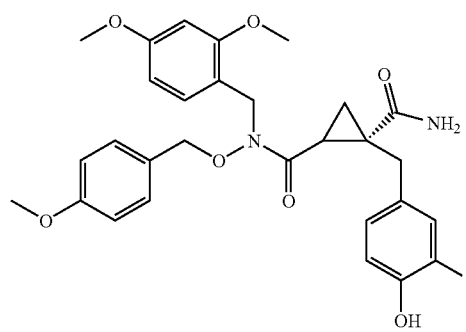

49

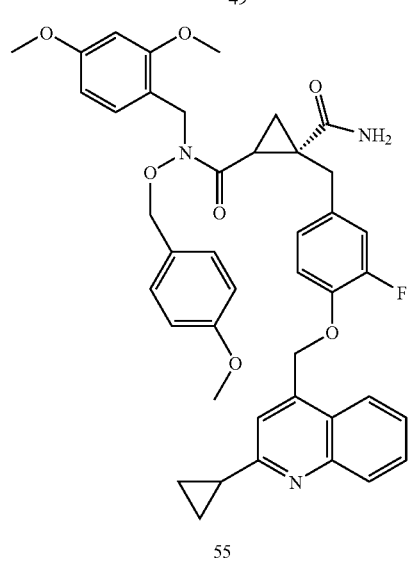

55

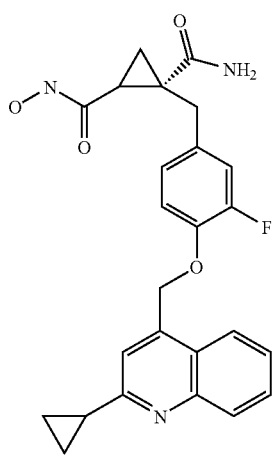

56

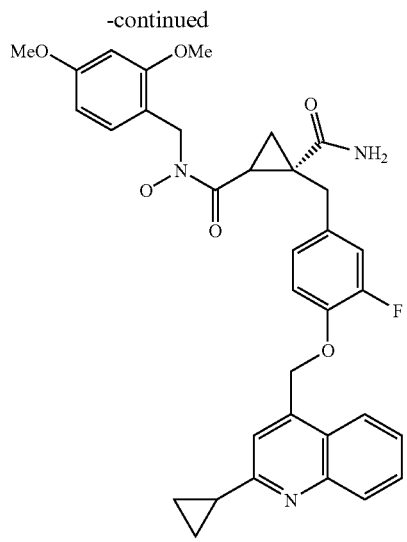

56a

Synthesis of Compound 55

To a 1 mL DMF solution of 20 mg of 49 (0.036 mmol); 9 mg of 54 as a HCl salt (0.035 mmol) and 2 mg of tetrabutylammonium iodide was: added with 200 mg of potassium carbonate and the mixture was stirred overnight. After removal of DMF, the residue was chromatographed to give 23 mg of product 55.

Synthesis of Compound 56

To a solution of compound 55 in 1 mL of DCM was added 5 eq of triethylsilane and 1 mL TFA. The solution was let stand for 2 h and the solvent evaporated. The residue was chromatographed with a C-30 reverse phase HPLC eluted with 5-95% acetonitrile in water to give 15 mg of 56.

$^1$H NMR (CD$_3$OD): δ 8.08 (m, 1H); 7.95 (m, 1H); 7.75 (m, 1H); 7.55 (m, 1H); 7.4 (s, 1H); 7.0-7.2 (m, 3H); 5.6(s, 2H); 3.1-3.3 (m, 2H); 2.3 (m, 1H); 2.15(m, 1H); 1.55(m, 1H); 1.45(m, 1H); 1.05-1.2 (m, 4H).

Method 18

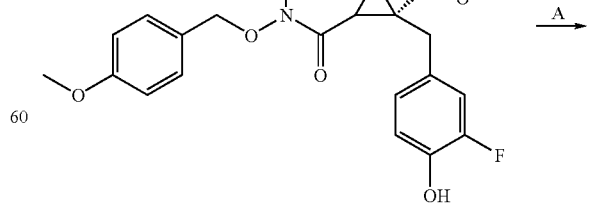

47

-continued

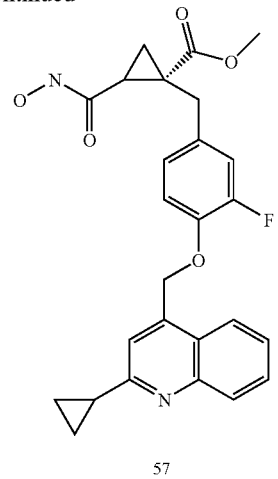

57

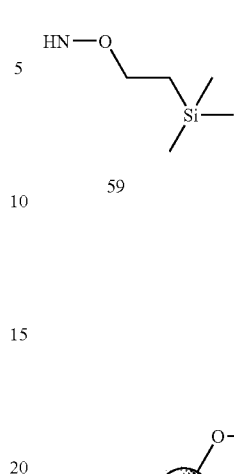

59

A →

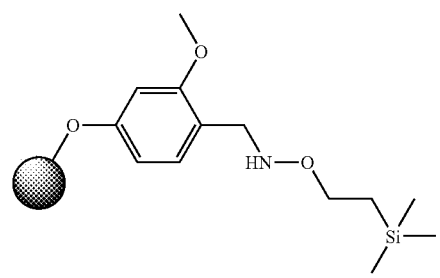

60

Synthesis of Compound 57

Compound 57 was synthesized following procedures similar to the transformation of 49 to 56 (Method 17).

$^1$H NMR (CD$_3$OD): δ 8.08 (m, 1H); 7.95 (m, 1H); 7.75 (m, 1H); 7.55 (m, 1H); 7.4 (s, 1H); 7.0-7.2 (m, 3H); 5.6(s, 2H); 3.61 (s, 3H); 3.0-3.25 (m, 2H); 2.3 (m, 2H); 1.55 (m, 2H); 1.05-1.2 (m, 4H).

Method 19

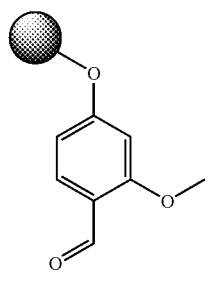

58

Synthesis of Resin 60

The mixture of 8.3 gram pre-swelled resin 58 (0.91 mmol/g) and 1.1 eq of 59 as a HCl salt in 20 mL of 10:20:70 solvent mixture of HOAc:MeOH:THF was agitated overnight. After the resin was washed with MeOH, THF and DCM, it was preswelled in 20 mL anhyd. DCM. After the mixture was cooled down to 0° C., 15 equivalent of BH$_3$.Py and 23 eq of dichloroacetic acid were added. After the reaction was agitated overnight, the resin was washed with MeOH, THF and DCM and dried in vacuo to give resin 60.

Method 20

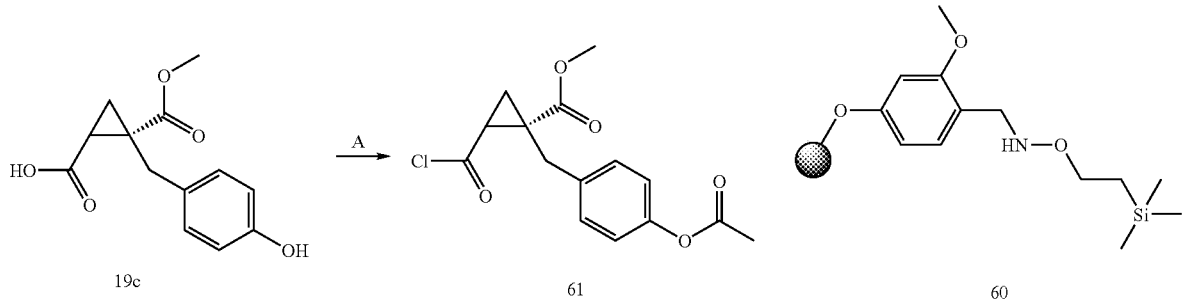

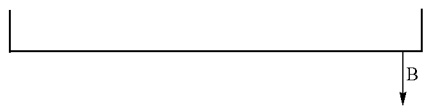

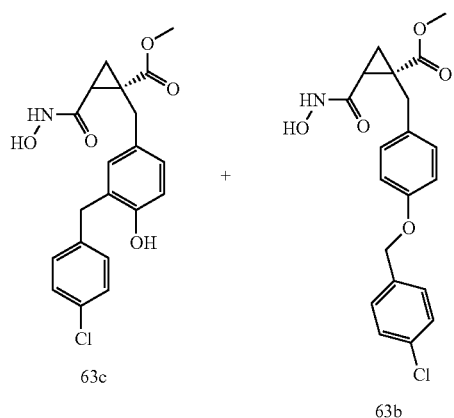

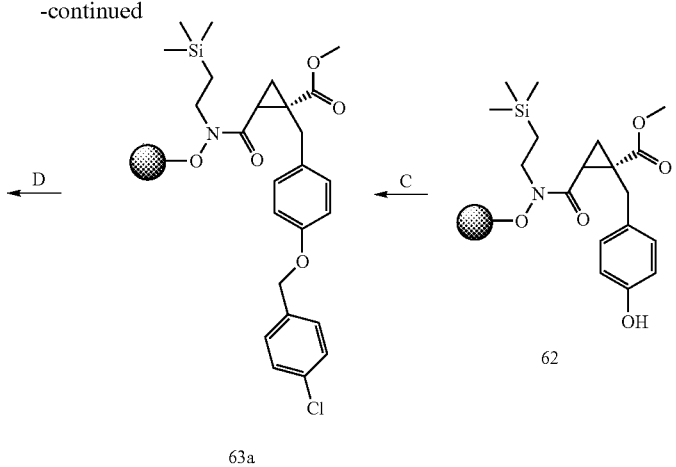

Synthesis of Compound 61

Compound 61 was synthesized following procedures similar to the transformation from 43 to 45 (Method 13).

Synthesis of Resin Bound Compound 62

Compound 61 (150 mg, 0.46 mmol) was dissolved in 2 mL of anhyd DCM and the solution was added to 178 mg of resin 6.0 with 0.2 mL of DIEA. The final mixture was agitated for 12 h before the resin was washed with 20% piperidine in DMF followed by wash with combination of MeOH, DCM and THF. The loading level of the final resin was determined to be 0.4 mmol/g after cleavage with 75% TFA in DCM overnight.

Synthesis of Resin Bound Compound 63b and 63c.

To preswelled resin 62 (75 mg) with anhyd THF was added 5 eq of 1,1'-(azodicarboxyl)dipiperidine, 5 eq of 2-3-dichlorobenzylalcohol and 7 eq. of tributylphosphine in 3 mL of THF under nitrogen. The final reaction mixture was heated to 70° C. with agitation overnight. After washing with MeOH, DCM and THF, the resin was cleaved with 75% TFA in DCM for 2 h. The residue after removal of the solvent was purified with a C-18 reverse phase column eluted with 5-95% of MeCN in water to give desired products 63b and 63c.

$^1$H NMR (CD$_3$OD) for 63b: δ 7.36-7.43 (m, 4H); 7.14-7.17 (m, 2H); 6.86-6.88 (m, 2H); 5.03 (2H, s); 3.61 (3H, s); 2.96-3.20 (2H, m); 2.23-2.27 (1H, m); 1.52-1.54 (2H, m).

$^1$H NMR (CD$_3$OD) for 63c: δ 7.17-7.23 (m, 4H); 6.89-6.93 (m, 2H); 6.65-6.67 (m, 1H); 3.87 (s, 2H); 3.54 (3H, s); 2.86-3.12 (2H, m) 2.18-2.22 (1H, m); 1.47-1.49 (2H, m).

Method 21

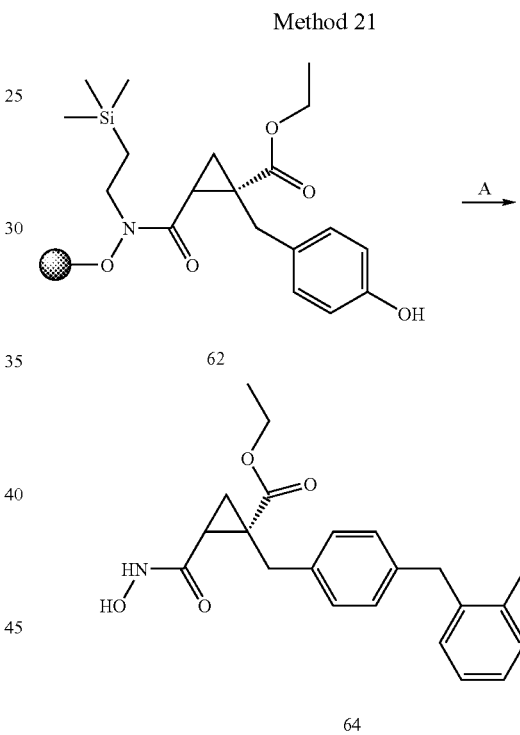

Synthesis of Compound 64

To pre-swelled resin 62 (75 mg) was added 100 mg 5 micron 4 Å molecular sieves, 2 eq. of anhyd. copper acetate, and 5 eq of 1-naphthylboronic acid followed by 2 mL of anhyd. DCM. The reaction mixture was agitated at rt overnight and the resin washed with THF. The above procedure was repeated before the resin was washed with MeOH, DCM, THF, and cleaved with 75% TFA in DCM for 2 h. After removal of organic solvent, the residue was purified with a C-18 reverse phase column eluted with 5-95% MeCN in water to give 4 mg of desired product 64.

$^1$H NMR (CD$_3$OD): δ 8.1 (m, 1H); 7.85 (m, 1H); 7.6 (m, 1H); 7.5 (m, 2H); 7.37 (m, 1H); 7.23 (m, 2H); 6.95 (m, 2H); 6.86 (m, 1H); 4.07(m, 2H); 3.1-3.3 (m, 2H); 2.23 (m, 1H); 1.55 (m, 2H); 1.16 (m, 3H).

Method 22

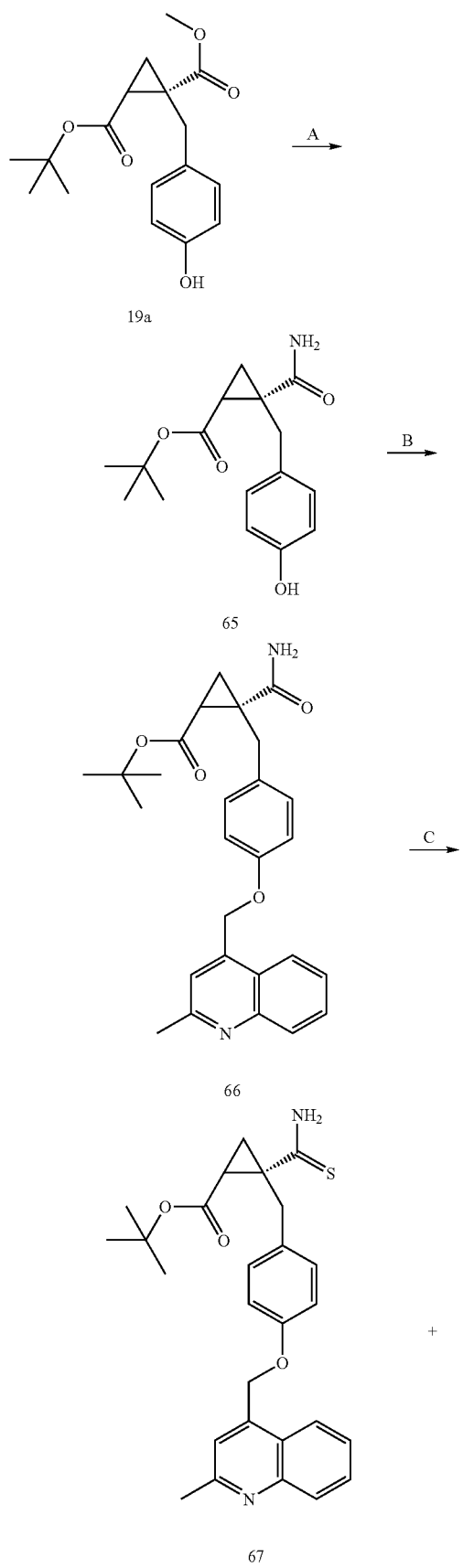

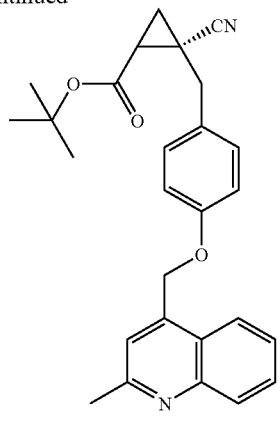

Synthesis of Compound 65

Compound 65 was synthesized from 19 following procedures similar to transformation from compound 9 to 11a (Method 3)

Synthesis of Compound 66

Compound 66 was synthesized from 65 following a procedure similar to transformation from compound 2 to 3 (Method 1) or 19a to 23 (Method 7).

Synthesis of Compound 67 and 68

Lawesson's reagent (250 mg, 0.62 mmol) was added to amide 66 (544 mg, 1.2 mmol) in toluene and the reaction was refluxed for an hour before another 0.5 equiv of Lawesson's reagent was added. The reaction was heated for one more hour and the mixture was diluted with DCM, washed with a saturated sodium bicarbonate (3×) and water (3×). The organic extract was dried over sodium sulfate and concentrated. The crude material was purified via flash chromatography eluting with a 0-2% 2N $NH_3/CH_3OH:CH_2Cl_2$ gradient affording a 1:4 ratio of thioamide 67 to nitrile 68.

Method 23

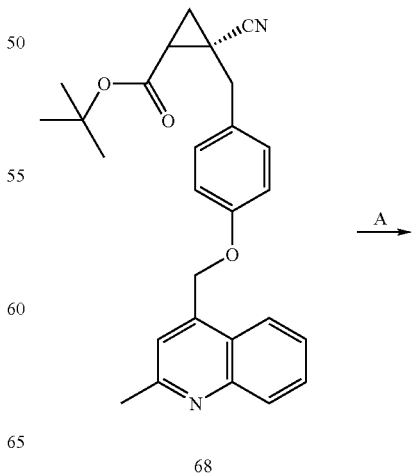

-continued

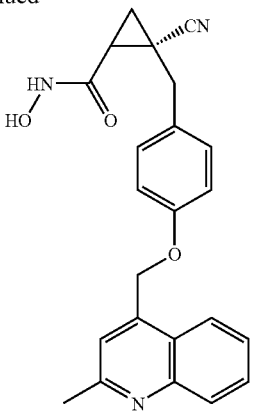

69

Synthesis of Compound 69

Compound 69 was synthesized from 68 following procedures similar to the transformation of 7 to 10 (Method 2).

$^1$H NMR (CD$_3$OD): δ 8.45 (m, 1H); 8.16 (m, 3H); 7.97 (m, 1H) 7.3 (m, 2H); 7.15 (m, 2H); 5.87 (s, 2H); 3.09 (s, 2H); 3.07 (s, 3H); 2.25 (m, 1H); 1.6 (m, 2H).

Method 24

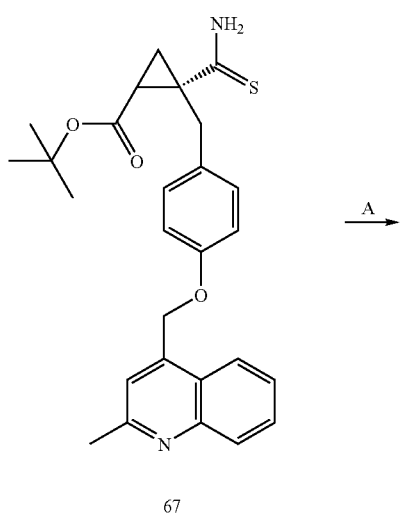

67

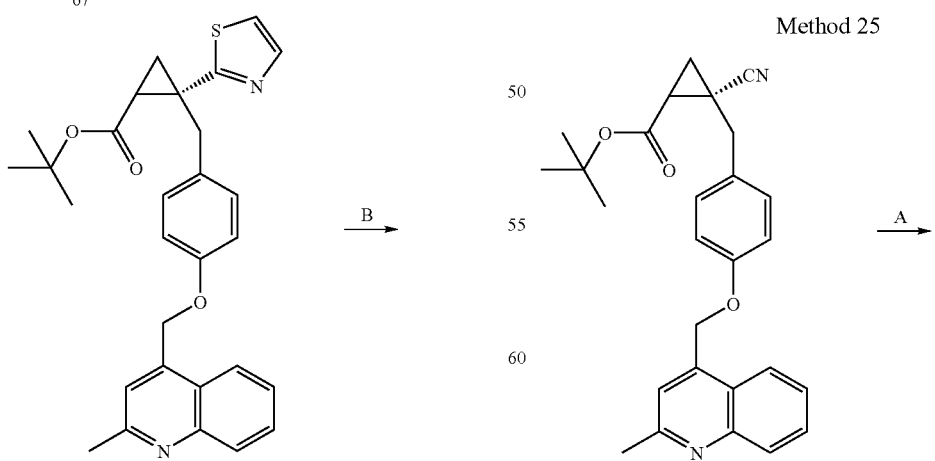

70

-continued

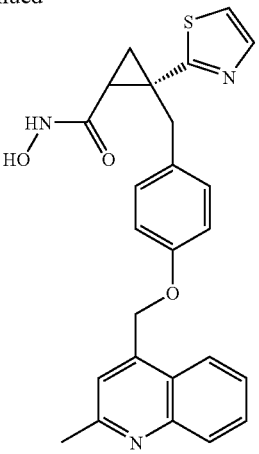

71

Synthesis of Compound 70

A 50% aq. chloroacetaldehyde solution (0.100 mL, 0.79 mmol) and potassium bicarbonate (80 mg, 0.8 mmol) was added to thioamide 67 (74 mg, 0.16 mmol) in tetrahydrofuran. The solution was stirred overnight at room-temperature. The reaction was concentrated and the residue was partitioned between DCM and water. The organic extracts were washed with water (3×), dried over sodium sulfate and concentrated. The crude material was dissolved in DCM (2 mL) with diisopropylethylamine (0.056 mL, 0.032 mL) and the solution was cooled to 0° C. before trifluoroacetic anhydride (0.040 mL, 0.03 mmol) was added. The reaction was stirred at room temperature for 1.5 hr before it was concentrated. The residue was dissolved in DCM, washed with a saturated bicarbonate (3×), and water (3×). The organic extracts were dried over sodium sulfate and concentrated. The crude material was purified via flash chromatography eluted with 0-3% 2N NH$_3$ in CH$_3$OH/CH$_2$Cl$_2$ gradient to afford 70.

Synthesis of Compound 71

Compound 71 was synthesized following procedures similar to the transformation of 7 to 10 (Method 2).

$^1$H NMR (CD$_3$OD): δ 8.45 (m, 1H); 8.10 (m, 2H); 8.08 (m, 1H); 7.97 (m, 1H) 7.58 (m, 1H); 7.36 (m, 1H); 7.14 (m, 2H); 7.01 (m, 2H); 5.80 (s, 2H); 3.3-3.5 (m,); 2.95 (s, 3H); 2.25 (m, 1H); 1.83 (m, 1H); 1.77 (m, 1H).

Method 25

69

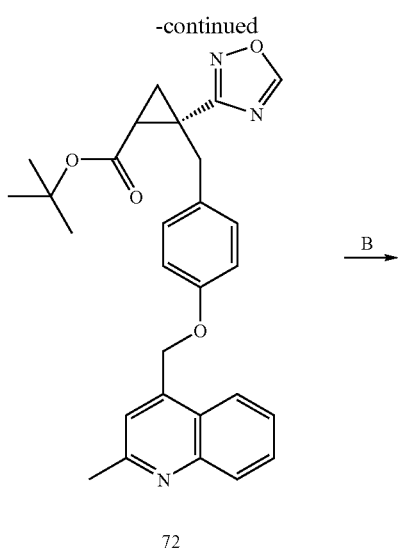

72

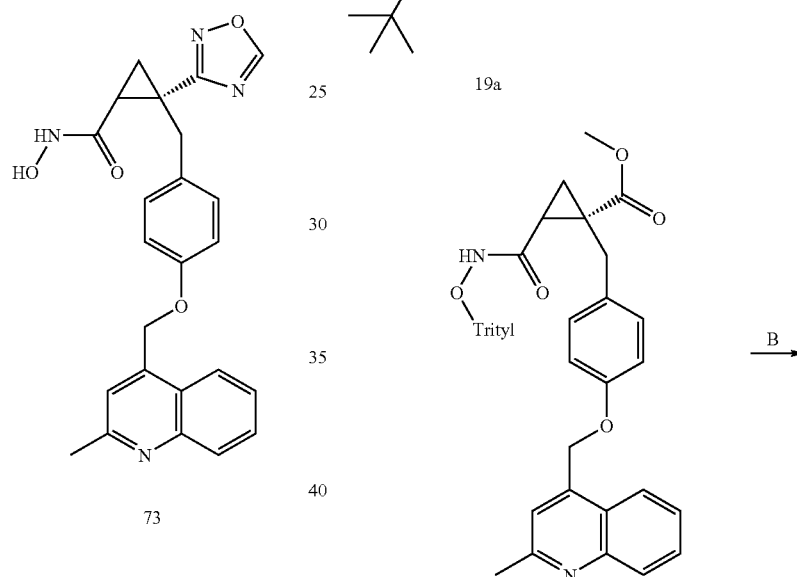

73

Synthesis of Compound 72

Hydroxylamine hydrochloride (186 mg, 2.7 mmol) and diisopropylethylamine (0.47 mL, 2.7 mmol) were combined in ethanol and agitated for 30 minutes before compound 69 (105 mg, 0.25 mmole) was added to the solution. The reaction was irradiated in a microwave for five minutes at 100° C. followed by addition of 10 eq of both hydroxylamine hydrochloride and diisopropylethylamine. The reaction was irradiated with a microwave for five additional minutes at 100° C. before the reaction was concentrated. The residue was dissolved in DCM and washed with a saturated aqueous solution of sodium bicarbonate (3×) and water (3×). The organic extracts were dried over sodium sulfate and concentrated to afford 113 mg of crude-material. Pyridinium-p-toluenesulfonate (63 mg, 0.25 mmol) and triethylorthoformate (1 mL, 6.0 mmol) were added to the above crude material in ethanol followed by irradiation in a microwave for 5 minutes at 100° C. The reaction was concentrated and the resulting oil was dissolved in DCM, washed with a sat sodium bicarbonate (3×) and water (3×). The organic extracts were dried over sodium sulfate and concentrated. The crude material was chromatographed with a silica gel column eluted with a 0-3% 2N $NH_3$ in $CH_3OH/CH_2Cl_2$ gradient to afford 72.

Synthesis of Compound 73

Compound 73 was synthesized from 72 following procedures similar to the transformation of 7 to 10 (Method 2).

$^1$H NMR (CD$_3$OD): δ 9.05 (s, 1H); 8.41 (m, 1H); 8.10 (m, 3H); 7.91 (m, 1H); 7.25 (m, 2H); 7.02 (m, 2H); 5.80 (s, 2H); 3.3-3.5 (m,); 2.95 (s, 3H); 2.25 (m, 1H); 1.75 (m, 1H); 1.64 (m, 1H).

Method 26

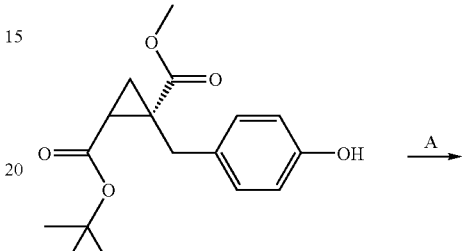

19a

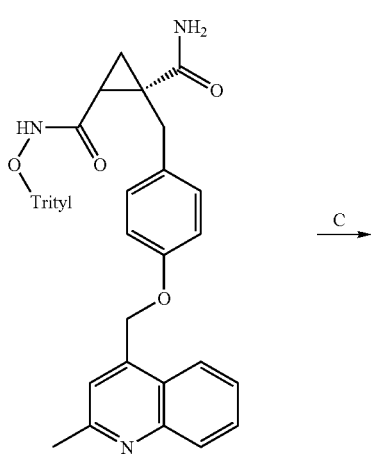

75

-continued

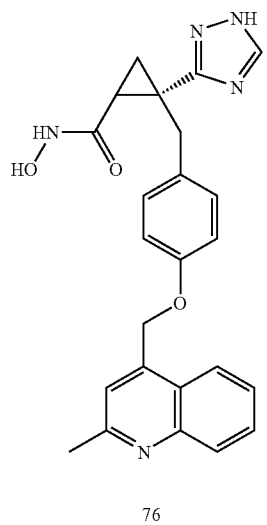

76

Synthesis of Compound 74

Compound 74 was synthesized from 19a following procedures similar to the transformation from 6b to 9 (Method 2).

Synthesis of Compound 75

Compound 75 was synthesized from 74 following procedures similar to the transformation from 9 to 11a (Method 3).

Synthesis of Compound 76

Amide 75 (10 mg) was dissolved in 1 mL of N,N'-dimethylforamide-dimethyl acetal and irradiated with a microwave at 100° C. for 5 minutes. After the solution was concentrated, the residue was dissolved in glacial acetic acid before hydrazine monohydrate was added. The reaction was irradiated again with a microwave for 100° C. for 5 minutes and the solution was concentrated. The final product mixture was purified via reverse phase HPLC eluting with a 0-95% $CH_3CN/H_2O$ gradient to give compound 76.

$^1$H NMR ($CD_3OD$): δ 8.35 (m, 1H); 8.7-8.17 (m, 4H); 7.91 (m, 1H); 7.10 (m, 2H); 6.98 (m, 2H); 5.76 (s, 2H); 3.3-3.5 (m,); 2.95 (s, 3H); 2.08 (m, 1H); 1.68 (m, 2H).

Method 27

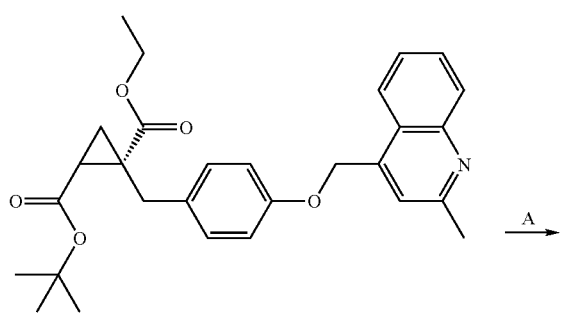

77

-continued

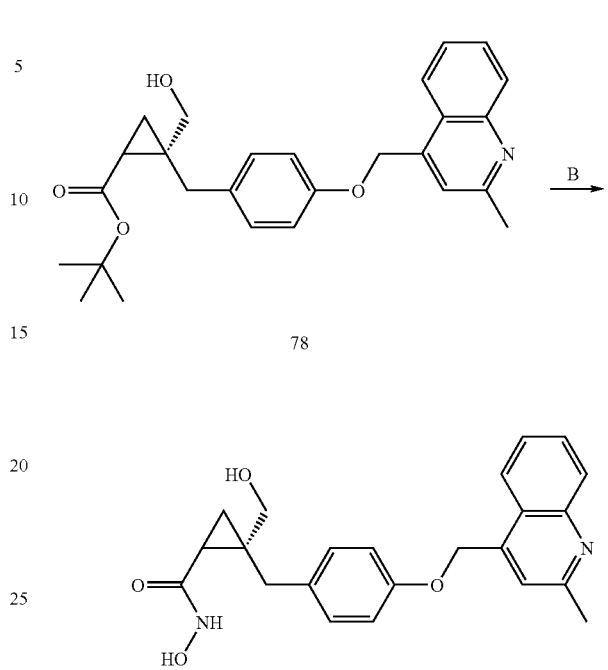

78

79

Synthesis of Compound 77

Compound 77 was synthesized from 28 following a procedure similar to transformation from compound 2 to 3 (Method 1) or 19 to 23 (Method 7).

Synthesis of Compound 78

Sodium borohydride (48 mg, 1.3 mmol) was added to a solution of 77 (60 mg, 0.13 mmol) in methanol under reflux. Additional amount of sodium borohydride was added until the starting material is completely consumed. After the reaction was concentrated, the residue was partitioned between DCM and water. The aqueous solution was extracted with DCM (3×) and the combined organic layers were washed with a sat. solution of $NaHCO_3$ (3×), $H_2O$ (3×), dried over sodium sulfate. After removal of solvent, the crude material was purified via flash chromatography eluted with ethyl acetate/hexane to afford 78.

Synthesis of Compound 79

Compound 78 was treated with 30% trifluoroacetic acid in DCM (1-2 mL) for 2.5 h followed by removal of solvent. The residue was treated with 2N $NH_3$ in methanol followed by removal of solvent. The residue was used for the synthesis of compound 79 following procedures similar to the transformation of 8 to 10 (Method 2).

$^1$H NMR ($CD_3OD$) of 79: δ 8.35 (m, 1H); 8.13 (m, 1H); 8.01 (m, 1H); 7.96 (s, 1H); 7.84 (m, 1H); 7.21 (m, 2H); 7.05 (m, 2H); 5.76 (s, 2H); 3.2-3.3 (m,); 2.93 (m, 5H); 1.54 (m, 1H); 1.29 (m, 1H); 0.96 (m, 1H).

Method 28

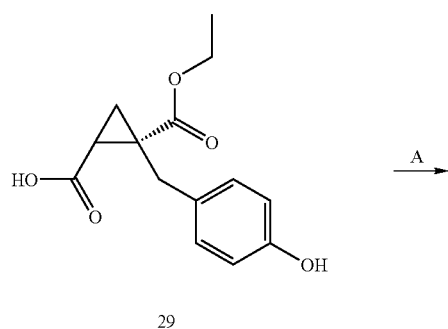

Synthesis of Compound 80 and 81

To a 2 mL solution of 0.264 g (1 mmol) of 29 was added N-chlorosuccinate (1.1 eq) and the solution was stirred for 2 h. After removal of solvent, the product mixture was purified via a C-18 reverse phase column eluted with 5-95% acetonitrile in water get pure 0.20 g of 80 and 0.05 g of 81.

Synthesis of Compound 82

Compound 82 was synthesized from 81 following a procedure similar to transformation from 29 to 30 (Method 9) and 30 to 33 (Method 10).

$^1$H NMR (CDCl$_3$): δ 8.10 (m, 1H); 7.85 (m, 1H); 7.70 (m, 1H); 7.54 (m, 1H); 7.26 (m, 2H); 6.98 (m, 1H); 6.71 (m, 1H); 5.41 (s, 2H); 4.1 (m, 2H); 3.14 (m, 2H); 2.73 (s, 3H); 2.23 (m, 1H); 1.65 (m, 1H); 1.56 (m, 1H); 1.16 (m, 3H).

Method 29

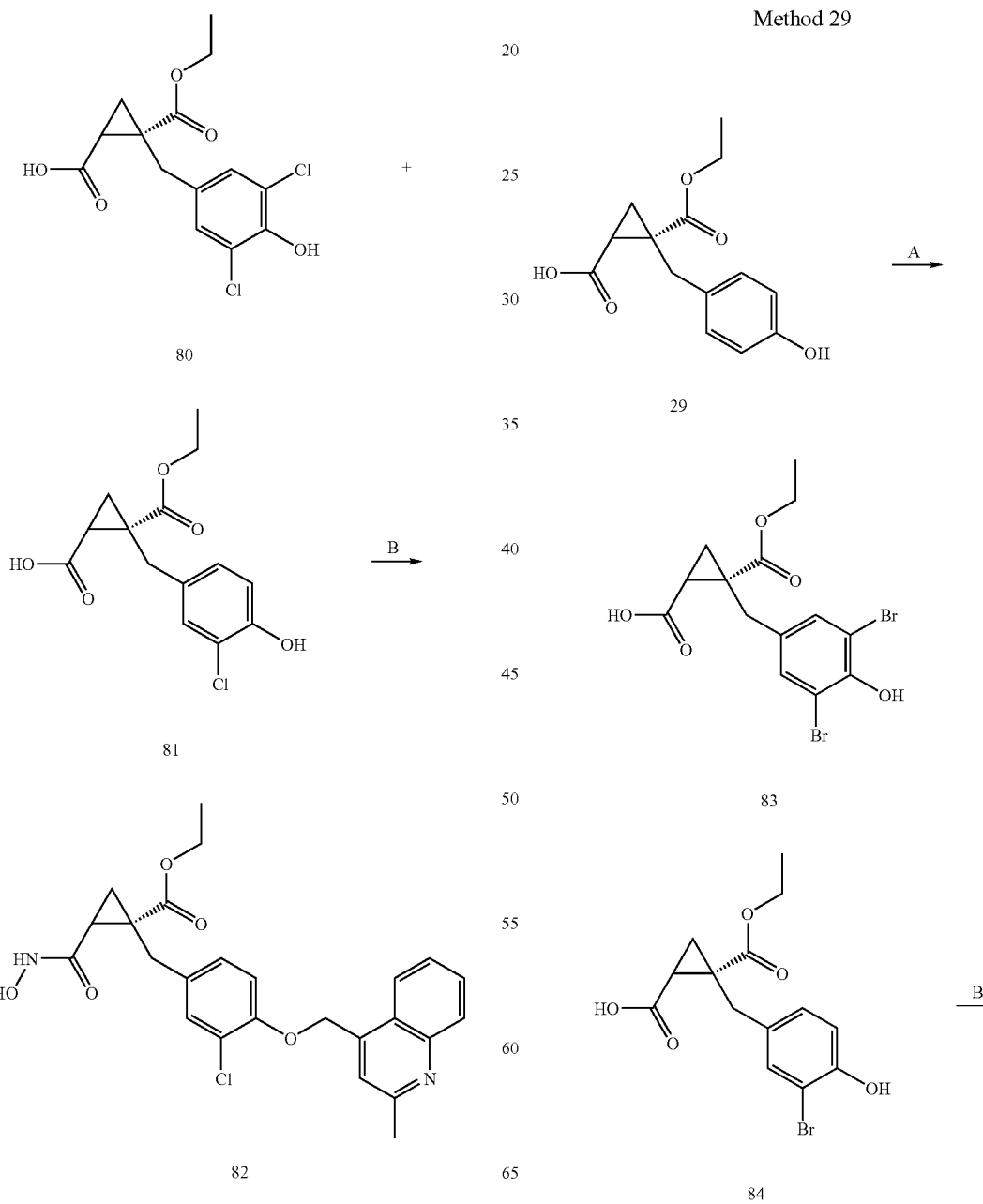

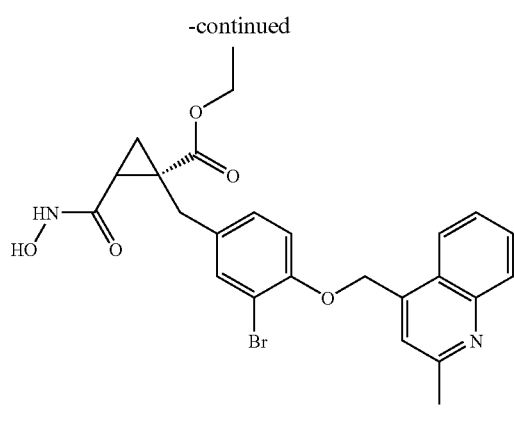

85

Synthesis of Compound 83 and 84

Compounds 83 and 84 were synthesized from 29 following procedures similar to transformation of 29 to 80 and 81 (Method 28).

Synthesis of Compound 85

Compound 85 was synthesized from 84 following a procedure similar to transformation from 29 to 30 (Method 9) and from 30 to 33 (Method 10).

$^1$H NMR (CD$_3$OD): δ 8.41 (m, 1H); 8.06-8.22 (m, 3H); 7.94 (m, 1H); 7.54 (m, 1H); 7.26 (m, 2H); 5.88 (s, 2H); 4.07 (m, 2H); 2.98-3.25 (m, 2H); 2.87 (s, 3H); 2.23 (m, 1H); 1.54 (m, 2H); 1.16 (m, 3H).

Method 30

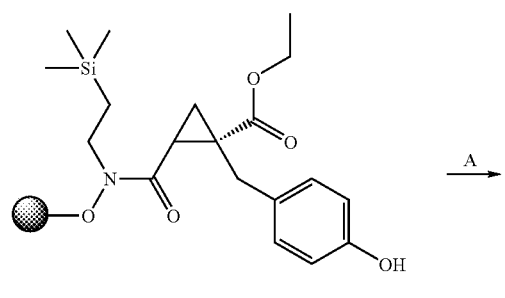

62

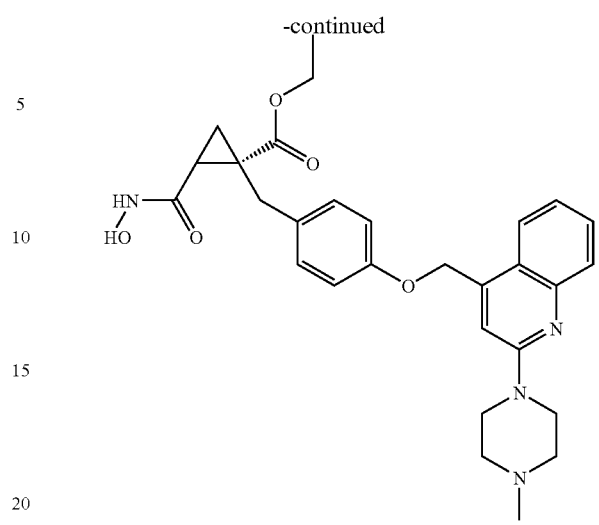

87

Synthesis of Compound 86

Compound 86 was synthesized following a procedure similar to the transformation of 62 to 63a (Method 20).

Synthesis of Compound 87

A mixture of resin 86 (0.070 g, ~0.7 mmol/g) and 1-methyl piperazine (0.5 mL) in toluene (1 mL) was agitated at 80° C. for 68 hours. The liquid was drained, and the resin was washed with an alternating cycle of CH$_2$Cl$_2$ (3×), THF (3×), and MeOH (3×). The resin was dried under vacuum for 10 minutes. The cartridge was charged with 75% TFA/CH$_2$Cl$_2$ and agitated at room temperature for 24 hours. The liquid was collected, and the resulting black resin was washed with CH$_2$Cl$_2$ (3×). The solvent was removed, and the residue was purified by reverse phase HPLC to provide 87.

$^1$H NMR (CD$_3$OD): δ 7.92-7.90 (m, 1H), 7.75-7.73 (m, 1H), 7.63-7.58 (m, 1H), 7.37-7.34 (m, 2H), 7.21-7.19 (m, 2H), 6.99-6.97 (m, 2H), 5.48 (s, 2H), 4.09-3.98 (m, 6H), 3.29-3.27 (m, 4H), 3.22-3.18 (m, 1H), 3.04-3.00 (m, 1H), 2.86 (s, 3H), 2.28-2.23 (m, 1H), 1.55-1.53 (m, 2H), 1.17-1.13 (m, 3H).

Method 31

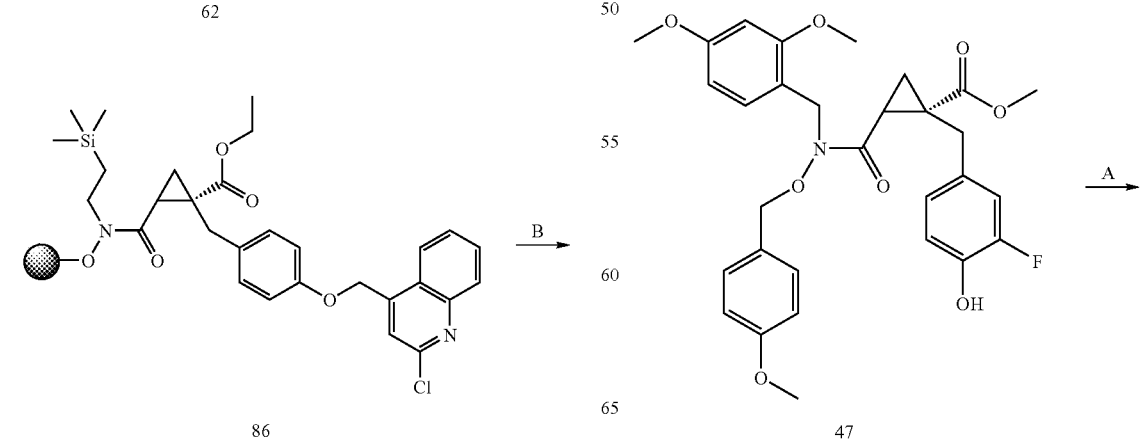

86    47

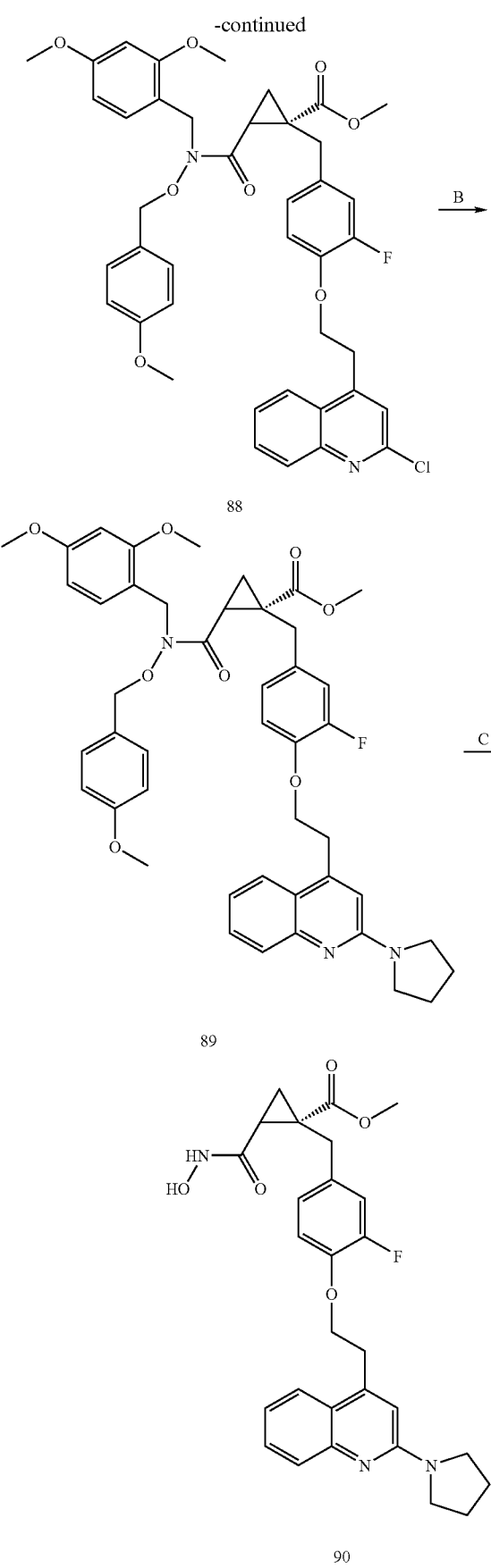

Synthesis of Compound 88
Compound 88 was prepared from 49 following a procedure similar to the transformation of 2 to 3 (Method 1).

Synthesis of Compound 89
A mixture of 88 and pyrrolidine in DME was irradiated in a microwave (100° C. for 25 minutes). The mixture was concentrated and purified by reverse phase HPLC to provide the product 89.

Synthesis of Compound 90
Compound 90 was prepared from 89 following a procedure similar to the transformation from 55 to 56 (Method 17).
$^1$H NMR (CD$_3$OD): δ 8.06-8.03 (m, 1H), 7.95-7.93 (m, 1H), 7.83-7.80 (m, 1H), 7.57-7.53 (m, 1H), 7.40-7.38 (m, 1H), 7.23-7.19 (m, 1H), 7.09-7.02 (m, 2H), 5.63 (s, 2H), 3.82-3.78 (m, 4H), 3.63 (s, 3H), 3.22-3.18 (m, 1H), 3.06-3.02 (m, 1H), 2.31-2.05 (m, 5H), 1.58-1.52 (m, 2H).

Method 32

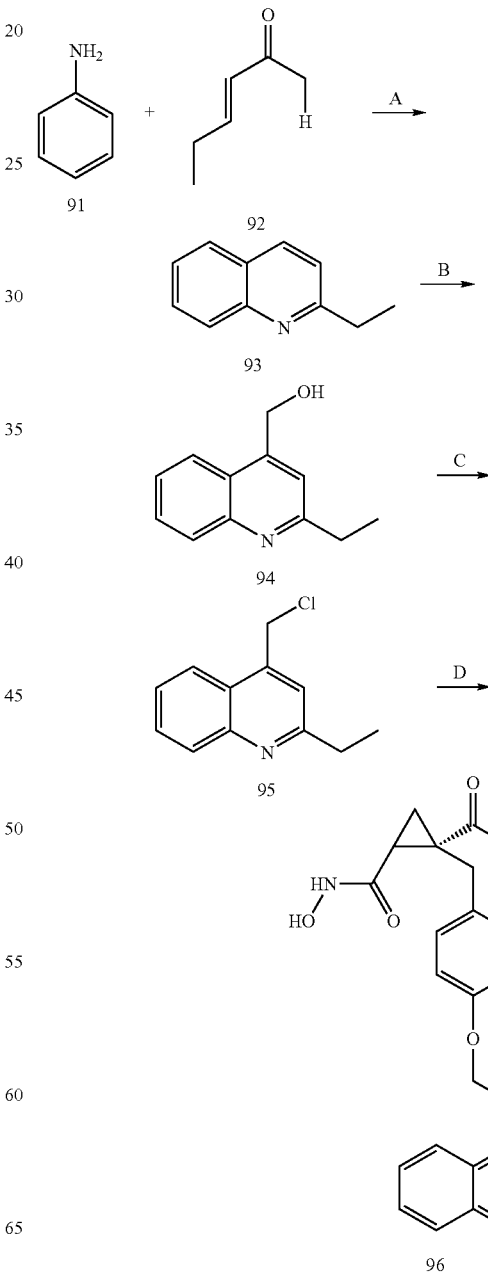

Synthesis of Compound 93

To a 250 mL round bottom flask containing aniline (1.8 mL, 20 mmol) was added concentrated HCl (5 mL) followed by chloranil (4.9 g 20 mmol) and n-BuOH. The mixture was heated to reflux and stirred vigorously at which time a solution of pentenal (2.4 mL, 24.5 mmol) in n-BuOH (2 mL) was added slowly over a 45 minute period. After the addition was complete, the mixture was refluxed for another 20 minutes and then cooled to room temperature. The mixture was diluted with ethyl acetate, and the organic layer was separated which was discarded. The aqueous phase was basicified with a saturated solution of $Na_2CO_3$ and extracted with ethyl acetate (3×). The collected organic layers were dried ($Na_2SO_4$), filtered, and concentrated. The brown oil was purified by flash chromatography to give compound 93.

Synthesis of Compound 94

To a solution of 93 (0.927, 5.9 mmol) in MeOH (12 mL) and $H_2O$ (6 ml) was added concentrated $H_2SO_4$ (0.300 mL) followed by iron powder (0.100 g, 1.8 mmol). The reaction was evacuated and flash with nitrogen (3×) and then cooled to 0° C. Hydroxylamine-O-sulfonic acid (2.0 g, 17.7 mmol) was added and the resulting mixture was stirred at 0° C. for 15 minutes and at room temperature for 5 hours. The mixture was basicified with a saturated $Na_2CO_3$ solution and diluted with $CH_2Cl_2$. The organic layer was removed, and the aqueous layer was extracted with $CH_2Cl_2$ (4×). The combined organic layers were dried ($Na_2SO_4$), filtered, and concentrated. The residue was purified by flash chromatography to give compound 94.

Synthesis of Compound 95

Compound 95 was synthesized from 94 following a procedure similar to the transformation of 53 to 54 (Method 16).

Synthesis of Compound 96

Compound 96 was synthesized from 95 following a procedure similar to the transformation of 47 to 57 (Method 18).

H NMR (CD$_3$OD): δ 8.10 (m, 1H), 8.03 (m, 1H), 7.79 (m, 1H), 7.67: (s, 1H), 7.63 (m, 1H), 7.12 (m, 1H), 7.05 (m, 1H), 6.98 (m, 1H); 5.63 (s, 2H), 3.57 (s, 3H), 3.0-3.2 (m, 2H), 3.0 (m, 2H), 2.26 (m, 1H); 1.52 (m, 2H); 1.35 (m, 3H).

Method 33

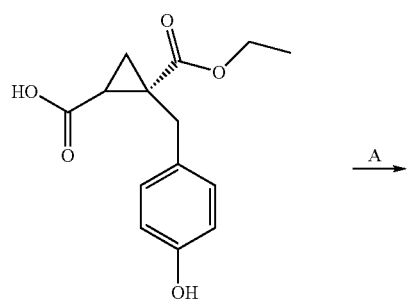

29a

A →

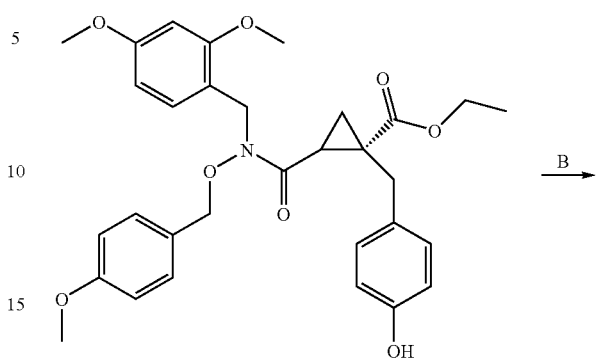

97

B →

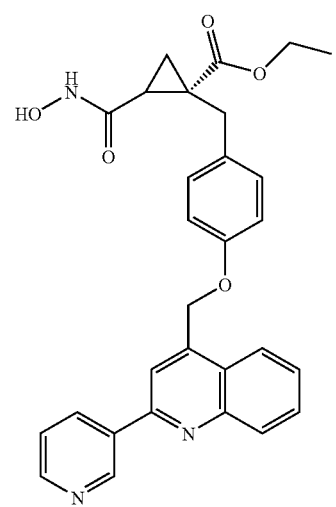

98

Synthesis of Compound 97

Compound 97 was synthesized from 29a following procedures similar to the transformation of 43 to 47 (Method 13) and 47 to 57 (Method 18).

Synthesis of Compound 98

Compound 98 was synthesized from 97 following procedures similar to the transformation of 50 to 56 (Method 17).

$^1$H NMR (CD$_3$OD): δ 9.48 (s, 1H); 9.07 (m, 1H); 8.80 (m, 1H); 8.30 (s, 1H), 8.21 (m, 2H), 7.98 (m, 1H), 7.87 (s, 1H), 7.73 (m, 1H), 7.22 (m, 2H), 7.04 (m, 2H), 5.70 (s, 2H), 4.04 (m, 2H), 2.95-3.22 (m, 2H), 2.24 (m, 1H), 1.51 (m, 2H); 1.12 (m, 3H).

Method 34

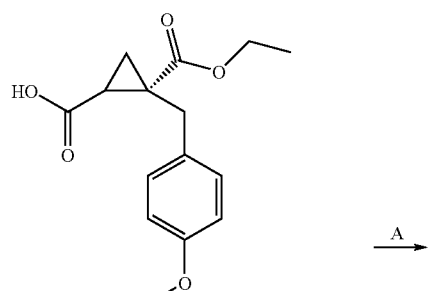

99

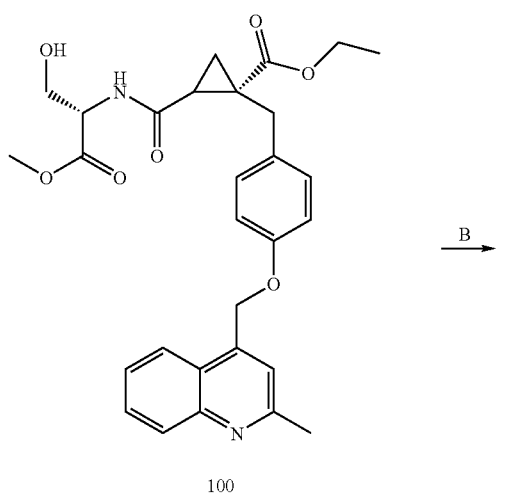

100

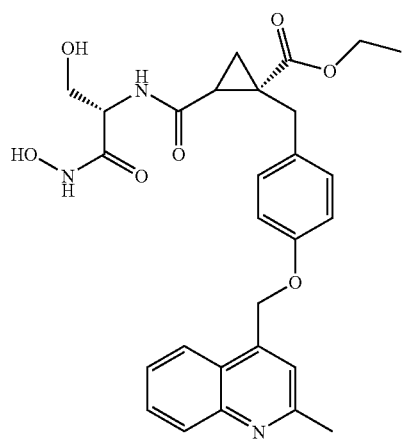

101

Synthesis of Compound 99

Compound 99 was synthesized from 30 following procedures similar to the transformation from 30 to 32 (Method 10).

Synthesis of Compound 100

Compound 99 (0.07 g, 0.17 mmol), (L)-serine methyl ester (26 mg, 0.17 mmol), and N-methyl morpholine (51 mg, 0.5 mmol) were dissolved in DMF. After addition of EDCl (48 mg, 0.25 mmol), the reaction mixture was stirred overnight at rt. The reaction mixture was diluted with EtOAc, washed with water, and concentrated. The crude product was purified via silica gel chromatography using a 2:1 EtOAc: Hexanes mobile phase to give 58 mg of compound 100.

Synthesis of Compound 101

Compound 101 was synthesized from 100 following a procedure similar to the transformation of 50a to compound 51 b (Method 15).

$^1$H NMR (300 MHz, CD$_3$OD): δ 8.08 (m, 1H), 7.98 (m, 1H), 7.74 (m, 1H), 7.57 (m, 2H), 7.18 (m, 2H), 6.95 (m, 2H), 5.54 (s, 2H), 4.4 (m, 1H), 4.04 (m, 2H); 3.72 (m, 2H); 2.94-3.22 (m, 2H), 2.70 (s, 3H); 2.51 (m, 1H), 1.52 (m, 2H), 1.14 (m, 3H).

Method 35

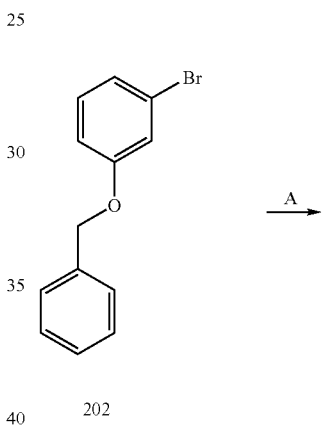

202

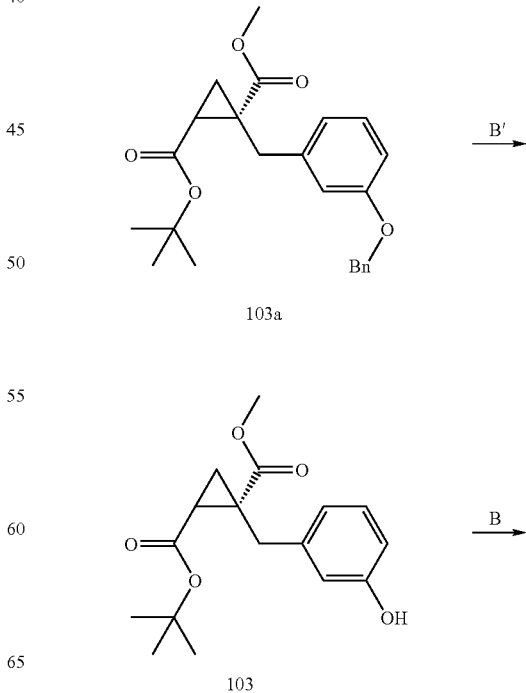

103a


103

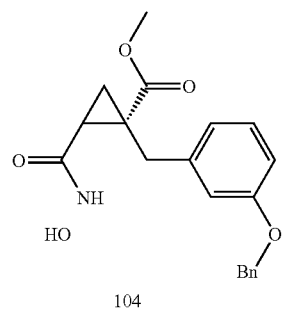
104
Synthesis of Compound 103
Compound 103 was synthesized from compound 102 following procedures similar to the transformation from 16 to 19 (Method 5).
Synthesis of Compound 104
Compound 104 was synthesized from 103 following procedures similar to the transformation from 6 to 10 (Method 2).
$^1$H NMR (CD$_3$CN): δ 7.41-7.61 (m, 55H), 7.25 (m, 1H), 6.92 (m, 3H), 5.17 (s, 2H), 3.67 (s, 3H), 3.08-3.33 (m, 2H), 2.35 (m, 1H), 1.64 (m, 1H); 1.56 (m, 1H).
Method 36
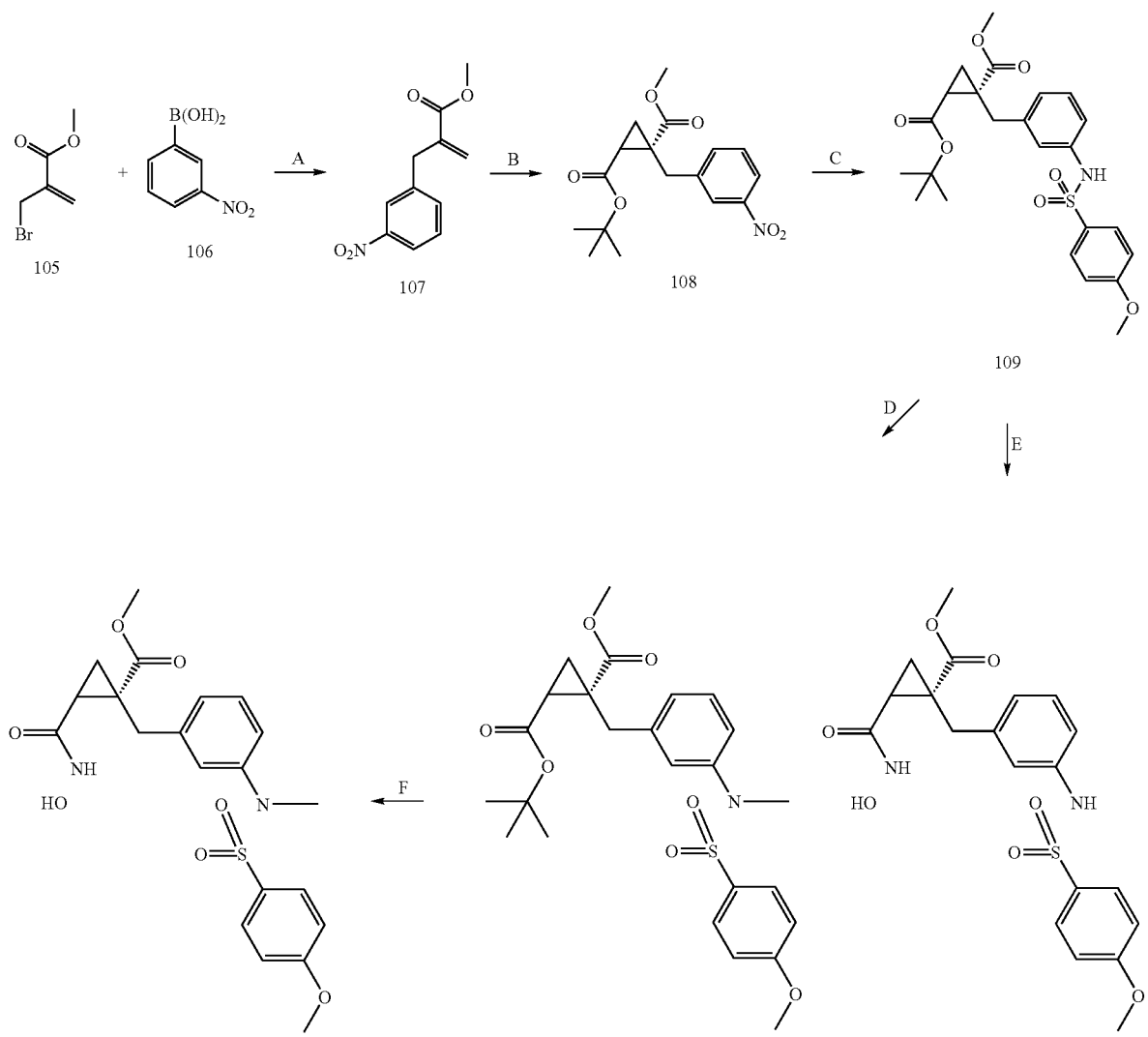

Synthesis of Compound 107

To a solution of methyl 2-(bromomethyl)acrylate 105 (2.0 mL, 16.6 mmol) and m-nitrophenylboronic acid 106 (3.0 g, 17.9 mmol) in toluene (150 mL) was added Pd(dppf)Cl$_2$.CHCl$_3$ (0.978 g, 1.34 mmol) and aqueous 3N K$_2$CO$_3$ (16 mL). The mixture was heated to reflux and stirred for 1 hour. The solution was cooled to room temperature and diluted with 1N NaOH (150 mL) and EtOAc (150 mL). The aqueous layer was removed, and the organic phase was washed with 1N Synthesis of Compound 110

Compound 110 was synthesized from 109 following procedures similar to the transformation of 7 to 10 (Method 2).

$^1$H NMR (CDCl$_3$) of 110: δ 7.67 (m, 2H), 7.09-6.97 (m, 3H), 6.88 (m, 2H), 6.72 (m, 1H), 3.81 (s, 3H), 3.62 (s, 3H), 3.34 (m, 1H), 3.02 (m, 1H), 2.41-2.37 (m, 1H), 1.65-1.62 (m, 1H), 1.55-1.52 (m, 1H).

Method 37

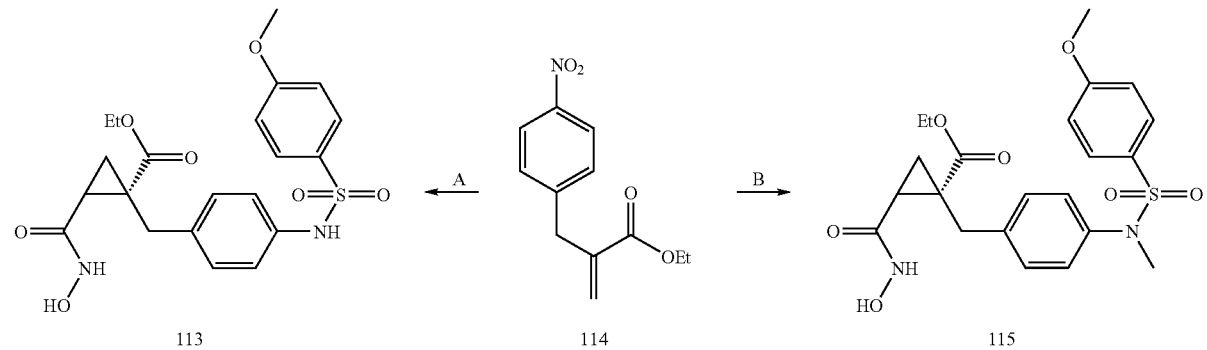

113        114        115

NaOH (2×). The organic phase was dried (Na$_2$CO$_3$), filtered, and concentrated. The mixture was purified by flash chromatography to furnish compound 107 (0.880 g).

Synthesis of Compound 108

Compound 108 was synthesized from 107 following a procedure similar to the transformation of 4 to 5 (Method 1).

Synthesis of Compound 109

A mixture of Compound 108 (0.450 g, 1.34 mmol) and 10% Pd/C (0.120 g) in MeOH was stirred at room temperature under an atmosphere of H$_2$ for 1.5 hours. The mixture was filtered through a pad of silica and concentrated to give the aniline, which was used for next step without purification.

To a solution of crude aniline (prepared above) and pyridine (0.230 mL, 2.84 mmol) in CH$_2$Cl$_2$ (20 mL) was added p-methoxyphenyl sulfonylchloride (0.284 g, 1.37 mmol). The mixture was stirred for 2 hours and then concentrated. The oil was purified by flash chromatography to provide compound 109 (0.541 g) as foam.

Synthesis of Compound 111

To a solution of Compound 109 (0.147 g, 0.31 mmol) and K$_2$CO$_3$ (0.135 g, 0.98 mmol) in DMF (0.700 mL) was added MeI (0.021 mL, 0.34 mmol). The reaction was stirred for 1.5 hours under nitrogen, quenched with H$_2$O, and diluted with EtOAc. The organic layer was separated, and the aqueous phase was extracted with EtOAc (3×). The combined organics were washed with H$_2$O (2×), dried (Na$_2$SO$_4$), filtered, and concentrated to provide compound 111 (0.141 mg).

Synthesis of Compound 112

Compound 112 was synthesized from 111 following procedures similar to the transformation of 7 to 10 (Method 2).

$^1$H NMR (CDCl$_3$): δ 7.50 (m, 2H), 7.14-7.17 (m, 3H), 6.92 (m, 2H), 6.57 (m, 1H), 3.86 (s, 3H), 3.73 (m, 1H), 3.70 (s, 3H), 3.10 (s, 3H), 3.01-2.97 (m, 1H), 1.71-1.59 (m, 2H), 1.27-1.24 (m, 1H).

Synthesis of Compound 113

Compound 113 was synthesized from 114 following procedures similar to the transformation of 107 to 110 (Method 36).

$^1$H NMR (CD$_3$OD): δ 7.65-7.63 (m, 2H), 7.10-7.08 (m, 2H), 6.97-6.94 (m, 4H), 4.03-3.98 (m, 2H), 3.82 (s, 3H), 3.16-3.12 (m, 1H), 3.02-2.98 (m, 1H), 2.27-2.24 (m, 1H), 1.53-1.50 (m, 2H), 1.08-1.05 (m, 3H).

Synthesis of Compound 115

Compound 115 was synthesized from 114 following procedures similar to the transformation of 107 to 112 (Method 36).

$^1$H NMR (CD$_3$OD): δ 7.45-7.42 (m, 2H), 7.20-7.18 (m, 2H), 7.02-6.96 (m, 4H), 4.09-4.04 (m, 2H), 3.87 (s, 3H), 3.23-3.20 (m, 1H), 3.13-3.10 (m, 1H), 3.12 (s, 3H), 2.32-2.28 (m, 1H), 1.57-1.54 (m, 2H), 1.14 (m, 3H).

Method 38

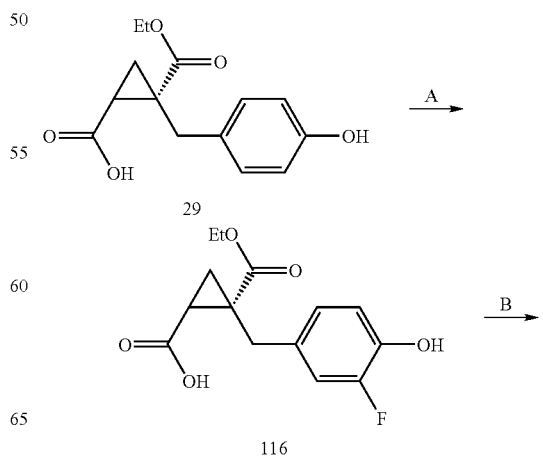

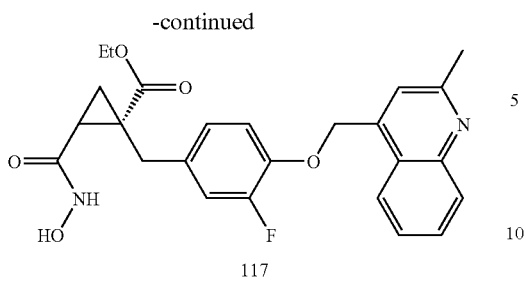

117

Synthesis of Compound 116

To a TFA solution of 219 mg (1.09 mmol) compound 29 was added 2 eq of Selectfluor and the solution was stirred overnight. After evaporation of solvent, the residue was chromatographed on a C-18 reverse phase column to give 24 mg of compound 116.

Synthesis of Compound 117

Compound 117 was synthesized from 116 following procedures similar to the transformation of 29 to 30 (Method 9) and then 30 to 33 (Method 10).

$^1$H NMR (CD$_3$OD): δ 8.19 (m, 1H), 8.05 (m, 1H), 7.87 (m, 1H), 7.75 (s, 1H); 7.70 (m, 1H); 7.15 (m, 1H); 7.06 (m, 1H); 7.00 (m, 1H); 5.70 (s, 2H), 4.06 (m, 2H), 3.02-3.21 (m, 2H), 2.79 (s, 3H), 2.26 (m, 1H), 1.53 (m, 2H), 1.14 (m, 3H)

Method 39

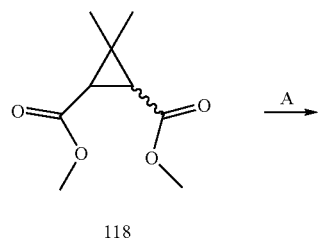

118

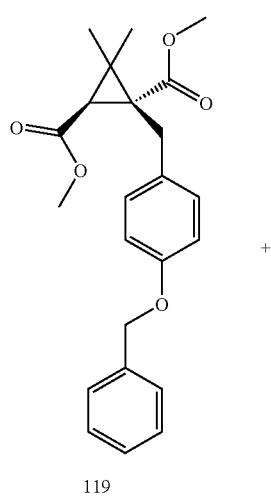

119

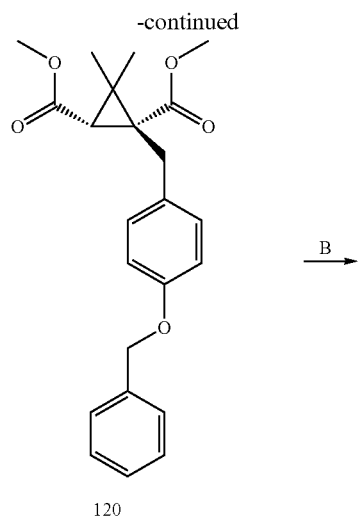

120

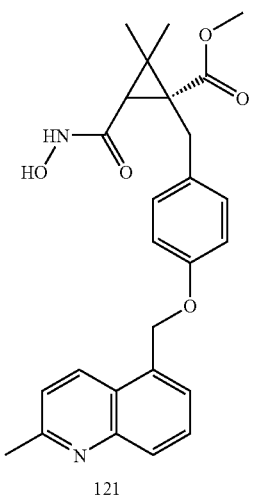

121

Synthesis of Compounds 119 and 120

To a solution of 118 (0.63 g, 3.30 mmol) in 8 mL of anhyd. THF at −78° C. was added 1.8 mL of 2 M LDA in THF, and the reaction mixture was stirred at −78° C. for 1 h. A solution of 4-benzyloxybenzylbromide (0.94 g, 3.39 mmol) in 2 mL of anhyd. THF was added via addition funnel. The reaction mixture was stirred and allowed to warm to 23° C. overnight. The reaction was quenched with 5 mL of saturated NH$_4$Cl and extract with 20 mL of diethyl ether. The organic solution was washed with 5 mL of brine, dried (MgSO$_4$), filtered, and concentrated in vacuo. Purification by flash silica gel chromatography gave 0.11 g (9%) of compound 119 and 0.40 g (31%) of compound 120.

Synthesis of Compound 121

Compound 121 was synthesized from 119 following procedures similar to the transformations of 18 to 19 (Method 5) and 30 to 33 (Method 10).

$^1$H NMR (DMSO): 610.74 (s, 1H), 8.79 (s, 1H), 8.07(m, 1H), 7.95 (m, 1H), 7.59-7.74 (m, 1H), 7.53-7.58 (m, 1H), 7.51 (s, 1H), 7.05 (m, 2H), 6.96 (m, 2H), 5.53 (s, 2H), 3.63 (m, 1H), 3.46 (s, 3H), 3.05 (m, 1H), 2.63 (s, 3H), 1.97 (s, 1H), 1.34 (s, 3H), 1.03 (s, 3H).

Method 40

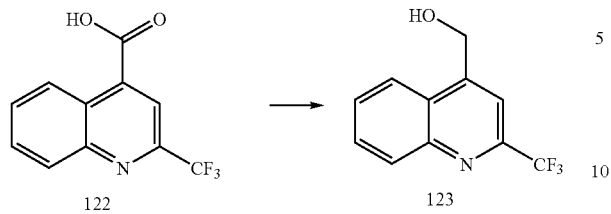

Synthesis of Compounds 122 and 123

Compound 122 was prepared from isatin according to the procedure described by H. W. Tsao, U.S. Pat. No. 4,267,33; May 12, 1981. The acid was reduced to the alcohol using cyanuric fluoride and sodium borohydride according to the procedure in G. Kokotos and C. Noula *J. Org. Chem.* 1996, 61, 6994-6996.

Method 41

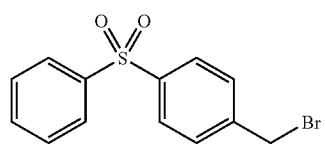

124

Compound 124 was prepared according to the procedure in A. G. Taveras et al US Patent 2002 US 632,747.

Method 42

125

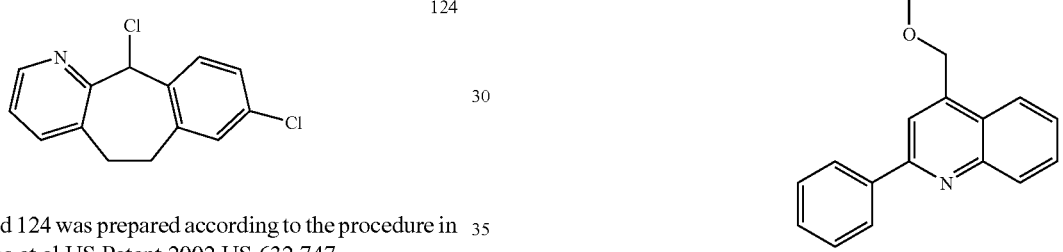

Compound 125 was prepared according to a procedure similar to the one described by F. J. Lotspeich *J. Org. Chem.* 1967, 32, 1274-1277.

Method 42

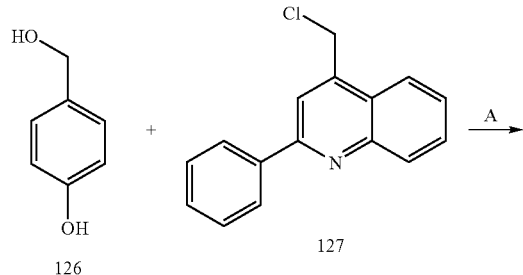

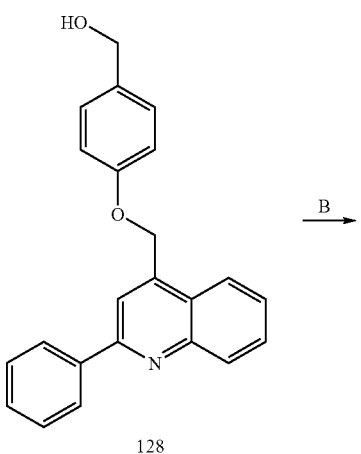

128

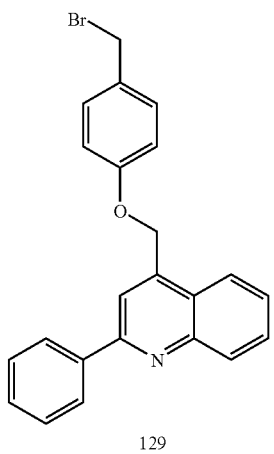

129

Synthesis of Compound 128

Compound 128 was synthesized from 127 following a procedure similar to the transformation of 19a to 23.

Synthesis of Compound 129

A solution of compound 128 (4.0 g, 11.73 mmol) in anhyd CH$_2$Cl$_2$ (60 mL) was cooled to 0° C. with a ice-water bath before PBr$_3$ (1.1 mL, 11.73 mmol, in 5 mL anhyd CH$_2$Cl$_2$) was added. The solution was stirred at 0° C. for 4 hours and at rt for 12 hours before it was poured into a cold saturated aq NaHCO$_3$ (250 mL) with stirring. The aq layer was extracted with CH$_2$Cl$_2$ (4×). The combined organic layers were washed with brine (100 mL), dried over anhyd Na$_2$SO$_4$, and concentrated. The residue was dried under vacuum for 4 hours to give compound 129 (4.3 g, 91%).

Method 43

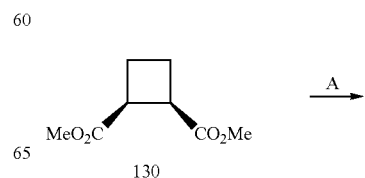

130

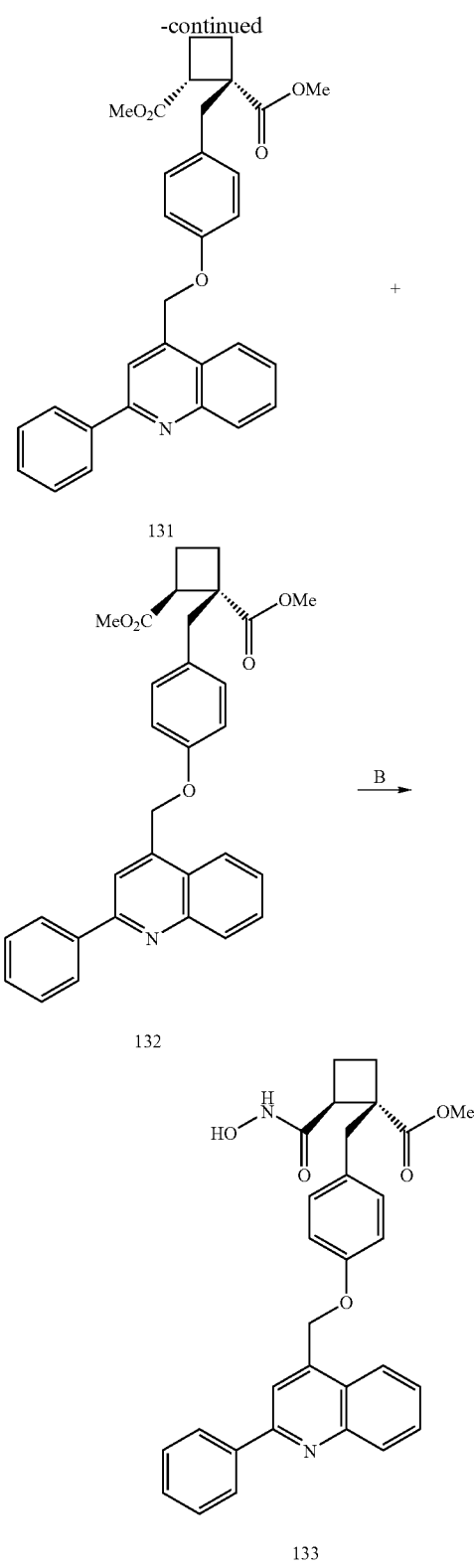

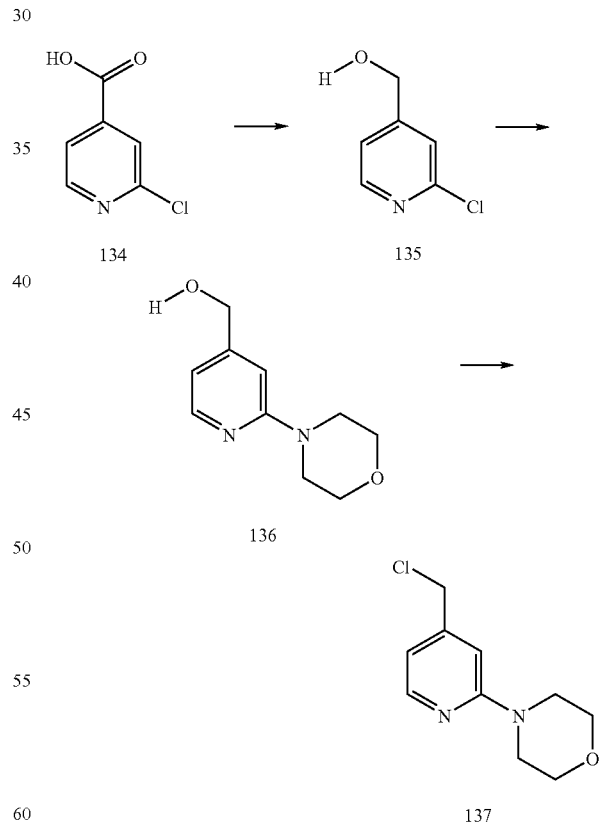

Synthesis of Compound 131 and 132

To a 100 mL round bottom flask was added diisopropyl amine (1.0 mL, 7.16 mmol) and anhyd THF (10 mL). The solution was cooled to −40° C. before n-BuLi (1.45 M, 4.5 mL, 6.52 mmol) was added dropwise via a syringe. The solution was gradually warmed up to −20° C. in 20 minutes before it was cooled to −78° C. The above solution was added to a solution of cis-dimethyl 1,2-cyclobutane diester 130 (1.02 g, 5.92 mmol) in anhyd THF (10 mL) at −78° C. via a cannula. The solution was stirred at −78° C. for an hour followed by addition of compound 129 (1.9 g, 4.74 mmol) in anhyd THF (5 mL). The solution was stirred at −78° C. for 4 h, and allowed to gradually warmed up to room temperature overnight before sat aq NH$_4$Cl (50 mL) was added. The aq layer was extracted with EtOAc (3×) and the combined organic layers were dried over anhyd Na$_2$SO$_4$, and concentrated. The residue was chromatographed to give compounds 131 and 132 (110 mg).

Synthesis of Compound 133

Compound 133 was synthesized from 132 following a procedure similar to the transformation of 50a to 51 b (Method 15).

$^1$H-NMR (CD$_3$OD, 300 MHz): δ 8.16 (m, 2H), 8.08 (m, 3H), 7.81 (m, 1H), 7.65 (m, 1H), 7.58-7.50 (m, 3H), 7.06 (m, 2H), 7.01 (m, 2H), 5.66 (s, 2H), 3.63 (s, 3H), 3.18 (m, 1H), 3.11 (m, 1H), 3.05 (m, 1H), 2.37 (m, 2H), 2.13 (m, 1H), 1.94 (m, 1H).

Method 44

Synthesis of Compound 135

Compound 135 was synthesized from 134 following a procedure similar to the transformation of 51 to 53 (Method 16).

Synthesis of Compound 136

Compound 135 (1.45 g/10.1 mmol) was dissolved in 20 mL of toluene and morpholine (8.6 mL) was added. The reaction mixture was stirred under N₂ at 110 C over the weekend then concentrated to give 8.2 g of a yellow oil which was purified to give compound 136.

Synthesis of Compound 137

Compound 137 was synthesized from 136 following a procedure similar to the transformation of 53 to 54 (Method 16).

Table 1 below provides preferred compounds of the present invention and associated LCMS and/or HNMR data.

TABLE 1

| | Structures | Rt (min) | M + 1 (Obs) | 1H NMR | Method |
|---|---|---|---|---|---|
| A | 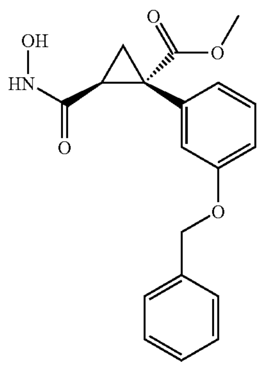 | 4.56 | 342 | 1H NMR (CD3CN): d 7.6-7.4 (m, 5H); 7.3 (m, 1H); 6.95 (m, 3H); 5.2 (m, 2H); 3.7 (s, 3H); 2.6 (m, 1H); 2.05 (m, 1H); 1.85 (m, 1H). | 2 |
| B | 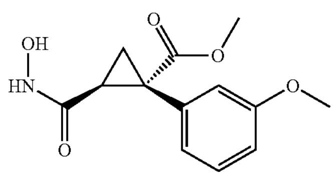 | 2.91 | 266 | 1H NMR (CD3CN): d 7.35 (m, 1H); 6.95 (m, 3H); 3.9 (s, 3H); 3.71 (s, 3H); 2.6 (m, 1H); 2.05 (m, 1H); 1.85 (m, 1H). | 2 |
| C | 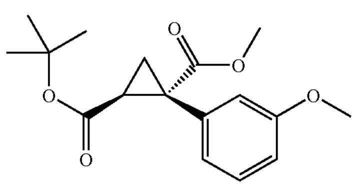 | | 307 | | 2A |
| D | 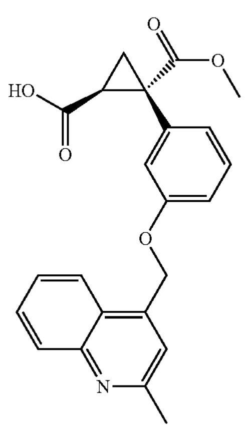 | | 392 | | 2AB |

TABLE 1-continued

| | | | | |
|---|---|---|---|---|
| E | *(structure: 1-(3-benzyloxyphenyl)-N'-hydroxycyclopropane-1,2-dicarboxamide)* | 3.46  327 | 1H NMR (CD3CN): d 7.6-7.35 (m, 5H); 7.4 (m, 1H); 7.05 (m, 3H); 6.4 (br s, 1H); 5.85 (br s, 1H); 5.2 (m, 2H); 2.6 (m, 1H); 1.9 (m, 1H); 1.75 (m, 1H). | 3 |
| F | *(structure: 1-(3-methoxyphenyl)-N'-hydroxycyclopropane-1,2-dicarboxamide)* | 2.05  251 | 1H NMR (CD3CN): d 7.4 (m, 1H); 7.02 (m, 3H); 6.1 (br s, 1H); 5.75 (br s, 1H); 3.9 (s, 3H); 2.6 (m, 1H), 1.9 (m, 1H); 1.75 (m, 1H). | 2ABC; 3 |
| G | *(structure: 1-(4-benzyloxyphenyl)-N'-tert-butoxycyclopropane-1,2-dicarboxamide)* | 383 | | 4A'; 2BC; 3AB |
| H | *(structure: ethyl 1-(4-benzyloxyphenyl)-2-(tert-butoxycarbonyl)cyclopropane-1-carboxylate)* | 5.56  397 | | 4A' |

TABLE 1-continued

| | Structure | | | | |
|---|---|---|---|---|---|
| I | (structure) | 4.31 | 384 | | 4A'; 3A |
| J | (structure) | | 412 | 1H NMR (CDCl3): d 7.3-7.5(m, 5H); 7.20 (m, 2H); 6.9 (m, 2H); 5.0 (s, 2H); 4.1 (m, 2H); 3.15 (m, 0.3H); 2.5 (m, 0.5 H); 2.05 (m, 1H); 1.7-1.9 (m, 1.2 H); 1.3 (br. s, 3 H) 1.2 (m, 3H); 1.1 (br. s, 6 H) | 4A' |
| K | (structure) | 4.66 | 341 | | 4A'; 2B |
| L | (structure) | | 411 | | 5AB |

TABLE 1-continued

| | | | |
|---|---|---|---|
| M | (structure) | 4.26  395 | 6 |
| N | (structure) | 3.86  355 | 6 |
| O | (structure) | 2.45  496 | 7A; 6 |
| P | (structure) | 1.95  497 | 7A; 6 |

TABLE 1-continued
| Q | 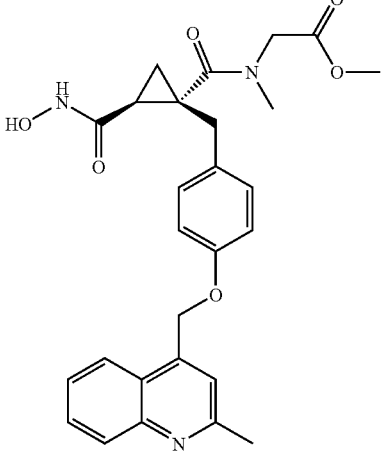 | 3.64 | 492 | 7A; 6 |
| R | 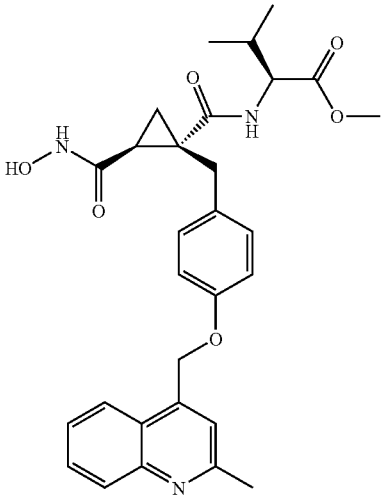 | 3.98 | 520 | 7A; 6 |
| S | 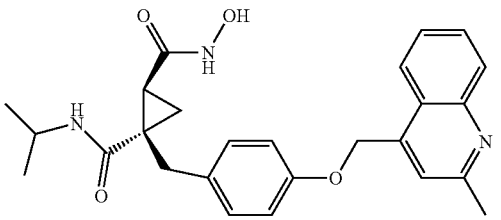 | 2.25 | 448 | 7A; 6 |
| T | 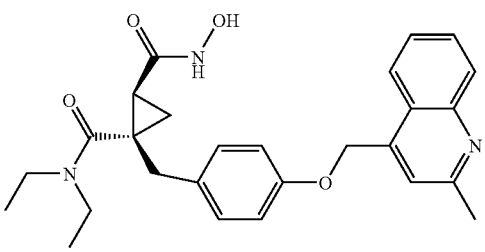 | 3.88 | 462 | 7A; 6 |

TABLE 1-continued

| | | | |
|---|---|---|---|
| U | [structure] | 3.68 448 | 7A; 6 |
| V | [structure] | 2 420 | 7A; 6 |
| W | [structure] | 3.84 462 | 7A; 6 |
| X | [structure] | 2.6 510 | 7A; 6 |
| Y | [structure] | 1.95 497 | 7A; 6 |
| Z | [structure] | 3.84 462 | 7A; 6 |

TABLE 1-continued

| | | | |
|---|---|---|---|
| AA | | 3.95 474 | 7A; 6 |
| AB | | 4.11 510 | 7A; 6 |
| AC | | 4.32 524 | 7A; 6 |
| AD | | 2.5 488 | 7A; 6 |
| AE | | 2.35 489 | 7A; 6 |
| AF | | 4.08 482 | 7A; 6 |

TABLE 1-continued
| | | | | | |
|---|---|---|---|---|---|
| AG | 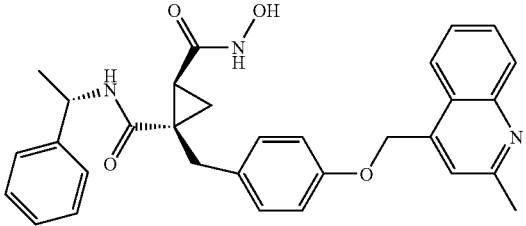 | 2.55 | 510 | | 7A; 6 |
| AH | 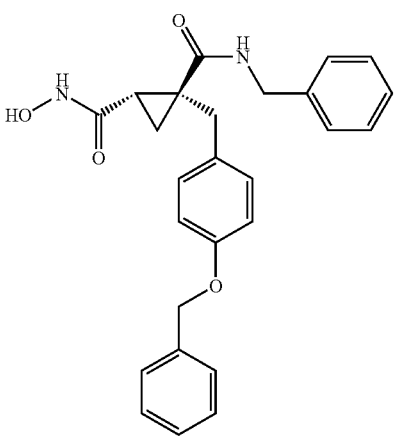 | 4.41 | 431 | 1H NMR (CD3CN/D2O, 2:1): d 7.29-7.44 (m, 6H), 7.14–7.07 (m, 4H), 6.84 6.81 (m, 4H), 5.03 (s, 2H), 4.22-4.13 (m, 2H), 3.12-2.93 (m, 2H), 2.07-2.03 (m, 1H), 1.49-1.46 (m, 1H), 1.40 1.38 (m, 1H). | 6 |
| AI | 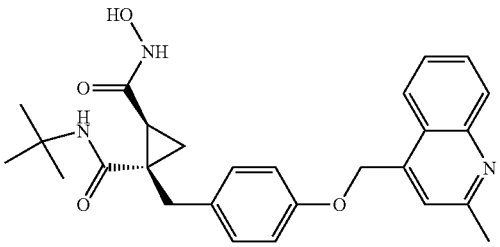 | 3.91 | 462 | | 7A; 6 |
| AJ | 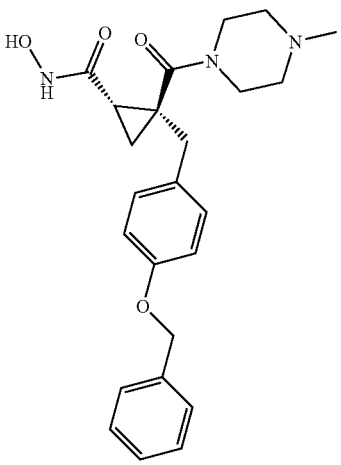 | 3.66 | 424 | | 6 |

TABLE 1-continued
| | | | | |
|---|---|---|---|---|
| AK | 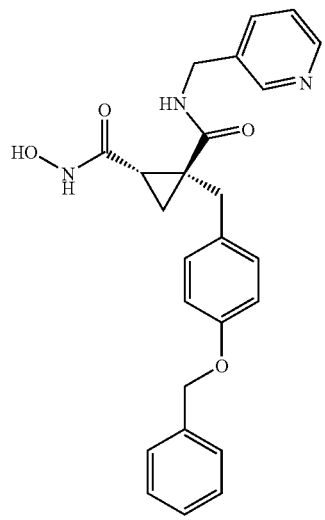 | 3.61 | 432 | 6 |
| AL | 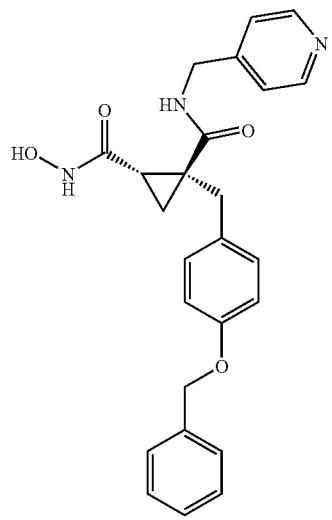 | 3.61 | 432 | 6 |
| AM | 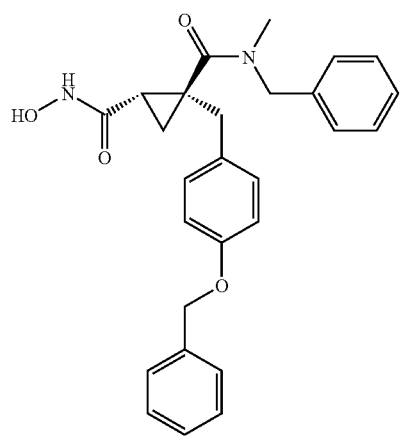 | 4.61 | 445 | 6 |

TABLE 1-continued
| | | | | |
|---|---|---|---|---|
| AN | 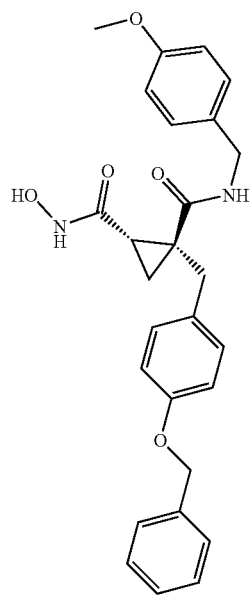 | 4.41 | 461 | 6 |
| AO | 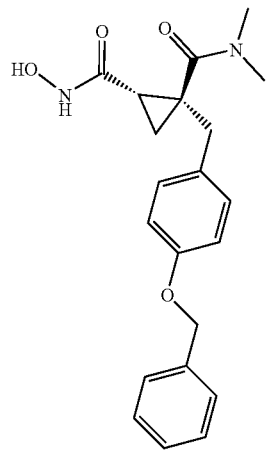 | 4.01 | 369 | 6 |
| AP | 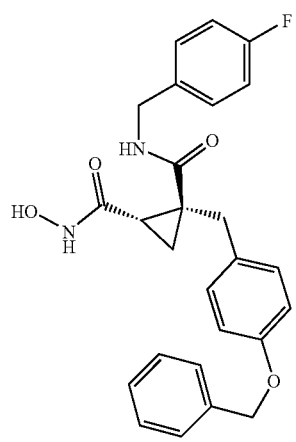 | 4.46 | 449 | 6 |

TABLE 1-continued
| | | | | |
|---|---|---|---|---|
| AQ | 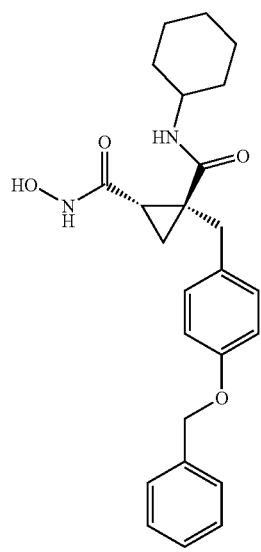 | 4.56 | 423 | 6 |
| AR | 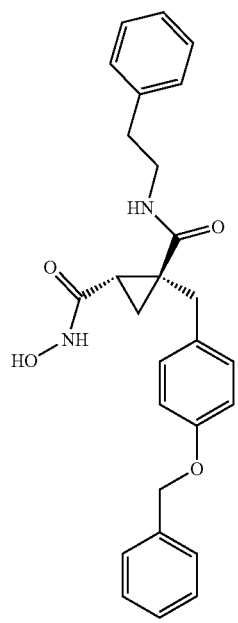 | 4.56 | 445 | 6 |

TABLE 1-continued
| | | | | |
|---|---|---|---|---|
| AS | 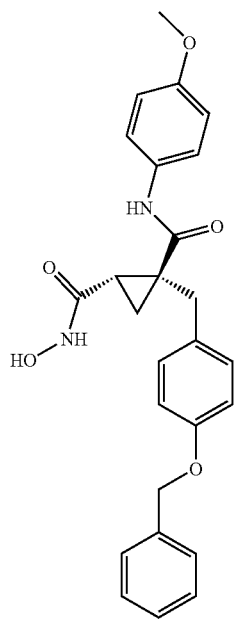 | 4.41 | 447 | 6 |
| AT | 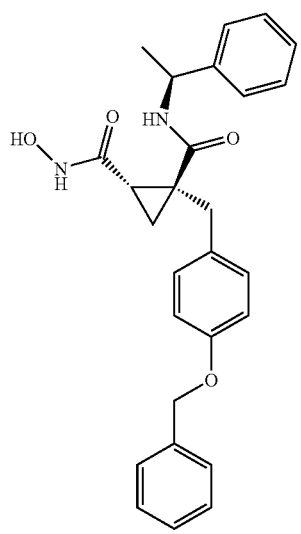 | 4.56 | 445 | 6 |

TABLE 1-continued
| | | | | |
|---|---|---|---|---|
| AU | 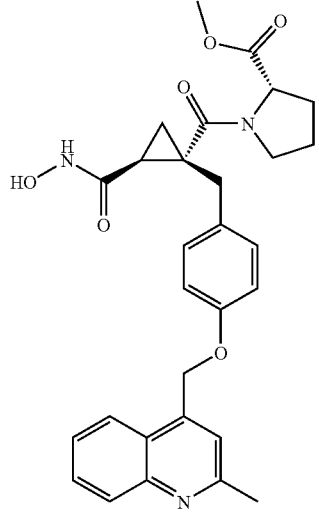 | 3.78 | 518 | 7A; 6 |
| AV | 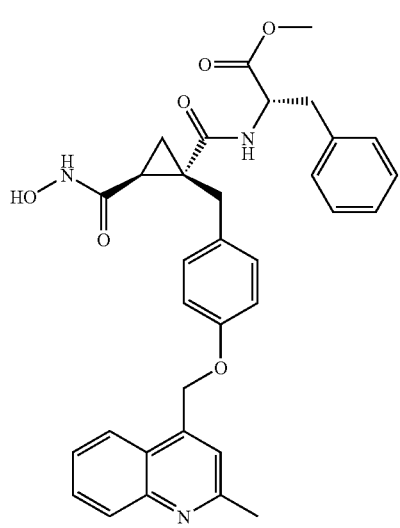 | 4.18 | 568 | 7A; 6 |
| AW | 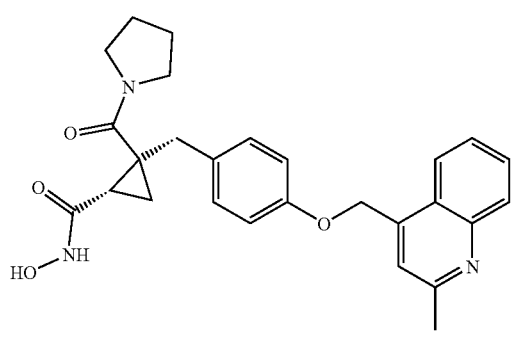 | 3.68 | 460 | 7A; 6 |
| AX | 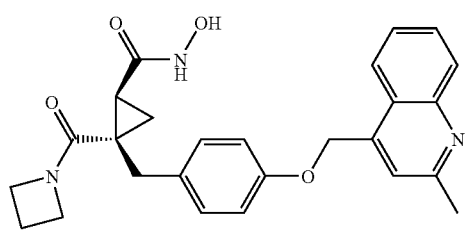 | 3.48 | 446 | 7A; 6 |

TABLE 1-continued
| | | | |
|---|---|---|---|
| AY | 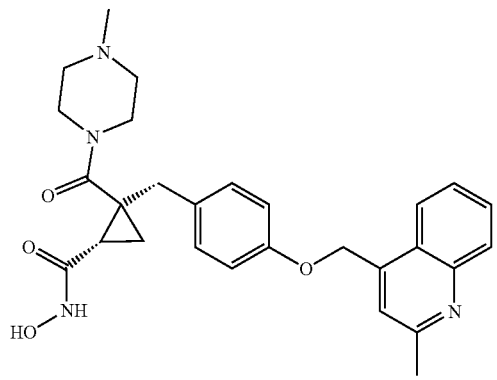 | 3.21 489 | 7A; 6 |
| AZ | 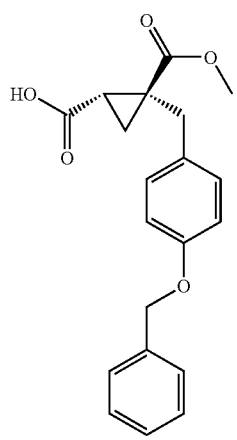 | 341 | 5AB; 2B |
| BA | 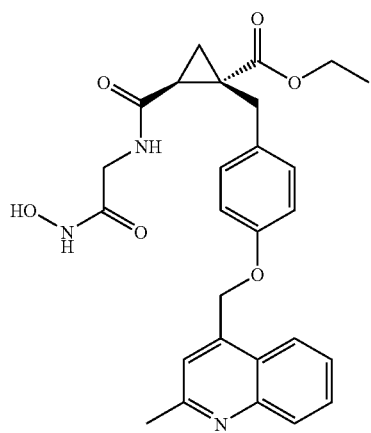 | 492 | 34 |

TABLE 1-continued
| | | | |
|---|---|---|---|
| BB | 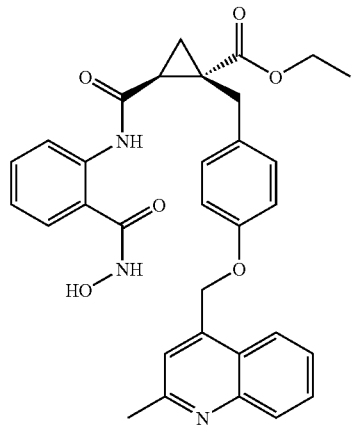 | 554 | 34 |
| BC | 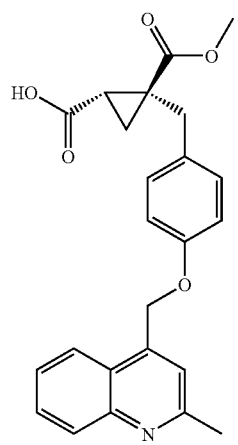 | 4.01 406 | 7AB |
| BD | 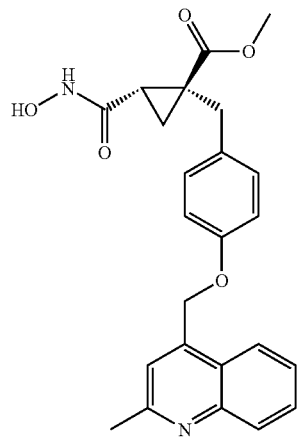 | 3.76 421 | 7 |

TABLE 1-continued
| | | | | | |
|---|---|---|---|---|---|
| BE | 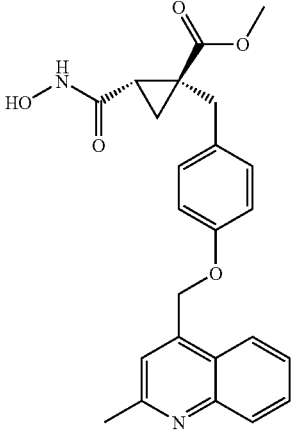 | 3.76 | 421 | | 7 |
| BF | 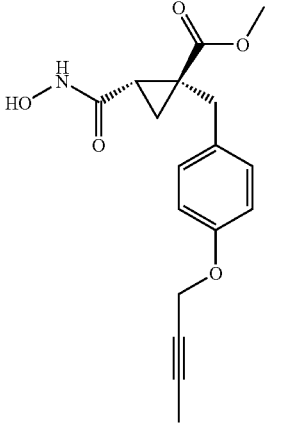 | 3.96 | 318 | 1H NMR (CD3CN): d 7.15 (m, 2H), 6.84 (m, 2H), 4.64-4.62 (m, 2H), 3.58 (s, 3H), 3.15-2.94 (m, 2H), 2.22-2.18 (m, 1H), 1.83-1.81 (m, 3H), 1.52-1.46 (m, 2H). | 7 |
| BG | 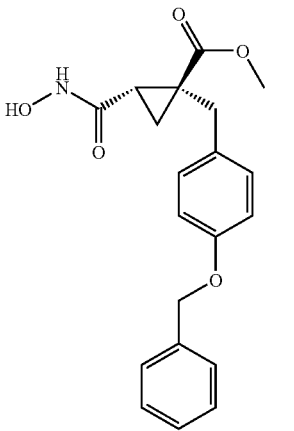 | 4.71 | 356 | 1H NMR (CDCl3): d 7.42-7.31 (m, 5H), 7.12 (m, 2H), 6.86 (m, 2H), 5.01 (s, 2H), 3.63 (s, 3H), 3.20-3.09 (m, 2H), 2.17 (m, 1H), 1.64-1.58 (m, 2H) | 7 |

TABLE 1-continued

| | | | | |
|---|---|---|---|---|
| BH | (structure) | 3.96 | 406 | 7AB |
| BI | (structure) | 5.05 | 449 | 8AB |
| BJ | (structure) | 2.65 | 449 | 8AB |
| BK | (structure) | 2.8 | 463 | 8AB |
| BL | (structure) | 2.15 | 434 | 1H NMR (CD3OD): d 8.42-8.40 (m, 1H), 8.19-8.09 (m, 3H), 7.96-7.92 (m, 1H), 7.14-7.05 (m, 4H), 5.82 (s, 2H), 3.07 (s, 2H), 3.01 (s, 3H), 2.99 (s, 3H), 2.82 (s, 3H), 1.91-1.88 (m, 1H), 1.54-1.51 (m, 1H),1.37-1.34 (m, 1H). | 8AC |

TABLE 1-continued
| BM | 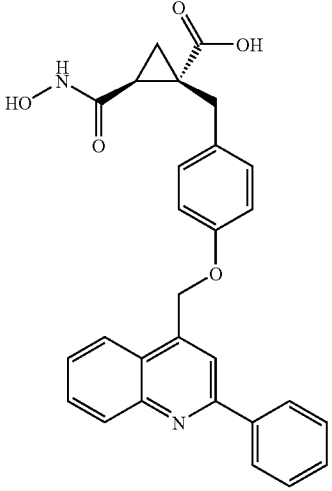 | 3.58 | 469 | 10AB; 7C; 8A; 2D |
| BN | 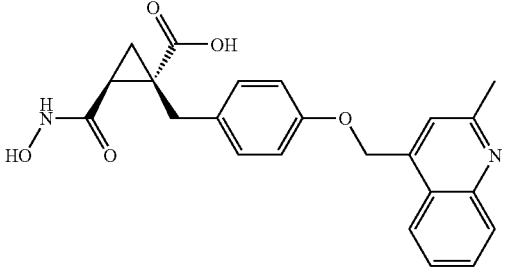 | 3.36 | 407 | 8A; 2D |
| BO | 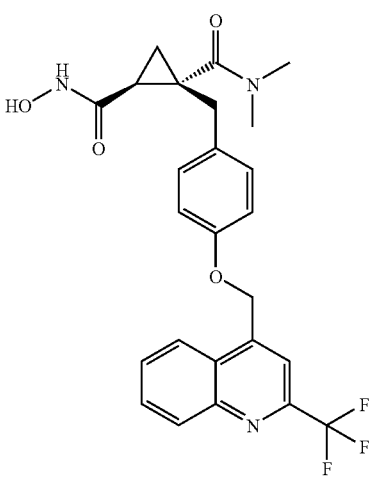 | | 488 | 15A; 10BD |

TABLE 1-continued
| | | | |
|---|---|---|---|
| BP 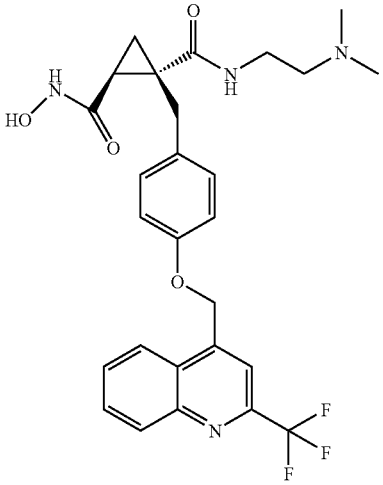 | 531 | | 15A; 10BD |
| BQ 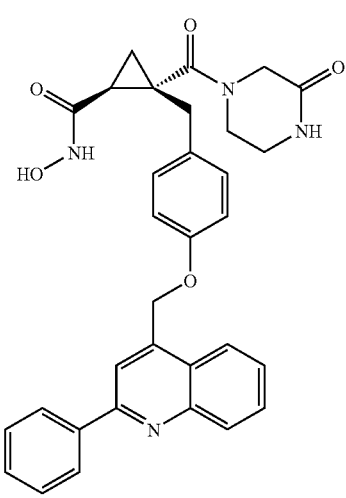 | 551 | 1H NMR (CD3OD): δ 8.02-8.18 (m, 5H); 7.72-7.82 (m, 2H); 7.42-7.68 (m, 4H); 7.04-7.18 (m, 2H); 6.96-7.04 (m, 2H); 5.59 (s, 2H); 3.82-4.02 (m, 2H); 3.44-3.70 (m, 2H); 2.96-3.20 (m, 4H); 1.82-1.96 (m, 1H); 1.50-1.62 (m, 1H); 1.28-1.40 (m, 1H). | 10ABD |
| BR 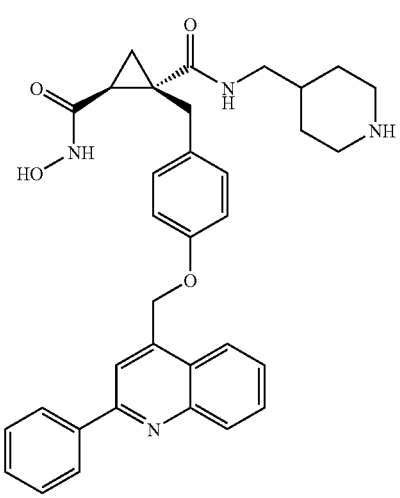 | 565 | 1H NMR (CD3OD): δ 8.0-8.18 (m, 5H); 7.72-7.80 (m, 1H); 7.56-7.62 (m, 1H); 7.42-7.56 (m, 3H); 7.14-7.26 (m, 2H); 6.98-7.08 (m, 2H); 5.55 (s, 2H); 3.08-3.26 (m, 2H); 2.76-2.92 (m, 4H); 2.24-2.42 (m, 2H); 2.04-2.16 (m, 1H); 1.40-1.56 (m, 2H); 1.16-1.40(m, 3H); 0.76-0.96 (m, 2H). | 10ABD |

TABLE 1-continued
| | | | | |
|---|---|---|---|---|
| BS | 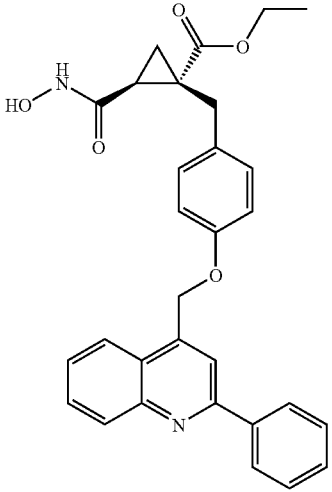 | 4.88 | 497 | 1H NMR (CD3OD): δ 8.54-8.51 (m, 2H), 8.44-8.42 (m, 1H), 8.24-8.20 (m, 1H), 8.13-8.11 (m, 2H), 8.05-8.01 (m, 1H), 7.83-7.75 (m, 3H), 7.28 7.25 (m, 2H), 7.13-7.10 (m, 2H), 5.95 (s, 2H), 4.08-4.02 (m, 2H), 3.24-3.20 (m, 1H), 3.04-3.00 (m, 1H), 2.28-2.24 (m, 1H), 1.56-1.54 (m, 2H), 1.16 1.12 (m, 3H). | 10ABC |
| BT | 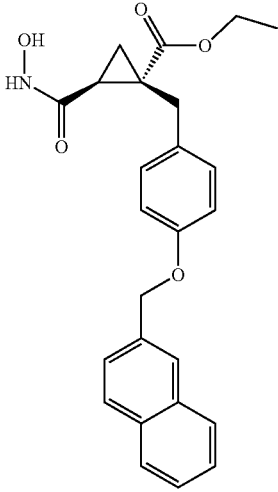 | 5.22 | 420 | | 10ABC |
| BU | 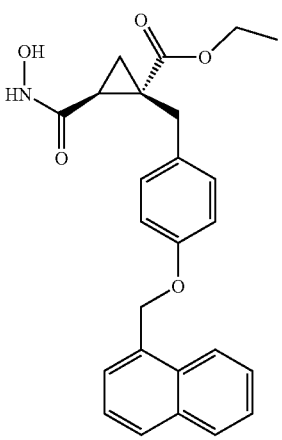 | 5.15 | 420 | | 10ABC |

TABLE 1-continued
| | | | | |
|---|---|---|---|---|
| BV | 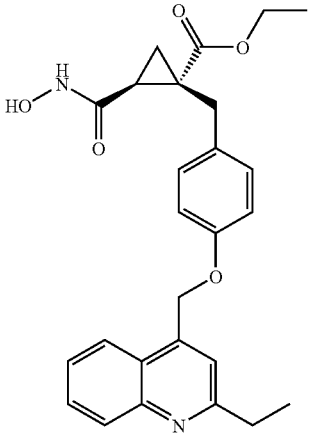 | 4.71 | 449 | 1H NMR (400 MHZ, CD3OD): d 8.14-8.02 (m, 2H); 7.79-7.74 (m, 1H); 7.62-7.58 (m, 2H); 7.22-7.20 (m, 2H); 7.00-6.98 (m, 2H); 5.57 (s, 2H); 4.08-4.03.(m, 2H), 3.22-3.18 (m, 1H), 3.03-2.96 (m, 3H); 2.27-2.24 (m, 1H); 1.55-1.53 (m, 2H); 1.39-1.34 (m, 3H), 1.16 (m, 3H). | 10ABC |
| BW | 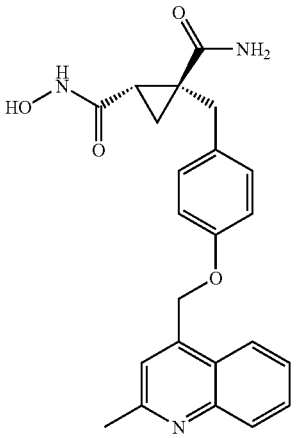 | 3.11 | 406 | | 8AC |
| BX | 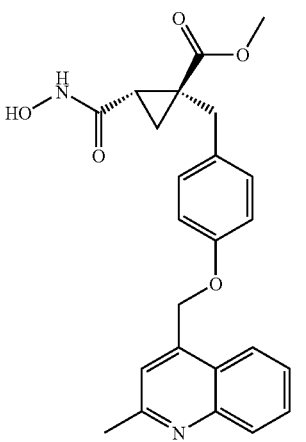 | 3.61 | 421 | 1H NMR (CD3CN): d 8.38 (m, 1H), 8.28 (m, 1H), 8.06-8.02 (m, 2H), 7.90 7.86 (m, 1H), 7.23 (d, 2H), 7.04 (d, 2H), 5.72 (s, 2H), 3.59 (s, 3H), 3.16-2.99 (m, 2H), 2.96 (s, 3H), 2.25-2.21 (m, 1H), 1.54-1.47 (m, 2H) | 7 |

TABLE 1-continued
| | | | | |
|---|---|---|---|---|
| BY | 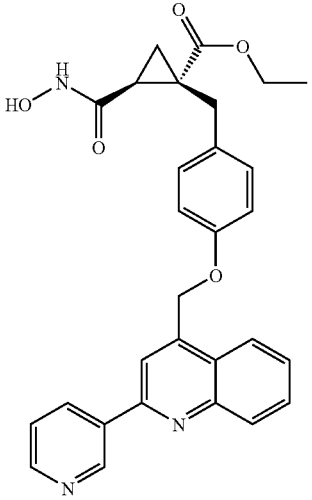 | | 498 | 1H NMR (400 MHz, CD3OD): d 9.48 (s, 1H); 9.07 (m, 1H); 8.80 (m, 1H); 8.30 (s, 1H), 8.21 (m, 2H), 7.98 (m, 1H), 7.87 (s, 1H), 7.73 (m, 1H), 7.22 (m, 2H), 7.04 (m, 2H), 5.70 (s, 2H), 4.04 (m, 2H), 2.95-3.22 (m, 2H), 2.24 (m, 1H), 1.51 (m, 2H); 1.12 (m, 3H). | 10ABC |
| BZ | 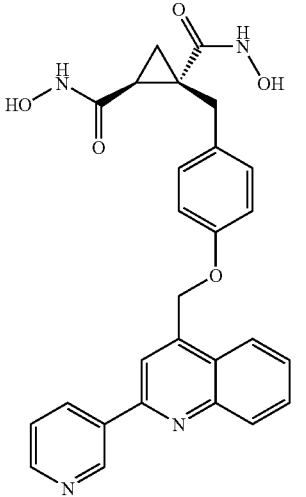 | 3.71 | 485 | | 10ABD |
| CA | 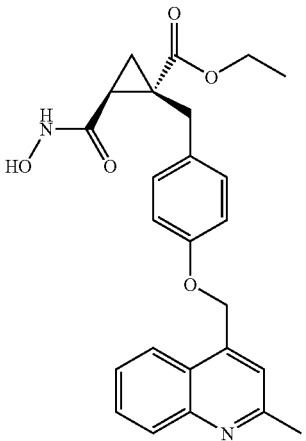 | | 435 | 1HNMR (300 MHz, CD3OD): δ 8.01 (m, 1H), 7.96 (m,1H), 7.74-7.69 (m, 1H), 7.57-7.52 (m, 1H), 7.52 (s, 1H), 7.19 (m, 2H),6.943 (m, 2H), 5.47 (s, 2H), 4.05 (m, 2H), 3.29-3.02 (m, 2H), 2.66 (s, 3H), 2.30-2.20 (m, 1H), 1.60-1.48 (m, 2H), 1.10 (m, 3H). | 15 |

TABLE 1-continued

| | | |
|---|---|---|
| CB | 507 | 15 |
| CC | 489 | 15 |
| CD | 507 | 15 |

TABLE 1-continued

| | | | |
|---|---|---|---|
| CE | (structure) | 474 | 15A; 10B |
| CF | (structure) | 519 | 15 |
| CG | (structure) | 518 | 15 |

TABLE 1-continued
| | | | |
|---|---|---|---|
| CH | 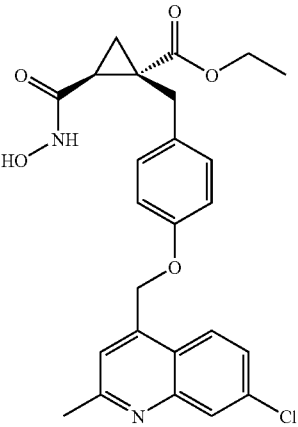 | 469 | 15 |
| CI | 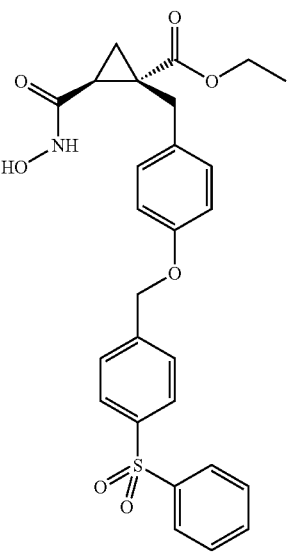 | 510 | 15 |
| CJ | 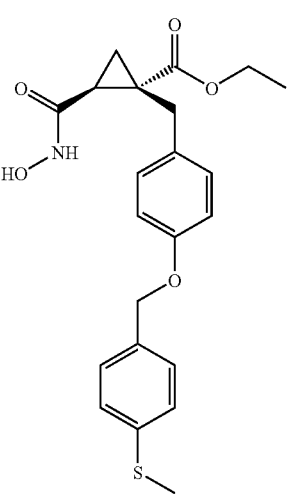 | 416 | 15 |

TABLE 1-continued
| | | | |
|---|---|---|---|
| CK | 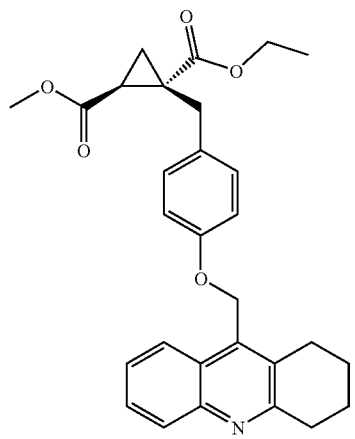 | 474 | 15 |
| CL | 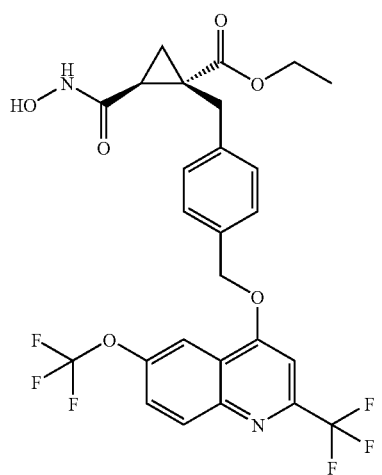 | 573 | 15 |
| CM | 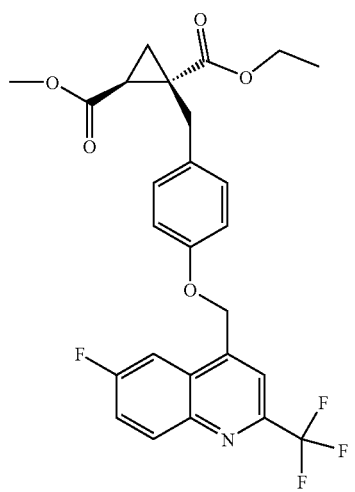 | 506 | 15A |

TABLE 1-continued
| | | | | |
|---|---|---|---|---|
| CN 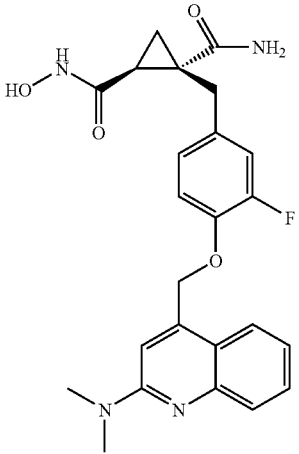 | 3.71 | 453 | 1HNMR (400 MHz, CD3OD): d 7.97-7.92 (m, 1H), 7.82-7.80 (m, 1H), 7.67 7.64 (m, 1H), 7.39-7.34 (m, 2H), 7.21 7.02 (m,3H), 5.57 (s, 2H), 3.31-3.29 (m,) 2.19-2.14 (m, 1H), 1.55-1.51 (m, 1H), 1.46-1.43 (m, 1H), | 14, 31 |
| CO 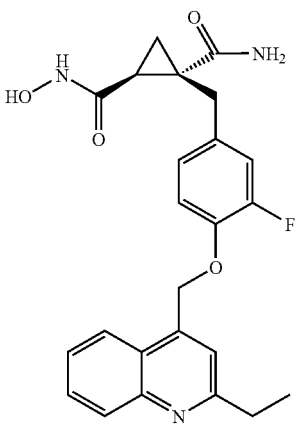 | 3.61 | 438 | 1HNMR (400 MHz, CD3OD): d 8.16-8.04 (m, 2H), 7.86-7.82 (m, 1H), 7.74 (s, 1H), 7.69-7.65 (m, 1H), 7.18-7.00 (m, 3H), 5.65 (s, 2H), 3.26-3.13 (m, 2H), 3.07-3.02 (m, 2H), 2.18-2.14 (m, 1H), 1.56-1.53 (m, 1H), 1.46-1.37 (m, 4H). | 17 |
| CP 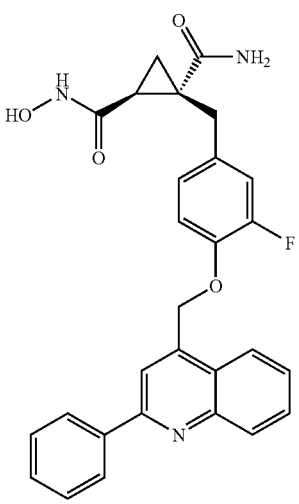 | 4.78 | 486 | 1H NMR (400 MHz, CD3OD): d 8.35 (m, 2H); 8.3 (m, 1H); 8.15 (m, 2H); 8.05 (m, 1H); 7.85 (m, 1H); 7.65 (m. 3H); 7.25 (m,, 1H); 7.0-7.15 (m, 2H); 5.95 (s, 2H); 3.1-3.3 (m, 2H); 2.15 (m, 1H); 1.55 (m, 1H); 1.45 (m, 1H). | 17 |

TABLE 1-continued
| | | | | |
|---|---|---|---|---|
| CQ 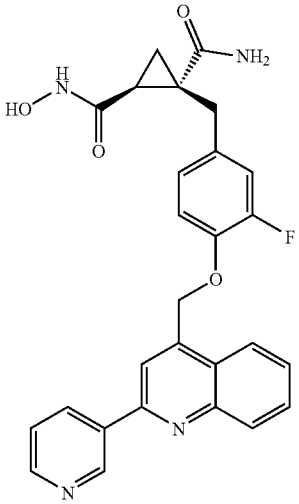 | 3.84 | 487 | 1H NMR (400 MHz, CD3OD): d 9.4 (br. s, 1H); 8.7-8.9 (m, 2H); 8.15-8.25 (m, 3H); 8.1 (s, 1H); 7.78-7.85 (m, 2H); 7.6-7.7 (m, 2H); 7.0-7.25 (m, 3H); 5.6 (s, 2H); 3.1-3.25(m, 2H); 2.15 (m, 2H); 1.5 (m, 1H); 1.45 (m, 1H). | 17 |
| CR 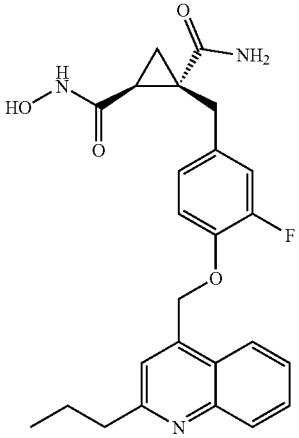 | 3.64 | 452 | 1H NMR (400 MHz, CD3OD): d 8.15 (m, 1H); 8.05 (m, 1H); 7.75 (m, 1H); 7.6 (m, 2H); 6.95-7.2 (m, 3H); 5.62 (s, 2H); 3.1-3.15 (m, 2H); 2.95 (m, 2H); 2.15 (m, 1H); 1.8 (m, 2H); 1.55 (m, 1H); 1.45 (m, 1H); 1.0 (m, 3H). | 17 |
| CS 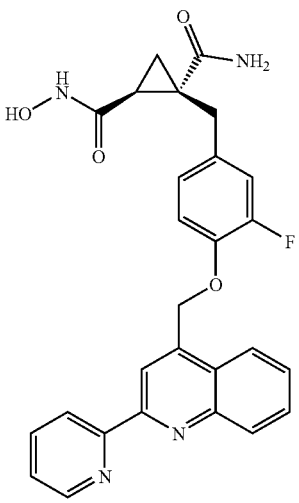 | | 487 | | 17 |

TABLE 1-continued
| | | | | | |
|---|---|---|---|---|---|
| CT | 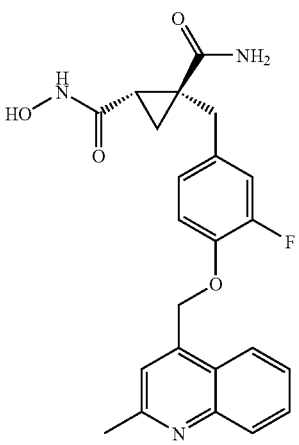 | 2.84 | 424 | 1H NMR (400 MHz, CD3OD): d 8.41 (m, 1H); 8.1-8.2 (m, 3H); 7.95 (m, 1H); 7.25 (m, 1H); 7.05-7.15 (m, 2H); 5.95 (s, 2H); 3.1-3.3 (m, 2H); 3.02 (s, 3H); 2.18 (m, 1H); 1.55 (m, 1H); 1.45 (m, 1H). | 12; 10ABD |
| CU | 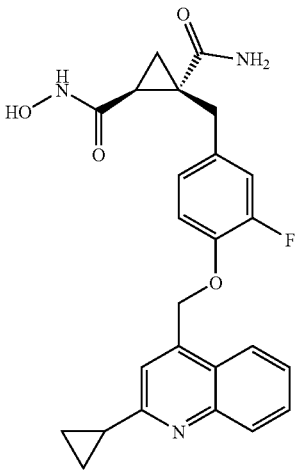 | 4.01 | 450 | 1H NMR (CD3OD): δ 8.08 (m, 1H); 7.95 (m, 1H); 7.75 (m, 1H); 7.55 (m, 1H); 7.4 (s, 1H); 7.0-7.2 (m, 3H); 5.6 (s, 2H); 3.1-3.3 (m, 2H); 2.3 (m, 1H); 2.15 (m, 1H); 1.55 (m, 1H); 1.45 (m, 1H); 1.05-1.2 (m, 4H). | 17 |
| CV | 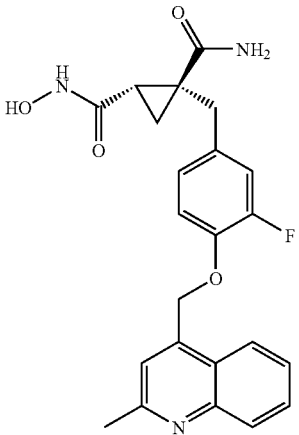 | 3.04 | 424 | | 17 |

TABLE 1-continued
| | | | |
|---|---|---|---|
| CW 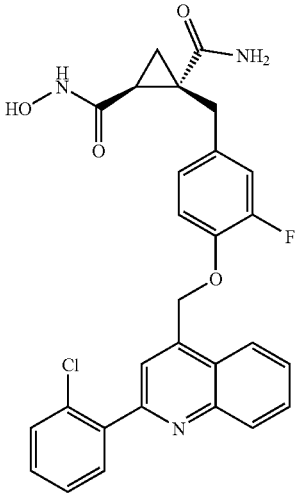 | 4.48 | 520 | 17 |
| CX 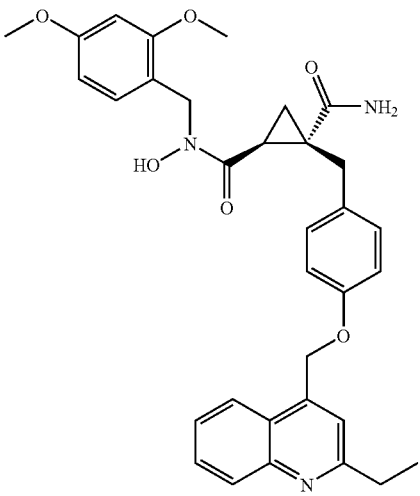 | 4.01 | 570 | 17 |
| CY 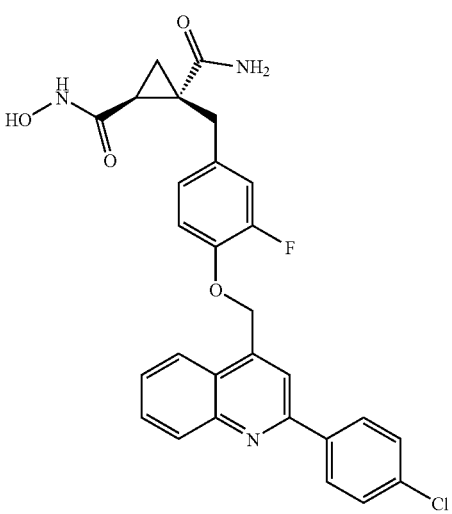 | | 520 NMR | 17 |

TABLE 1-continued
| CZ | 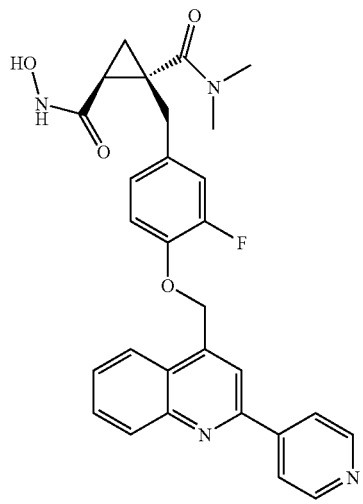 | 515 | 14B; 17 |
| --- | --- | --- | --- |
| DA | 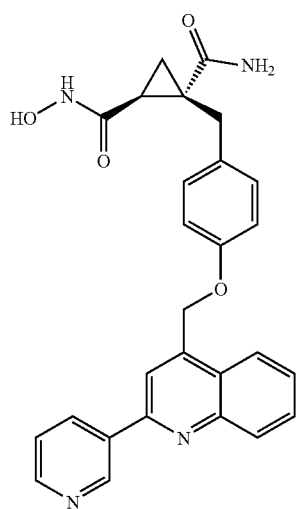 | 3.28  469 | 17 |
| DB | 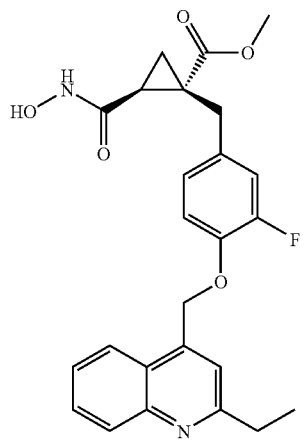 | 4.41  453 | 18 |

TABLE 1-continued
| | | | | | |
|---|---|---|---|---|---|
| DC | 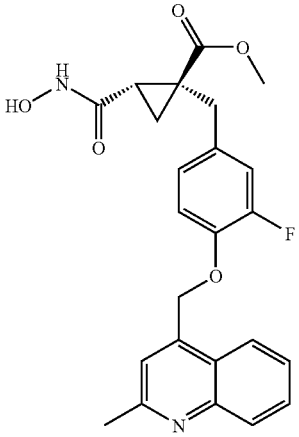 | 3.59 | 439 | | 18 |
| DD | 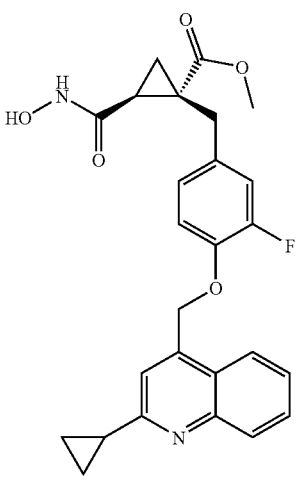 | 3.74 | 465 | | 18 |
| DE | 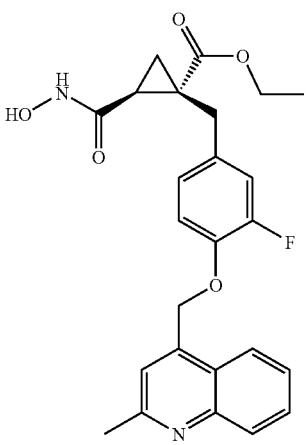 | 4.55 | 453 | 1H NMR (CD3OD): δ 8.19 (m, 1H), 8.05 (m,1H), 7.87 (m, 1H), 7.75 (s, 1H); 7.70 (m, 1H); 7.15 (m, 1H); 7.06 (m, 1H); 7.00 (m, 1H); 5.70 (s, 2H), 4.06 (m, 2H); 3.02-3.21 (m, 2H), 2.79 (s, 3H), 2.26 (m, 1H), 1.53 (m, 2H), 1.14 (m, 3H) | 18 |

TABLE 1-continued
| | | | |
|---|---|---|---|
| DF 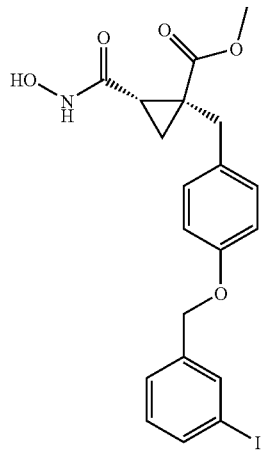 | 4.81 | 482 | 20 |
| DG 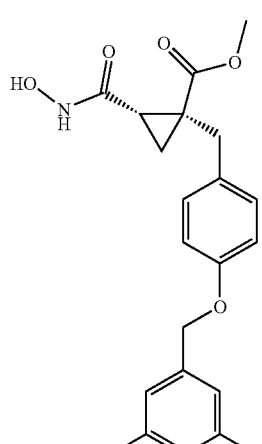 | 4.96 | 424 | 20 |
| DH 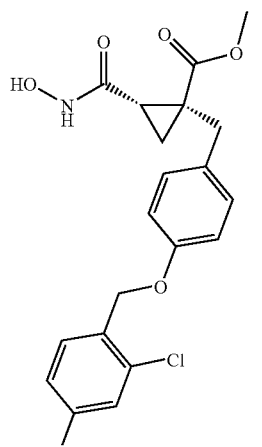 | 4.91 | 424 | 20 |

TABLE 1-continued

| | | | |
|---|---|---|---|
| DI [structure] | 4.86 | 424 | 20 |
| DJ [structure] | 4.68 | 423 | 20AB; 6C |
| DK [structure] | 4.61 | 390 | 20 |

TABLE 1-continued
| | | | |
|---|---|---|---|
| DL 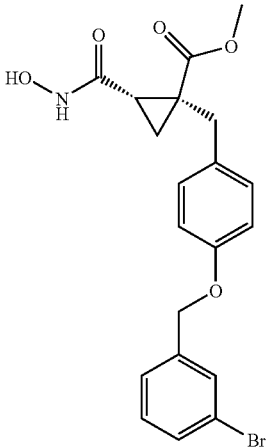 | 4.71 | 435 | 20 |
| DM 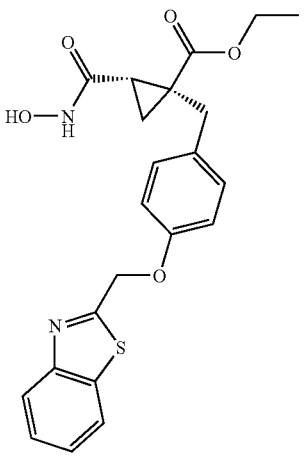 | 4.35 | 427 | 20 |
| DN 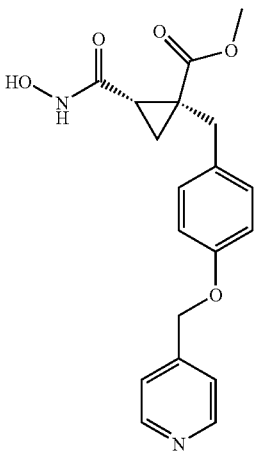 | 3.16 | 357 | 20 |

TABLE 1-continued

| | | | |
|---|---|---|---|
| DO | [structure] | 4.26  390<br>4.66 | 20 |
| DP | [structure] | 4.91  438 | 20 |
| DQ | [structure] | 4.08  437 | 20 |

TABLE 1-continued
| | | | |
|---|---|---|---|
| DR 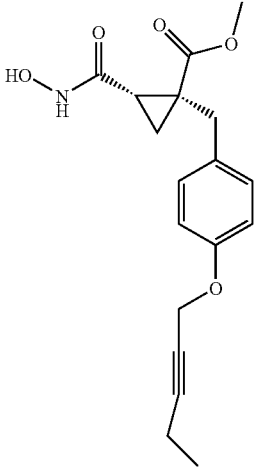 | 4.21 | 332 | 20 |
| DS 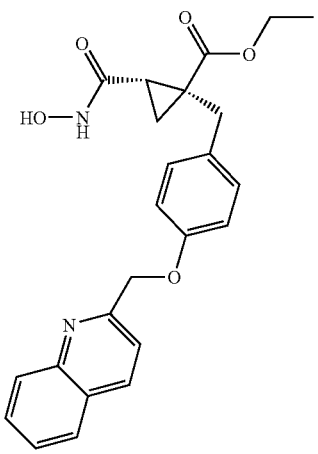 | 3.88 | 421 | 20 |
| DT 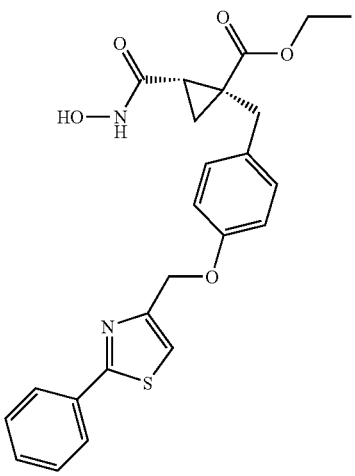 | 4.58 | 453 | 20 |

TABLE 1-continued
| DU | 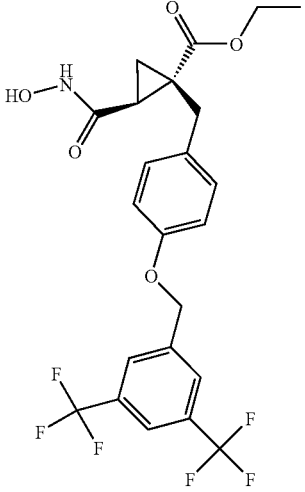 | 5.02 | 506 | 20 |
| DV | 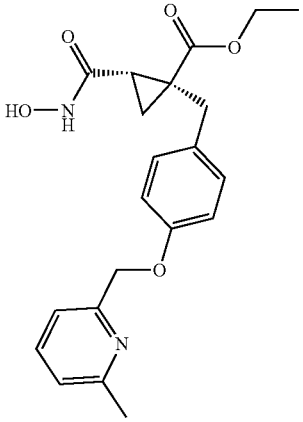 | 3.44 | 385 | 20 |
| DW | 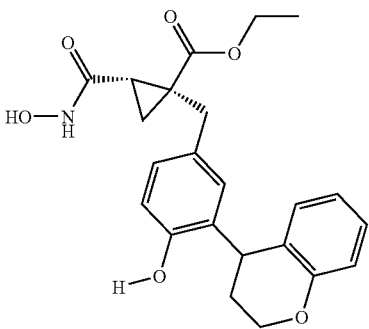 | 4.05 | 412 | 20 |

TABLE 1-continued

| | | | | |
|---|---|---|---|---|
| DX | | 4.31 | 406 | 20 |
| DY | | 3.21 | 374 | 20 |
| DZ | | 4.91 | 362 | 20 |
| EA | | 3.78 | 450 | 20 |

TABLE 1-continued
| | | | | |
|---|---|---|---|---|
| EB | 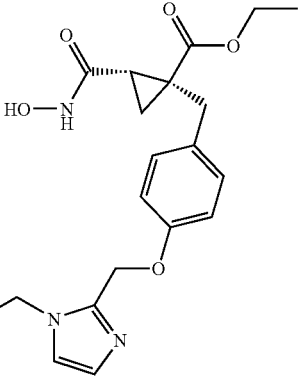 | 4.11 | 484 | 20 |
| EC | 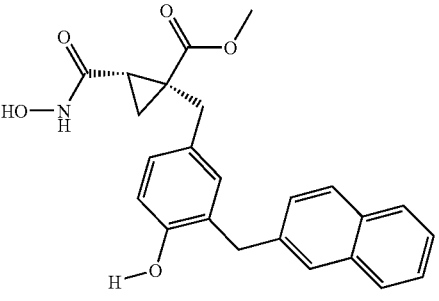 | 4.36 | 406 | 20 |
| ED | 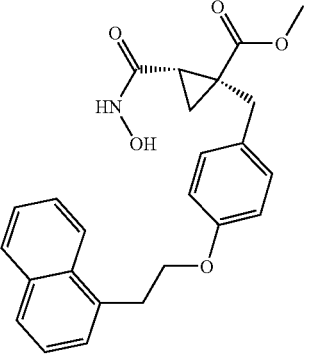 | 4.86 | 420 | 20 |
| EE | 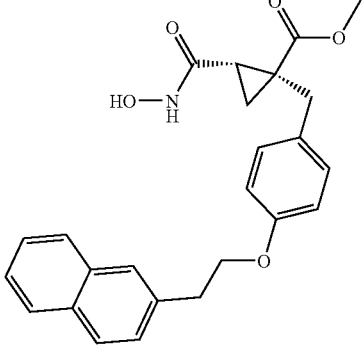 | | 420 | 20 |

TABLE 1-continued
| EF | 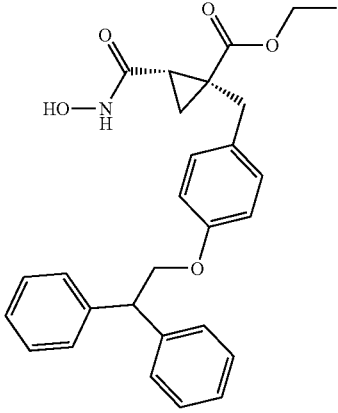 | 460 | 20 |
| --- | --- | --- | --- |
| EG | 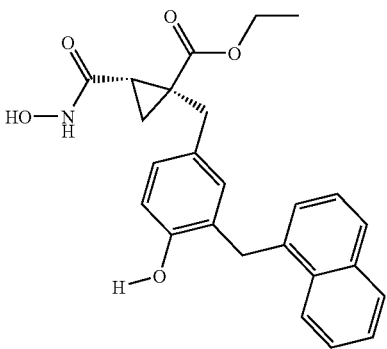 | 420 | 20 |
| EH | 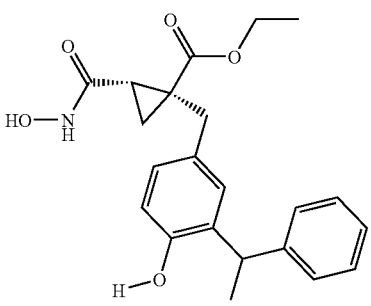 | 384 | 20 |
| EI | 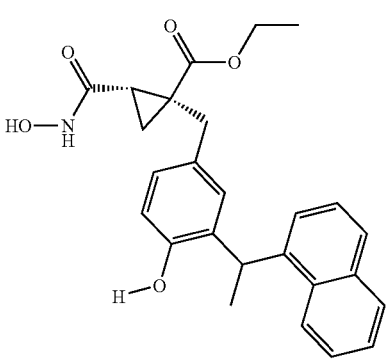 | 434 | 20 |

TABLE 1-continued
| | | | |
|---|---|---|---|
| EJ | 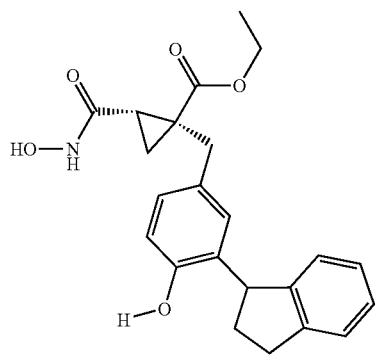 | 396 | 20 |
| EK | 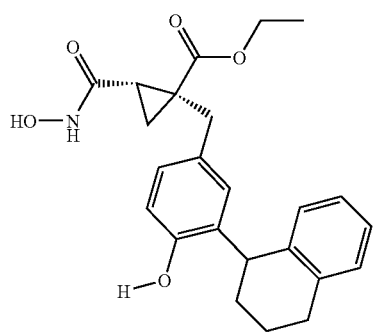 | 410 | 20 |
| EL | 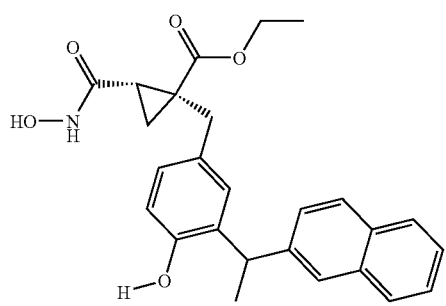 | 434 | 20 |
| EM | 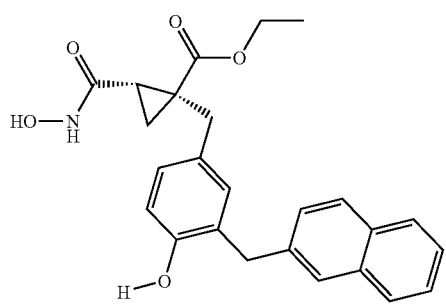 | 420 | 20 |

TABLE 1-continued

| | | | |
|---|---|---|---|
| EN | (structure) | 5.15  406 | 21 |
| EO | (structure) | 4.78  415 | 21 |
| EP | (structure) | 4.91  424 | 21 |
| EQ | (structure) | 4.55  400 | 21 |

| | | | |
|---|---|---|---|
| ER 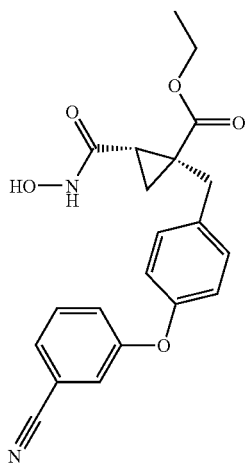 | | 4.51 381 | 21 |
| ES 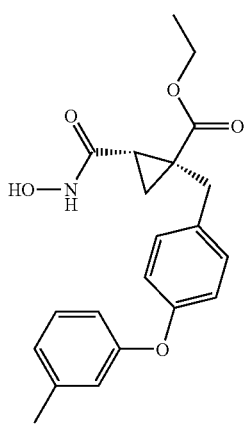 | | 4.78 370 | 21 |
| ET 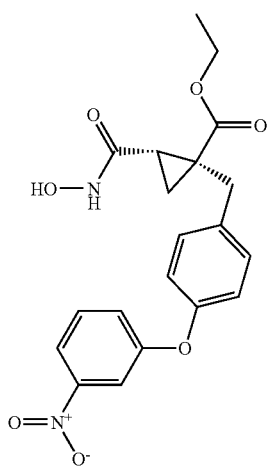 | | 4.65 401 | 21 |

TABLE 1-continued
| | | | |
|---|---|---|---|
| EU | 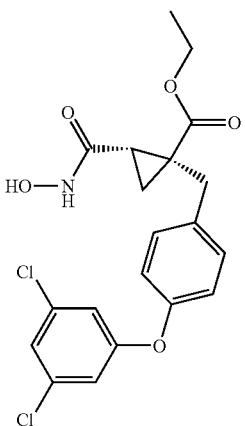 | 5.18  424 | 21 |
| EV | 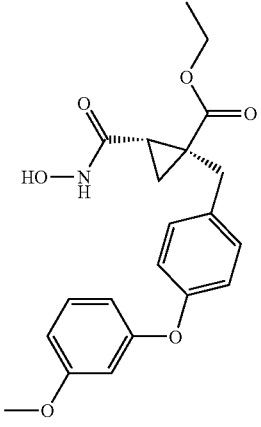 | 4.61  386 | 21 |
| EW | 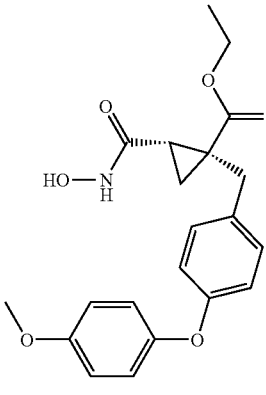 | 4.58  386 | 21 |

TABLE 1
| EX | 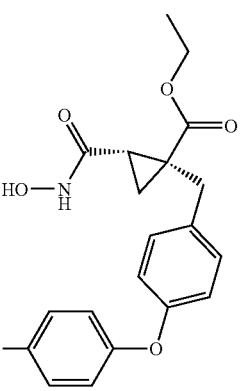 | 4.65 | 401 | 21 |
|----|---|------|-----|----|
| EY | 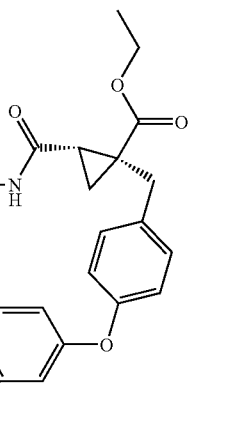 | 4.88 | 390 | 21 |
| EZ | 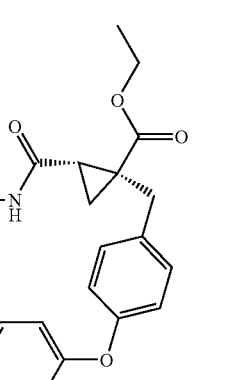 | 4.61 | 356 | 21 |
| FA | 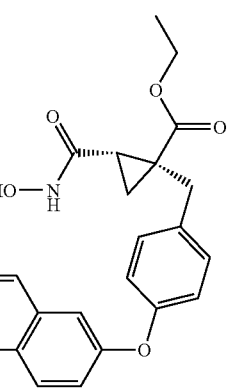 | 4.95 | 406 | 21 |

TABLE 1-continued

| | | | |
|---|---|---|---|
| FB | (structure) | 4.85  390 | 21 |
| FC | (structure) | 4.78  370 | 21 |
| FD | (structure) | 4.18  434 | 21 |
| FE | (structure) | 4.98  384 | 21 |

TABLE 1-continued
| | | | |
|---|---|---|---|
| FF 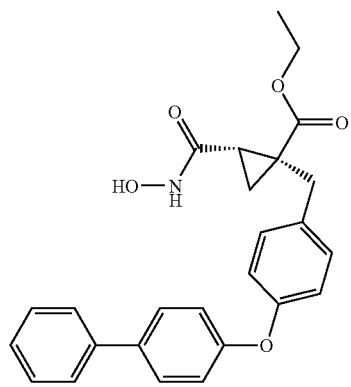 | | 432 | 21 |
| FG 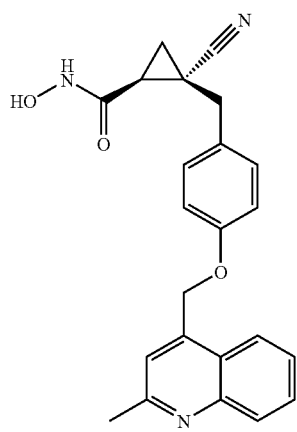 | 4.28 | 388 | 23 |
| FH 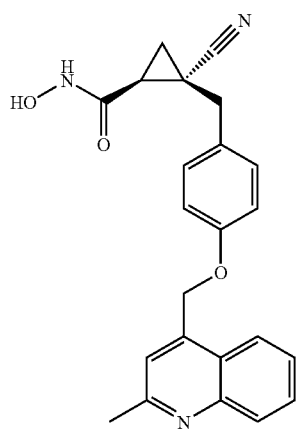 | 3.38 | 388 | 23 |

TABLE 1-continued

| | | | | |
|---|---|---|---|---|
| FI | (structure) | 3.48 | 460 | 24 |
| FJ | (structure) | 3.95 | 446 | 24 |
| FK | (structure) | 4.01 | 431 | 25 |

TABLE 1-continued
| | | | | |
|---|---|---|---|---|
| FL | 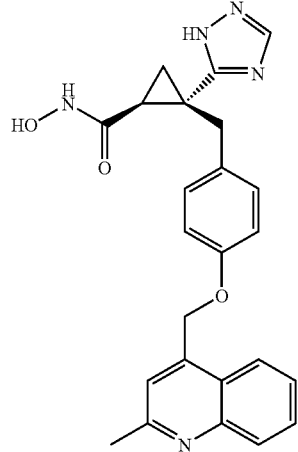 | 3.78 | 430 | 26 |
| FM | 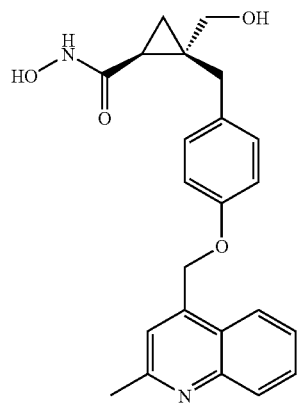 | | 393 | 27 |
| FN | 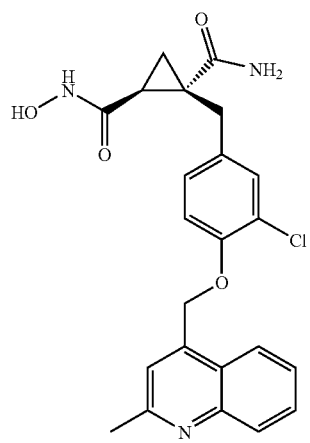 | 3.75 | 440 | 28A; 9C; 10ABD |

TABLE 1-continued

| | | | |
|---|---|---|---|
| FO | (structure) | 4.61  469 | 28 |
| FP | (structure) | 503 | 28 |
| FQ | (structure) | 3.78  485 | 29A;<br>9C;<br>10ABD |

TABLE 1-continued
| | | | |
|---|---|---|---|
| FR | 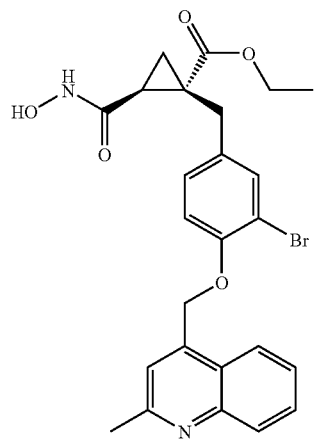 | 4.28  514 | 29 |
| FS | 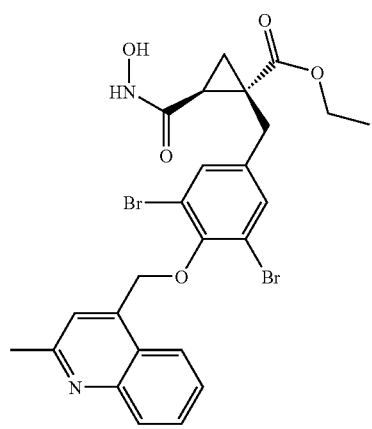 | 593 | 29 |
| FT | 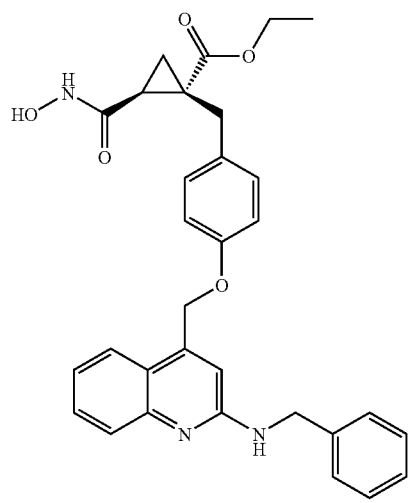 | 5.18  526 | 30 |

| | | | | | |
|---|---|---|---|---|---|
| FU | 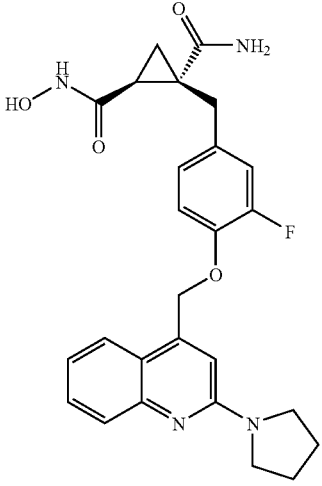 | 4.05 | 479 | 1HNMR (400 MHz, CD3OD): d 8.05-8.03 (m, 1H), 7.95-7.93 (m 1H), 7.84-7.80 (m, 1H), 7.57-7.53 (m, 1H), 7.39 (m, 1H), 7.25-7.20 (m, 1H), 7.11-7.04 (m, 2H), 5.63 (m, 2H), 3.81-3.78 (m, 4H), 3.27-3.14 (m, 2H), 2.21-2.17 (m, 5H), 1.57-1.53 (m, 1H), 1.45 1.43 (m, 1H). | 14; 31 |
| FV | 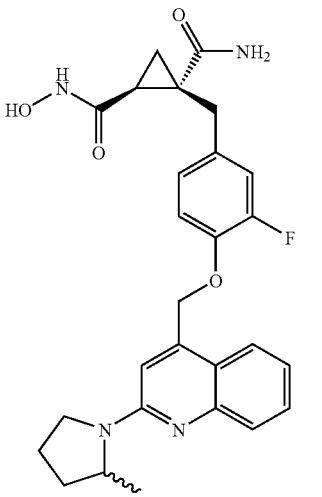 | 4.18 | 493 | 1HNMR (400 MHz, CD3OD): d 8.01-7.99 (m, 1H), 7.92-7.90 (m, 1H), 7.79 7.75 (m, 1H), 7.52-7.48 (m, 1H), 7.34 (s, 1H), 7.22-7.18 (m, 1H), 7.11-7.03 (m, 2H), 5.63 (m,2H), 4.51-4.46 (m, 1H), 3.91-3.88 (m, 1H), 3.71-3.64 (m, 1H), 3.27-3.12 (m, 2H), 2.30-2.13 (m, 4H), 1.95-1.93 (m, 1H), 1.55 1.53 (m, 1H), 1.45-1.43 (m, 1H), 1.33 1.31 (m, 3H). | 14; 31 |
| FW | 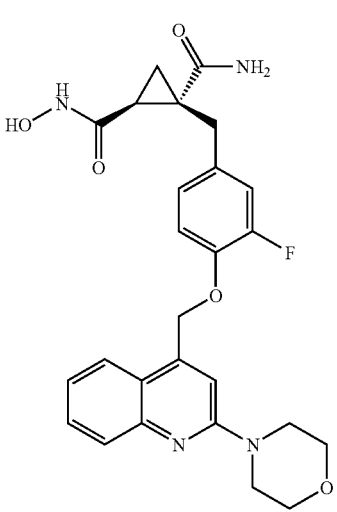 | 3.64 | 495 | 1HNMR (400 MHz, CD3OD): d 7.90-7.88 (m, 1H), 7.73-7.71 (m, 1H), 7.60 7.56 (m, 1H), 7.34-7.30 (m, 2H), 7.16 6.99 (m, 3H), 5.51 (s, 2H), 3.82-3.80 (m, 4H), 3.71-3.69 (m, 4H), 3.25-3.12 (m, 2H), 2.17-2.14 (m, 1H), 1.55 1.52 (m, 1H), 1.47-1.43 (m, 1H). | 14; 31 |

TABLE 1-continued
| | | | | |
|---|---|---|---|---|
| FX 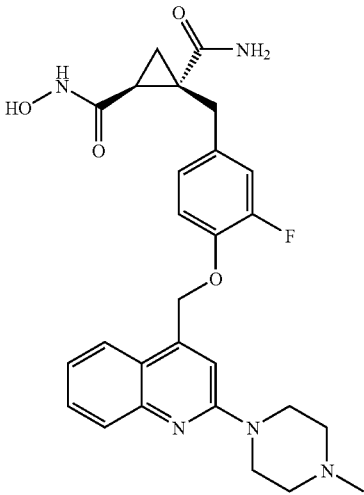 | | 3.31 | 508 | 1H NMR (CD3OD): δ 8.08-8.06 (m, 2H), 7.85-7.81 (m, 1H), 7.63-7.57 (m, 2H), 7.23-7.18 (m, 1H), 7.10-7.03 (m, 2H), 5.63 (s, 2H), 4.28-4.14 (m, 4H), 3.58-3.50 (m, 4H), 3.27-3.14 (m, 2H), 3.00 (s, 3H), 2.25-2.18 (m, 1H), 1.56-1.53 (m, 1H), 1.45-1.42 (m, 1H). | 14; 31 |
| FY 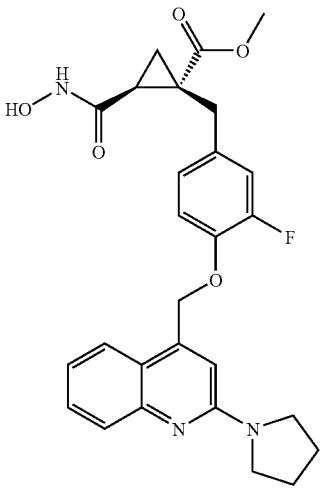 | | 4.45 | 494 | | 31 |
| FZ 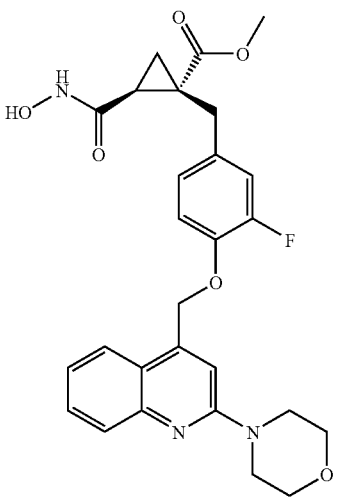 | | 4.48 | 510 | | 31 |

TABLE 1-continued
| | | | |
|---|---|---|---|
| GA 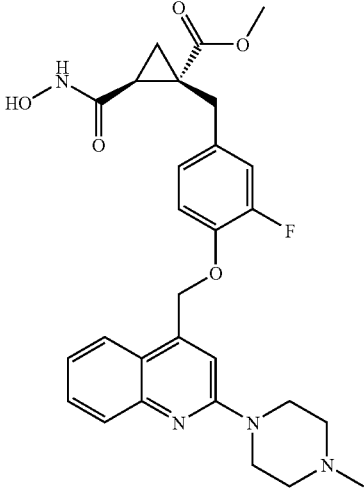 | 3.78 | 523 | 31 |
| GB 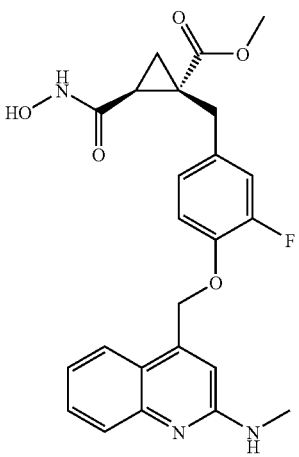 | 4.01 | 454 | 31 |
| GC 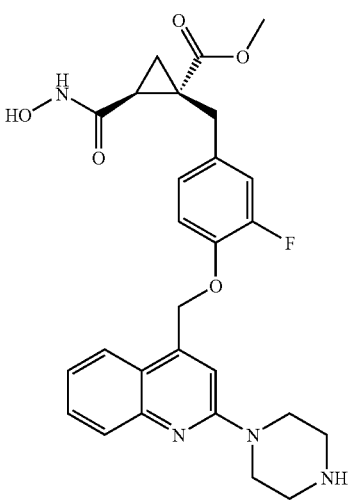 | 3.58 | 509 | 31 |

| | | | |
|---|---|---|---|
| GD | 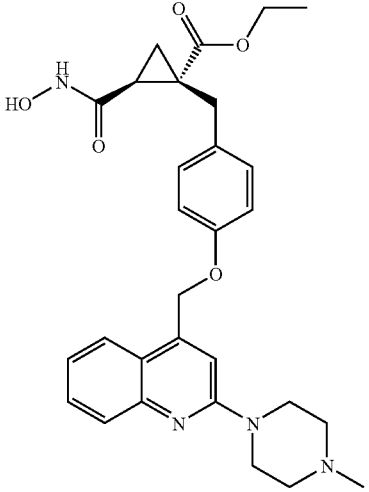 | 4.05 519 | 30 |
| GE | 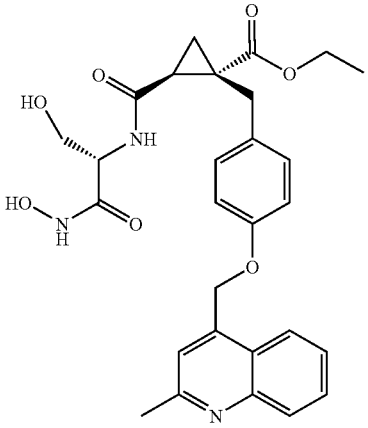 | 522 | 34 |
| GF | 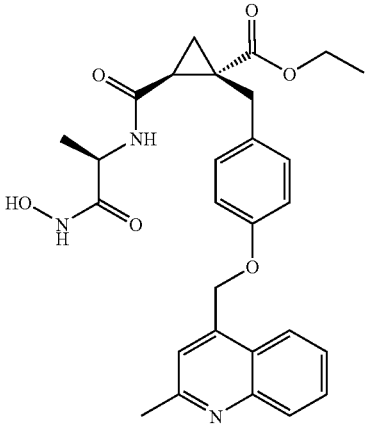 | 506 | 34 |

TABLE 1-continued
| GG | 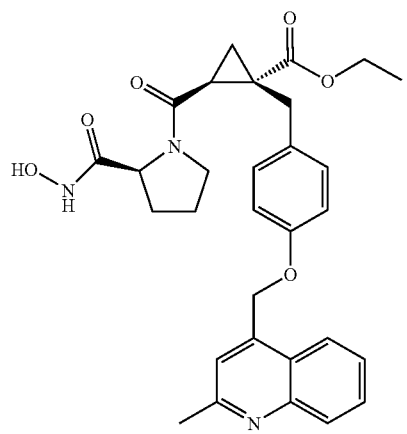 | 532 | 34 |
| GH | 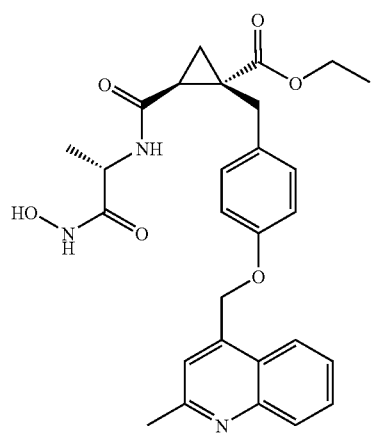 | 506 | 34 |
| GI | 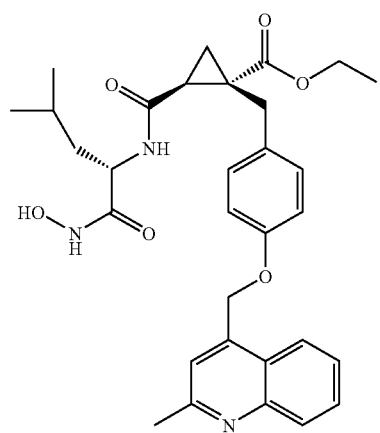 | 548 | 34 |

| | | | | | |
|---|---|---|---|---|---|
| GJ | 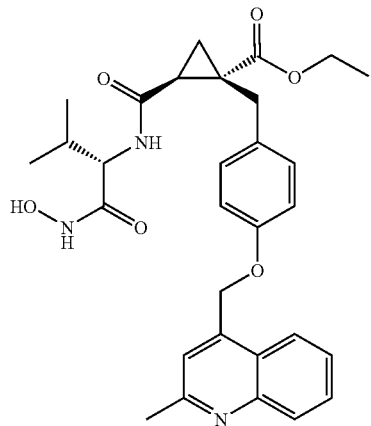 | | 534 | | 34 |
| GK | 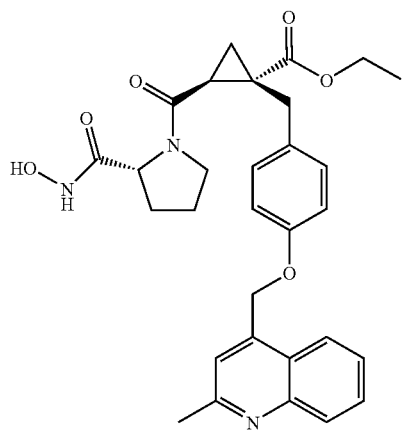 | | 532 | | 34 |
| GL | 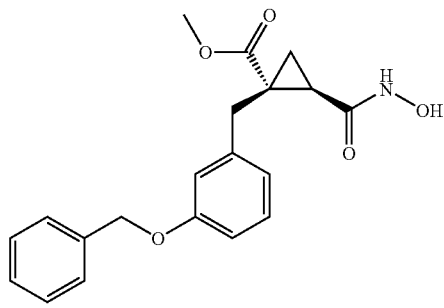 | 4.76 | 356 | 1H NMR (CD3CN): d 7.6-7.4 (m, 5H); 7.3 (m, 1H); 6.95 (m, 3H); 5.2 (s, 2H); 3.7 (s, 3H); 3.3-3.1 (m, 2H); 2.4 (m, 1H); 1.65-1.55 (m, 2H). | 35 |
| GM | 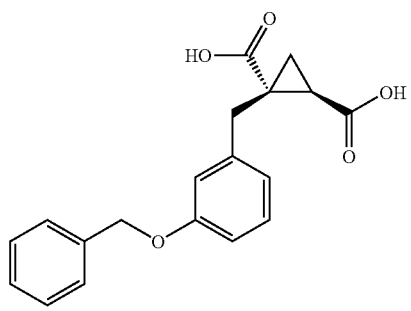 | | 327 | | 35A; 3A; 2B |

TABLE 1-continued
| GN | 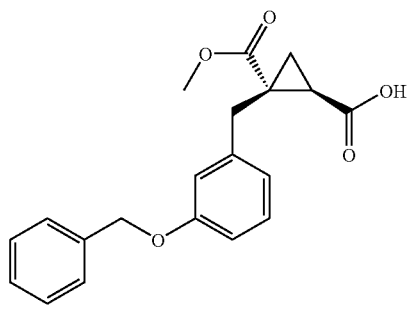 | 341 | 35A; 2B |
| GO | 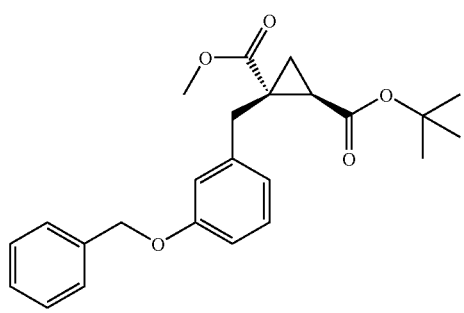 | 6.06 397 | 35A |
| GP | 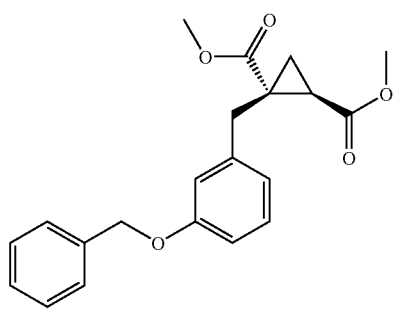 | 355 | 35A; 3A; 2B; 9C |
| GQ | 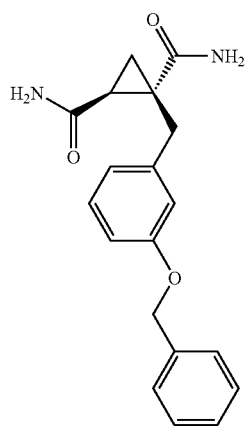 | 3.91 325 | 35A; 3A; 2B; 8C |

TABLE 1-continued
| | | | | | |
|---|---|---|---|---|---|
| GR | 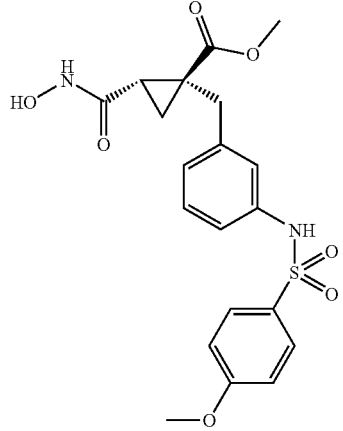 | 3.86 | 435 | 1H NMR (CDCl3): d 7.67 (m, 2H), 7.09-6.97 (m, 3H), 6.88 (m, 2H), 6.72 (m, 1H), 3.81 (s, 3H), 3.62 (s, 3H), 3.34 (m, 1H), 3.02 (m, 1H), 2.41-2.37 (m, 1H), 1.65-1.62 (m, 1H), 1.55-1.52 (m, 1H) | 36ABCE |
| GS | 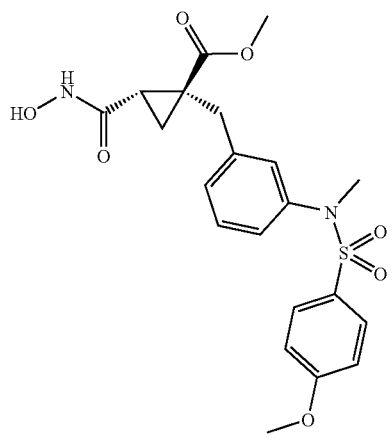 | 4.11 | 449 | 1H NMR (CDCl3): d 7.50 (m, 2H), 7.14-7.17 (m, 3H), 6.92 (m, 2H), 6.57 (m, 1H), 3.86 (s, 3H), 3.73 (m, 1H), 3.70 (s, 3H), 3.10 (s, 3H), 3.01-2.97 (m, 1H), 1.71-1.59 (m, 2H), 1.27-1.24 (m, 1H). | 36ABCDF |
| GT | 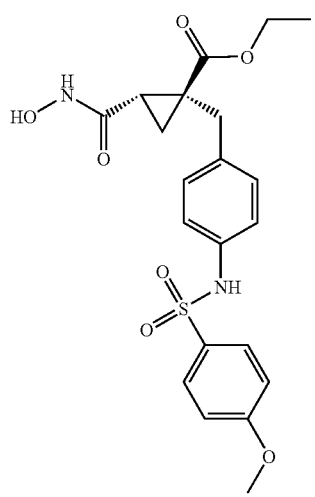 | 4.06 | 449 | 1H NMR (CD3OD): d 7.65-7.63 (m, 2H), 7.10-7.08 (m, 2H), 6.97-6.94 (m, 4H), 4.00 (q, 2H), 3.82 (s, 3H), 3.16-2.98 (m, 2H), 2.27-2.24 (m, 1H), 1.53-1.49 (m, 2H), 1.06 (m, 3H) | 37A |

TABLE 1-continued
| | | | | | |
|---|---|---|---|---|---|
| GU | 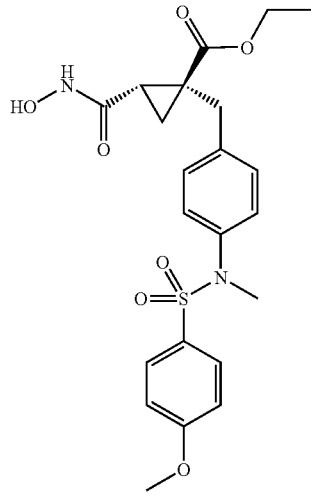 | 4.36 | 463 | 1H NMR (CD3OD): d 7.45-7.42 (m, 2H), 7.20-7.18 (m, 2H), 7.02-6.96 (m, 4H), 4.06 (q, 2H), 3.87 (s, 3H), 3.23-3.09 (m, 2H), 3.12 (s, 3H), 2.32-2.28 (m, 1H), 1.57-1.54 (m, 2H), 1.14 (m, 3H) | 37B |
| GV | 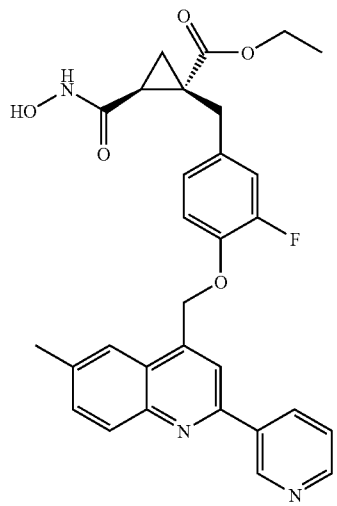 | 4.71 | 530 | | 38 |
| GW | 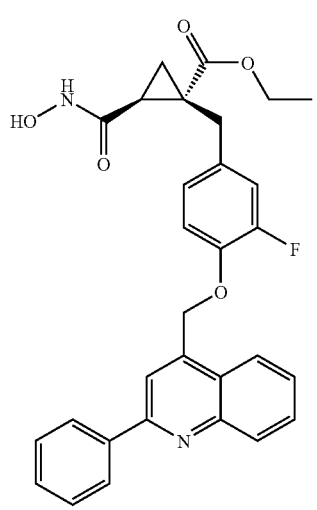 | 4.41 | 515 | | 38 |

| | | | | |
|---|---|---|---|---|
| GX | | 449 | 1HNMR (300 MHz, DMSO), d 10.74 (s, 1H), 8.79 (s, 1H), 8.07 (m, 1H), 7.95 (m, 1H), 7.74-7.59 (m, 1H), 7.58-7.53 (m, 1H), 7.51 (s, 1H), 7.05 (m, 2H), 6.96 (m, 2H), 5.53 (s, 2H), 3.63 (m, 1H), 3.46 (s, 3H), 3.05 (m, 1H), 2.63 (s, 3H), 1.97 (s, 1H), 1.34 (s, 3H), 1.03 (s, 3H) | 39 |
| GY | | 449 | 1HNMR (300 MHz, DMSO), d 10.42 (s, 1H), 8.71 (s, 1H), 8.08 (m, 1H), 7.95 (m, 1), 7.75-7.68 (m, 1H), 7.58-7.48 (m, 2H), 7.10 (m, 2H), 7.02 (m, 2H), 5.55 (s, 2H), 3.39 (s, 3H), 3.21 (m, 1H), 2.77 (m, 1H), 2.64 (s, 3H), 1.43 (s, 1H), 1.32 (s, 3H), 1.25 (s, 3) | 39 |
| GZ | | 434 | | 39A; 10B |
| HA | | 4.56 410 | | 1; 2B; 20 |
| HB | | 4.41 468 | | 1; 2B; 20 |

TABLE 1-continued
| HC | 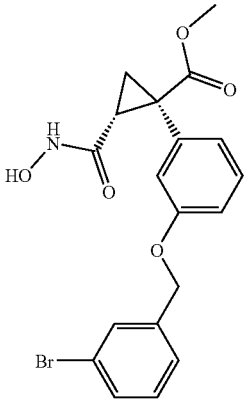 | 4.46 | 421 | 1; 2B; 20 |
| HD | 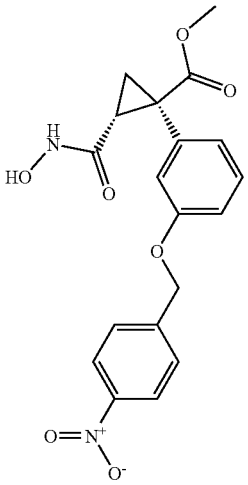 | 4.21 | 387 | 1; 2B; 20 |
| HE | 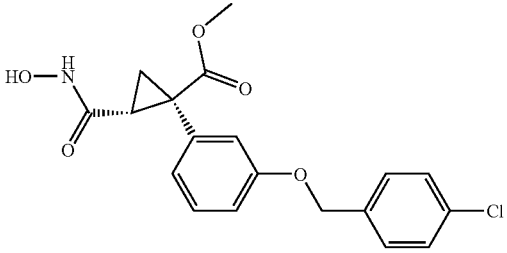 | 4.01<br>4.21<br>4.41 | 376 | 1; 2B; 20 |
| HF | 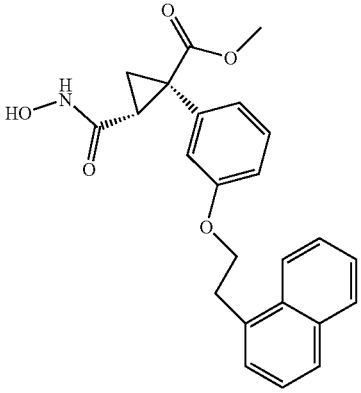 | 4.66 | 406 | 1; 2B; 20 |

TABLE 1-continued
| | | | | |
|---|---|---|---|---|
| HG | 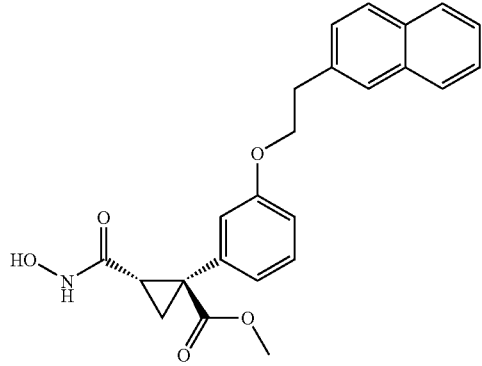 | 4.66 | 406 | 1; 2B; 20 |
| HH | 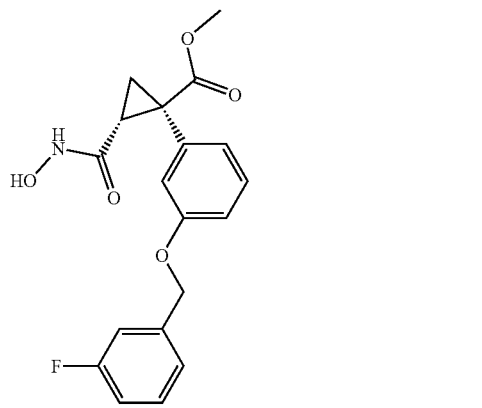 | 4.21 | 360 | 1; 2B; 20 |
| HI | 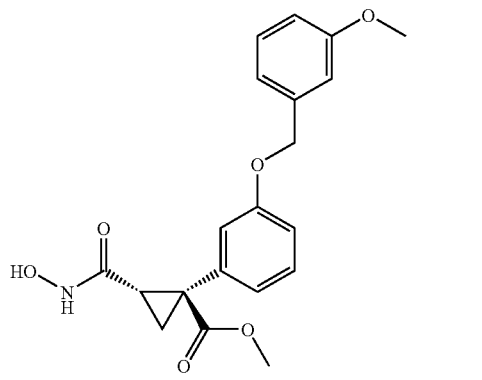 | 4.16 | 372 | 1; 2B; 20 |
| HJ | 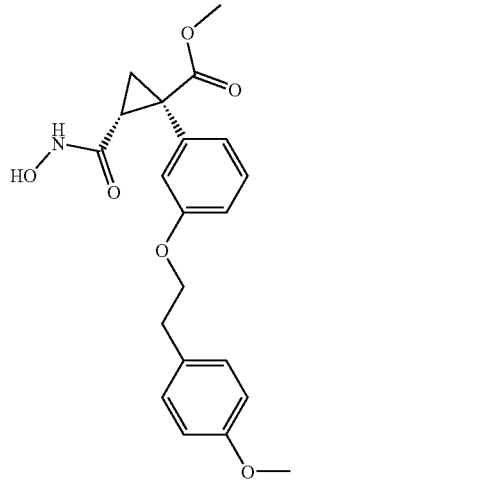 | 4.31 | 386 | 1; 2B; 20 |

TABLE 1-continued
| | | | |
|---|---|---|---|
| HK | 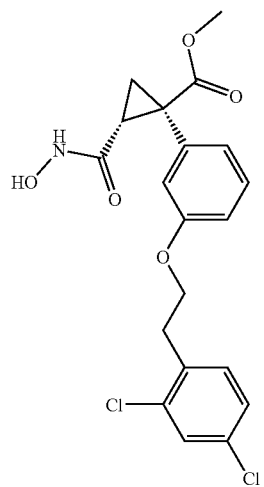 | 4.81 424 | 1; 2B; 20 |
| HL | 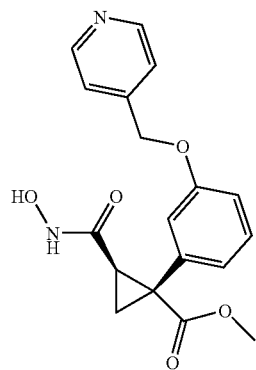 | 2.75 343<br>2.96 | 1; 2B; 20 |
| HM | 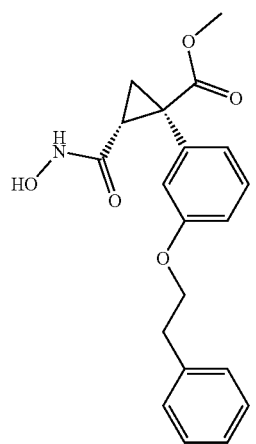 | 4.31 356 | 1; 2B; 20 |

TABLE 1-continued
| | | | | |
|---|---|---|---|---|
| HN 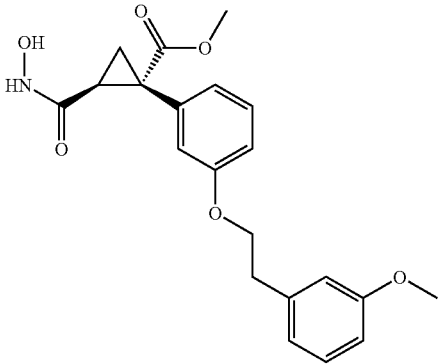 | 4.31 | 386 | | 1; 2B; 20 |
| HO 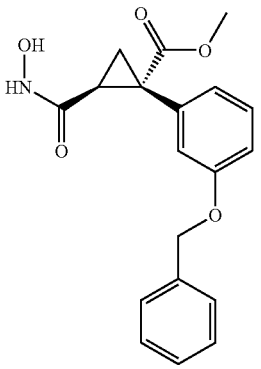 | 4.06 | 342 | 1H NMR (CD3CN): d 7.65-7.4 (m, 5H); 7.35 (m, 1H); 7.0 (m, 3H); 5.19 (m, 2H); 3.7 (s, 3H); 2.4 (m, 1H); 2.05 (m,); 1.85(m, 1H) | 1; 2B; 20 |
| HP 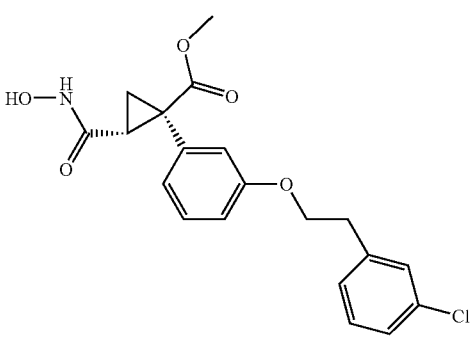 | 4.56 | 390 | | 1; 2B; 20 |
| HQ 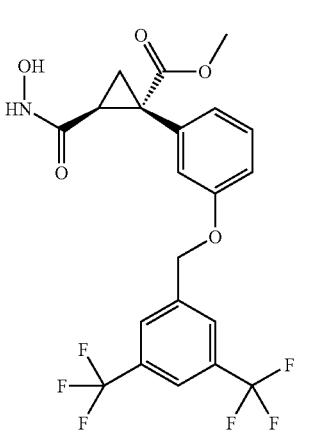 | 4.86 | 478 | | 1; 2B; 20 |

TABLE 1-continued

| | | | |
|---|---|---|---|
| HR | (structure) | 3.91  370 | 1; 2B; 20 |
| HS | (structure) | 3.96  318 | 1; 2B; 20 |
| HT | (structure) | 4.61  348 | 1; 2B; 20 |
| HU | (structure) | 2.91  343 | 1; 2B; 20 |

TABLE 1-continued

| | | | |
|---|---|---|---|
| HV | (structure) | 3.76  304 | 1; 2B; 20 |
| HW | (structure) | 4.11  320 | 1; 2B; 20 |
| HX | (structure) | 4.31  396 | 1; 2B; 20 |
| HY | (structure) | 3.76  306 | 1; 2B; 20 |

TABLE 1-continued
| | | | |
|---|---|---|---|
| HZ | 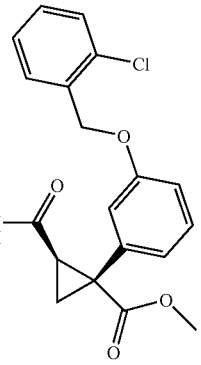 | 4.36 376 | 1; 2B; 20 |
| IA | 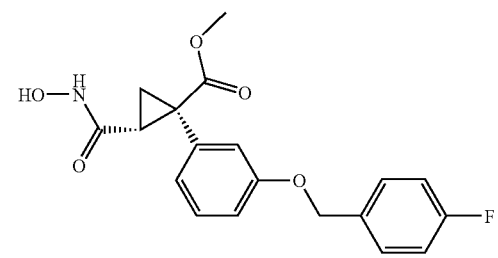 | 3.76 4.01 360 | 1; 2B; 20 |
| IB | 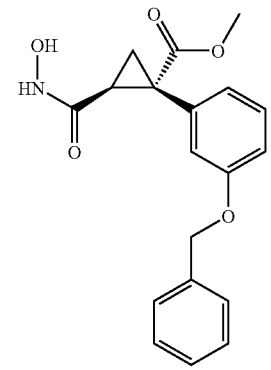 | 4.11 342 | 1; 2B; 20 |
| IC | 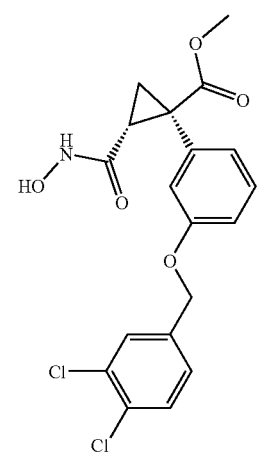 | 4.66 410 | 1; 2B; 20 |

TABLE 1-continued
| ID | | | | |
|---|---|---|---|---|
| ID | 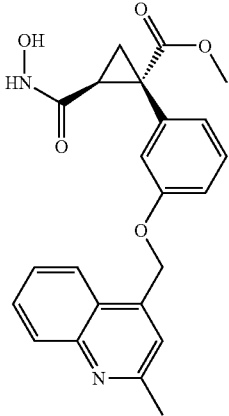 | 3.31 | 407 | 1H NMR (CD3CN): d 8.45 (d, 1H); 8.25-8.05 (m, 3H); 7.95 (m, 1H); 7.25 (m, 1H); 7.05-6.95 (m, 3H); 5.85 (m, 2H); 3.6 (s, 3H); 3.0 (s, 3H); 2.55 (m, 1H); 2.0 (m, 1H); 1.8 (m, 1H). | 1; 2B; 20 |
| IE | 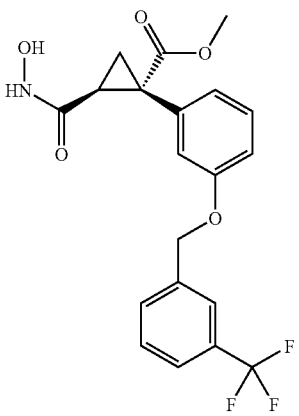 | 4.51 | 410 | | 1; 2B; 20 |
| IF | 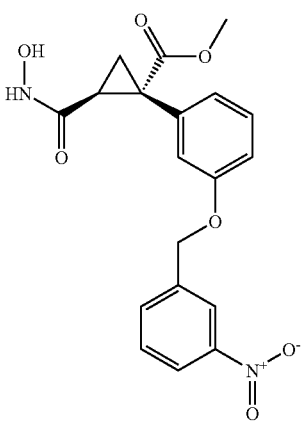 | 4.16 | 387 | | 1; 2B; 20 |

TABLE 1-continued

| | | | | |
|---|---|---|---|---|
| IG | [structure] | 2.86 | 392 | 1H NMR (CD3CN): d 8.45 (m, 1H); 8.25-8.05 (m, 3H); 7.95 (m, 1H); 7.25 (m, 1H); 7.05-6.95 (m, 3H); 5.85 (m, 2H); 3.0 (s, 3H); 2.55 (m, 1H); 2.0 (m, 1H); 1.8 (m, 1H). | 1; 2B; 20 |
| IH | [structure] | 4.18 | 387 | | 1; 2B; 20AB; 21 |
| II | [structure] | 4.35 | 378 | | 1; 2B; 20AB; 21 |
| IJ | [structure] | 4.31 | 356 | | 1; 2B; 20AB; 21 |
| IK | [structure] | 4.11 | 342 | | 1; 2B; 20AB; 21 |

TABLE 1-continued

| | Structure | | | |
|---|---|---|---|---|
| IL | (acetylphenoxy-phenyl cyclopropane hydroxamate methyl ester) | 3.78 | 370 | 1; 2B; 20AB; 21 |
| IM | (benzodioxol-oxy-phenyl cyclopropane hydroxamate methyl ester) | | 372 | 1; 2B; 20AB; 21 |
| IN | (methylphenoxy-phenyl cyclopropane hydroxamate methyl ester) | 4.11 | 342 | 1; 2B; 20AB; 21 |
| IO | (methoxyphenoxy-phenyl cyclopropane hydroxamate methyl ester) | 3.88 | 358 | 1; 2B; 20AB; 21 |
| IP | (cyanophenoxy-phenyl cyclopropane hydroxamate methyl ester) | 3.81 | 353 | 1; 2B; 20AB; 21 |

TABLE 1-continued
| | | | | |
|---|---|---|---|---|
| IQ | 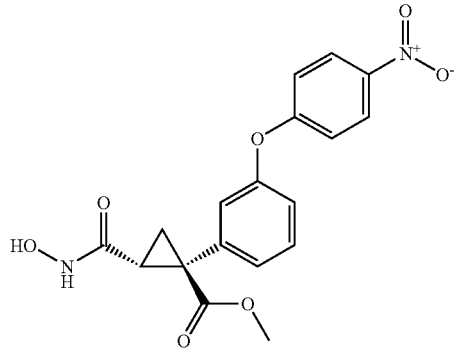 | 3.98 | 373 | 1; 2B; 20AB; 21 |
| IR | 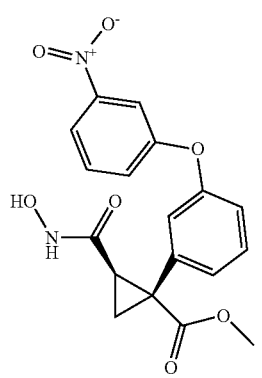 | 4.01 | 373 | 1; 2B; 20AB; 21 |
| IS | 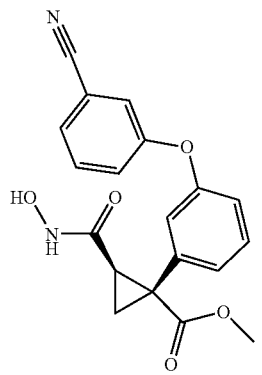 | 3.84 | 353 | 1; 2B; 20AB; 21 |
| IT | 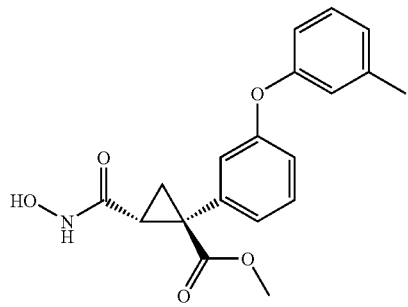 | 4.31 | 342 | 1; 2B; 20AB; 21 |

TABLE 1-continued
| IU | 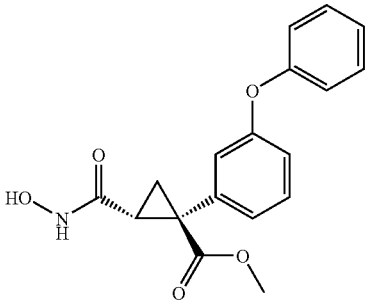 | 3.91 | 328 | 1; 2B; 20AB; 21 |
| IV | 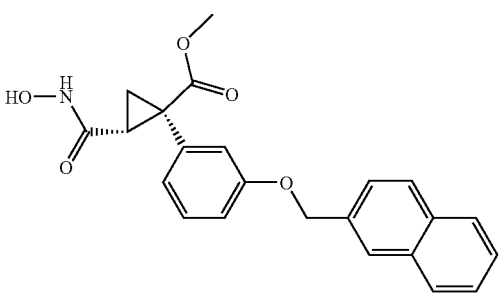 | 4.11, 4.36 | 392 | 1; 2B; 20AB; 21 |
| IW | 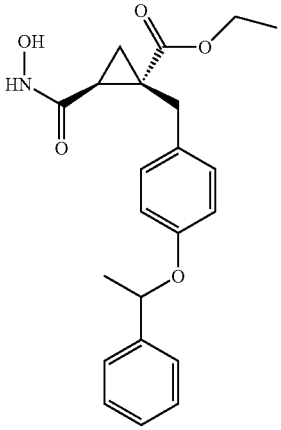 | 4.95 | 384 | 10ABC |
| IX | 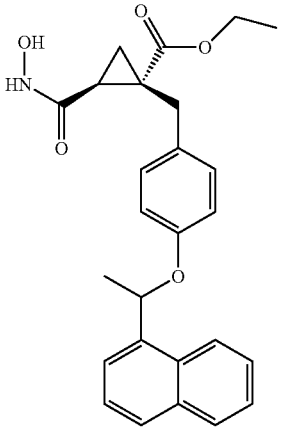 | | 434 | 10ABC |

| | | | | |
|---|---|---|---|---|
| IY 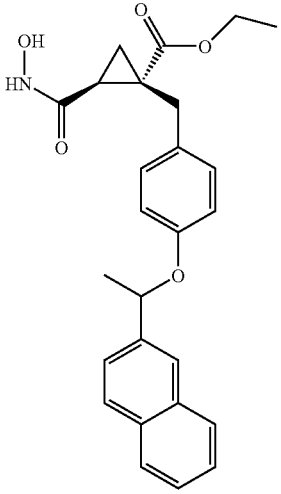 | | 434 | | 10ABC |
| IZ 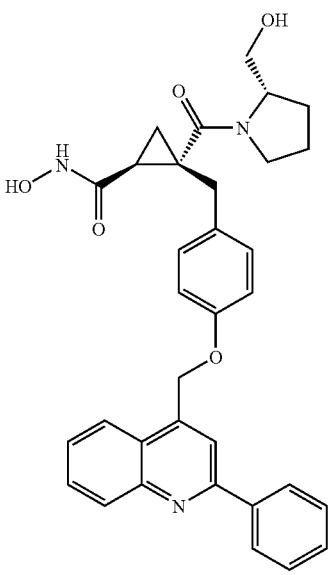 | 3.91 | 552 | 1H NMR (400 MHz, CD3OD): d 8.42-8.32 (m, 3H), 8.12-8.06 (m, 3H), 7.92 7.88 (m, 1H), 7.72-7.68 (m, 3H), 7.17 7.15 (m, 2H), 7.09-7.07 (m, 2H), 5.85 (s, 2H), 3.97-3.88 (m, 1H), 3.52-3.35 (m, 4H), 3.20-3.08 (m, 2H), 2.02-1.98 (m, 1H), 1.88-1.82 (m, 1H), 1.77 1 | 10ABD |
| JA 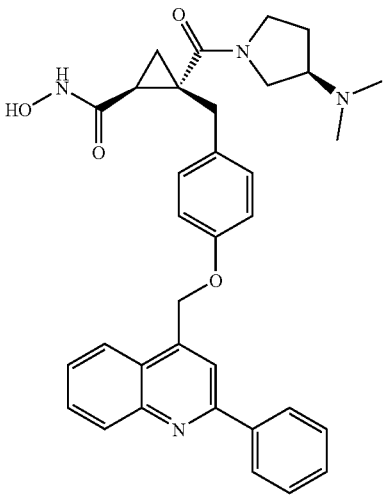 | 4.21 | 565 | 1H NMR (400 MHz, CD3OD): d 8.35-8.28 (m, 3H), 8.13-8.11 (m, 2H), 8.04 7.98 (m, 1H), 7.86-7.81 (m, 1H), 7.67 7.65 (m, 3H), 7.20-7.17 (m, 2H), 7.12 7.10 (m, 2H), 5.81 (s, 2H), 3.80-3.43 (m, 5H), 3.14-3.11 (m, 1H), 3.03-2.97 (m, 1H), 2.92-2.80 (m, 6H), 2.36 2 | 10ABD |

| | | | | | |
|---|---|---|---|---|---|
| JB | 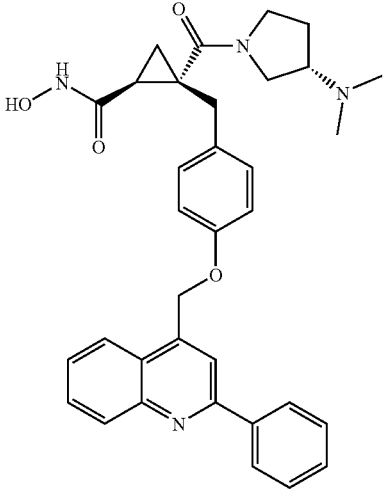 | 4.21 | 565 | | 10ABD |
| JC | 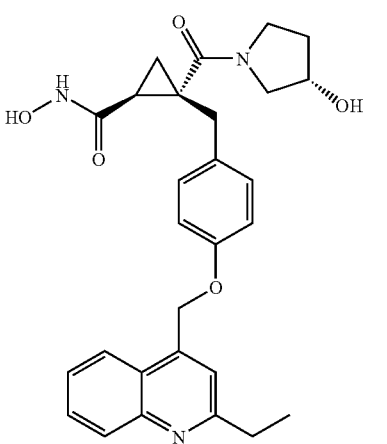 | 3.64 | 490 | 1HNMR (400 MHz, CD3OD): d 8.46-8.44 (m, 1H), 8.24-8.14 (m, 3H), 8.00 7.96 (m, 1H), 7.19-7.06 (m, 4H), 5.85 (s, 2H), 4.38-4.35 (m, 1H), 3.65-3.36 (m, 4H), 3.33-3.27 (m,), 3.15-2.99 (m, 2H), 1.96-1.78 (m, 3H), 1.54-1.45 (m, 5H). | 10ABD |
| JD | 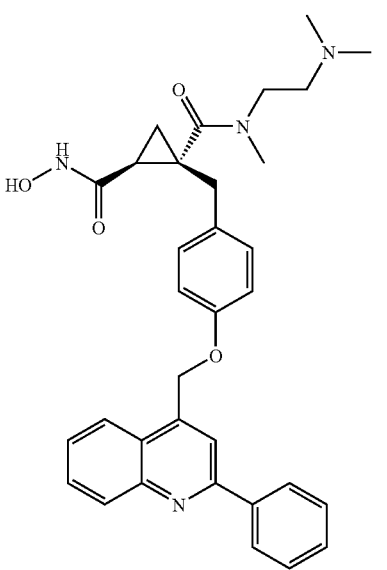 | 3.61 | 553 | 1H NMR (400 MHz, CD3OD): d 8.41-8.33 (m, 3H), 8.12-8.10 (m, 3H), 7.93 7.90 (m, 1H), 7.71 -7.69 (m, 3H), 7.18 7.10 (m, 4H), 5.85 (s, 2H), 3.63-3.49 (m, 2H), 3.1 6-3.09 (m, 7H), 2.92-2.78 (m, 6H), 2.03-2.01 (m, 1H), 1.53 1.51 (m, 1H), 1.45-1.42 (m, 1H). | 10ABD |

TABLE 1-continued
| | | | |
|---|---|---|---|
| JE 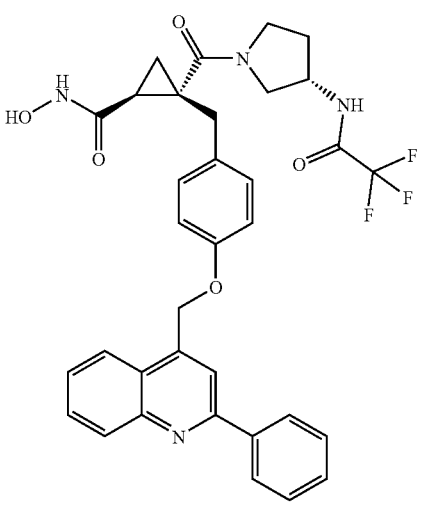 | 3.94 | 633 | 10ABD |
| JF 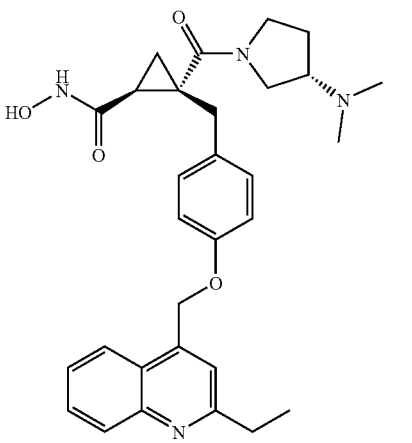 | 3.81 | 517 | 10ABD |
| JG 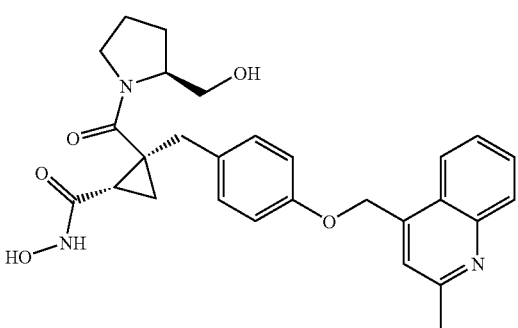 | 3.48 | 490 | 10ABD |

TABLE 1-continued

| | | | | |
|---|---|---|---|---|
| JH | | 3.11 | 406 | 1H NMR (CD3OD): d 8.44 (m, 1H); 8.16 (m, 3H); 7.97 (m, 1H); 7.27 (m, 2H); 7.09 (m, 2H);5.85 (s, 2H); 3.20 (m, 2H); 3.01 (s, 3H); 2.17-2.13 (m, 1H), 1.56-1.52 (m, 1H), 1.48-1.45 (m, 1H) | 10ABD |
| JI | | 3.21 | 476 | | 10ABD |
| JJ | | 3.21 | 476 | | 10ABD |
| JK | | 3.11 | 406 | | 10ABD |

TABLE 1-continued

| | | | |
|---|---|---|---|
| JL (structure) | 4.01 | 522 | 10ABD |
| JM (structure) | 3.91 | 439 | 12; 10AB; 2C; 3A; 3C |
| JN (structure) | 4.98 | 514 | 1H NMR (400 MHz, CD3OD): d 8.4 (d, 1H); 8.39 (s, 1H); 8.35 (m, 1H); 8.1 (m, 2H); 8.05 (m, 1H); 7.9 (m, 2H); 7.7 (m, 2H); 7.22 (m. 1H); 6.9-7.0 (m, 2H); 5.9 (s, 2H); 3.1 (br. 2H); 3.0 (br, 3H); 2.8 (br, 3H); 2.9 (m, 1H); 1.5 (m, 1H); 1.39 (m, 1H). | 12; 10ABD |

TABLE 1-continued
| | | | | |
|---|---|---|---|---|
| JO | 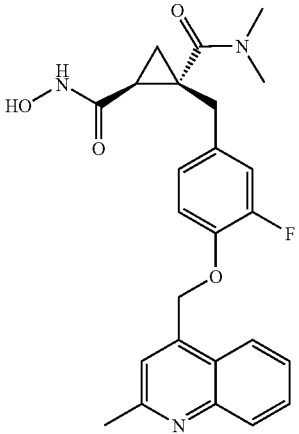 | 4.55 | 452 | 12; 10ABD |
| JP | 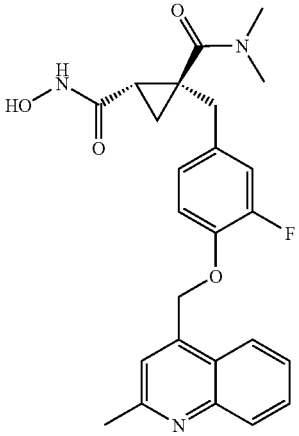 | 3.18 | 452 | 12; 10ABD |
| JQ | 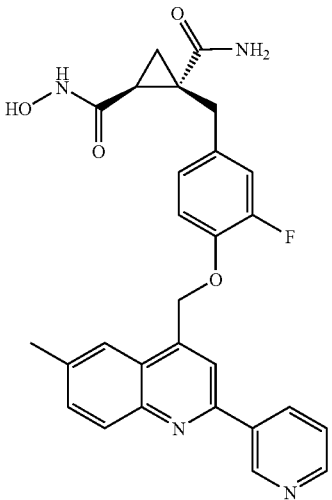 | 4.05 | 501 | 12; 10ABD |

TABLE 1-continued
| | | | | |
|---|---|---|---|---|
| JR 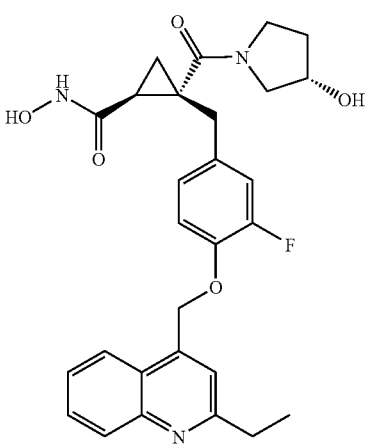 | 3.68 | 508 | 1HNMR (400 MHz, CD3OD): d 8.44-8.42 (m, 1H), 8.24-8.14 (m, 3H), 7.99-7.95 (m, 1H), 7.27-7.21 (m, 1H), 7.07-6.98 (m, 2H), 5.91 (s, 2H), 4.43-4.37 (m, 1H), 3.67-3.63 (m, 2H), 3.49-3.40 (m, 2H), 3.33-3.27 (m,), 3.16-3.03 (m, 2H), 1.94-1.86 (m, 2H), 1.54-1.46 (m, 6H). | 12; 10ABD |
| JS 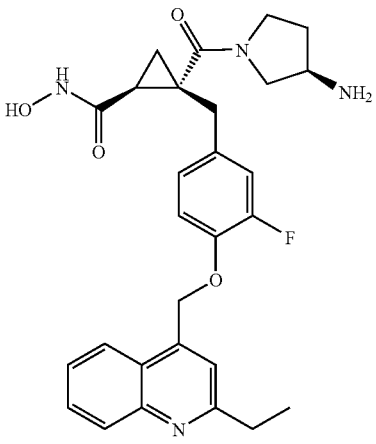 | 3.48 | 507 | | 12; 10ABD |
| JT 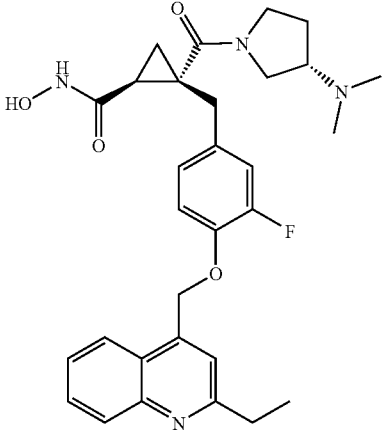 | 3.61 | 535 | | 12; 10ABD |

TABLE 1-continued
| | | | | |
|---|---|---|---|---|
| JU | 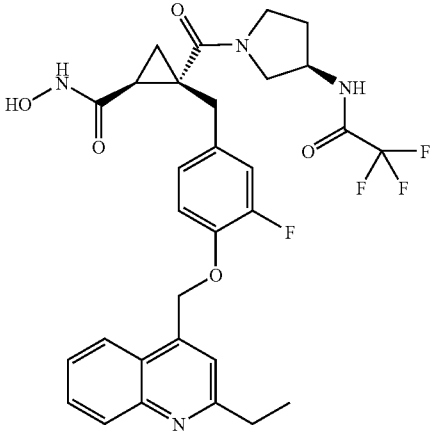 | 3.61 603 | | 12; 10ABD |
| JV | 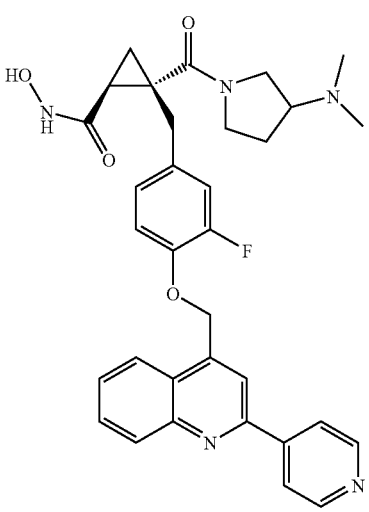 | 584 | | 12; 10ABD |
| JW | 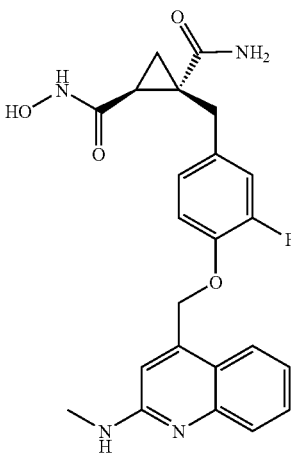 | 3.58 439 | 1HNMR (400 MHz, CD3OD): d 7.99-7.97 (m, 1H), 7.90-7.88 (m, 1H), 7.80-7.77 (m, 1H), 7.56-7.52 (m, 1H), 7.28 (s, 1H), 7.20-7.16 (m, 1H), 7.10-7.03 (m, 2H), 5.58 (s, 2H), 3.27-3.13 (m, 5H), 2.18-2.13 (m, 1H), 1.56-1.54 (m, 1H), 1.45-1.43 (m, 1H). | 14; 31 |
| JX | 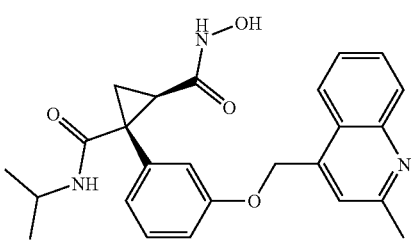 | 2.25 434 | | 2AB; 6 |

TABLE 1-continued
| | | | | |
|---|---|---|---|---|
| JY | 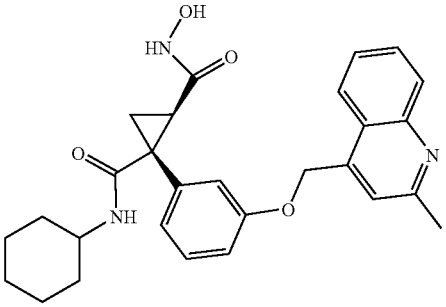 | 2.6 | 474 | 2AB; 6 |
| JZ | 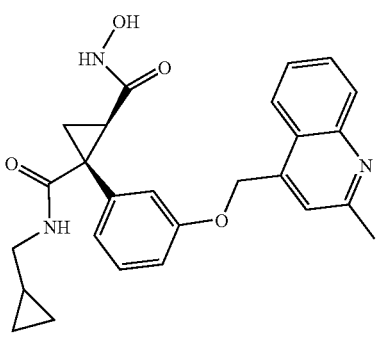 | 2.3 | 446 | 2AB; 6 |
| KA | 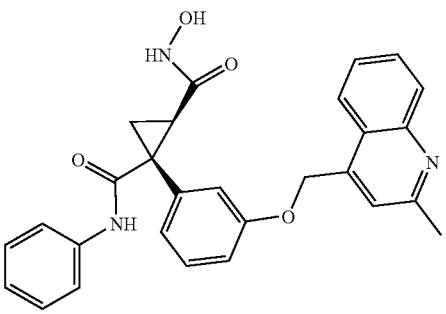 | 2.5 | 468 | 2AB; 6 |
| KB | 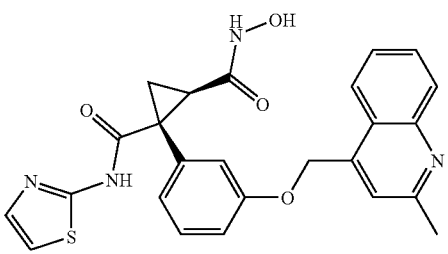 | 2.3 | 475 | 2AB; 6 |
| KC | 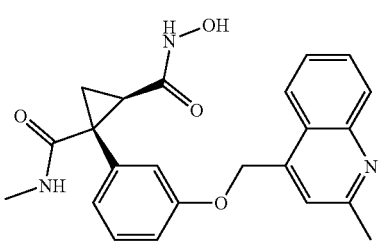 | 1.95 | 406 | 2AB; 6 |

TABLE 1-continued
| KD | 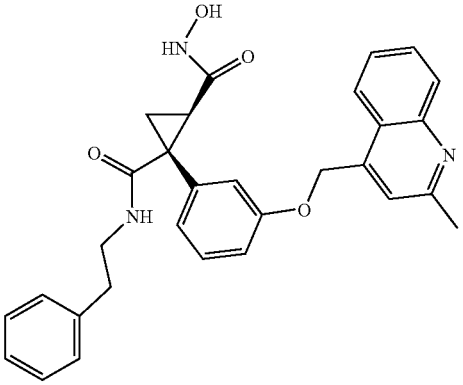 | 2.55 | 496 | 2AB; 6 |
| KE | 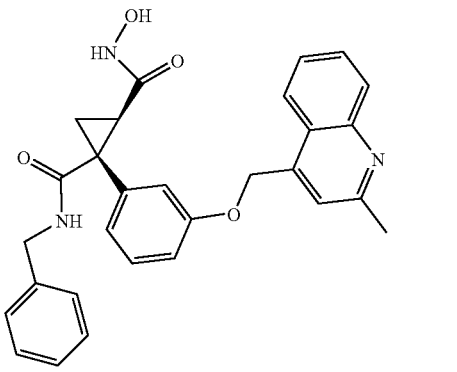 | 2.45 | 482 | 2AB; 6 |
| KF | 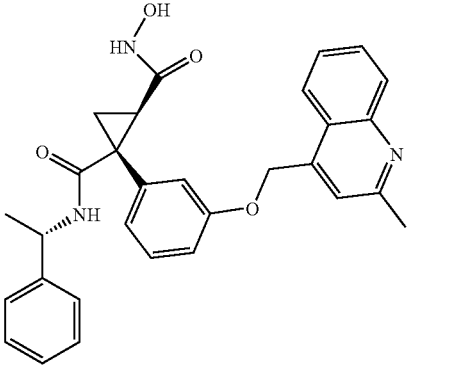 | 2.6 | 496 | 2AB; 6 |
| KG | 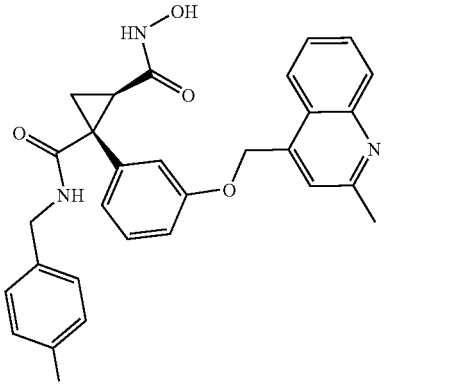 | 2.5 | 500 | 2AB; 6 |

TABLE 1-continued

| | | | |
|---|---|---|---|
| KH | (structure) | 1.85  483 | 2AB; 6 |
| KI | (structure) | 1.85  483 | 2AB; 6 |
| KJ | (structure) | 2.15  420 | 2AB; 6 |
| KK | (structure) | 2.6  496 | 2AB; 6 |

| | | | | |
|---|---|---|---|---|
| KL | | 1.8 | 475 | 2AB; 6 |
| KM | | 4.01 | 435 | 1; 7ABC; 8AB |
| KN | | 2.4 | 421 | 1; 7ABC; 8AB |
| KO | | 2.55 | 435 | 1; 7ABC; 8AB |
| KP | | 2.7 | 449 | 1; 7ABC; 8AB |

TABLE 1-continued
| | | | | |
|---|---|---|---|---|
| KQ | 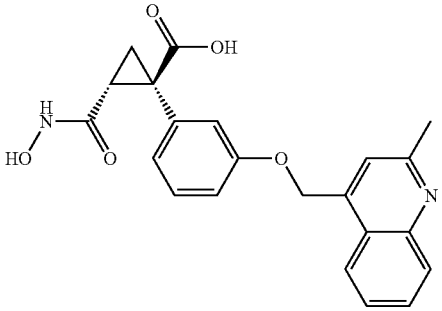 | 3.06 393 | | 1; 7ABC; 8A |
| KR | 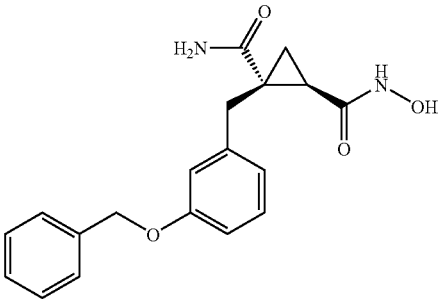 | 4.16 341 | 1H NMR (CD3CN): d 7.65-7.4 (m, 5H); 7.35 (m, 1H); 6.95 (m, 3H); 6.15 (br s, 1H); 5.95 (br s, 1H); 5.2 (s, 2H); 3.4-3.4 (m, 2H); 2.35 (m, 1H); 1.6 (m, 1H); 1.47 (m, 1H). | 35A; 7ABC; 8AC |
| KS | 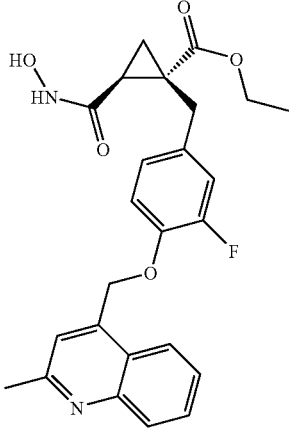 | 3.91 453 | 1H NMR (CD3OD): d 8.19 (m, 1H), 8.05 (m, 1H), 7.87 (m, 1H), 7.75 (s, 1H); 7.70 (m, 1H); 7.15 (m, 1H); 7.06 (m, 1H); 7.00 (m, 1H); 5.70 (s, 2H), 4.06 (m, 2H); (s, 3H), 3.02-3.21 (m, 2H), 2.79 (s, 3H), 2.26 (m, 1H), 1.53 (m, 2H), 1.14 (m, 3H) | 38 |
| KT | 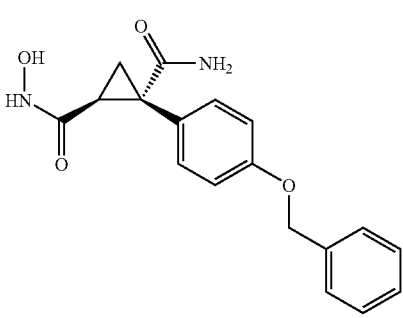 | 3.51 327 | 1H NMR (CD3CN): d 7.65-7.45 (m, 5H); 7.4 (m, 2H); 7.1 (m, 2H); 6.0 (br s, 1H); 5.65 (br s, 1H); 2.6 (m, 1H); 1.85 (m, 1H); 1.7 (m, 1H) | 4A; 2ABC; 3 |

TABLE 1-continued
| | | | | | |
|---|---|---|---|---|---|
| KU | 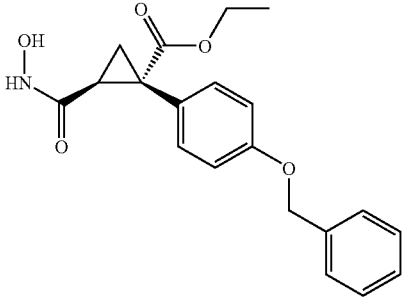 | 4.26 | 356 | 1H NMR (CD3CN): d 7.62-7.4 (m, 5H); 7.3 (m, 2H); 7.0 (m, 2H); 5.2 (s, 2H); 4.2 (m, 2H); 2.6 (m, 1H); 2.05 (m, 1H); 2.85 (m, 1H), 1.25 (m, 3H). | 4 |
| KV | 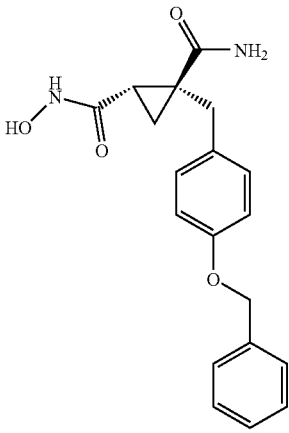 | 4.06 | 341 | 1H NMR (CD3CN:D20 (1:1)): d 7.40 7.29 (m, 5H), 7.12 (m, 2H), 6.88 (m, 2H), 5.03 (s, 2H), 3.08-2.85 (m, 2H), 2.06-2.02 (m, 1H), 1.50-1.46 (m, 1H), 1.38-1.35 (m, 1H) | 7ABC; 8Ac |
| KW | 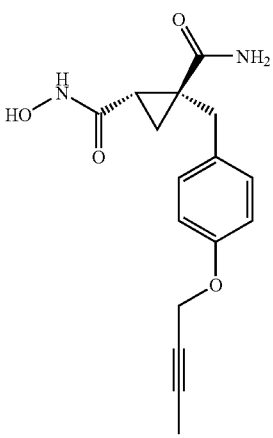 | 3.21 | 303 | 1H NMR (CD3OD): d 7.18 (m, 2H), 6.86 (m, 2H), 4.61 (s, 2H), 3.23-3.09 (m, 2H), 2.16-2.13 (m, 1H), 1.81 (m, 3H), 1.55-1.51 (m, 1H), 1.47-1.44 (m, 1H) | 7ABC; 8AC |

| | | | | |
|---|---|---|---|---|
| KX | [structure] | 4.65 | 468 | 1H NMR (400 MHz, CD3OD): d 8.43-8.33 (m, 3H), 8.12-8.09 (m, 3H), 7.94 7.90 (m, 1H), 7.73-7.68 (m, 3H), 7.28 7.26 (m, 2H), 7.11-7.09 (m, 2H), 5.85 (s, 2H), 3.27-3.12 (m, 2H), 2.16-2.12 (m, 1H), 1.56-1.53 (m, 1H), 1.47 1.44 (m, 1H) | 7ABC; 8AC |
| KY | [structure] | 3.85 | 538 | 1H NMR (400 MHz, CD3OD): d 8.40-8.30 (m, 3H), 8.12-8.04 (m, 3H), 7.90 7.87 (m, 1H), 7.69-7.67 (m, 3H), 7.18 7.06 (m, 4H), 5.84 (s, 2H), 4.35-4.28 (m, 1H), 3.63-3.37 (m, 3H), 3.22-2.96 (m, 3H), 1.90-1.66 (m, 3H), 1.54 1.51 (m, 1H), 1.46-1.42 (m, 1H). | 9; 10ABD |
| KZ | [structure] | 3.78 | 537 | 1HNMR (400 MHz, CD3OD): d 8.46-8.49 (m, 3H), 8.18-8.09 (m, 3H), 8.00 7.96 (m, 1H), 7.79-7.70 (m, 3H), 7.17 7.09 (m, 4H), 5.87 (s, 2H), 3.85-3.39 (m, 5H), 3.12-3.03 (m, 2H), 2.28-2.16 (m, 1H), 2.00-1.95 (m, 2H), 1.54 1.35 (m, 2H). | 9; 10ABD |

TABLE 1-continued
| | | | | | |
|---|---|---|---|---|---|
| LA | 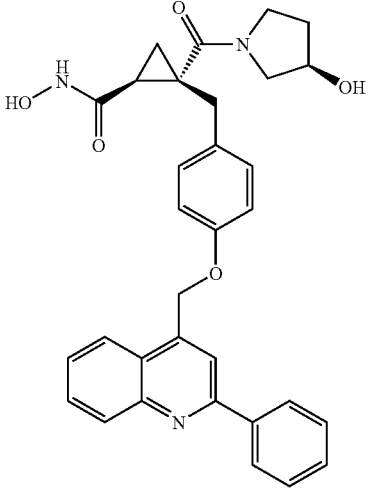 | 3.81 | 538 | 1H NMR (400 MHz, CD3OD): d 8.39-8.29 (m, 3H), 8.12-8.03 (m, 3H), 7.90 7.84 (m, 1H), 7.69-7.67 (m, 3H), 7.17 7.06 (m, 4H), 5.83 (s, 2H), 4.30-4.27 (m, 1H), 3.62-3.39 (m, 3H), 3.26-3.08 (m, 3H), 2.01 -1.63 (m, 3H), 1.55 1.45 (m, 1H), 1.37-1.29 (m, 1H). | 9; 10ABD |
| LB | 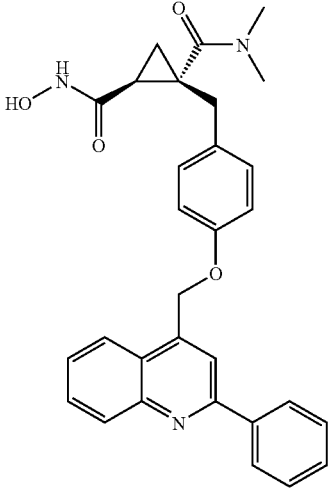 | 4.91 | 496 | 1H NMR (400 MHz, CD3QD): d 8.46-8.35 (m, 3H), 8.1 6-8.10 (m, 3H) 7.97-7.94 (m, 1H), 7.77-7.71 (m, 3H), 7.14 7.08 (m, 4H), 5.89 (s, 2H), 3.07 (s, 2H), 2.96 (s, 3H), 2.78 (s, 3H), 1.93-1.86 (m, 1H), 1.53-1.50 (m, 1H), 1.36 1.33 (m, 1H) | 9; 10ABD |
| LC | 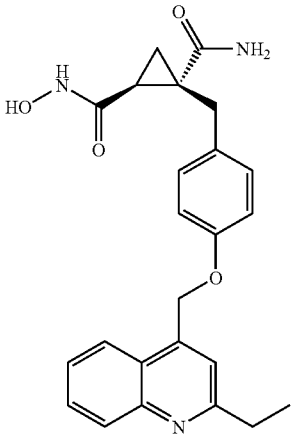 | 3.84 | 420 | | 9; 10ABD |

TABLE 1-continued
| LD | 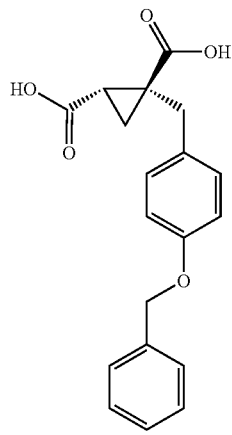 | 4.66 327 | 6A; 8A |
| LE | 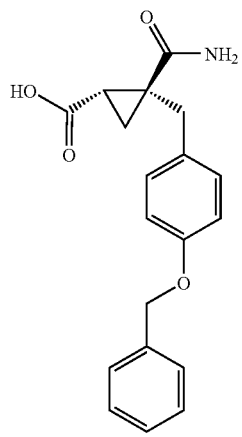 | 326 | 5AB; 8A; 3B; 2B |
| LF | 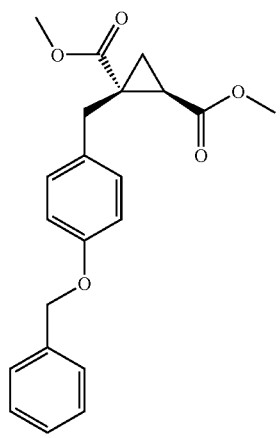 | 4.76 355 | 6A; 9C |

TABLE 1-continued
| | | | |
|---|---|---|---|
| LG | 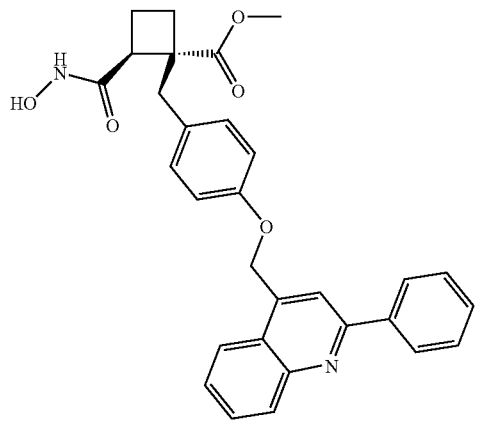 | 497 | 43 |
| LH | 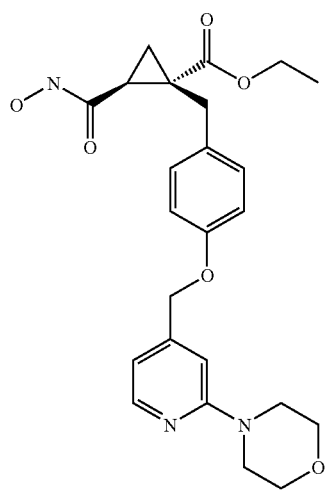 | 456 | 15 |
| LI | 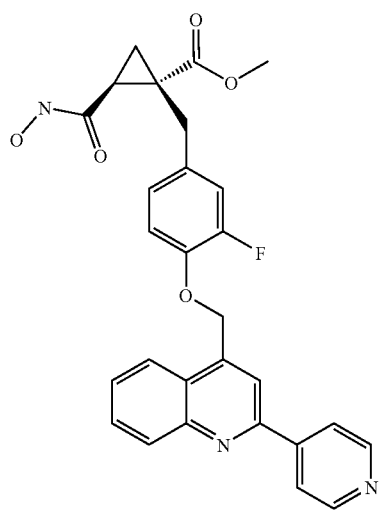 | 502 | 30B |

TABLE 1-continued
| | | | |
|---|---|---|---|
| LJ 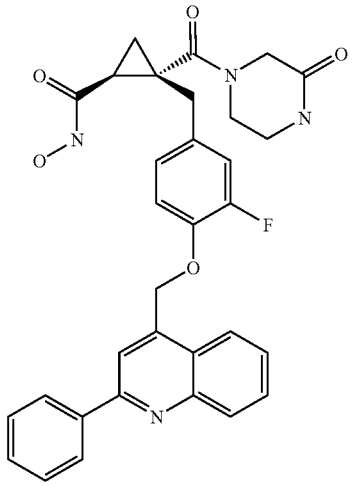 | | 569 | 12ABC, 13, 33, 3 |
| LK 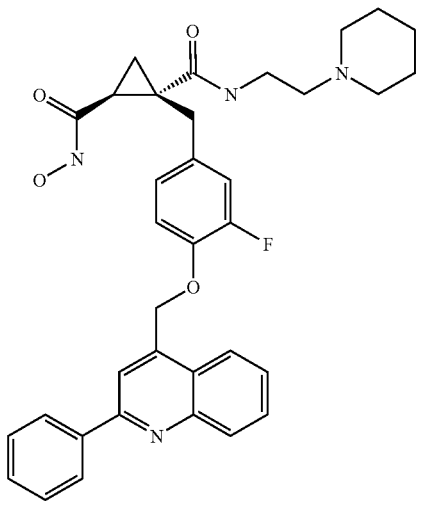 | | 597 | 12ABC, 13, 33, 3 |
| LL 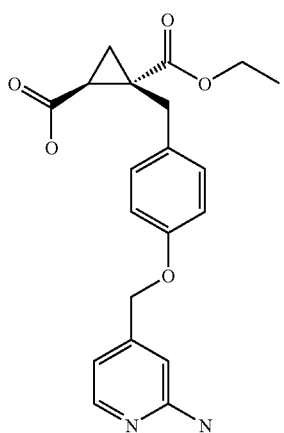 | | 371 | 15 |

TABLE 1-continued

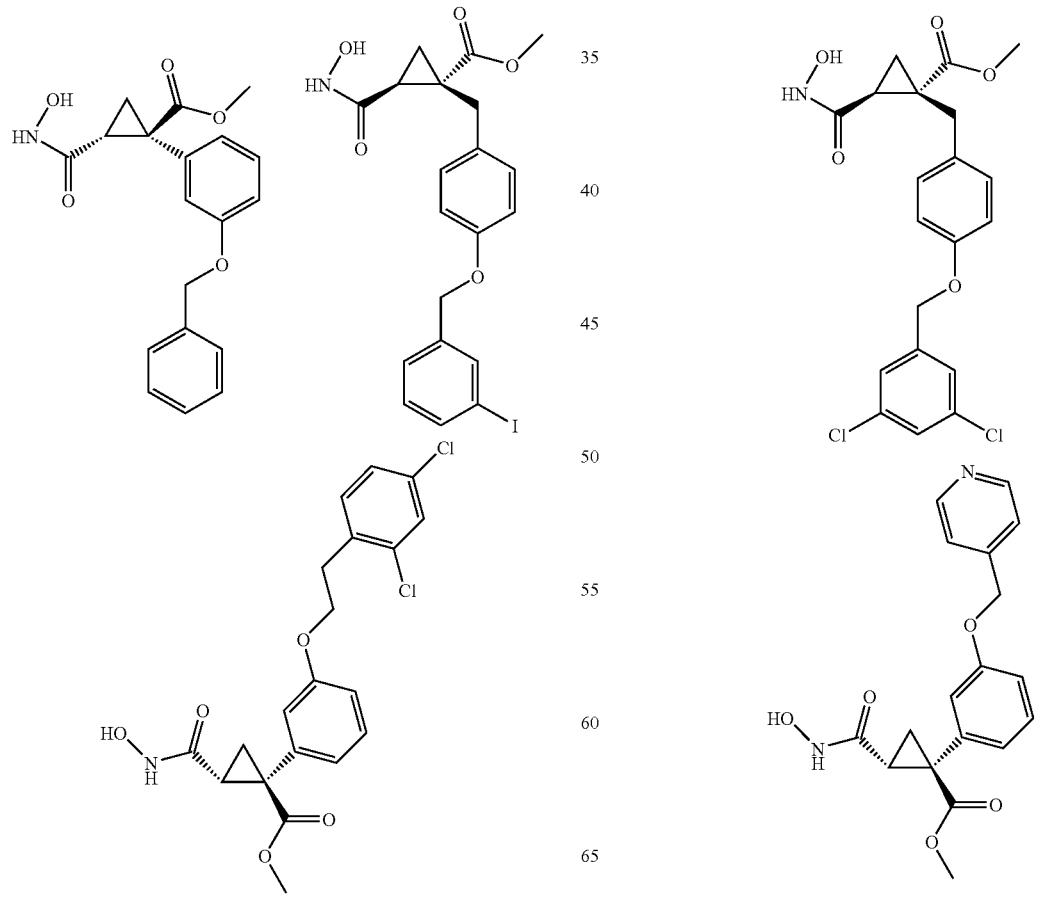

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

Therefore, we claim:

1. A compound selected from the group consisting of:

265 266
-continued -continued
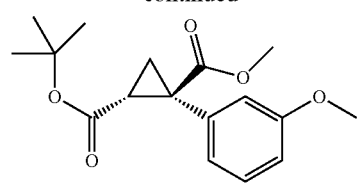
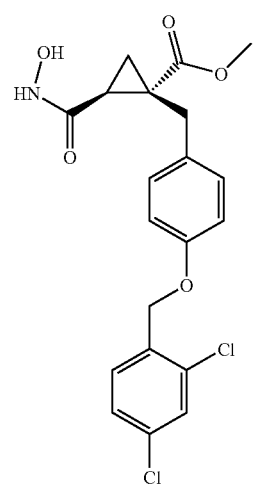
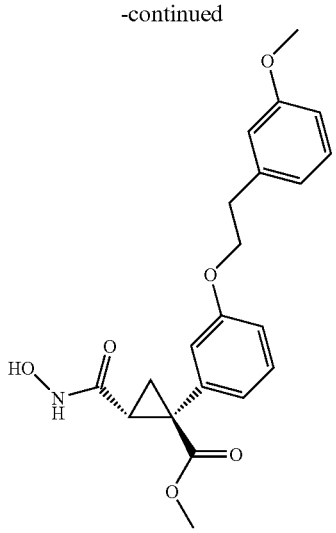
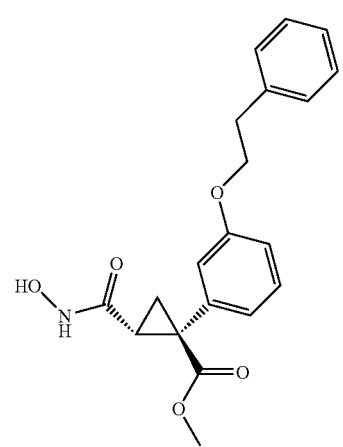
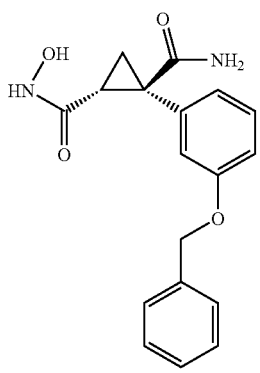
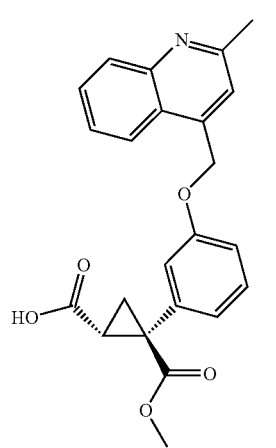 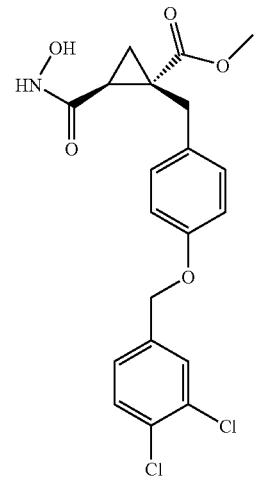 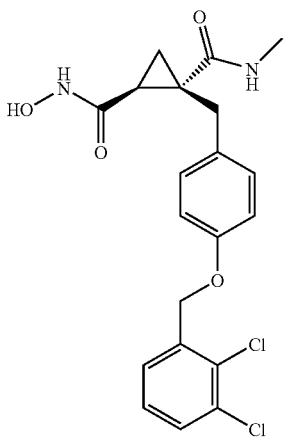

267
-continued
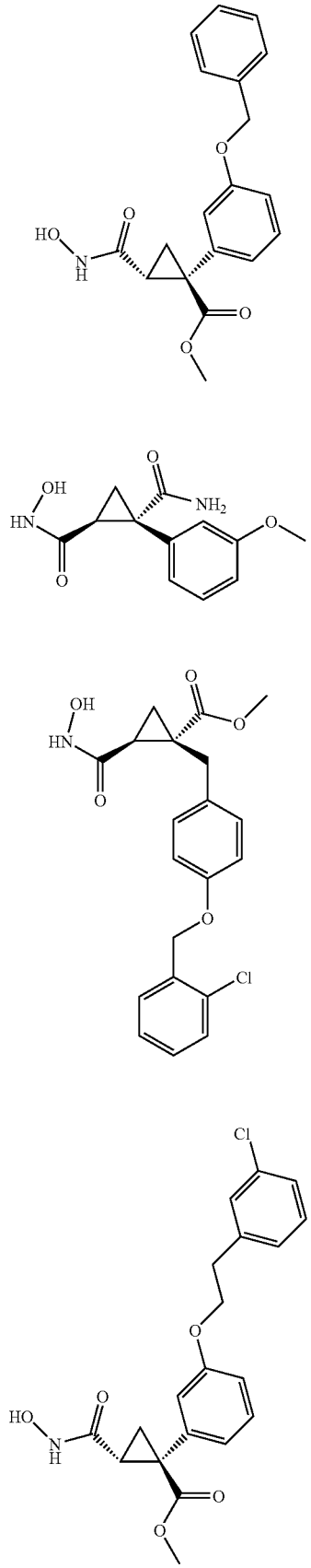
268
-continued
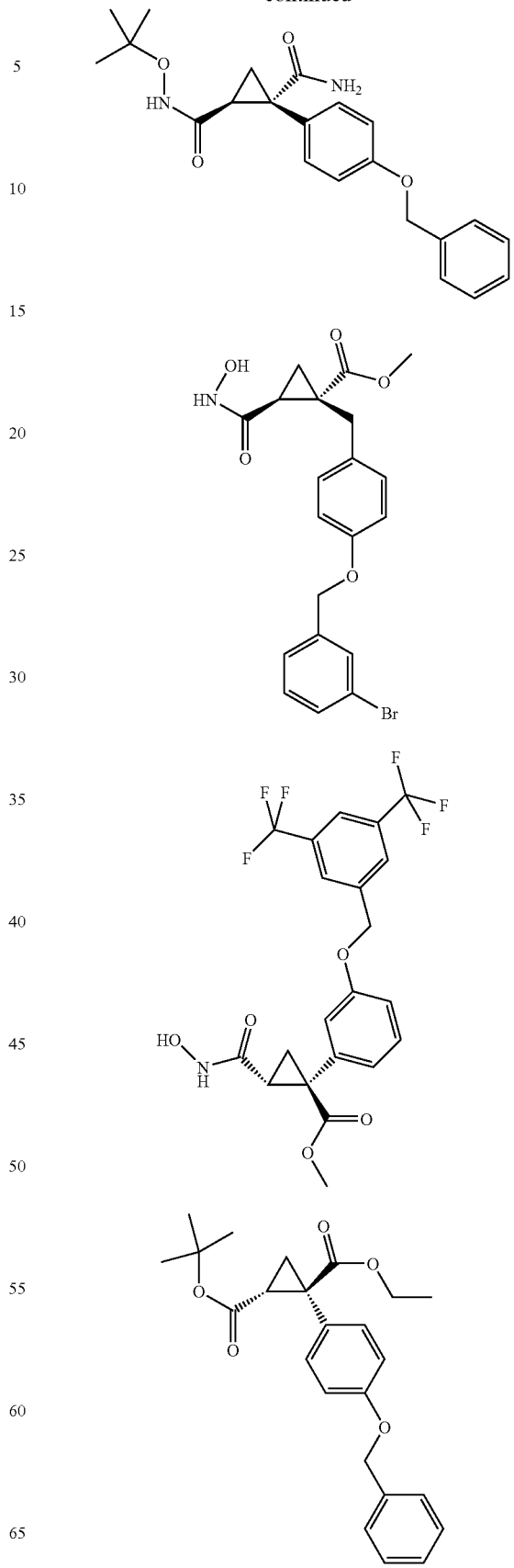

269
-continued
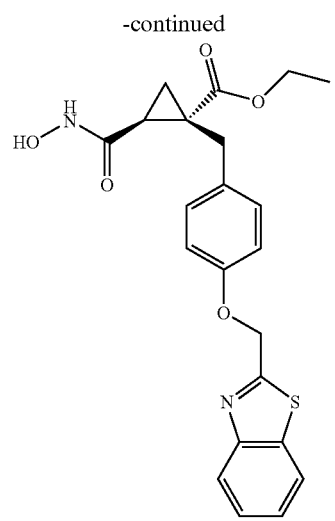
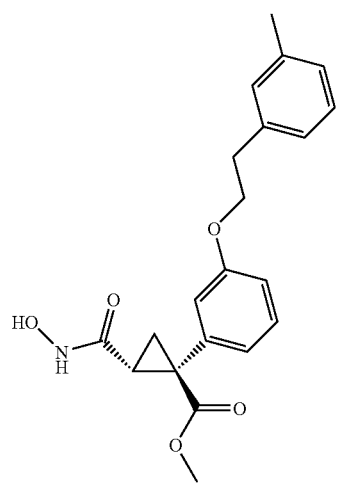
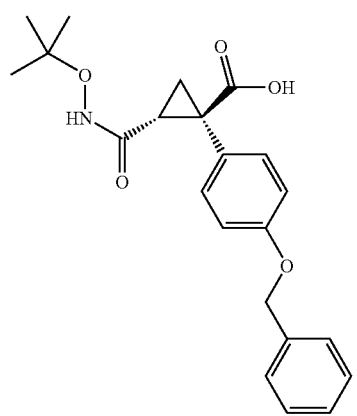
270
-continued
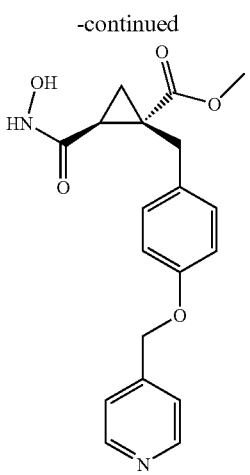
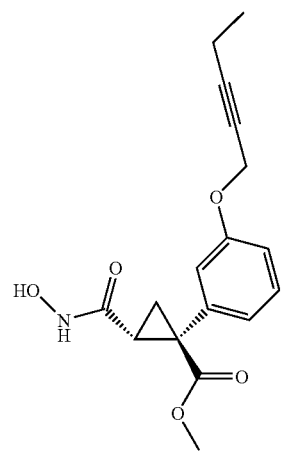
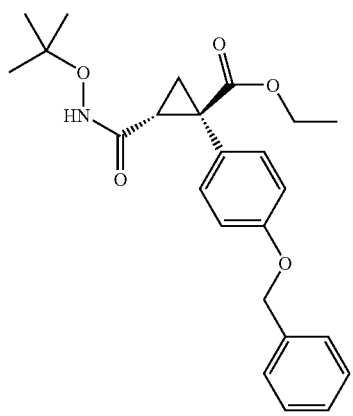

271
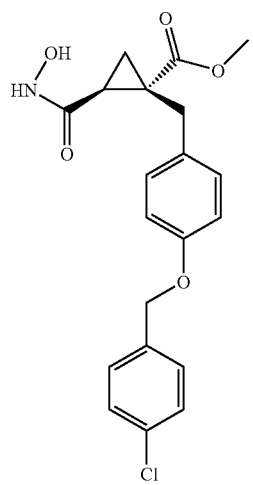
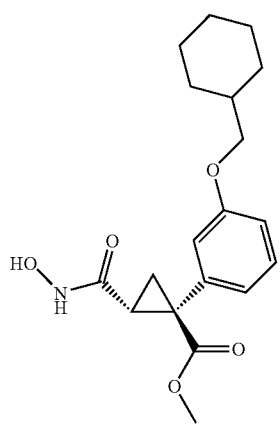
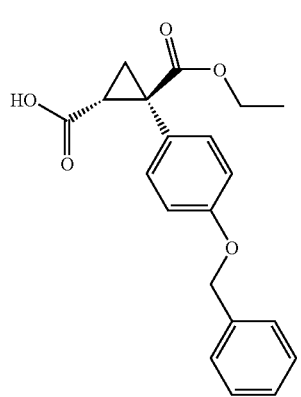
272
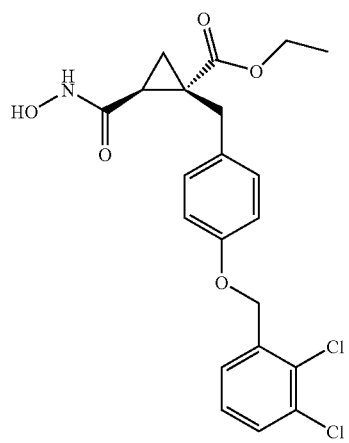
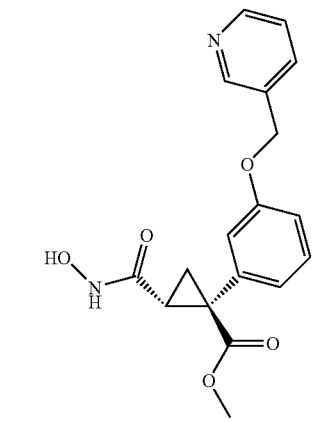
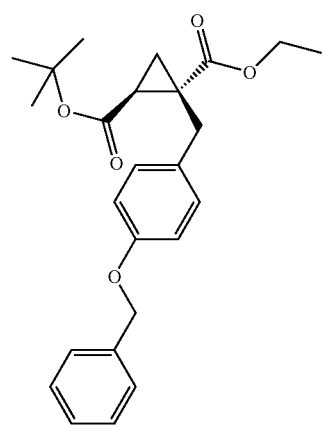

273
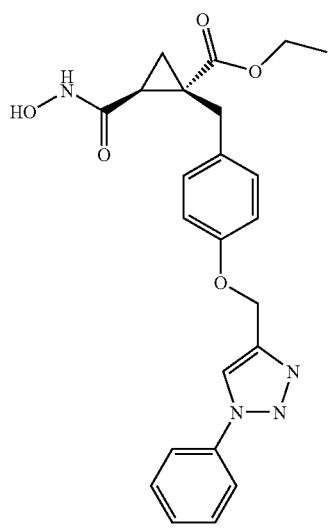
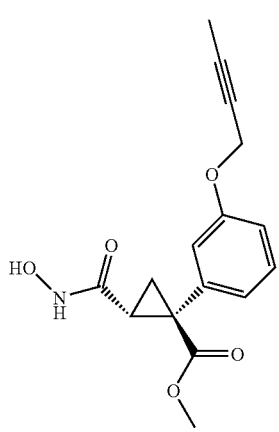
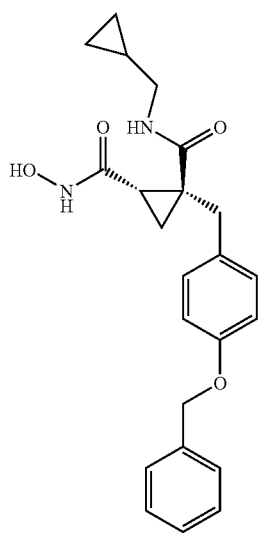
274
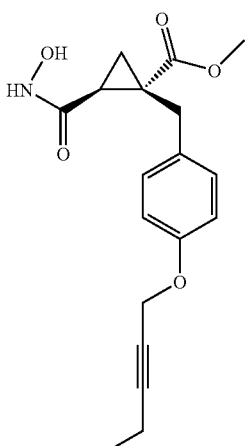
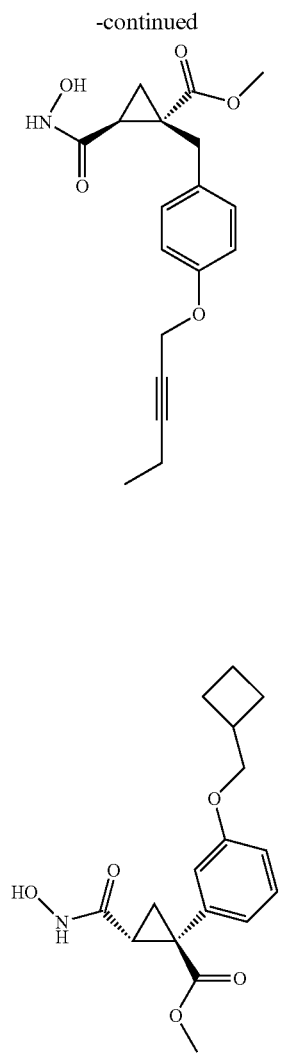
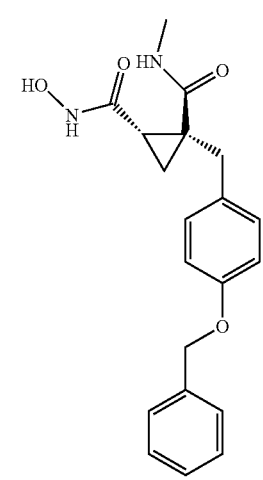

275
-continued
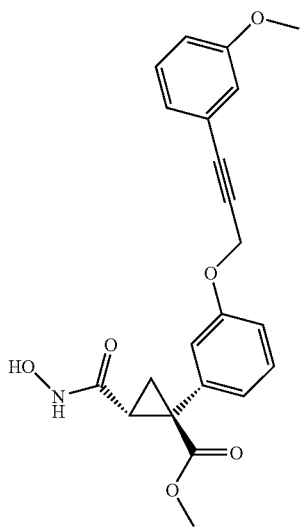
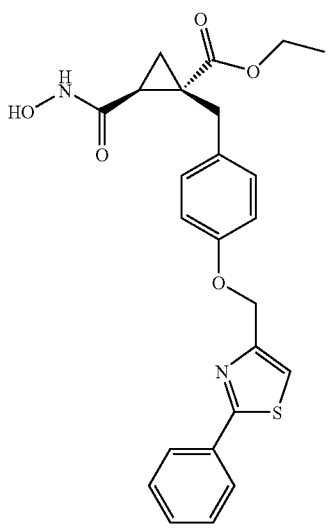
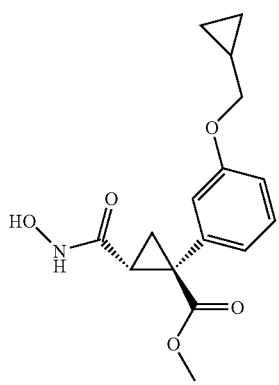
276
-continued
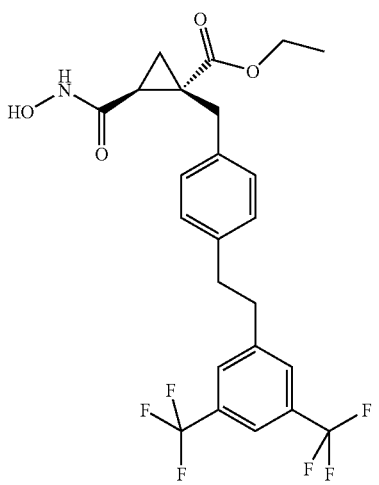
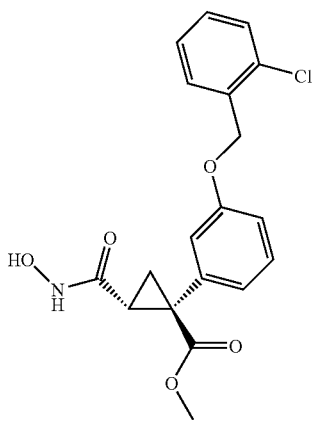
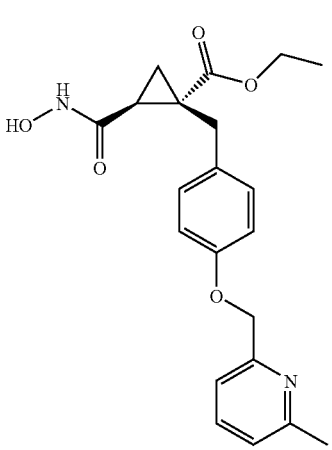

277
-continued
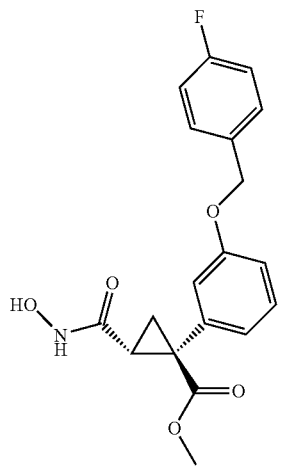
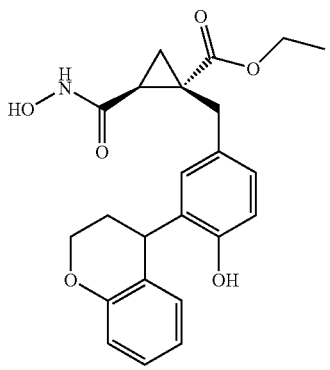
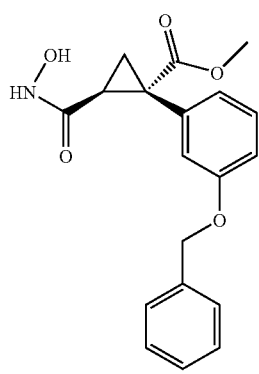
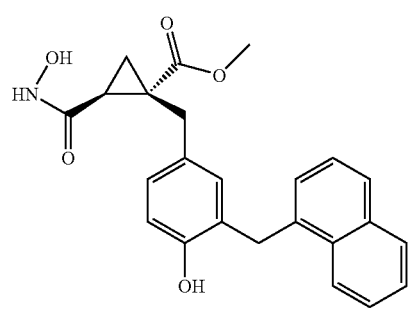
278
-continued
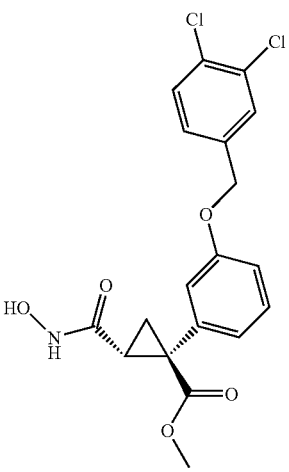
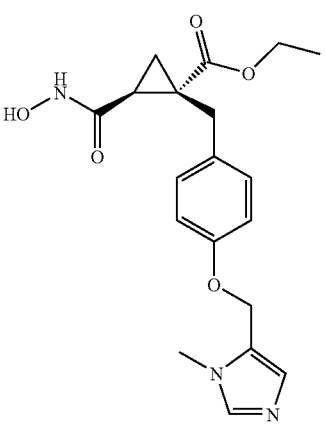
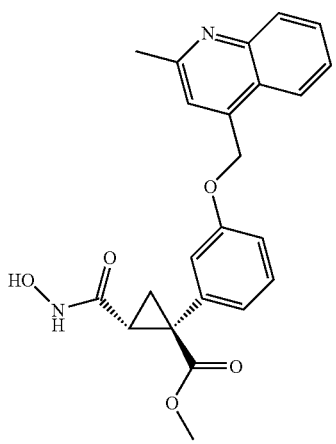

279
-continued
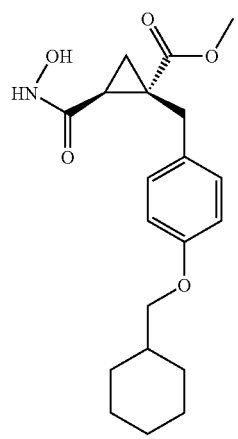
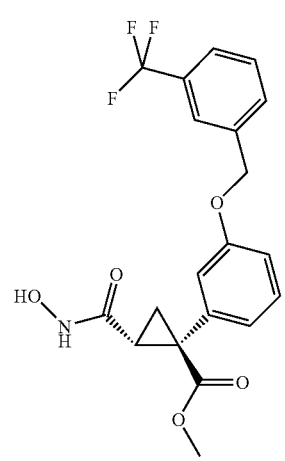
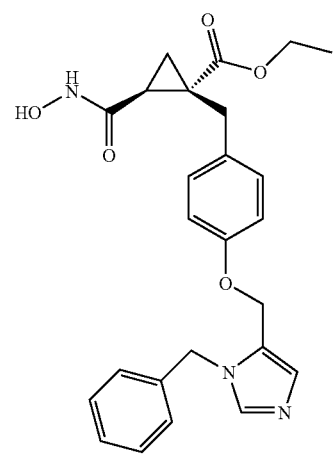
280
-continued
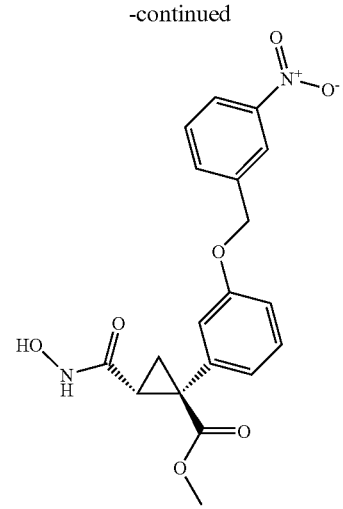
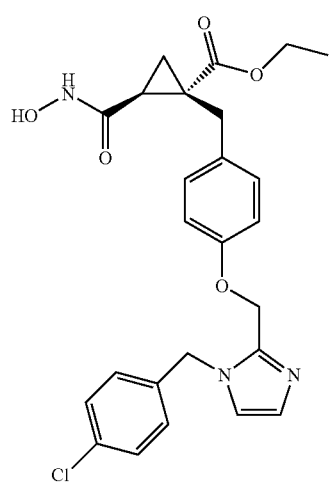
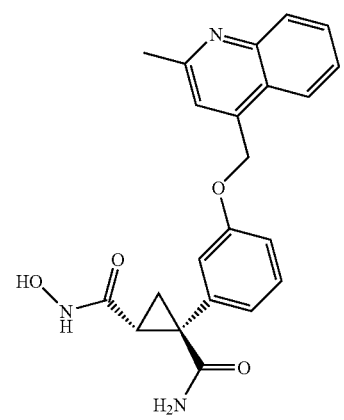

281
-continued
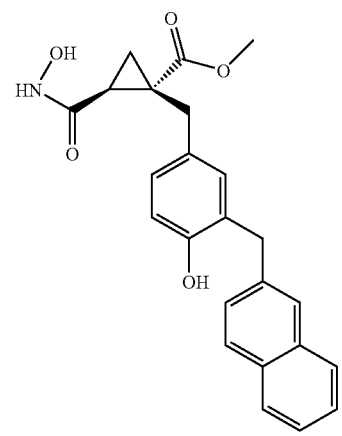
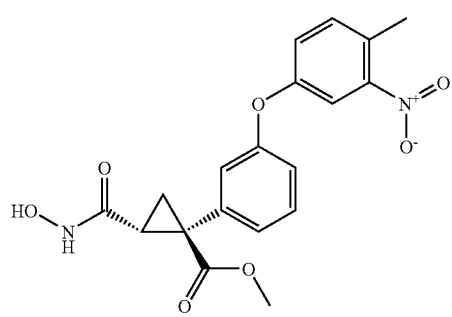
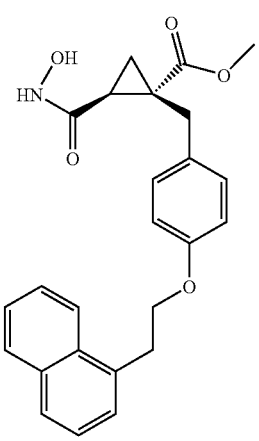
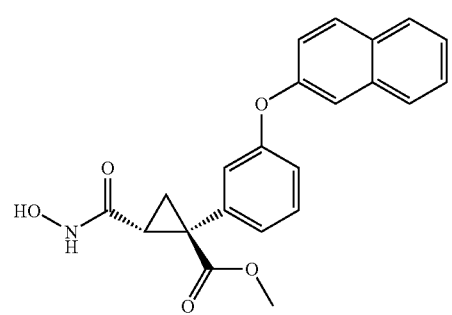
282
-continued
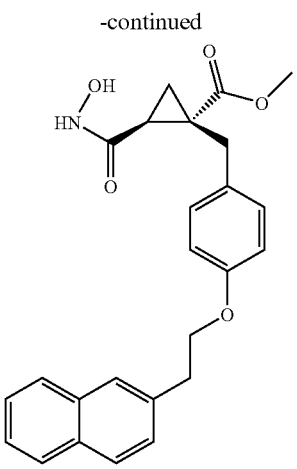
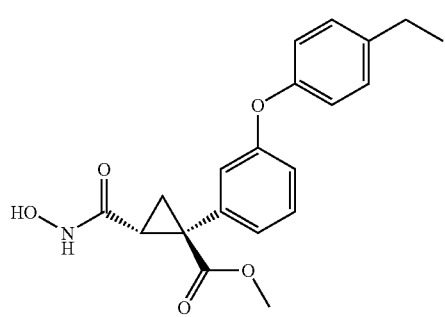
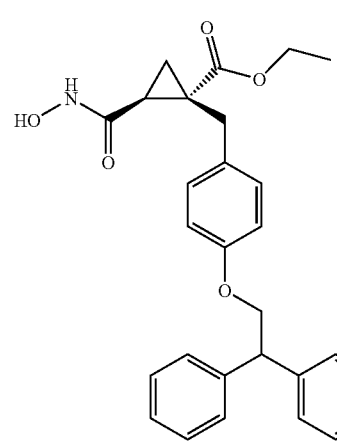
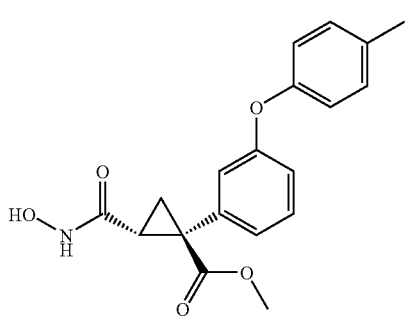

283
-continued
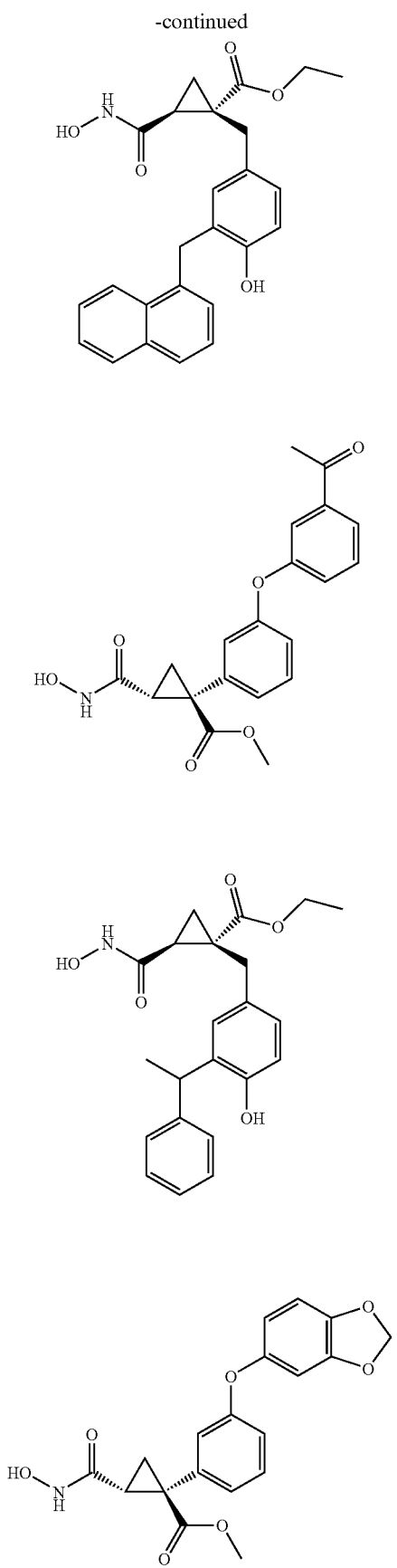
284
-continued
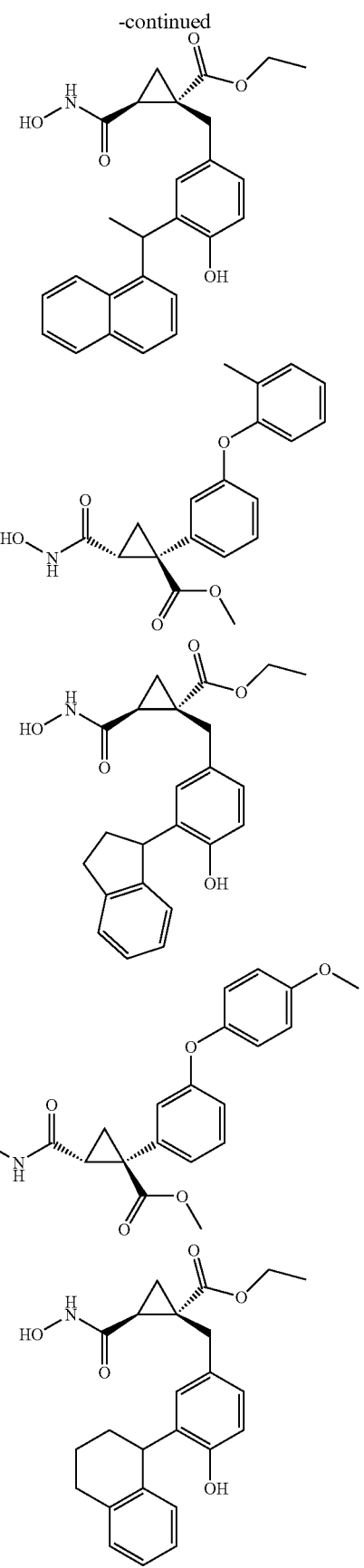

-continued
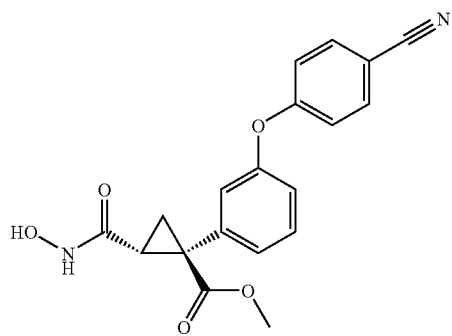
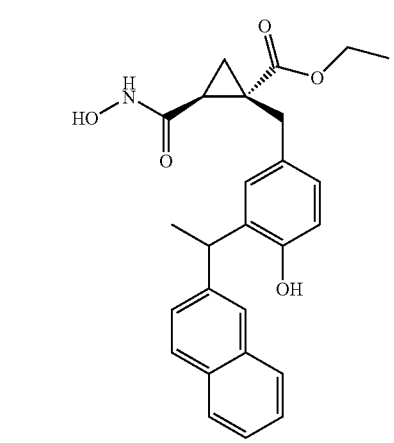
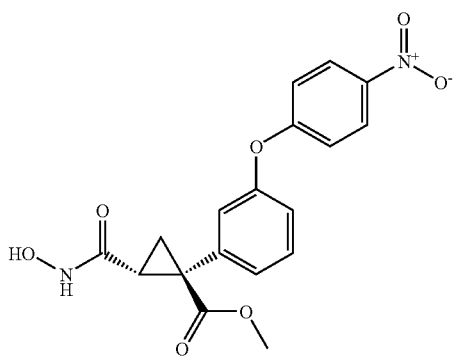
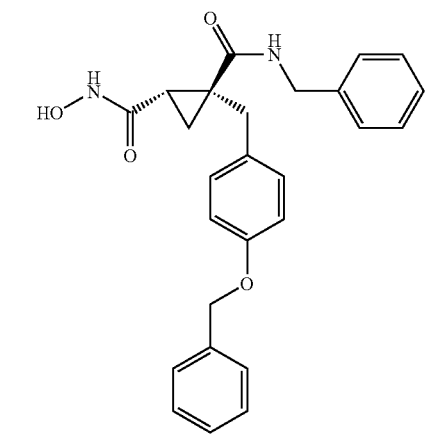
-continued
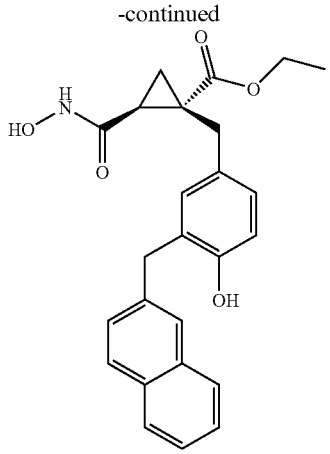
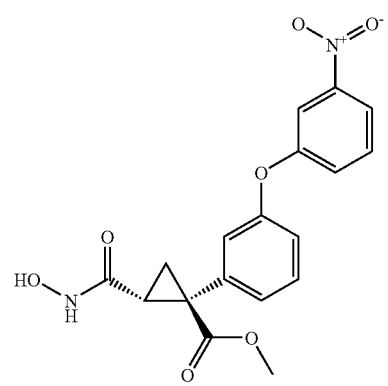
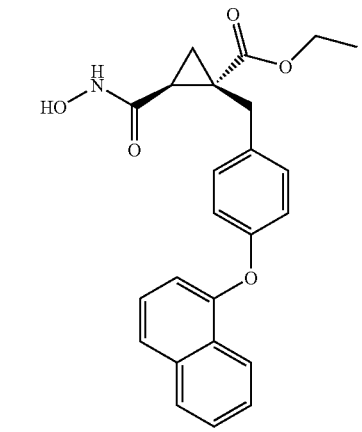
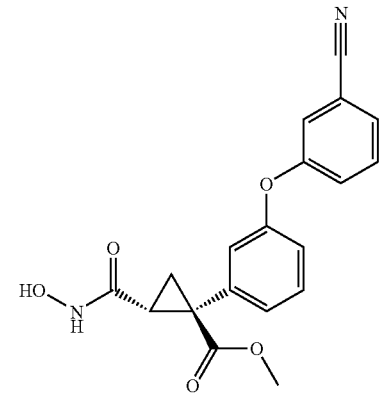

-continued
287
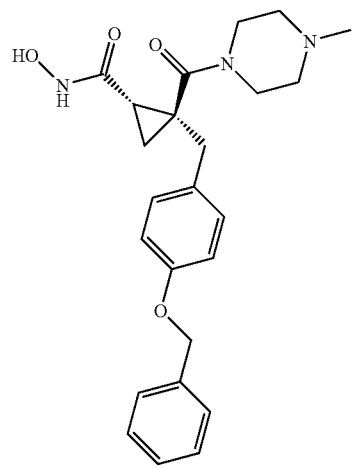
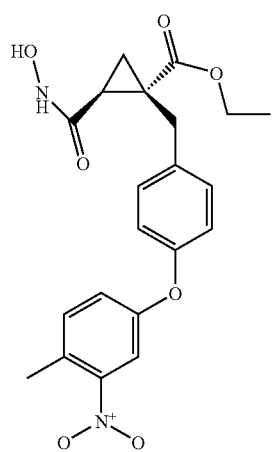
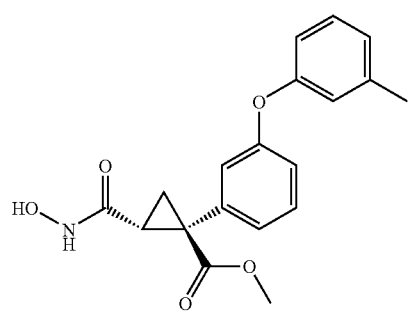
288
-continued
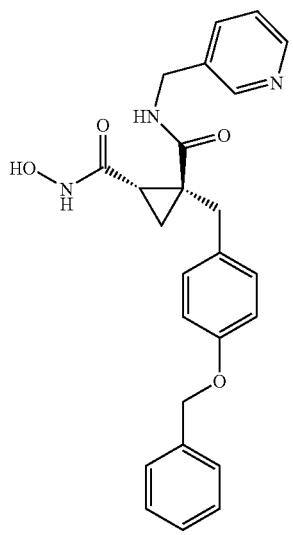
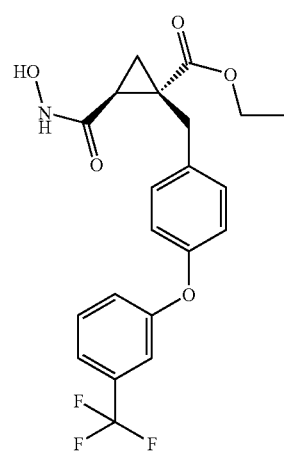
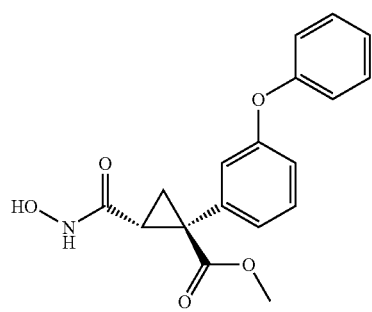

289
-continued
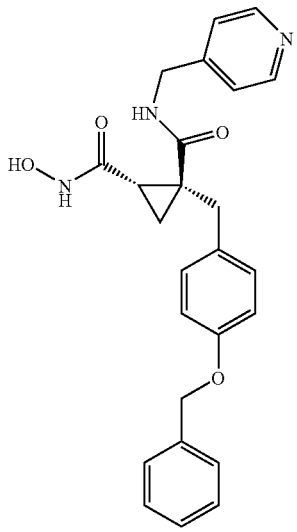
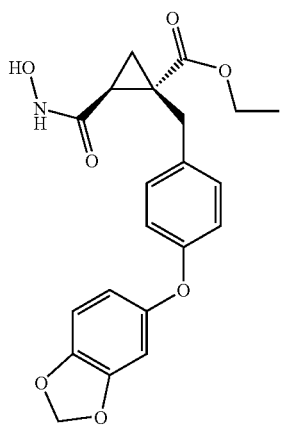
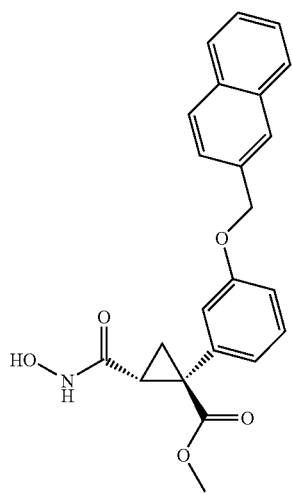
290
-continued
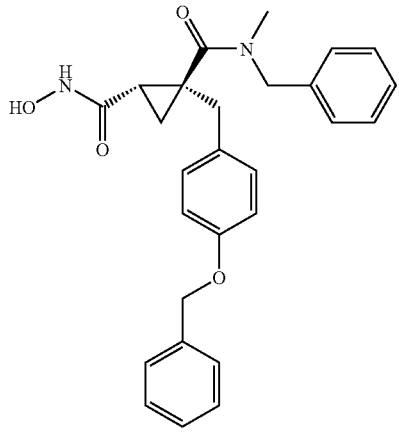
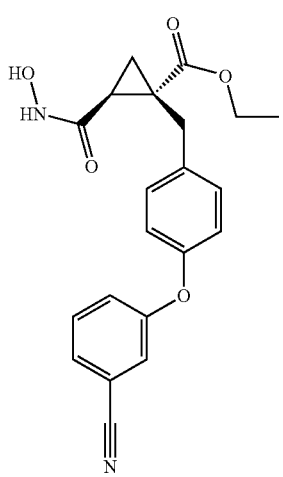
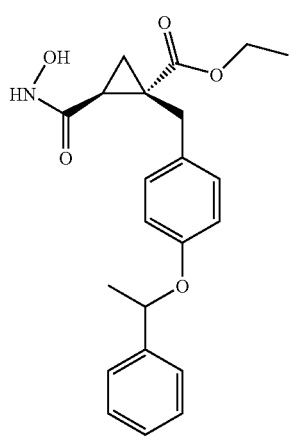

291
-continued
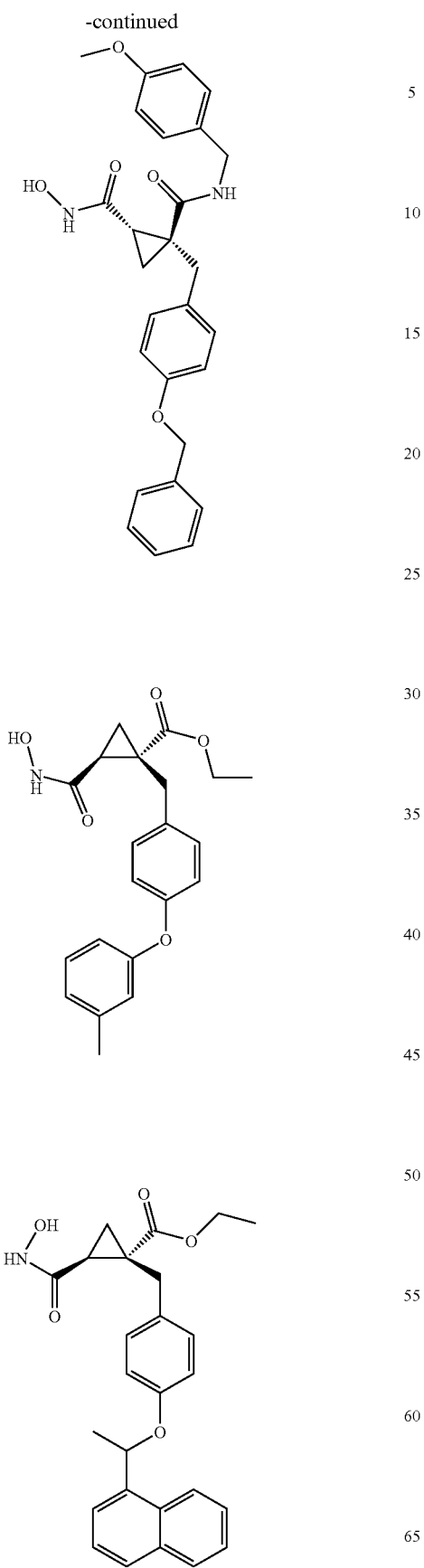
292
-continued
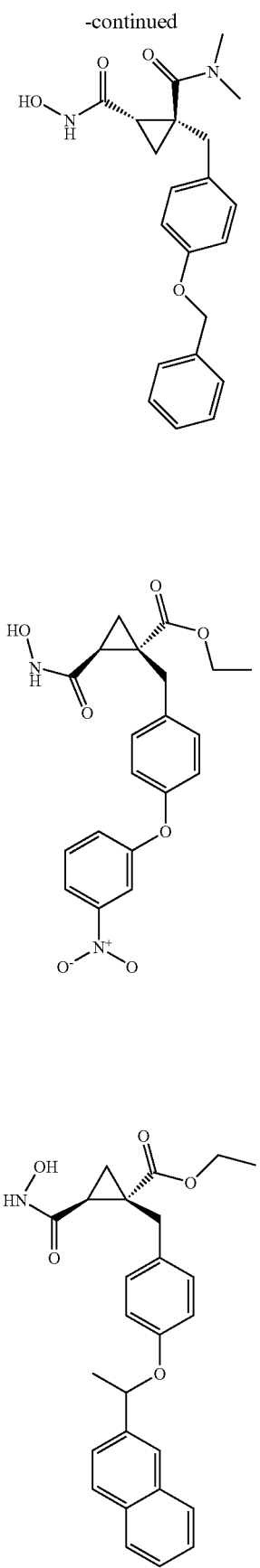

293 294
-continued -continued
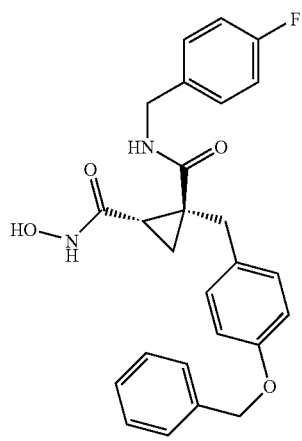
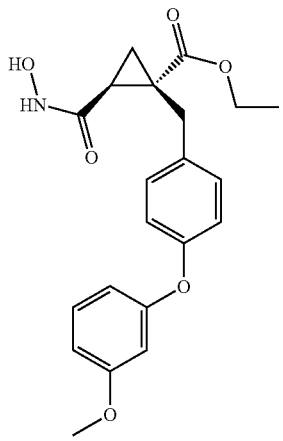
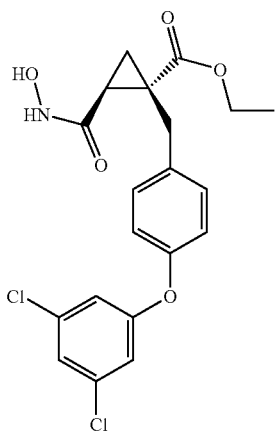
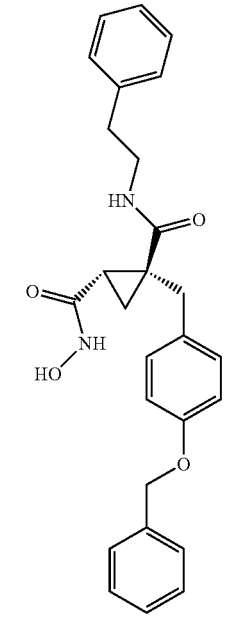
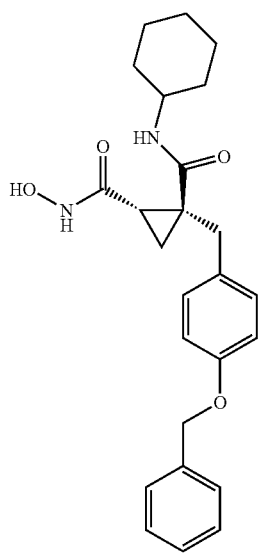
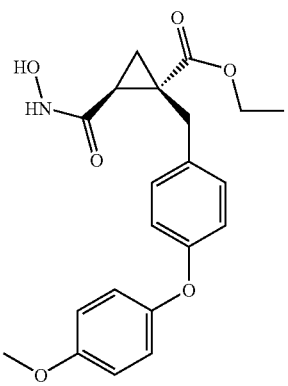

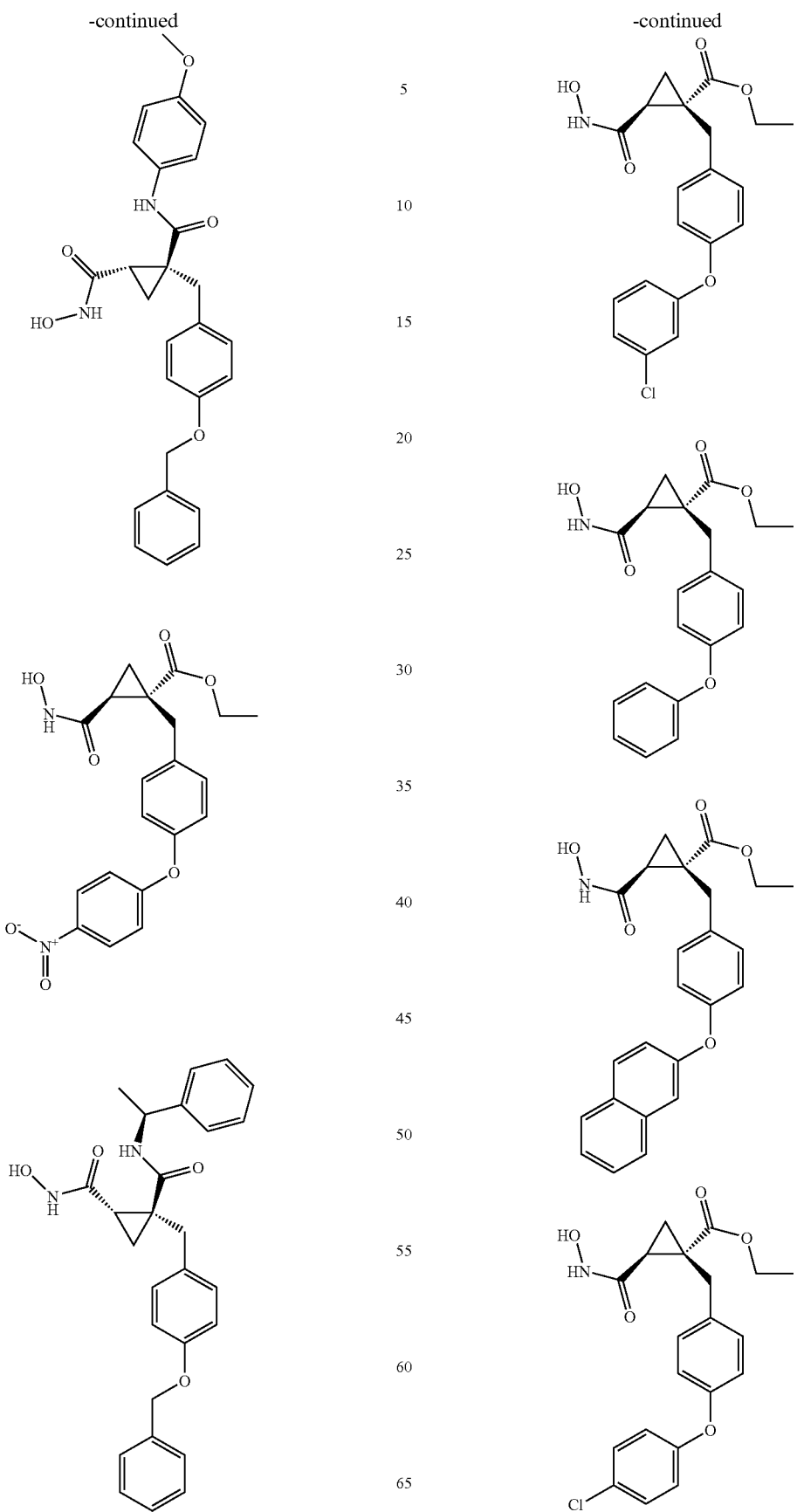

297
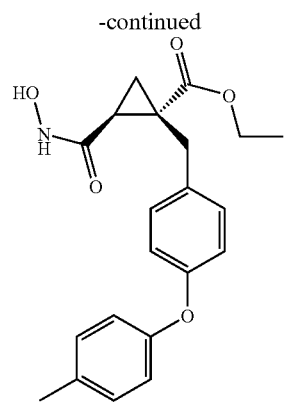
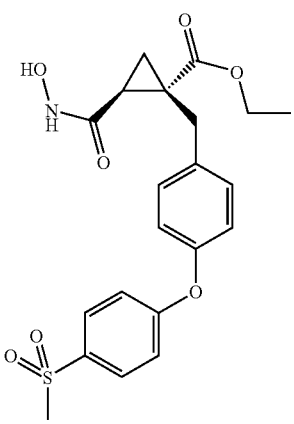
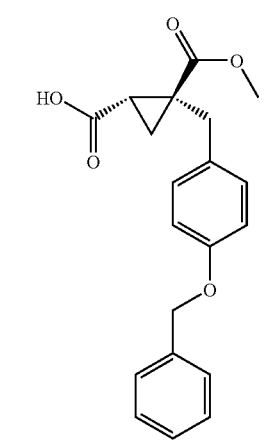
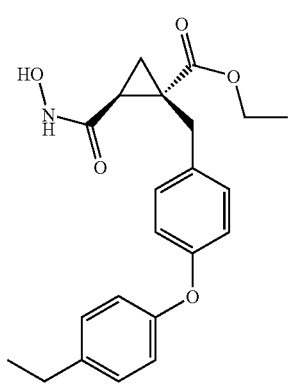
298
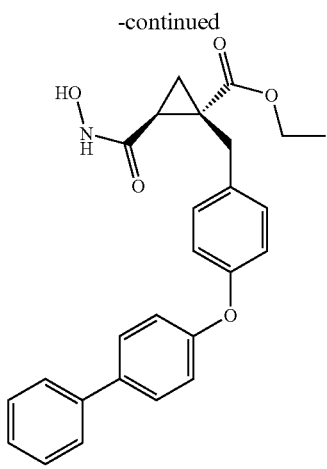
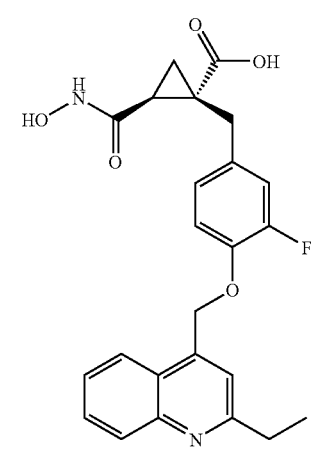
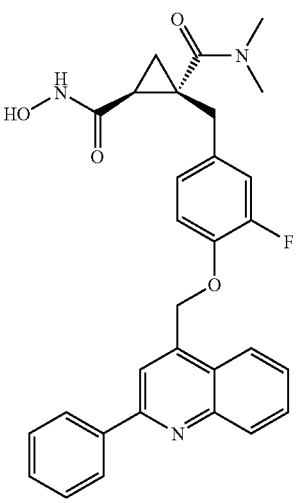

299
-continued
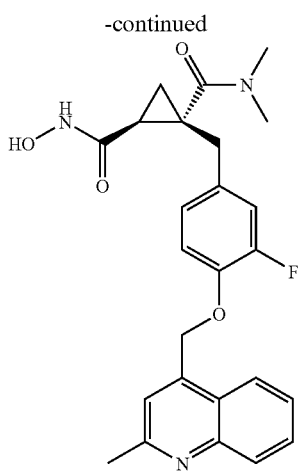
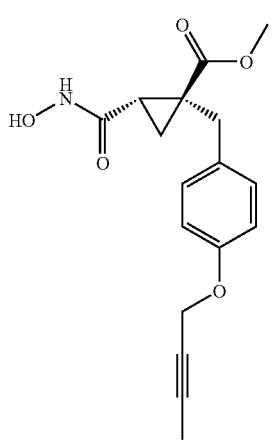
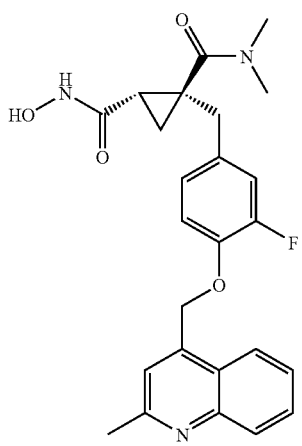
300
-continued
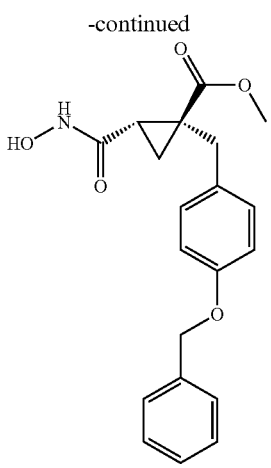
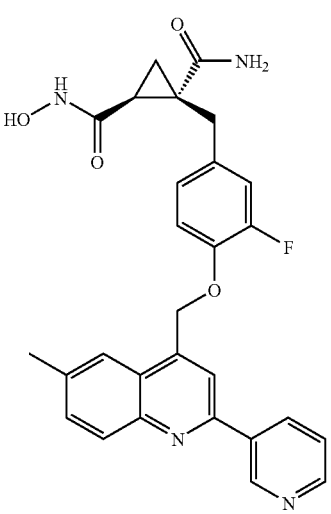
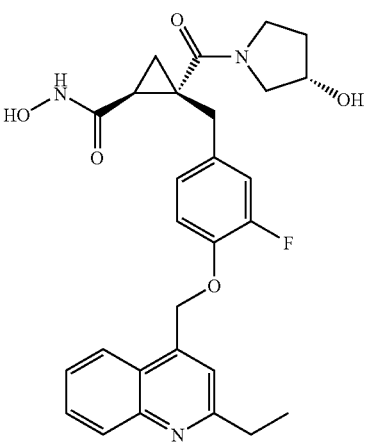

301
-continued
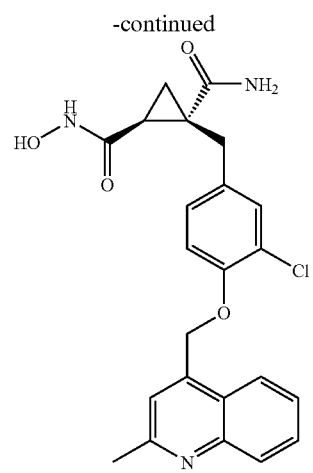
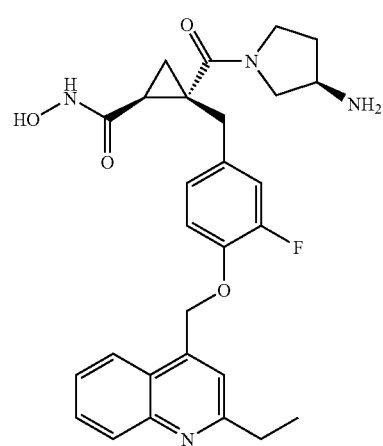
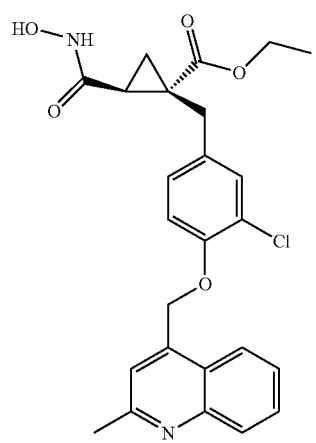
302
-continued
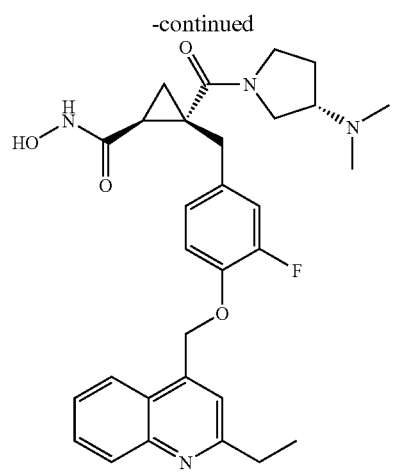
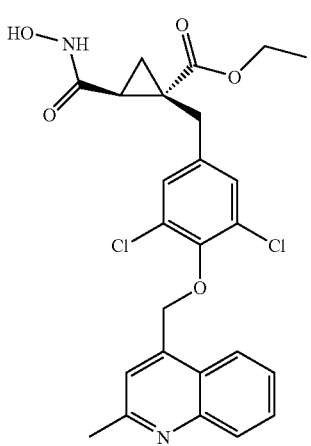
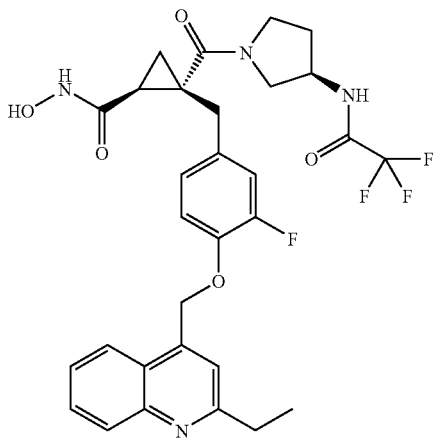

303
-continued
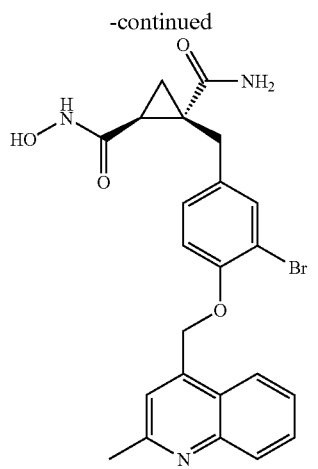
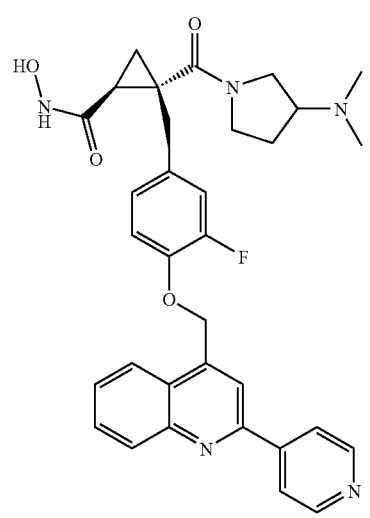
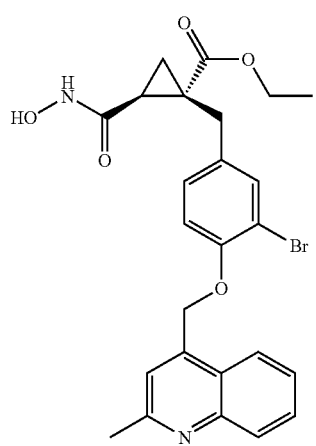
304
-continued
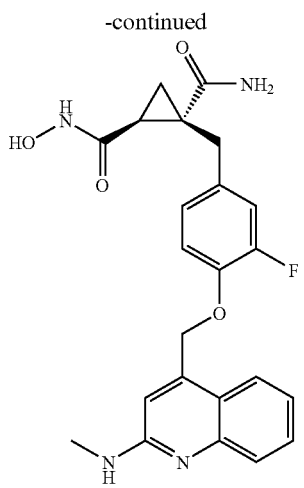
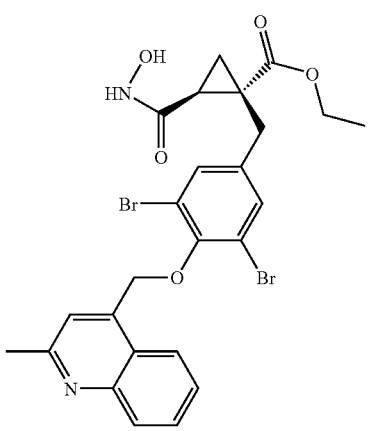
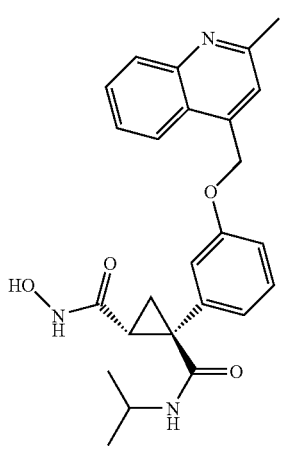

305 -continued
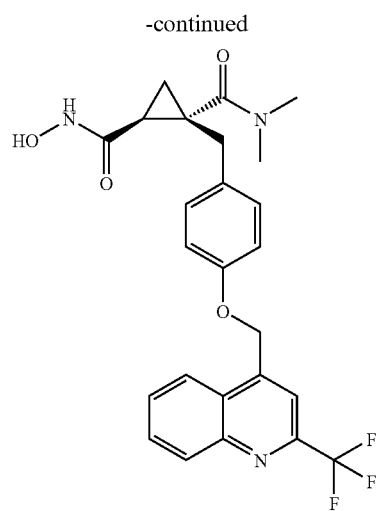
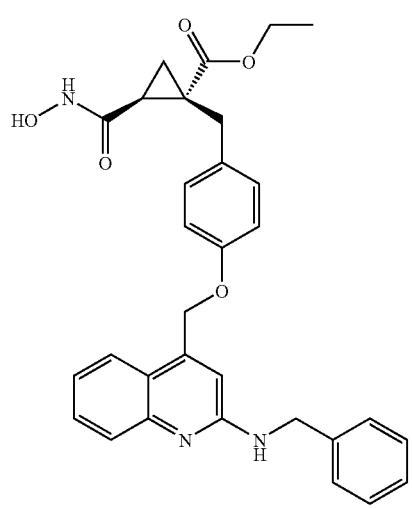
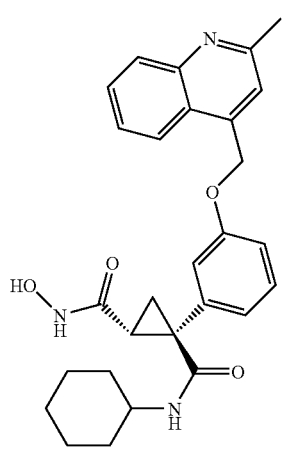
306 -continued
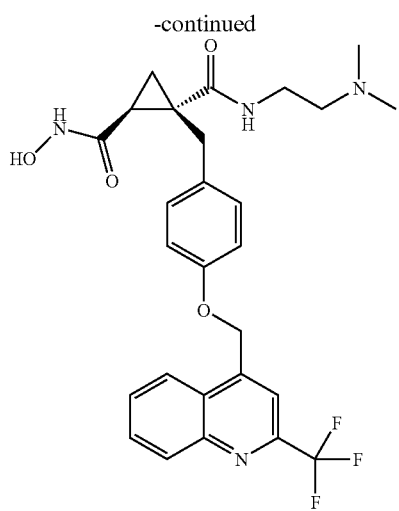
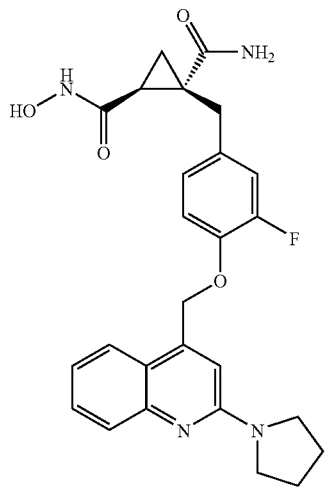
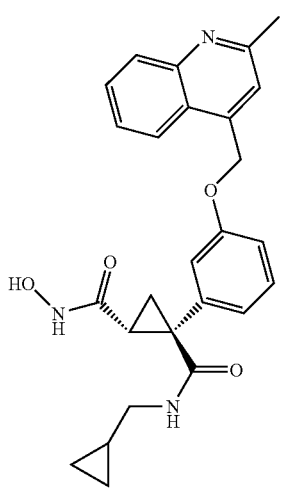

307
-continued
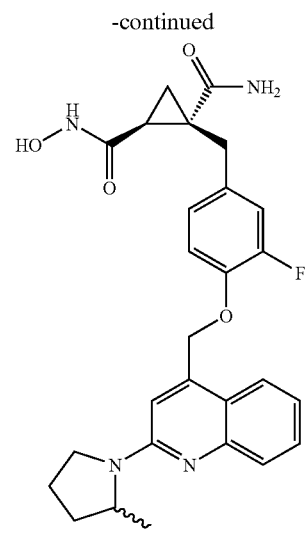
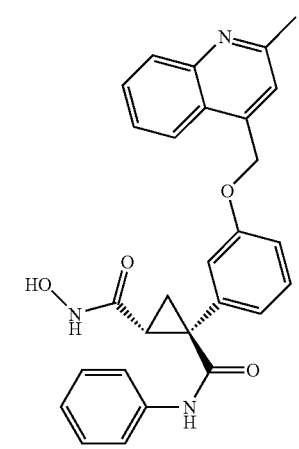
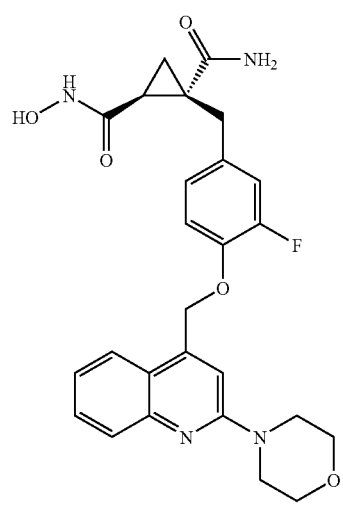
308
-continued
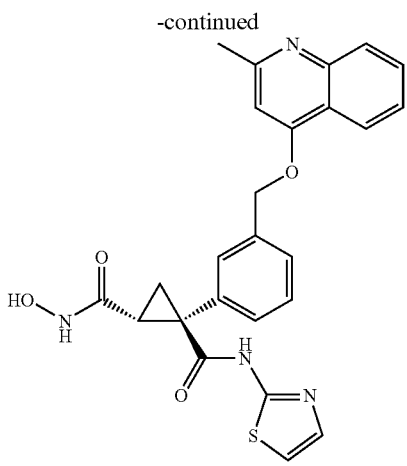
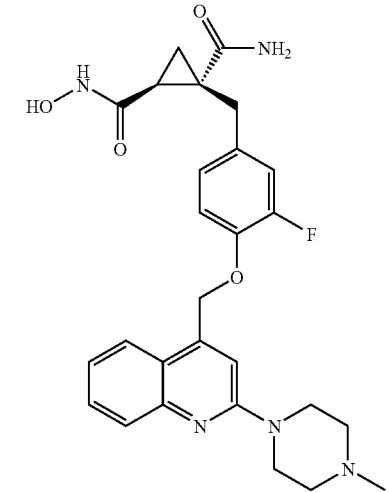
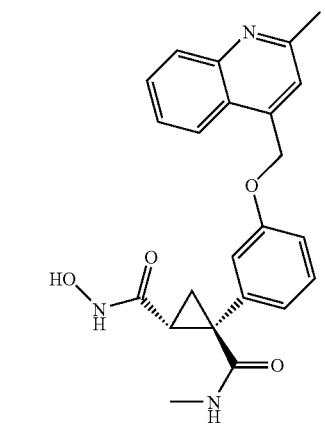

309
-continued
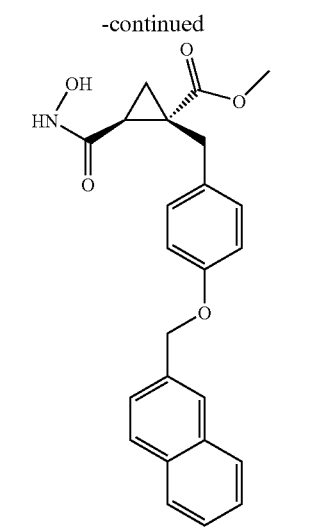
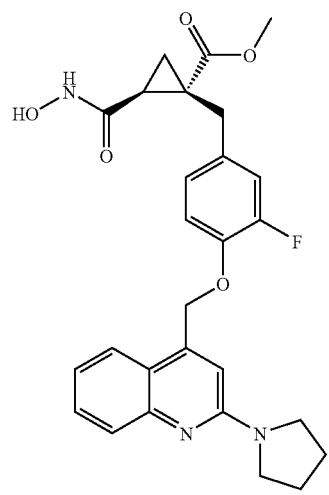
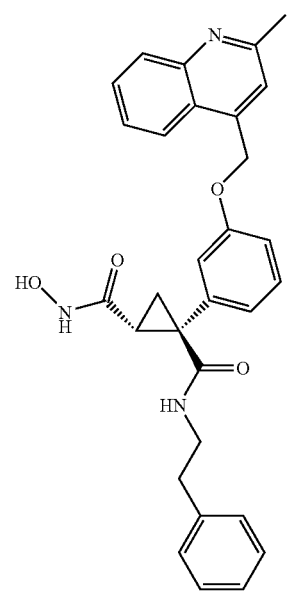
310
-continued
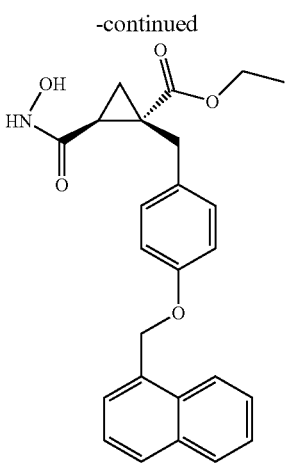
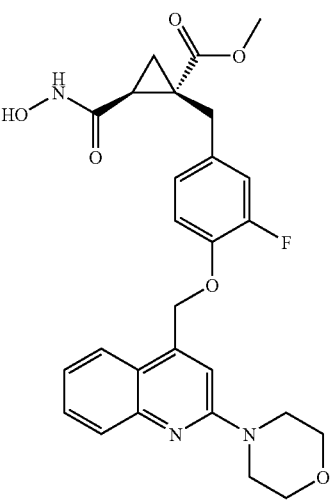
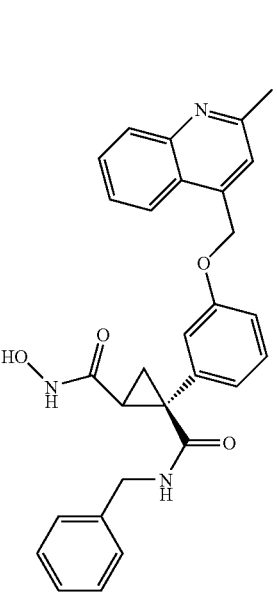

311
-continued
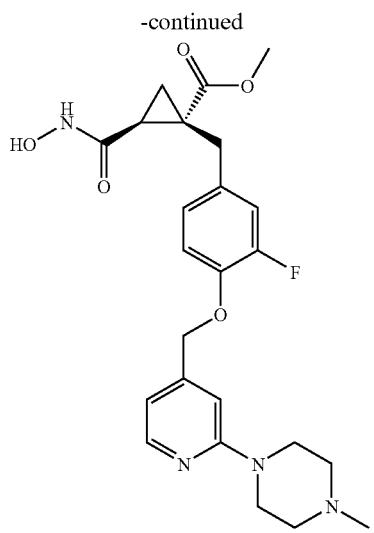
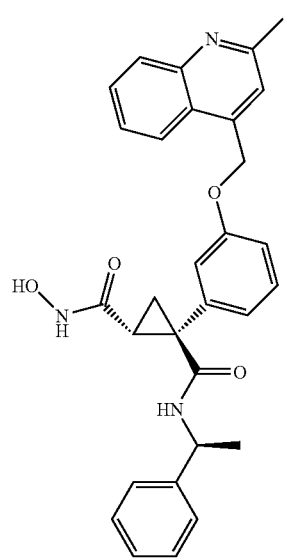
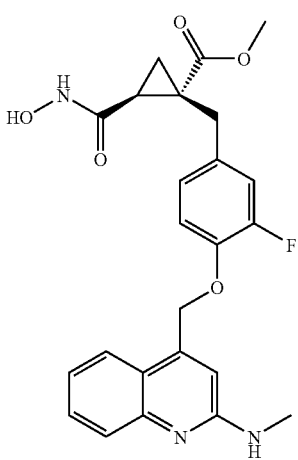
312
-continued
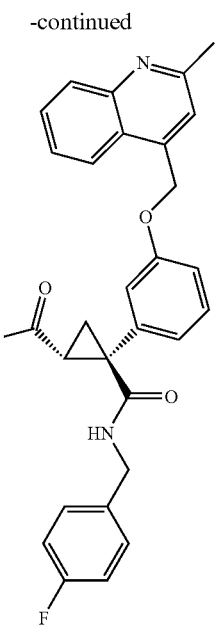
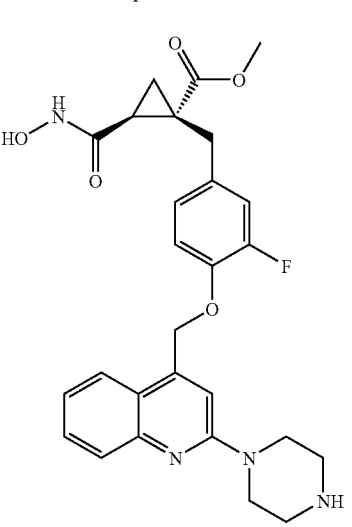
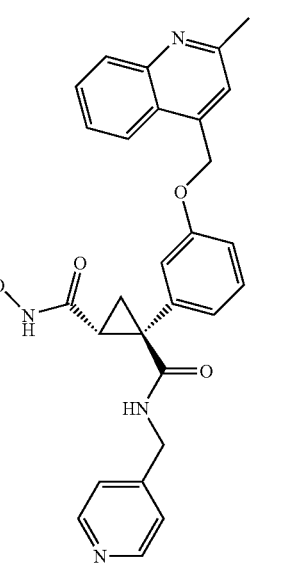

313
-continued
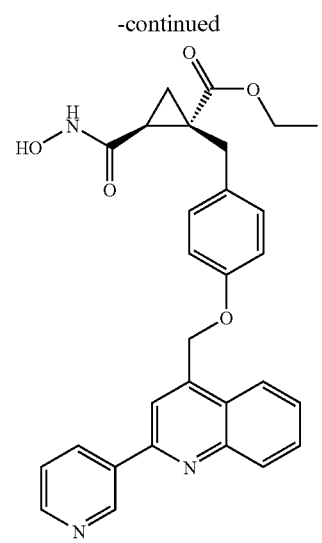
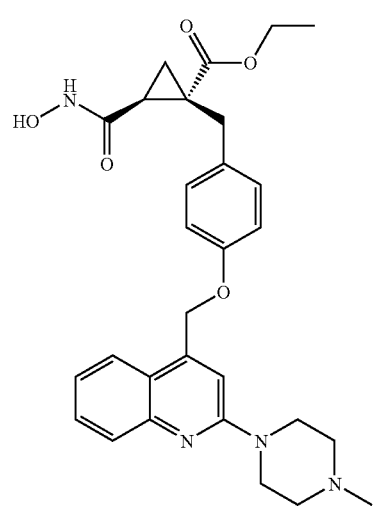
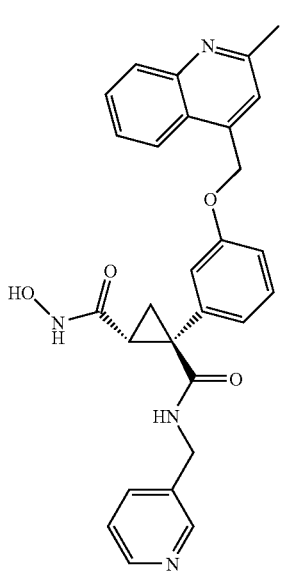
314
-continued
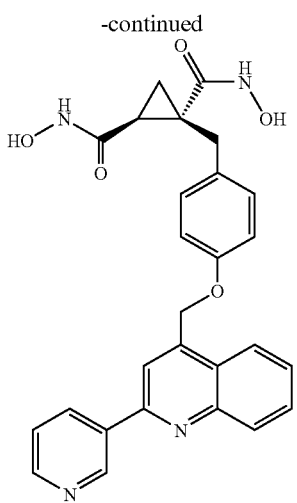
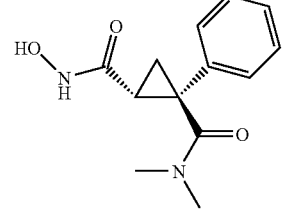
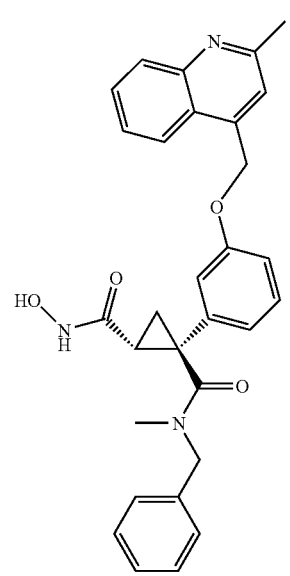

315
-continued
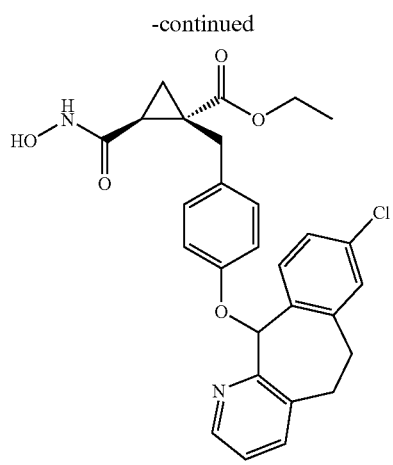
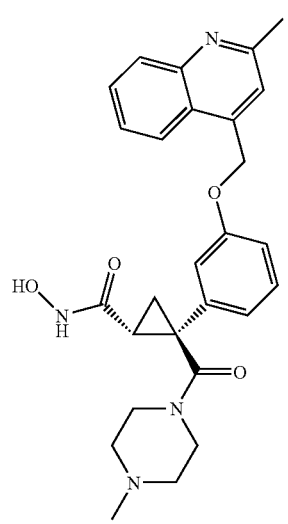
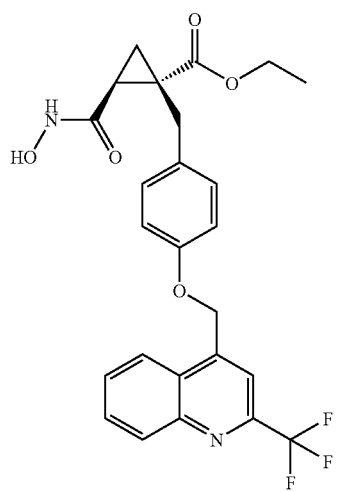
316
-continued
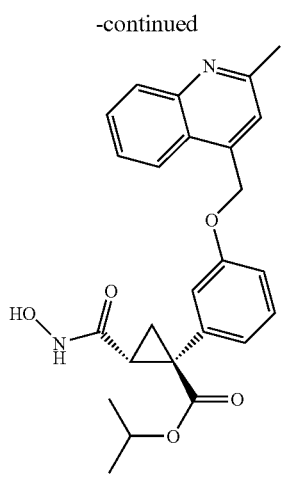
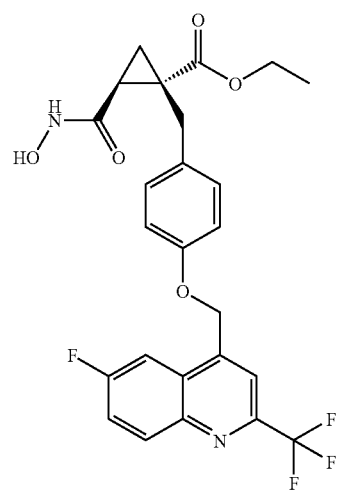
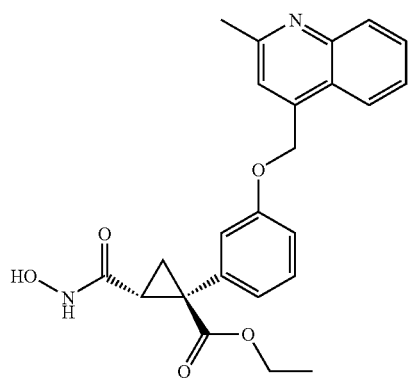

317 318
-continued -continued
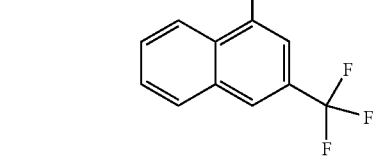
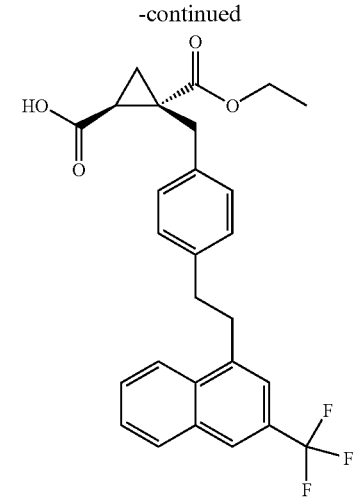
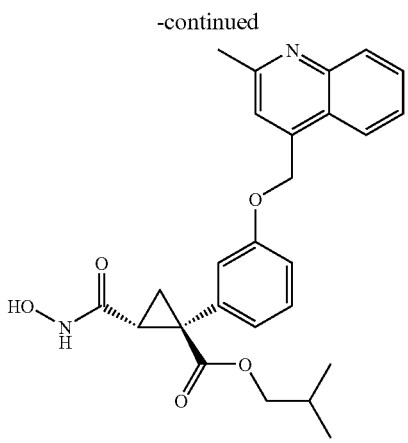
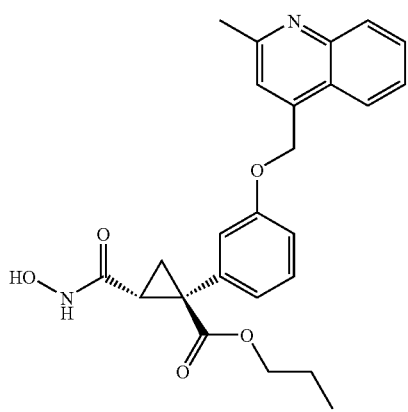
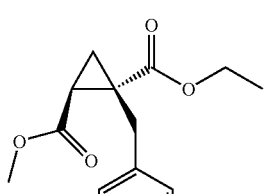
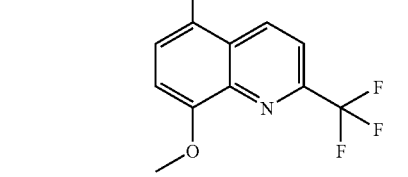
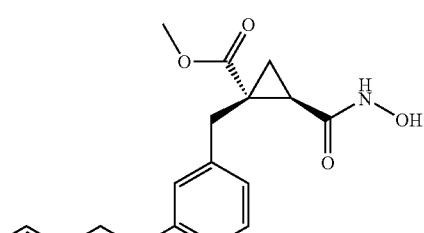
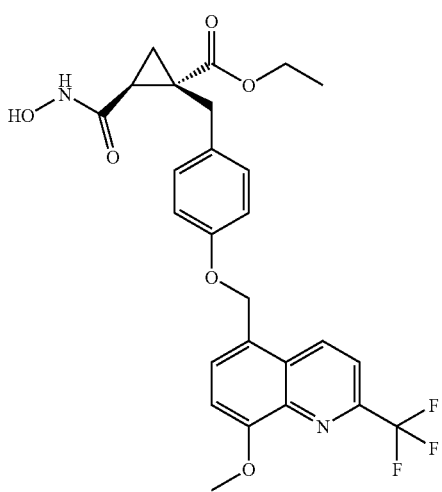
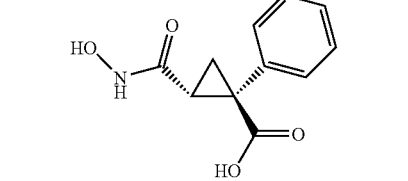

319
-continued
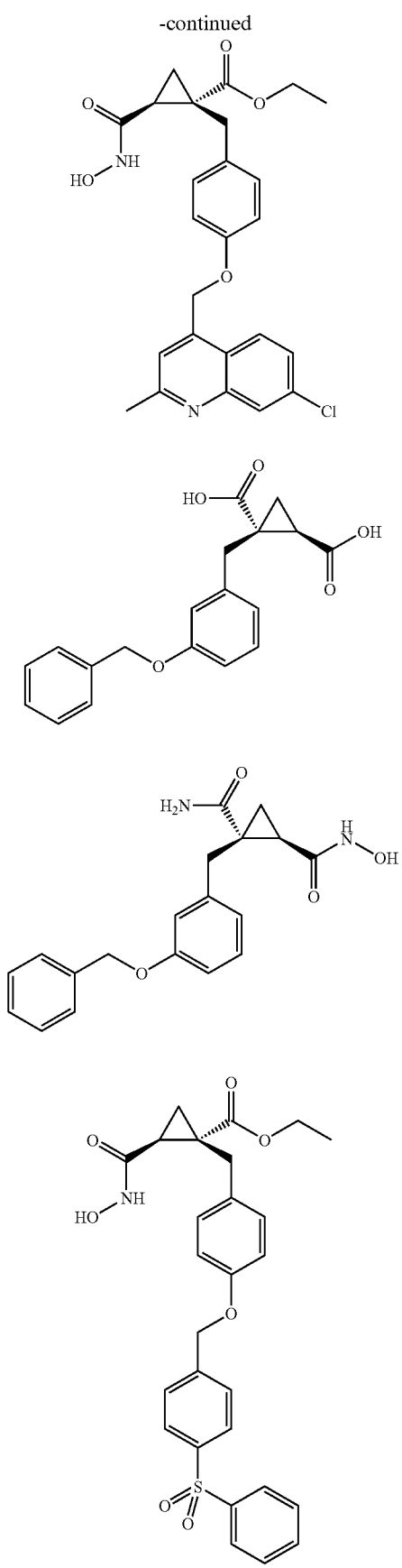
320
-continued
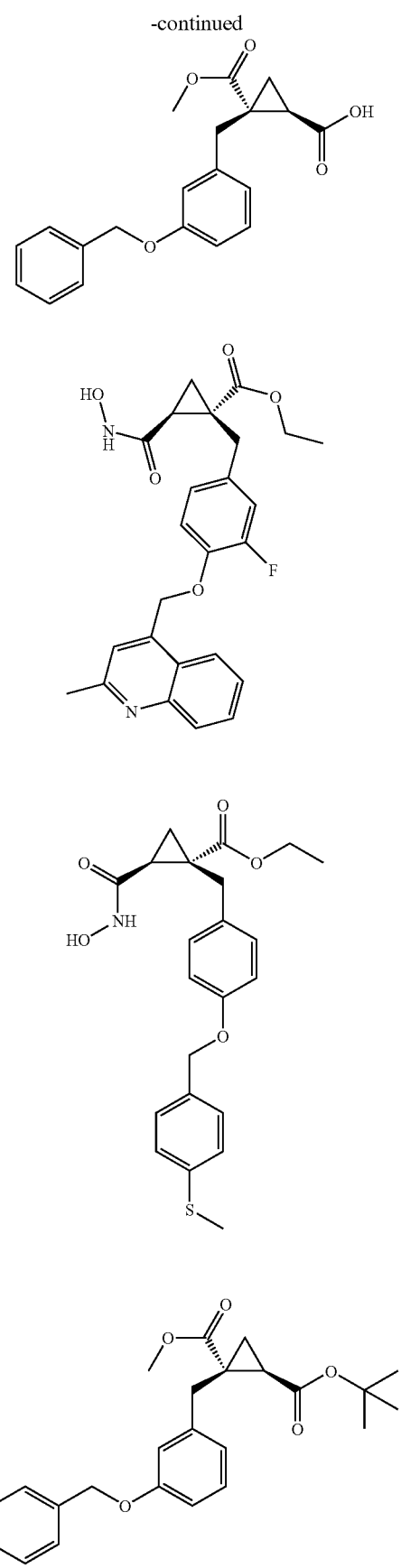

321
-continued
322
-continued
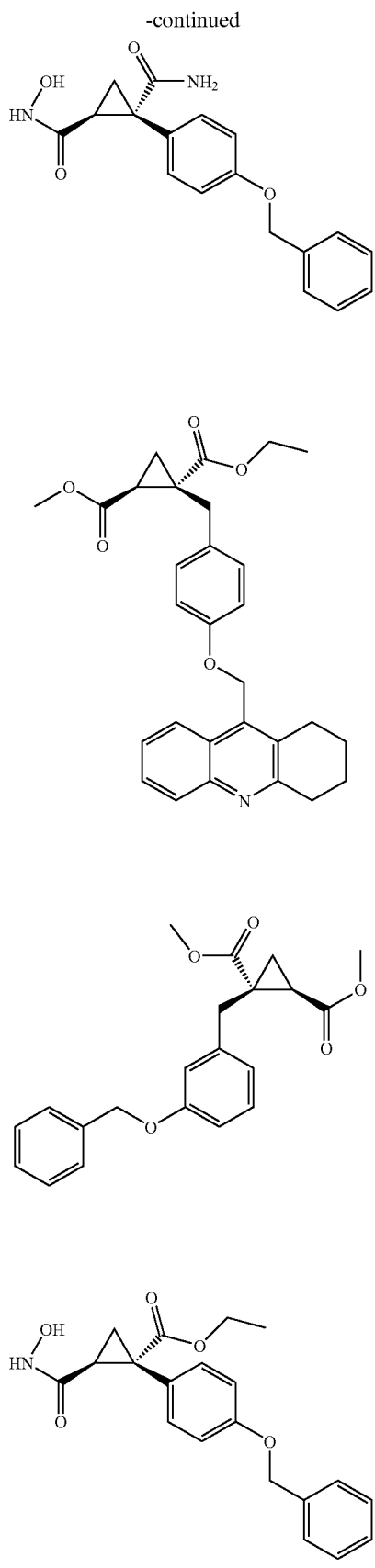
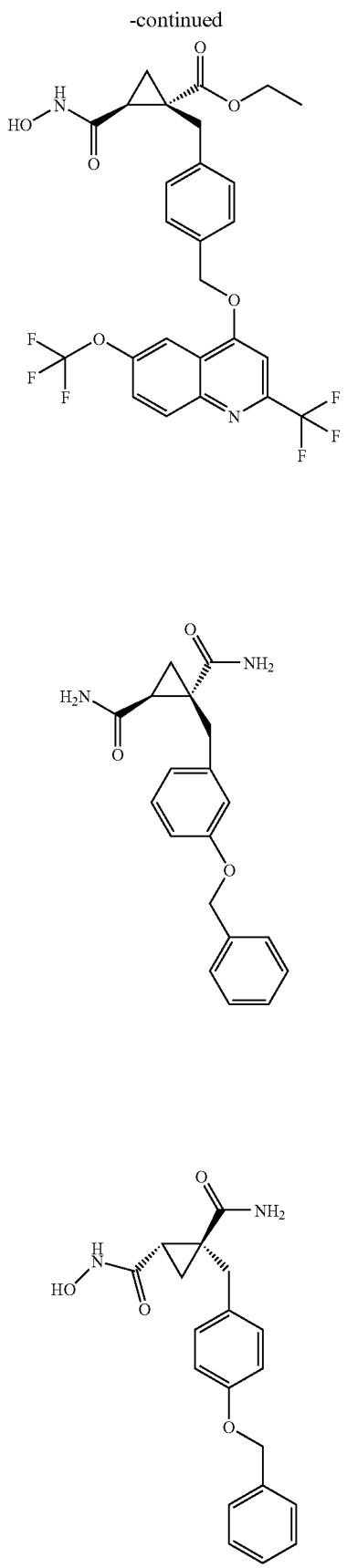

323
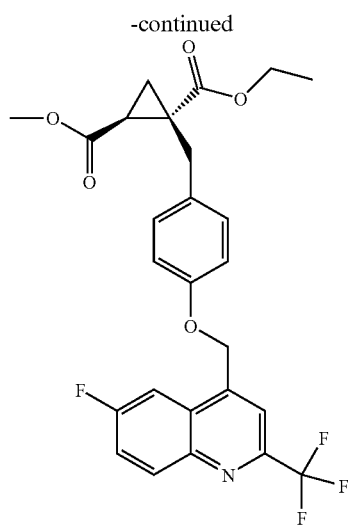
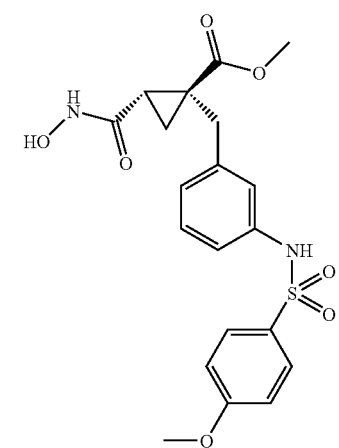
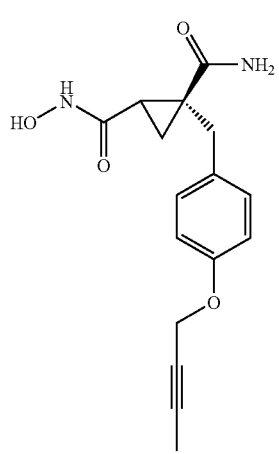
324
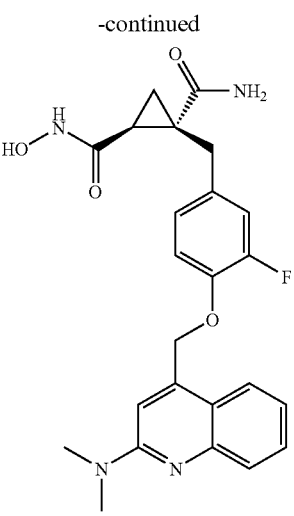
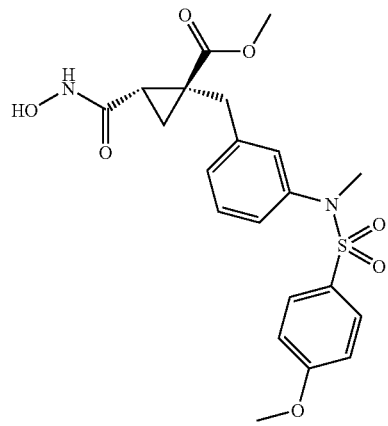
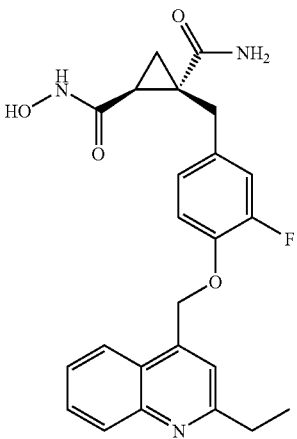

-continued
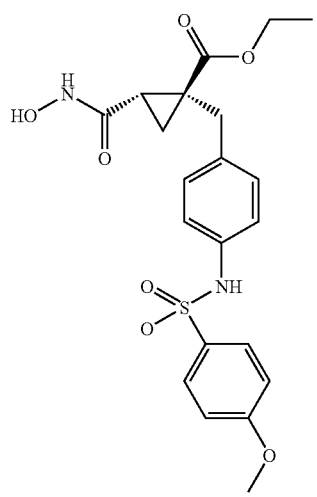
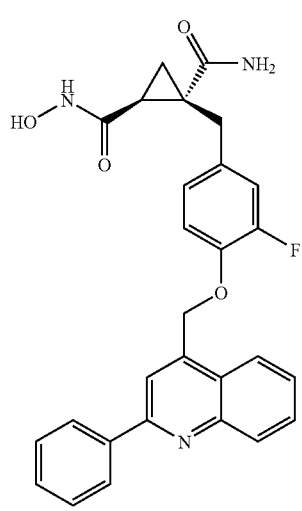
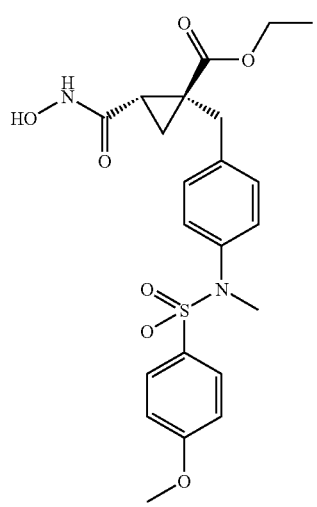
-continued
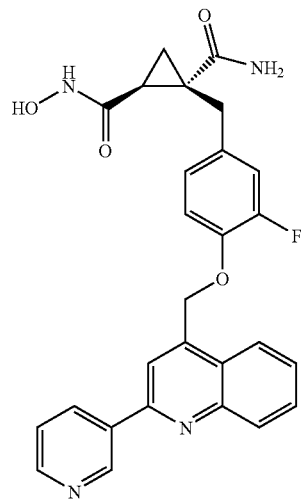
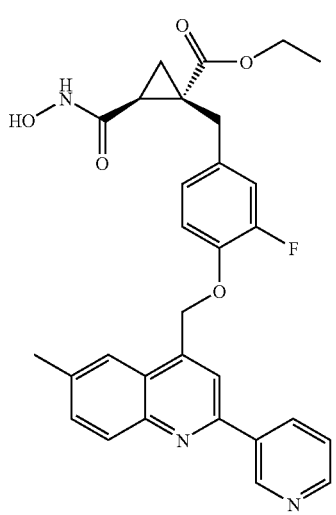
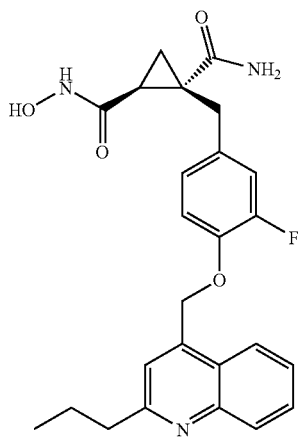

327
-continued
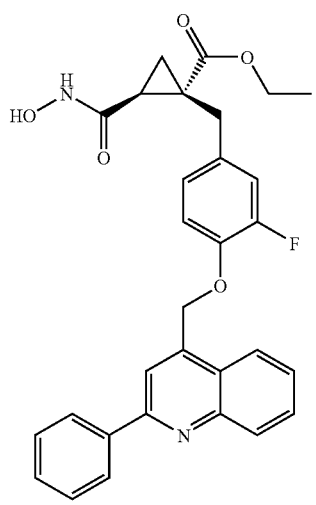
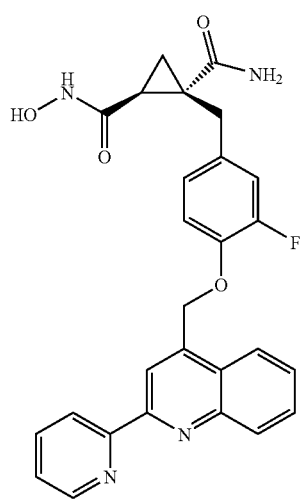
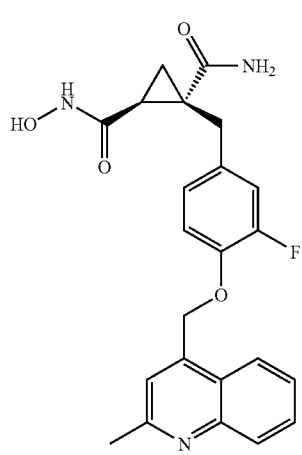
328
-continued
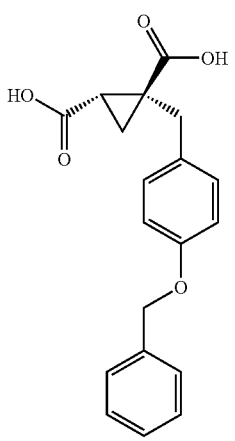
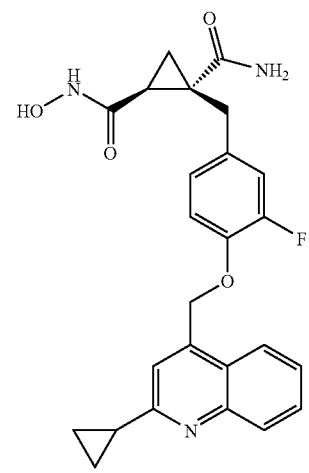
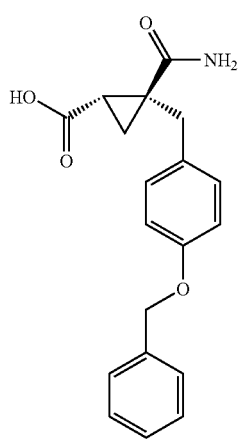

329
-continued
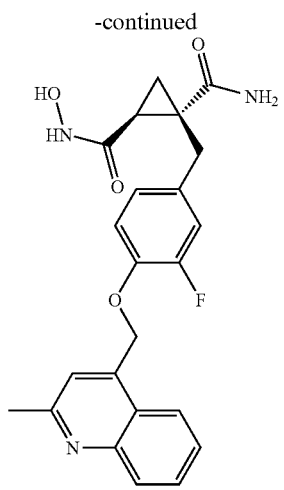
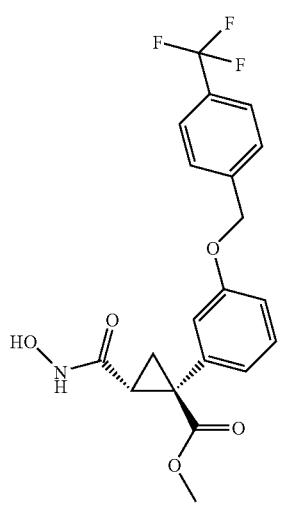
330
-continued
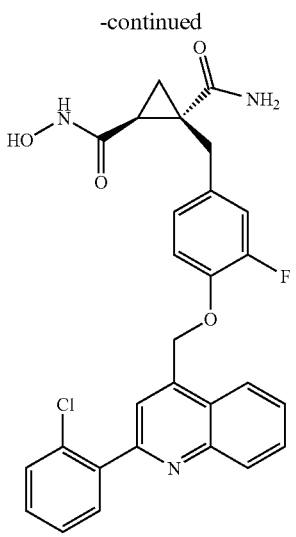
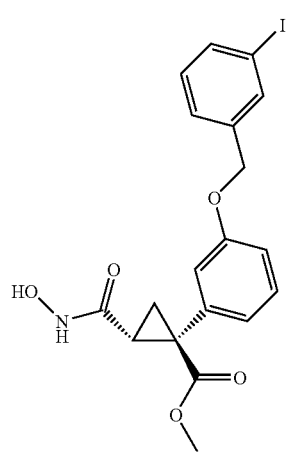
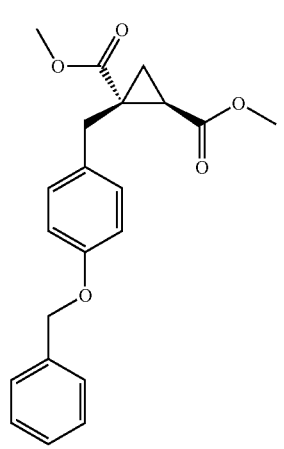
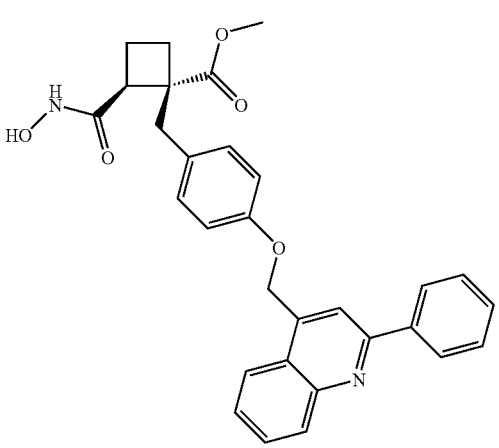

331
-continued
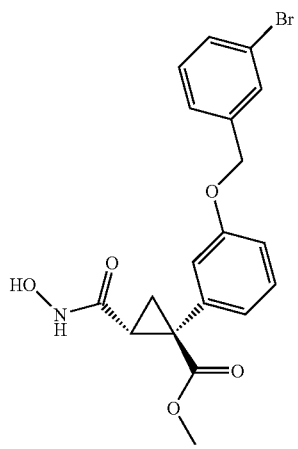
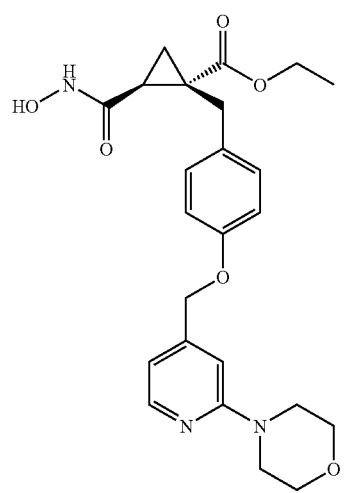
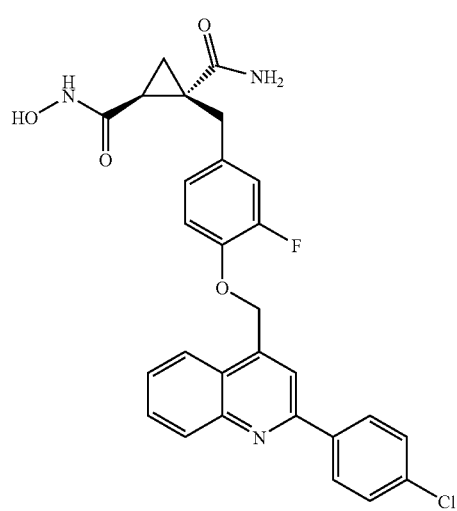
332
-continued
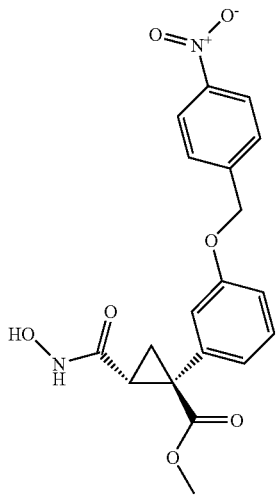
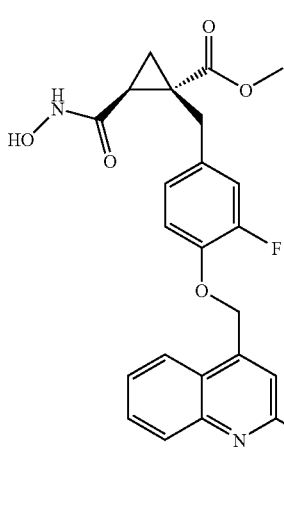
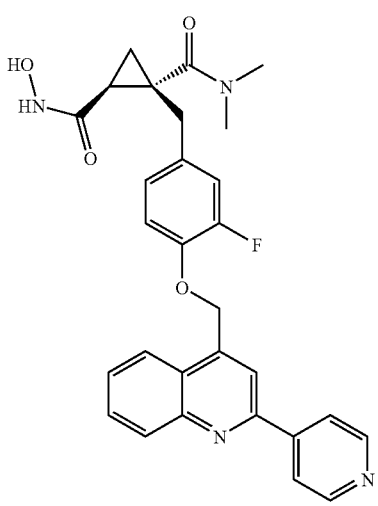

333
-continued
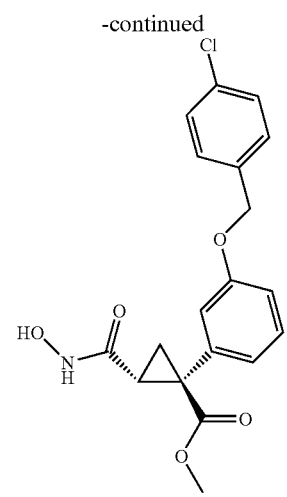
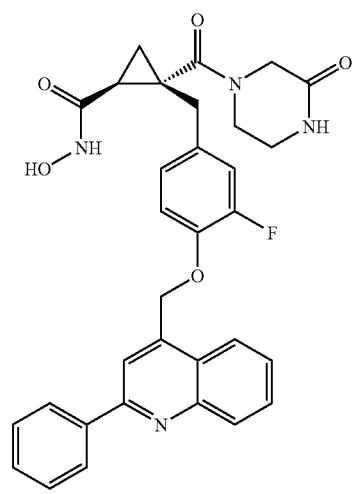
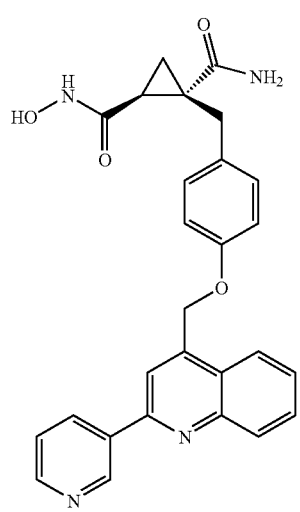
334
-continued
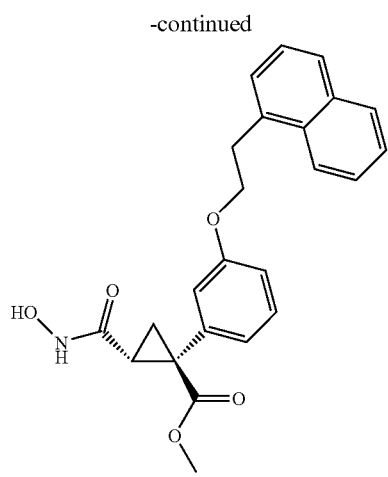
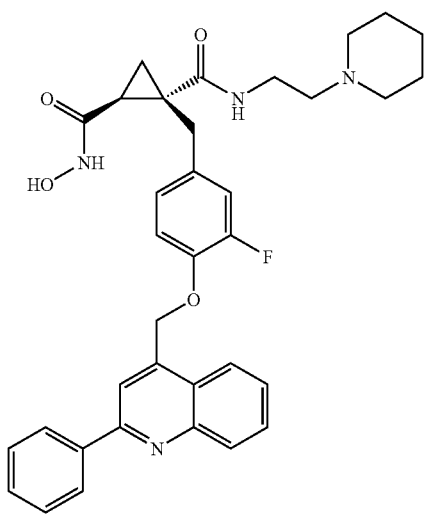
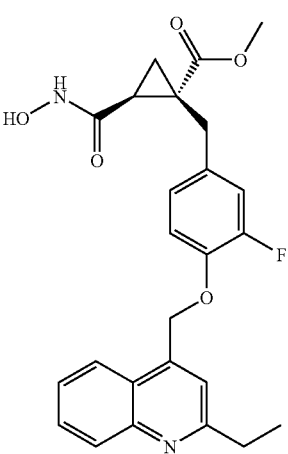

335
-continued
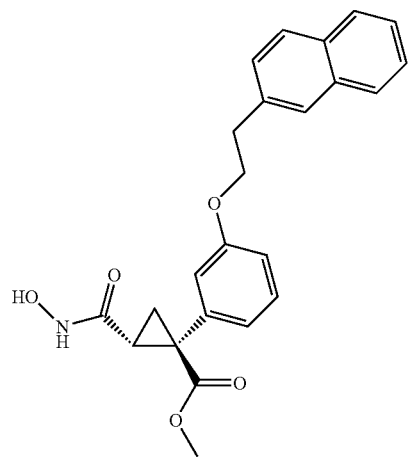
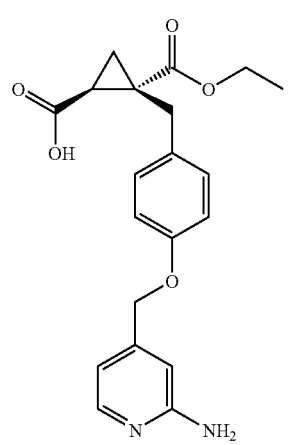
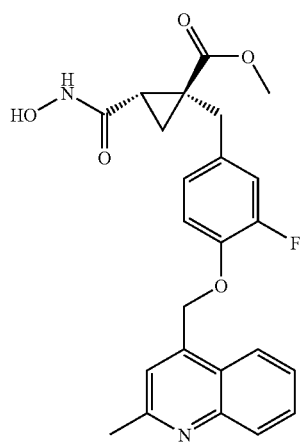
336
-continued
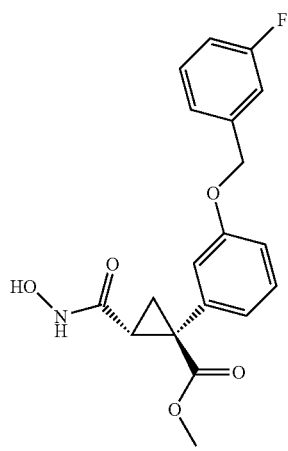
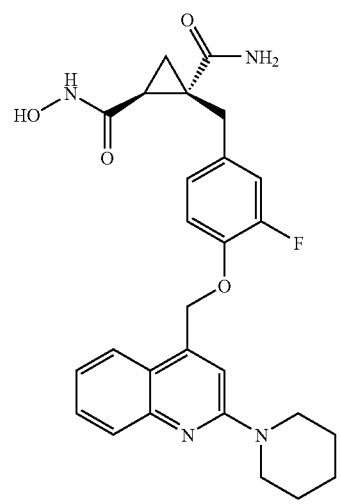
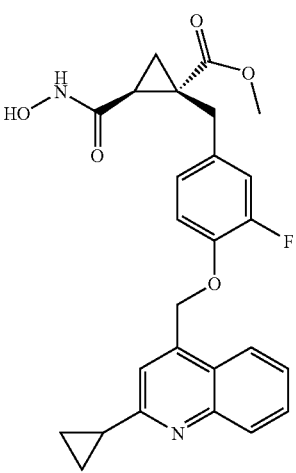

-continued
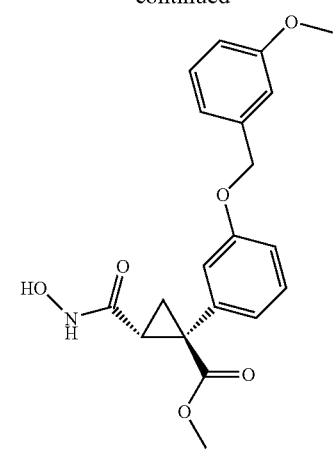
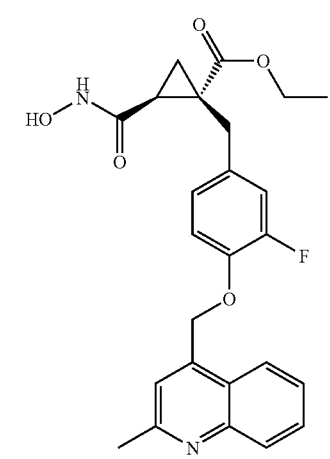
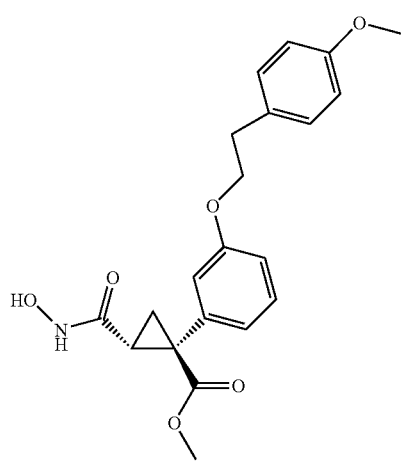
or a pharmaceutically acceptable salt or isomer thereof.
2. A compound according to claim 1, which is selected from the group consisting of
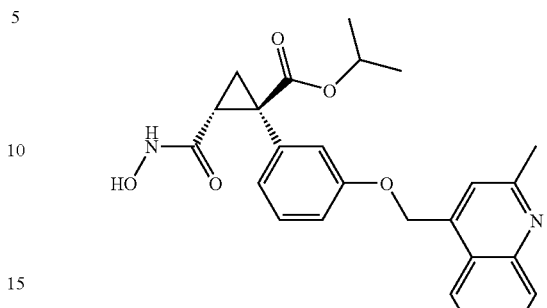
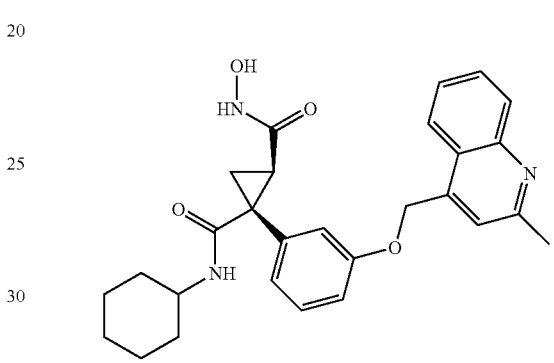
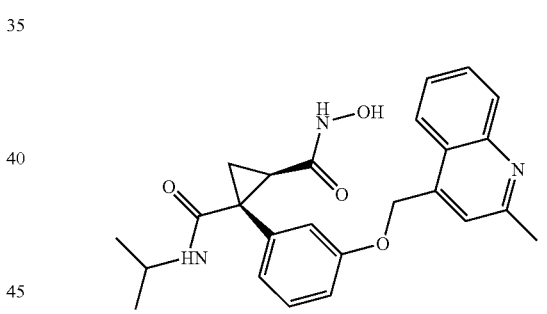
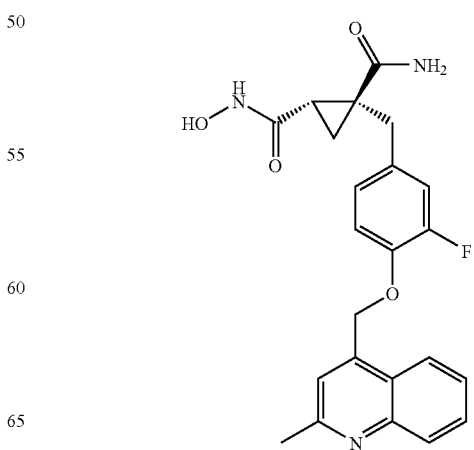

339
-continued
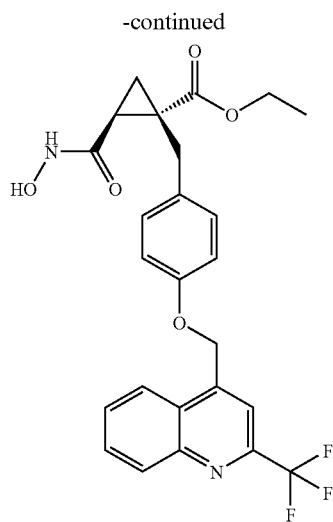
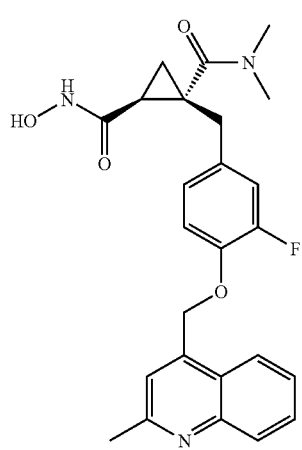
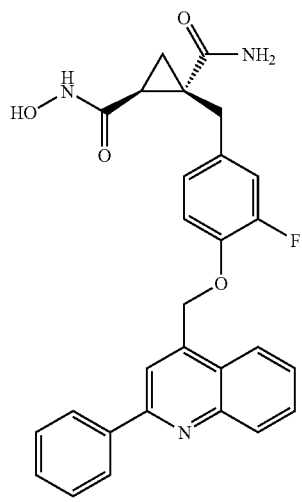
340
-continued
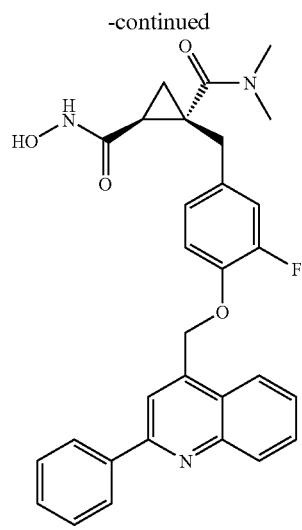
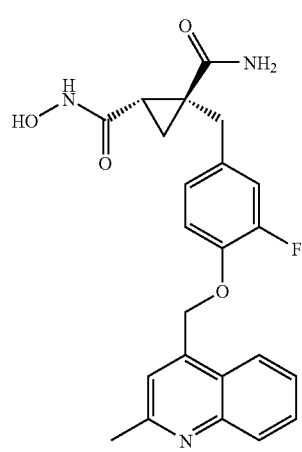
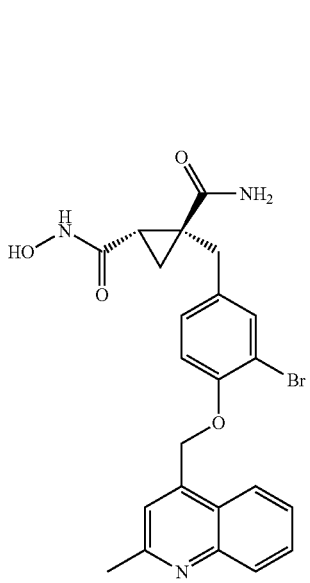

341
-continued
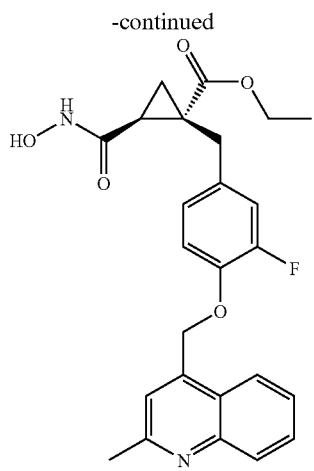
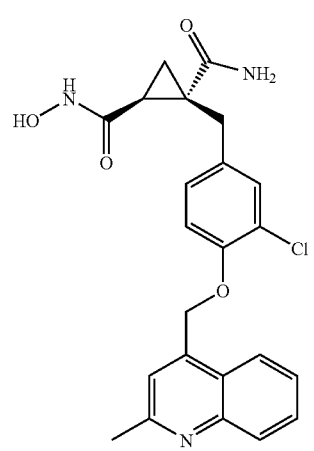
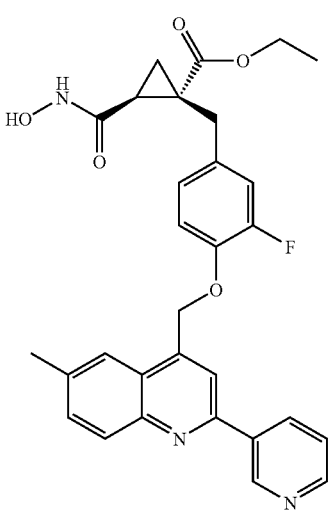
342
-continued
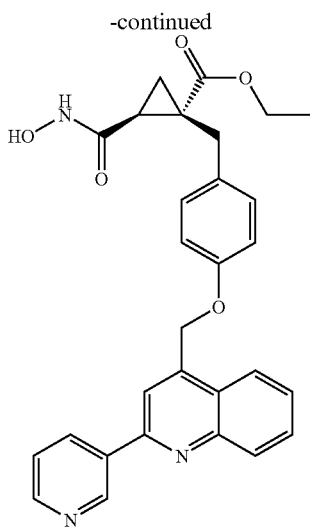
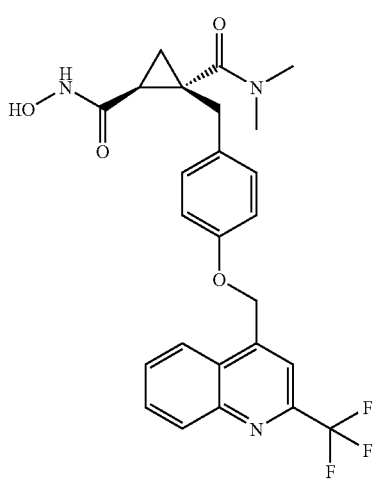
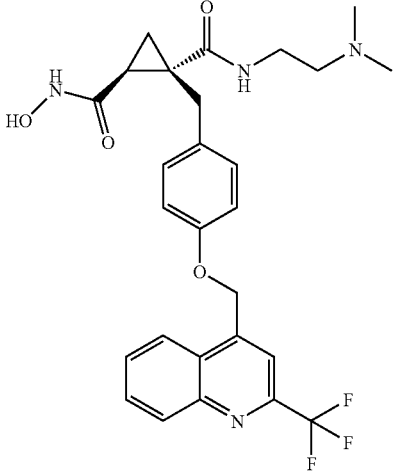

343
-continued
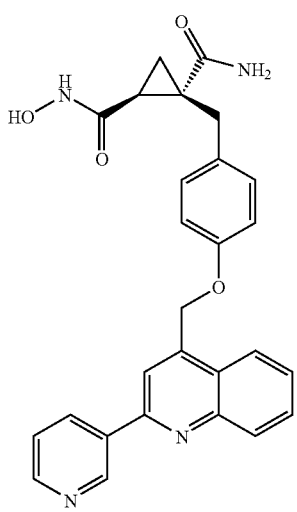
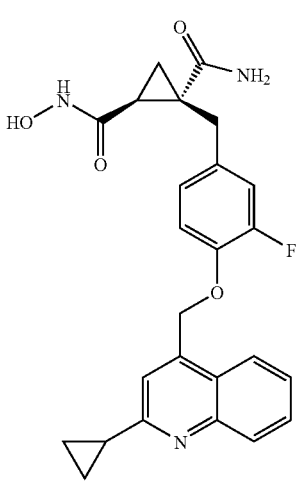
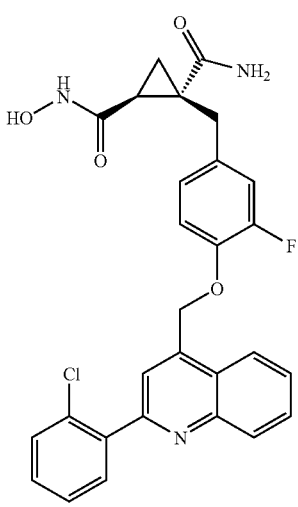
344
-continued
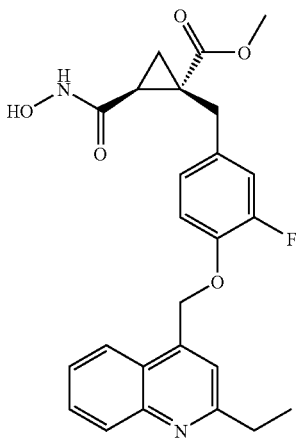
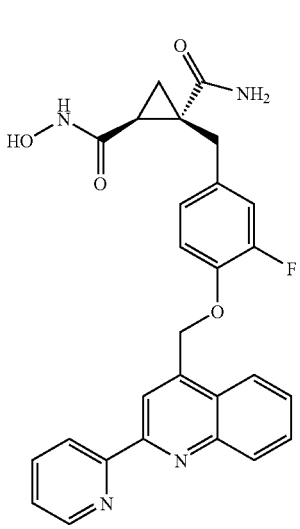
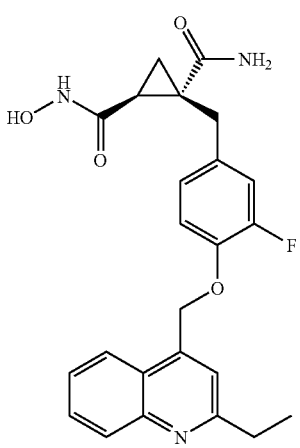

345
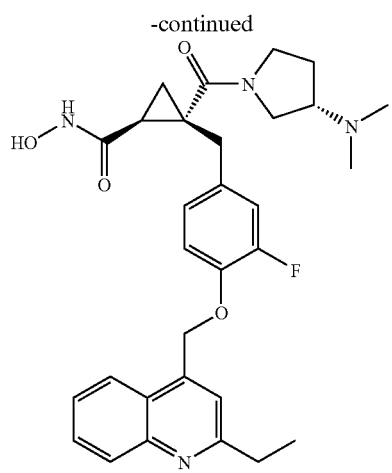
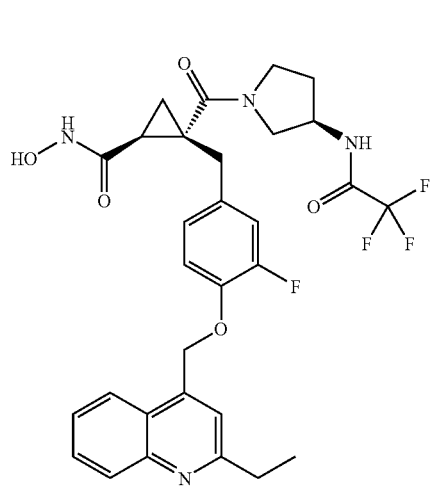
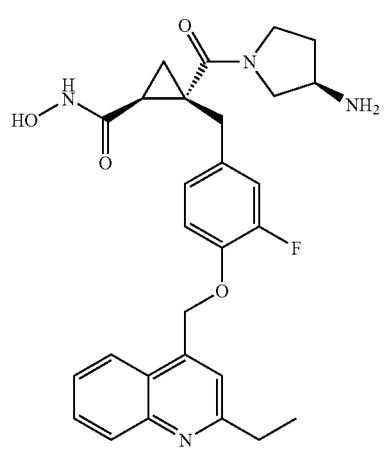
346
-continued
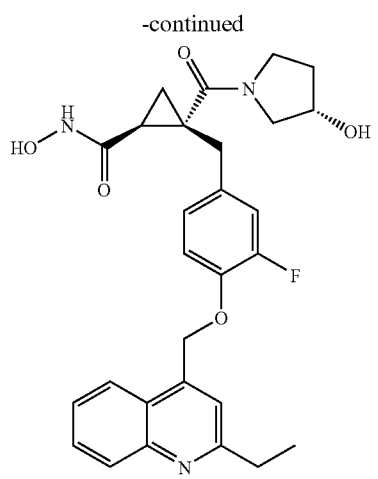
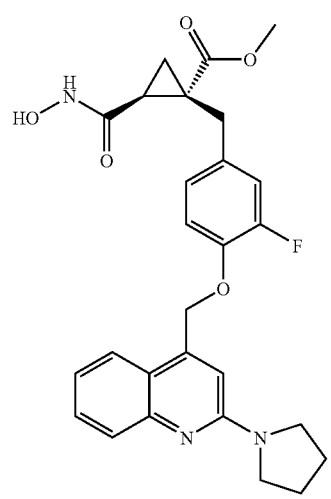
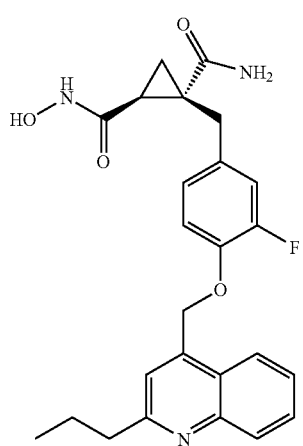

347
-continued
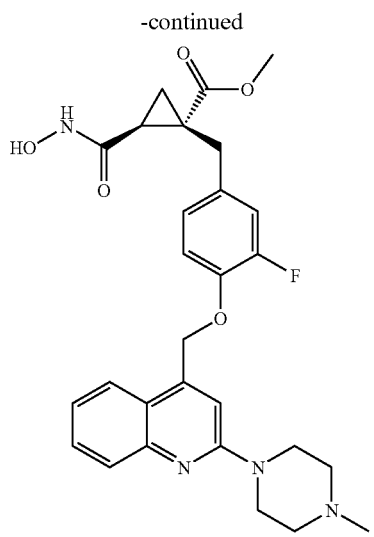
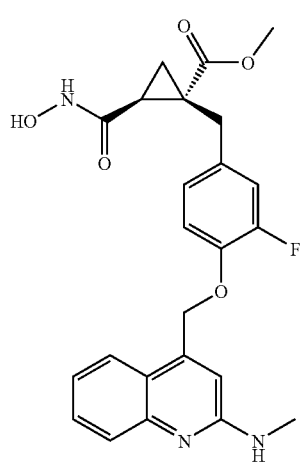
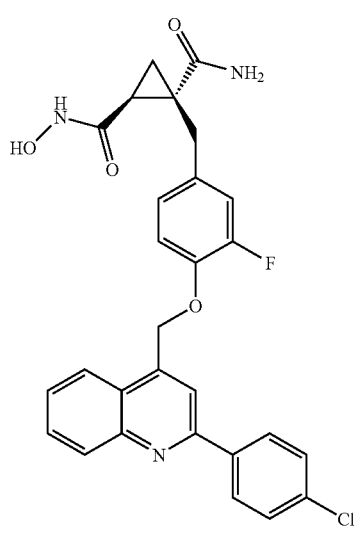
348
-continued
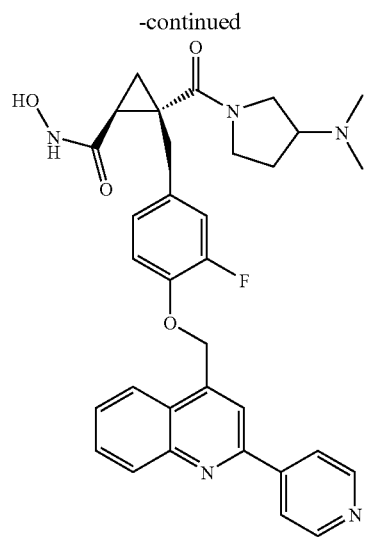
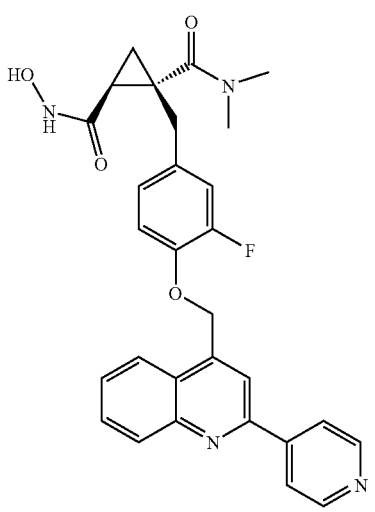
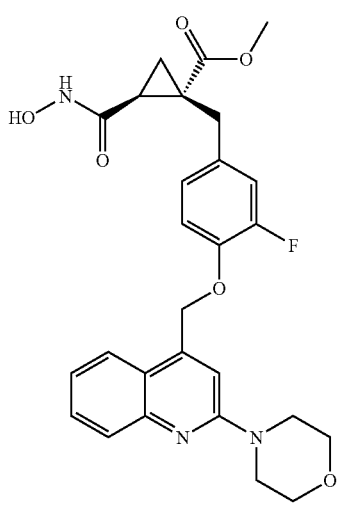

349
-continued
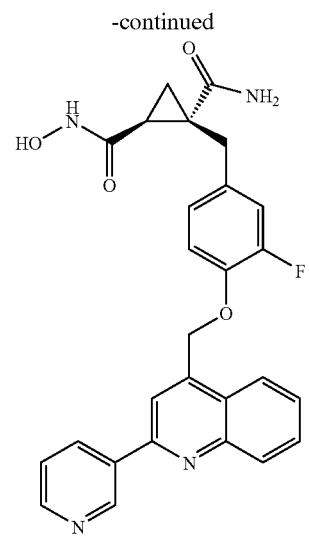
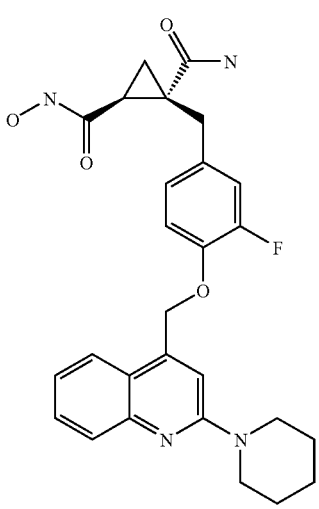
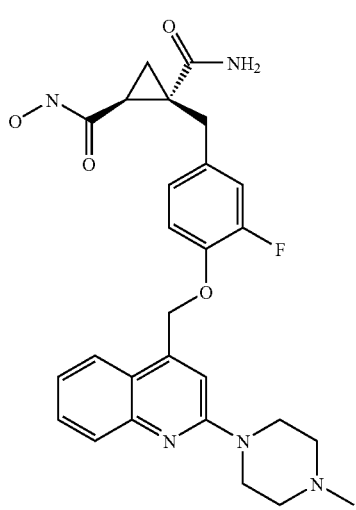
350
-continued
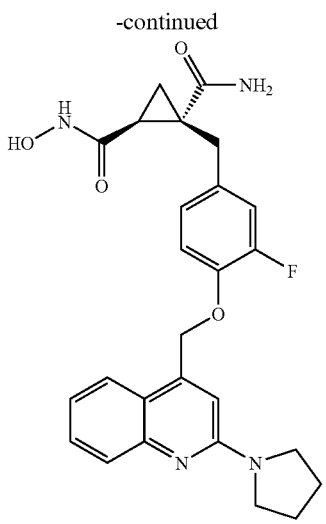
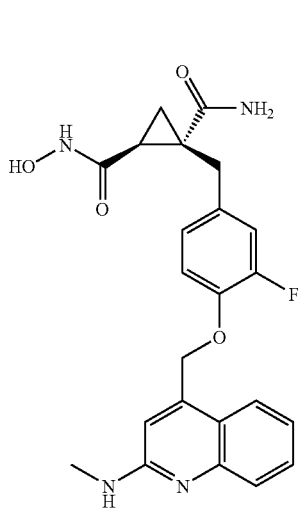

-continued
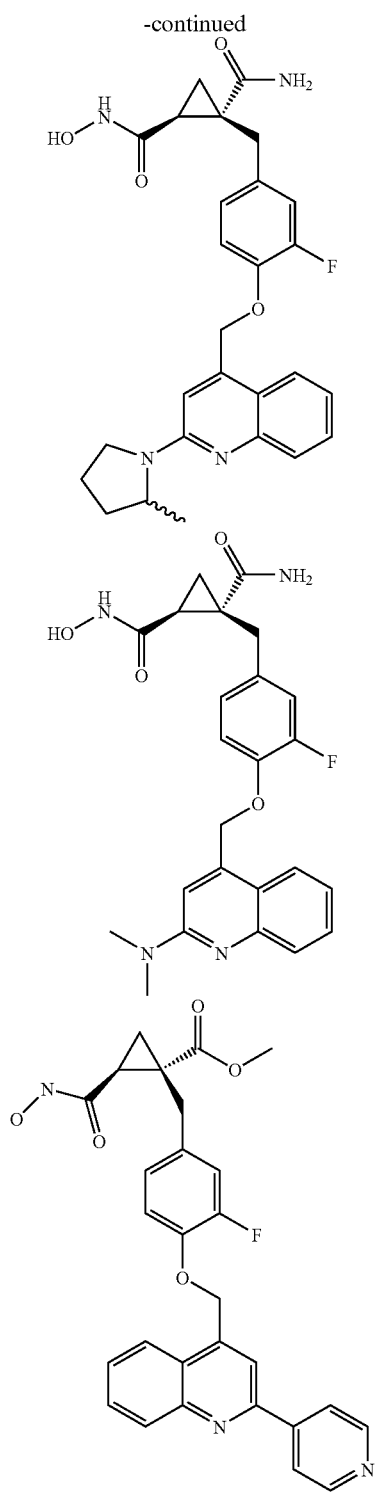
-continued
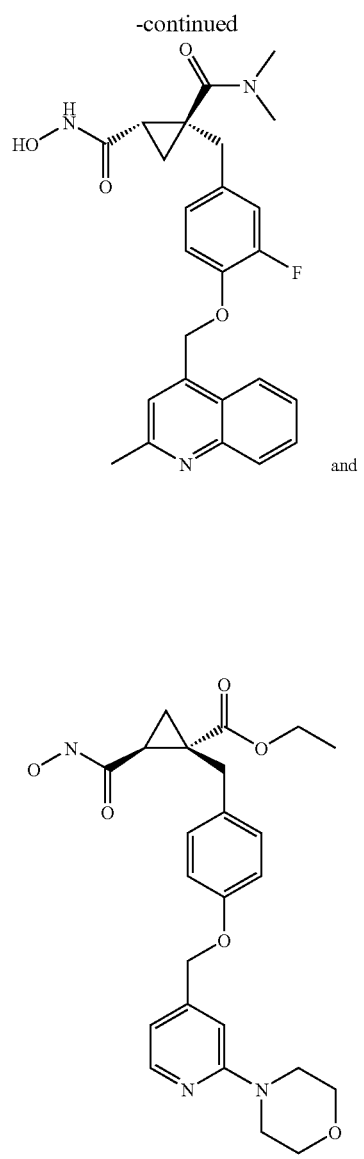
and
or a pharmaceutically acceptable salt or isomer thereof.
3. A pharmaceutical composition comprising a therapeutically effective amount of a compound of claim 1 or a pharmaceutically acceptable addition salt or isomer thereof, in combination with a pharmaceutically acceptable carrier.
* * * * *